(12) United States Patent
Duffy et al.

(10) Patent No.: US 9,249,125 B2
(45) Date of Patent: Feb. 2, 2016

(54) PYRAZOLE DERIVATIVES AS P38 MAP INHIBITORS

(71) Applicants: RESPIVERT LIMITED, High Wycombe, Buckinghamshire (GB); TOPIVERT PHARMA LIMITED, London (GB)

(72) Inventors: Lorna Anne Duffy, Nottingham (GB); John King-Underwood, Pendock (GB); Alistair Ian Longshaw, Nottingham (GB); Peter John Murray, London (GB); Stuart Thomas Onions, Nottingham (GB); David Michael Adrien Taddei, Nottingham (GB); Jonathan Gareth Williams, Nottingham (GB); Kazuhiro Ito, London (GB); Catherine Elisabeth Charron, London (GB)

(73) Assignees: RESPIVERT LIMITED, Buckinghamshire (GB); TOPIVERT PHARMA LIMITED, London (GB)

( * ) Notice: Subject to any disclaimer, the term of this patent is extended or adjusted under 35 U.S.C. 154(b) by 0 days.

(21) Appl. No.: 14/424,361

(22) PCT Filed: Aug. 28, 2013

(86) PCT No.: PCT/GB2013/052252
§ 371 (c)(1),
(2) Date: Feb. 26, 2015

(87) PCT Pub. No.: WO2014/033448
PCT Pub. Date: Mar. 6, 2014

(65) Prior Publication Data
US 2015/0203475 A1 Jul. 23, 2015

(30) Foreign Application Priority Data

Aug. 29, 2012 (GB) .................................. 1215357.3

(51) Int. Cl.
| *C07D 401/14* | (2006.01) |
| *C07D 403/14* | (2006.01) |
| *C07D 405/14* | (2006.01) |
| *C07D 409/14* | (2006.01) |
| *C07D 413/14* | (2006.01) |
| *C07D 417/14* | (2006.01) |
| *C07D 471/04* | (2006.01) |
| *A61K 31/5377* | (2006.01) |
| *A61K 31/506* | (2006.01) |

(52) U.S. Cl.
CPC ............ *C07D 403/14* (2013.01); *A61K 31/506* (2013.01); *A61K 31/5377* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01)

(58) Field of Classification Search
CPC .. C07D 401/14; C07D 403/14; C07D 405/14; C07D 409/14; C07D 413/14; C07D 417/14; C07D 471/04; A61K 31/5377; A61K 31/506
See application file for complete search history.

(56) References Cited

U.S. PATENT DOCUMENTS

| 6,319,921 | B1 | 11/2001 | Cirillo et al. |
| 6,492,393 | B1 | 12/2002 | Breitfelder et al. |
| 6,492,529 | B1 | 12/2002 | Kapadia et al. |
| 6,525,046 | B1 | 2/2003 | Cirillo et al. |
| 6,852,717 | B2 | 2/2005 | Cirillo et al. |

(Continued)

FOREIGN PATENT DOCUMENTS

| WO | WO 99/32110 A1 | 7/1999 |
| WO | WO 99/32455 A1 | 7/1999 |

(Continued)

OTHER PUBLICATIONS

U.S. Appl. No. 14/349,356, Ito et al., not publised yet.

*Primary Examiner* — Rebecca Anderson
(74) *Attorney, Agent, or Firm* — Knobbe, Martens, Olson & Bear, LLP

(57) ABSTRACT

Compounds of formula (I):

(I)

wherein $R^1$, $R^2$, J, Q, V, X, Y and Z are defined herein are disclosed. The compounds are inhibitors of the family of p38 mitogen-activated protein kinase enzymes (referred to herein as p38 MAP kinase inhibitors), particularly the alpha sub-type thereof, and of Syk kinase and the Src family of tyrosine kinases. The compounds may be used in therapy, including in pharmaceutical combinations, especially in the treatment of inflammatory diseases, in particular inflammatory diseases of the lung, such as asthma and COPD, as well as those of the gastrointestinal tract, such as ulcerative colitis and Crohn's disease and of the eye, such as uveitis.

12 Claims, No Drawings

(56) References Cited

U.S. PATENT DOCUMENTS

| | | |
|---|---|---|
| 6,894,173 B2 | 5/2005 | Zhang et al. |
| 6,916,814 B2 | 7/2005 | Moss et al. |
| 7,241,758 B2 | 7/2007 | Hao et al. |
| 7,678,811 B2 | 3/2010 | Dumas et al. |
| 7,838,524 B2 | 11/2010 | Lee et al. |
| 7,838,541 B2 | 11/2010 | Dumas et al. |
| 8,071,616 B2 | 12/2011 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,618,140 B2 | 12/2013 | Ito et al. |
| 8,642,773 B2 | 2/2014 | Ito et al. |
| 8,933,228 B2 | 1/2015 | Murray et al. |
| 2004/0152725 A1 | 8/2004 | Moss et al. |
| 2008/0300281 A1 | 12/2008 | Dumas et al. |
| 2009/0131437 A1 | 5/2009 | Furet et al. |
| 2010/0160355 A1 | 6/2010 | Degoey et al. |
| 2010/0168138 A1 | 7/2010 | Degoey et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0102607 A1 | 4/2013 | Cass et al. |
| 2013/0123260 A1 | 5/2013 | Charron et al. |
| 2014/0114061 A1 | 4/2014 | Kugimoto et al. |
| 2014/0249169 A1 | 9/2014 | Ito et al. |

FOREIGN PATENT DOCUMENTS

| | | |
|---|---|---|
| WO | WO 00/43384 | 7/2000 |
| WO | WO 01/04115 | 1/2001 |
| WO | WO 01/36403 | 5/2001 |
| WO | WO 01/64642 A1 | 9/2001 |
| WO | WO 02/092576 | 11/2002 |
| WO | WO 03/005999 | 1/2003 |
| WO | WO 03/068228 | 8/2003 |
| WO | WO 03/068229 | 8/2003 |
| WO | WO 03/072569 | 9/2003 |
| WO | WO 2005/110994 A1 | 11/2005 |
| WO | WO 2006/072589 A1 | 7/2006 |
| WO | WO 2010/038085 | 4/2010 |
| WO | WO 2010/038086 | 4/2010 |
| WO | WO 2010/067130 | 6/2010 |
| WO | WO 2010/067131 | 6/2010 |
| WO | WO 2010/075376 A1 | 7/2010 |
| WO | WO 2010/075380 A1 | 7/2010 |
| WO | WO 2010/112936 | 10/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124930 | 10/2011 |
| WO | WO 2011/158039 | 12/2011 |
| WO | WO 2011/158042 | 12/2011 |
| WO | WO 2011/158044 | 12/2011 |
| WO | WO 2013/050756 | 4/2013 |
| WO | WO 2013/050757 | 4/2013 |
| WO | WO 2014/027209 | 2/2014 |
| WO | WO 2014/033446 | 3/2014 |
| WO | WO 2014/033447 | 3/2014 |
| WO | WO 2014/033449 | 3/2014 |

PYRAZOLE DERIVATIVES AS P38 MAP INHIBITORS

FIELD OF THE INVENTION

The invention relates to compounds which are inhibitors of the family of p38 mitogen-activated protein kinase enzymes (referred to herein as p38 MAP kinase inhibitors), particularly the alpha sub-type thereof, and of Syk kinase and the Src family of tyrosine kinases, and to their use in therapy, including in pharmaceutical combinations, especially in the treatment of inflammatory diseases, in particular inflammatory diseases of the lung, such as asthma and COPD, as well as those of the gastrointestinal tract, such as ulcerative colitis and Crohn's disease and of the eye, such as uveitis.

BACKGROUND OF THE INVENTION

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively), each displaying different patterns of tissue expression, have been identified. The p38 MAPK alpha and beta isoforms are found ubiquitously in the body, being present in many different cell types. The alpha isoform is well characterized in terms of its role in inflammation. Although studies using a chemical genetic approach in mice indicate that the p38 MAPK beta isoform does not play a role in inflammation (O'Keefe, S. J. et al., *J Biol Chem.*, 2007, 282 (48):34663-71), it may be involved in pain mechanisms through the regulation of COX2 expression (Fitzsimmons, B. L. et al., *Neuroreport*, 2010, 21(4):313-7). These isoforms are inhibited by a number of previously described small molecular weight compounds. Early classes of inhibitors were highly toxic due to the broad tissue distribution of these isoforms which resulted in multiple off-target effects of the compounds. Furthermore, development of a substantial number of inhibitors has been discontinued due to unacceptable safety profiles in clinical studies (Pettus, L. H. and Wurz, R. P., *Curr. Top. Med. Chem.*, 2008, 8(16):1452-67). As these adverse effects vary with chemotype, and each of these compounds has distinct kinase selectivity patterns, the toxicities observed may be structure—rather than p38 mechanism-based.

Less is known about the p38 MAPK gamma and delta isoforms, which, unlike the alpha and beta isozymes are expressed in specific tissues and cells. The p38 MAPK-delta isoform is expressed more highly in the pancreas, testes, lung, small intestine and the kidney. It is also abundant in macrophages and detectable in neutrophils, CD4+T cells and in endothelial cells (Shmueli, O. et al., *Comptes Rendus Biologies*, 2003, 326(10-11):1067-1072; Smith, S. J. *Br. J. Pharmacol.*, 2006, 149:393-404; Hale, K. K., *J. Immunol.*, 1999, 162(7): 4246-52; Wang, X. S. et al., *J. Biol. Chem.*, 1997, 272(38): 23668-23674.) Very little is known about the distribution of p38 MAPK gamma although it is expressed more highly in brain, skeletal muscle and heart, as well as in lymphocytes and macrophages. (Shmueli, O. et al., *Comptes Rendus Biologies*, 2003, 326(10-11):1067-1072, (2003)/; Hale, K. K., *J. Immunol.*, 1999, 162(7):4246-52: Court, N. W. et al., *J. Mol. Cell. Cardiol.*, 2002, 34(4):413-26; Mertens, S. et al., *FEBS Lett.*, 1996, 383(3):273-6.)

Selective small molecule inhibitors of p38 MAPK gamma and p38 MAPK delta are not currently available, although one previously disclosed compound, BIRB 796, is known to possess pan-isoform inhibitory activity. The inhibition of p38 MAPK gamma and delta isoforms is observed at higher concentrations of the compound than those required to inhibit p38 MAPK alpha and p38 beta (Kuma, Y. *J. Biol. Chem.*, 2005, 280:19472-19479.). In addition BIRB 796 also impaired the phosphorylation of p38 MAPKs or JNKs by the upstream kinase MKK6 or MKK4. Kuma discussed the possibility that the conformational change caused by the binding of the inhibitor to the MAPK protein may affect the structure of both its phosphorylation site and the docking site for the upstream activator, thereby impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma, COPD (Chung, F., *Chest*, 2011, 139(6):1470-1479) and inflammatory bowel disease (IBD). There is now an abundant literature which demonstrates that p38 MAP kinase is activated by a range of pro-inflammatory cytokines and that its activation results in the recruitment and release of additional pro-inflammatory cytokines. Indeed, data from some clinical studies demonstrate beneficial changes in disease activity in patients during treatment with p38 MAP kinase inhibitors. For instance Smith describes the inhibitory effect of p38 MAP kinase inhibitors on TNFα (but not IL-8) release from human PBMCs.

The use of inhibitors of p38 MAP kinase in the treatment of chronic obstructive pulmonary disease (COPD) has also been proposed. Small molecule inhibitors targeted to p38 MAPK α/β have proved to be effective in reducing various parameters of inflammation in:

- cells and tissues obtained from patients with COPD, who are generally corticosteroid insensitive, (Smith, S. J., *Br. J. Pharmacol.*, 2006, 149:393-404);
- Biopsies from IBD patients (Docena, G. et al., *J. of Trans. Immunol.*, 2010, 162:108-115); and
- in vivo animal models (Underwood, D. C. et al., *Am. J. Physiol.*, 2000, 279:L895-902; Nath, P. et al., *Eur. J. Pharmacol.*, 2006, 544:160-167.).

Irusen and colleagues also suggested the possibility of involvement of p38 MAPKα/β on corticosteroid insensitivity via the reduction of binding affinity of the glucocorticoid receptor (GR) in nuclei (Irusen, E. et al., *J. Allergy Clin. Immunol.*, 2002, 109:649-657). Clinical experience with a range of p38 MAP kinase inhibitors, including AMG548, BIRB 796, VX702, SCIO469 and SCIO323 has been described (Lee, M. R. and Dominguez, C., *Current Med. Chem.*, 2005, 12:2979-2994.). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. A recent publication of Mercado (Mercado, N., et al., *Mol. Pharmacol.*, 2011, 80(6):1128-1135) demonstrates that silencing p38 MAPK γ has the potential to restore sensitivity to corticosteroids. Consequently there may be a dual benefit for patients in the use of a p38 MAP kinase inhibitor for the treatment of COPD and severe asthma.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

Epidemiologic investigations have revealed a strong association between viral infections of the upper respiratory tract and a substantial percentage of the exacerbations suffered by patients already diagnosed with chronic respiratory diseases. Some of the most compelling data in this regard derives from longitudinal studies of children suffering from asthma (Papadopoulos, N. G., Papi, A., Psarras, S. and Johnston, S. L., *Paediatr. Respir. Rev.* 2004, 5(3):255-260). A variety of additional studies support the conclusion that a viral infection can precipitate exacerbations and increase disease severity. For example, experimental clinical infections with rhinovirus have been reported to cause bronchial hyper-responsiveness to histamine in asthmatics which is unresponsive to treatment with corticosteroids (Grunberg, K., Sharon, R. F., et al., *Am. J. Respir. Crit. Care Med.,* 2001, 164(10):1816-1822). Further evidence derives from the association observed between disease exacerbations in patients with cystic fibrosis and HRV infections (Wat, D., Gelder, C., et al., *J. Cyst. Fibros.* 2008, 7:320-328). Also consistent with this body of data is the finding that respiratory viral infections, including rhinovirus, represent an independent risk factor that correlates negatively with the 12 month survival rate in paediatric, lung transplant recipients (Liu, M., Worley, S., et al., *Transpl. Infect. Dis.* 2009, 11(4):304-312).

Clinical research indicates that the viral load is proportionate to the observed symptoms and complications and, by implication, to the severity of inflammation. For example, following experimental rhinovirus infection, lower respiratory tract symptoms and bronchial hyper-responsiveness correlated significantly with virus load (Message, S. D., Laza-Stanca, V., et al., *PNAS,* 2008; 105(36):13562-13567). Similarly, in the absence of other viral agents, rhinovirus infections were commonly associated with lower respiratory tract infections and wheezing, when the viral load was high in immunocompetent paediatric patients (Gerna, G., Piralla, A., et al., *J. Med. Virol.* 2009, 81(8):1498-1507).

Interestingly, it has been reported recently that prior exposure to rhinovirus reduced the cytokine responses evoked by bacterial products in human alveolar macrophages (Oliver, B. G., Lim, S., et al., *Thorax,* 2008, 63:519-525). Additionally, infection of nasal epithelial cells with rhinovirus has been documented to promote the adhesion of bacteria, including *S. aureus* and *H. influenzae* (Wang, J. H., Kwon, H. J. and Yong, J. J., *The Laryngoscope,* 2009, 119(7):1406-1411). Such cellular effects may contribute to the increased probability of patients suffering a lower respiratory tract infection following an infection in the upper respiratory tract. Accordingly, it is therapeutically relevant to focus on the ability of novel interventions to decrease viral load in a variety of in vitro systems, as a surrogate predictor of their benefit in a clinical setting.

High risk groups, for whom a rhinovirus infection in the upper respiratory tract can lead to severe secondary complications, are not limited to patients with chronic respiratory disease. They include, for example, the immune compromised who are prone to lower respiratory tract infection, as well as patients undergoing chemotherapy, who face acute, life-threatening fever. It has also been suggested that other chronic diseases, such as diabetes, are associated with a compromised immuno-defence response. This increases both the likelihood of acquiring a respiratory tract infection and of being hospitalised as a result (Peleg, A. Y., Weerarathna, T., et al., *Diabetes Metab. Res. Rev.,* 2007, 23(1):3-13; Kornum, J. B., Reimar, W., et al., *Diabetes Care,* 2008, 31(8):1541-1545).

Whilst upper respiratory tract viral infections are a cause of considerable morbidity and mortality in those patients with underlying disease or other risk factors; they also represent a significant healthcare burden in the general population and are a major cause of missed days at school and lost time in the workplace (Rollinger, J. M. and Schmidtke, M., *Med. Res. Rev.,* 2010, Doi 10.1002/med.20176). These considerations make it clear that novel medicines, that possess improved efficacy over current therapies, are urgently required to prevent and treat rhinovirus-mediated upper respiratory tract infections. In general the strategies adopted for the discovery of improved antiviral agents have targeted various proteins produced by the virus, as the point of therapeutic intervention. However, the wide range of rhinovirus serotypes makes this a particularly challenging approach to pursue and may explain why, at the present time, a medicine for the prophylaxis and treatment of rhinovirus infections has yet to be approved by any regulatory agency.

Viral entry into the host cell is associated with the activation of a number of intracellular signalling pathways controlled by the relative activation and inactivation of specific kinases which are believed to play a prominent role in the initiation of inflammatory processes (reviewed by Ludwig, S, 2007; Signal Transduction, 7:81-88) and of viral propagation and subsequent release.

It has been disclosed previously that compounds that inhibit the activity of both c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). For the reasons summarised above, in combination with the inhibition of p38 MAPKs, these are particularly advantageous inherent properties for compounds designed to treat chronic respiratory diseases.

Certain p38 MAPK inhibitors have also been described as inhibitors of the replication of respiratory syncitial virus (Cass, L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. Due to the ubiquitous expression of p38 in inflammatory cells it has become an obvious target for investigation in IBD models. Studies investigating the efficacy of p38 inhibitors in animal models of IBD and human biopsies from IBD patients indicated that p38 could be a target for the treatment of IBD (Hove, T. ten et al., *Gut*, 2002, 50:507-512, Docena, G. et al., *J. of Trans. Immunol.* 2010, 162:108-115). However, these findings are not completely consistent with other groups reporting no effect with p38 inhibitors (Malamut G. et al., *Dig. Dis. Sci,* 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology,* 2006, 4:325-334). A small clinical study investigating the efficacy of CNI-1493, a P38 and Jnk inhibitor, in patients with severe Crohn's disease showed significant improvement in clinical score over 8 weeks (Hommes, D. et al. *Gastroenterology.* 2002 122:7-14).

T cells are known to play key role in mediating inflammation of the gastrointestinal tract. Pioneering work by Powrie and colleagues demonstrated that transfer of naive CD4+ cells into severly compromised immunodeficient (SCID) animals results in the development of colitis which is dependent on the presence of commensal bacteria (Powrie F. et al. *Int Immunol.* 1993 5:1461-71). Furthermore, investigation of mucosal membranes from IBD patients showed an upregulation of CD4+ cells which were either Th1 (IFNg/IL-2) or Th2 (IL5/TGFb) biased depending on whether the patient had Crohn's disease or ulcerative colitis (Fuss I J. et al. J Immunol. 1996 157:1261-70.). Similarly, T cells are known to play a key role in inflammatory disorders of the eye with several studies reporting increased levels of T cell associated cytokines (IL-17 and IL-23) in sera of Beçhets patients (Chi W. et al. *Invest Ophthalmol Vis Sci.* 2008 49:3058-64). In support, Direskeneli and colleagues demonstrated that Behcets patients have increased Th17 cells and decreased Treg cells in their peripheral blood (Direskeneli H. et al. J Allergy Clin Immunol. 2011 128:665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science.* 1994 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum.* 2008 58:3309-18). Syk kinase is widely expressed in cells of the hematopoietic system, most notably in B cells and mature T cells. Through interaction with immunoreceptor tyrosine-based activation (ITAM) motifs it plays an important role in regulating T cell and B cell expansion as well as mediating immune-receptor signalling in inflammatory cells. Syk activation leads to IL-6 and MMP release—inflammatory mediators commonly found upregulated in inflammatory disorders including IBD and rheumatoid arthritis (Wang Y D. et al *World J Gastroenterol* 2007; 13: 5926-5932, Litinsky I et al. *Cytokine.* 2006 January 33:106-10).

In addition to playing key roles in cell signalling events which control the activity of pro-inflammatory pathways, kinase enzymes are now also recognised to regulate the activity of a range of cellular functions. Among those which have been discussed recently are the maintenance of DNA integrity (Shilo, Y. *Nature Reviews Cancer,* 2003, 3:155-168) and co-ordination of the complex processes of cell division. An illustration of recent findings is a publication describing the impact of a set of inhibitors acting upon the so-called "Olaharsky kinases" on the frequency of micronucleus formation in vitro (Olaharsky, A. J. et al., *PLoS Comput. Biol.,* 2009, 5(7):e1000446.). Micronucleus formation is implicated in, or associated with, disruption of mitotic processes and is therefore an undesirable manifestation of potential toxicity. Inhibition of glycogen synthase kinase 3α (GSK3α) was found to be a particularly significant factor that increases the likelihood of a kinase inhibitor promoting micronucleus formation. Recently, inhibition of the kinase GSK3β with RNAi was also reported to promote micronucleus formation (Tighe, A. et al., *BMC Cell Biology,* 2007, 8:34).

It may be possible to attenuate the adverse effects arising from drug interactions with Olaharsky kinases, such as GSK3α, by optimisation of the dose and/or by changing the route of administration. However, it would be more advantageous to identify therapeutically useful molecules that demonstrate low or undetable activity against these off-target enzymes and consequently elicit little or no disruption of mitotic processes, as measured in mitosis assays.

It is evident from consideration of the literature cited hereinabove that there remains a need to identify and develop new p38 MAP kinase inhibitors that have improved therapeutic potential over currently available treatments. Desirable compounds are those that exhibit a superior therapeutic index by exerting, at the least, an equally efficacious effect as previous agents but, in one or more respects, are less toxic at the relevant therapeutic dose. The present invention therefore inter alia provides such novel compounds that inhibit the enzyme activity of p38 MAP kinase, for example with certain sub-type specificities, together with Syk kinase and tyrosine kinases within the Src family (particularly c-Src) thereby possessing good anti-inflammatory properties, and suitable for use in therapy.

In one or more embodiments the compounds exhibit a long duration of action and/or persistence of action in comparison to other previously disclosed allosteric p38 MAP kinase inhibitors such as, for example, BIRB796 (Pargellis, C. et al., *Nature Struct. Biol.,* 2002, 9(4):268-272).

SUMMARY OF THE INVENTION

Thus in one aspect of the invention there is provided a compound of formula (I):

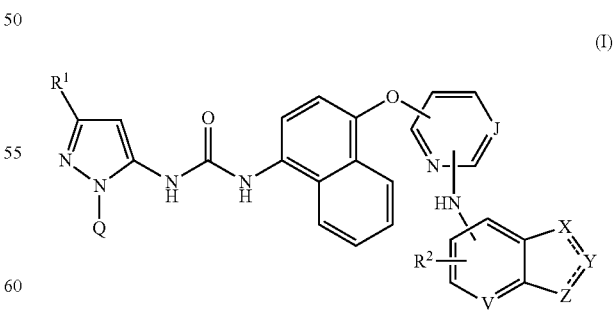

wherein:
R$^1$ represents C$_{1-6}$ alkyl, C$_{1-6}$ hydroxyalkyl, C$_{0-2}$ alkylene-C$_{3-8}$ cycloalkyl optionally substituted by C$_{1-3}$ alkyl, halo substituted C$_{1-6}$ alkyl or a 4-6 membered heterocycle optionally substitute with C$_{1-3}$ alkyl, Q represents thienyl, phenyl, pyridine or pyridone, each optionally substituted by 1 to 3 substituents independently selected from, hydroxyl, halogen, $C_{1-6}$ alkyl, $C_{1-6}$ alkoxy, haloalkoxy, $C_{1-6}$ hydroxyalkyl, $OC_{2-6}$ alkyleneOR$^A$, $OC_{2-6}$ alkyleneOC$_{2-6}$ alkyleneOR$^A$, $OC_{2-6}$ alkyleneNR$^A$R$^A$, $C_{1-6}$ alkylene-5-10 membered heterocycle, and $C_{0-3}$ alkylene-O—$C_{1-6}$ alkylene-5-10 membered heterocycle, R$^A$ represents H or $C_{1-3}$ alkyl,
R$^2$ represents H, $C_{1-3}$ alkyl, $C_{1-3}$ alkoxy or halo,
J represents CH or N,
V represents CR$^2$ or N,
X represents S, N, NR$^3$, CR$^4$, C=O, O, CR$^5$R$^6$, or —OCR$^5$R$^6$— thereby forming a six membered ring,
Y represents O, N, NR$^7$, CR$^8$, C=O, SO$_n$ or CR$^9$R$^{10}$,
Z represents O, S, N, NR$^{11}$, C=O, CR$^{12}$, CR$^{12}$R$^{13}$, or —OCR$^{12}$R$^{13}$— thereby forming a six membered ring,
with the proviso that when Z represents —OCR$^{12}$R$^{13}$— then X represents S, N, NR$^3$, CR$^4$, C=O, O or CR$^5$R$^6$,
R$^3$ represents H, $C_{1-3}$ alkyl or $C_{1-6}$ alkylene-5-10 membered heterocycle,
R$^4$ represents H, hydroxyl, $C_{1-8}$ alkyl, $C_{2-8}$ alkenyl, $C_{2-8}$ alkynyl, $C_{1-3}$ haloalkyl, $C_{0-6}$ alkyleneNR$^{14}$R$^{15}$ or $C_{0-6}$ alkylene-5-10 membered heterocycle, wherein each alkylene group or alkyl group optionally bears 1 oxo substituent and optionally one or two carbons in the alkylene chain or alkyl chain is replaced by a heteroatom selected from O, N, NR$^{14}$ or S(O)$_p$,
R$^5$ represents H or $C_{1-3}$ alkyl,
R$^6$ represents H or $C_{1-3}$ alkyl,
R$^7$ represents H, $C_{1-3}$ alkyl or $C_{1-6}$ alkylene-5-10 membered heterocycle,
R$^8$ represents H, hydroxyl, $C_{1-8}$ alkyl, $C_{2-8}$ alkenyl, $C_{2-8}$ alkynyl, $C_{1-3}$ haloalkyl, $C_{0-6}$ alkyleneNR$^{14}$R$^{15}$ or $C_{0-6}$ alkylene-5-10 membered heterocycle, wherein each alkylene group or alkyl group optionally bears 1 oxo substituent and optionally one or two carbons in the alkylene chain or alkyl chain is replaced by a heteroatom selected from O, N, NR$^{14}$ or S(O)$_p$,
R$^9$ represents H or $C_{1-3}$ alkyl,
R$^{10}$ represents H or $C_{1-3}$ alkyl,
R$^{11}$ represents H, $C_{1-3}$ alkyl or $C_{1-6}$ alkylene-5-10 membered heterocycle,
R$^{12}$ represents H, hydroxyl, $C_{1-8}$ alkyl, $C_{2-8}$ alkenyl, $C_{2-8}$ alkynyl, $C_{1-3}$ haloalkyl, $C_{0-6}$ alkyleneNR$^{14}$R$^{15}$ or $C_{0-6}$ alkylene-5-10 membered heterocycle, wherein each alkylene group or alkyl group optionally bears 1 oxo substituent and optionally one or two carbons in the alkylene chain or alkyl chain is replaced by a heteroatom selected from O, N, NR$^{14}$ or S(O)$_p$,
R$^{13}$ represents H or $C_{1-3}$ alkyl,
R$^{14}$ represents H or $C_{1-3}$ alkyl,
R$^{15}$ represents H or $C_{1-3}$ alkyl,
a dashed bond represents as required by valency, a double or single bond,
n represents 0, 1 or 2,
p represents 0, 1 or 2
or a pharmaceutically acceptable salt thereof, including all stereoisomers and tautomers thereof Compounds of the invention are inhibitors of p38 MAP kinase especially of the alpha sub-type.

In at least some embodiments, compounds of the present invention have low B-Raf binding, for example less than 40% inhibition of B-Raf kinase binding at 500 nM, such as 30% inhibition or less in an assay such as the Kinomescan method (see Biological Testing Experimental Methods section below).

B-Raf is a member of the Raf kinase family of serine/threonine-specific protein kinases. This protein plays a role in regulating the MAP kinase/ERKs signaling pathway, which affects cell division, differentiation, and secretion. A mutation of the gene has been associated with cancer in humans (Davies, H. et al., *Nature,* 2002, 417(6892):949-54).

The compounds disclosed herein have significantly different properties to molecules such as sorafenib which are inhibitors of several tyrosine protein kinases such as VEGFR and PDGFR and of Raf kinases such as C-Raf and B-Raf. Sorafenib is used in the treatment of advanced inoperable hepatocellular cancer and advanced renal cell cancer (Iver, R. et al., *Expert Opin. Pharmacother.,* 2010, 11(11):1943-1955). Sorafenib also interacts with B-Raf, mutants which commonly occur in human melanoma. However, cell signalling can bypass selective inhibition of B-Raf with undesirable consequences (Lo, R. S., *Cell Research*, advance online publication 8 May 2012; doi: 10.1038/cr.2012.78). It is therefore preferable that kinase inhibitors intended for use as anti-inflammatory medicines should have minimal potential to interact with B-Raf.

In contrast to anticancer treatments such as sorafenib the compounds of the present invention possess Syk and/or c-Src inhibitory activity which is expected to promote an advantageous therapeutic profile.

Compounds of the present invention also display low affinity for GSK3α kinase manifested as weak activity in a binding assay or weak activity in an enzyme inhibition assay, which is considered to be beneficial in a therapeutic context, in particular in relation to minimising toxicity in vivo.

In at least some embodiments, compounds of the present invention have p59-HCK inhibitory activity which may also augment their advantageous therapeutic profile.

DETAILED DESCRIPTION OF THE INVENTION

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example —$C_{1-3}$ alkylOC$_{1-3}$ alkyl, such as —CH$_2$CH$_2$OCH$_3$ or —CH$_2$OCH$_3$. Thus in one embodiment the alkoxy is linked through carbon to the remainder of the molecule. In one embodiment the alkoxy is linked through oxygen to the remainder of the molecule, for example —OC$_{1-6}$ alkyl. In one embodiment the disclosure relates to straight chain alkoxy.

Halo or halogen includes fluoro, chloro, bromo or iodo, in particular fluoro, chloro or bromo, especially fluoro or chloro.

Alkyl substituted by halo (haloalkyl) as employed herein refers to alkyl groups having 1 to 6 halogen atoms, for example 1 to 5 halogens, such as per haloalkyl, in particular perfluoroalkyl, more specifically —CF$_2$CF$_3$ or CF$_3$.

Alkyl substituted by hydroxy (hydroxyalkyl) as employed herein refers to alkyl groups having 1 to 3 hydroxy groups, for example 1 or 2 hydroxy substituents thereon, for example —CH$_2$CH$_2$OH, —C(CH$_3$)CH$_2$OH, —C(CH$_3$)$_2$CH$_2$OH or similar.

Alkoxy substituted by halo (haloalkoxy) as employed herein refers to alkoxy groups having 1 to 6 halogen atoms, for example 1 to 5 halogens, such as per haloalkoxy, in particular perfluoroalkoxy, more specifically —OCF$_2$CF$_3$ or —OCF$_3$.

Alkylene as employed herein is a straight chain or branched chain carbon linking group, for example comprising methylenes, between two other moieties. It will be clear to those skilled in the art that groups defined as, for example $C_{2-8}$ alkenyl and $C_{2-8}$ alkynyl may comprise an alkylene portion.

$C_{1-6}$ alkyl includes $C_1$, $C_2$, $C_3$, $C_4$, $C_5$ and $C_6$.

$C_{1-6}$ alkoxy includes $C_1$, $C_2$, $C_3$, $C_4$, $C_5$ and $C_6$.

The term 5-10 membered heterocycle, as employed herein refers to a 5 to 10 membered saturated or partially unsaturated non-aromatic ring comprising one or more, for example 1, 2, 3 or 4 heteroatoms independently selected from O, N and S, wherein optionally one or two carbons in the ring may bear an oxo substituent. Any valencies of a heteroatom not employed in forming or retaining the ring structure may be filled by hydrogen or a substituent, as appropriate. Thus the optional substituents on the heterocycles may be attached to a carbon or on a heteroatom, such as nitrogen as appropriate. Examples of 5-10 membered heterocycles include, pyrroline, pyrrolidine, tetrahydrofuran, thiepane, oxepane piperidine, piperazine, morpholine, thiomorpholine, dioxane, tetrahydrothiophene, pyrazoline, imidazoline, pyrazolidine, oxoimidazolidine, dioxolane, thiazolidine, isoxazolidine, dihydropyran, dihydroindene, dihydroisobenzofuran, isoindolin-1-one, chroman, 1,2,3,4-tetrahydroquinoline, 2,3-dihydrobenzo[b][1,4]dioxineazocane, and the like.

The term 5-6 membered heterocycle as employed herein refers to a 5 to 6 membered saturated or partially unsaturated non-aromatic ring comprising one or more, for example 1, 2, 3 or 4 heteroatoms independently selected from O, N and S wherein optionally one or two carbons in the ring may bear an oxo substituent. The definition of $C_{5-8}$ heterocycle as employed herein refers to a 5 to 6 membered saturated or partially unsaturated non-aromatic carbocyclic ring comprising one or more, for example 1, 2, 3 or 4 heteroatoms independently selected from O, N and S, wherein each heteroatom replaces a carbon atom and optionally one or two carbons may bear an oxo substitutent. Clearly any valencies of a heteroatom not employed in forming or retaining the ring structure may be filled by hydrogen or a substituent, as appropriate. Thus substituents on heterocycles may be on carbon or on a heteroatom, such as N as appropriate. Examples of heterocycles and $C_{5-6}$ heterocycles include pyrroline, pyrrolidine, tetrahydrofuran, tetrahydrothiophene, pyrazoline, imidazoline, pyrazolidine, imidazolidine, oxoimidazolidine, dioxolane, thiazolidine, isoxazolidine, pyran, dihydropyran, piperidine, piperazine, morpholine, dioxane, thiomorpholine and oxathiane.

When employed herein, the group morpholinyl suitably represents N-morpholinyl.

In one embodiment $R^1$ is $C(CH_3)_2CH_2OH$ or $CH(CH_3)CH_2OH$.

In one embodiment $R^1$ is 1-hydroxy-2-methylpropan-2-yl.

In one embodiment $R^1$ is t-butyl.

In one embodiment $R^1$ is isopropyl.

In one embodiment $R^2$ is H, $C_{1-6}$ alkyl or halo, for example H, methyl or chloro.

In one embodiment $R^2$ is chloro, methyl or methoxy.

In one embodiment $R^3$ is H, methyl or $C_{1-6}$ alkylene-5-6-membered heterocycle, such as H or methyl.

In one embodiment $R^4$ represents H, halogen, $C_{1-6}$ alkyl optionally substituted by hydroxyl, $C_{1-6}$ alkoxy, $CO_2C_{1-3}$ alkyl, $C_{0-6}$ alkyleneNR$^{14}$R$^{15}$ or $C_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

In one embodiment $R^4$ represents H, $CO_2C_{1-3}$ alkyl, $C_{0-6}$ alkyleneNR$^{14}$R$^{15}$ or $C_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

In one embodiment $R^4$ is H, methyl, OCH$_2$CH$_2$morpholinyl, C(O)NHCH$_2$CH$_2$morpholinyl, C(O)morpholinyl or C(O)N(C$_{1-3}$ alkyl)$_2$ In one embodiment $R^5$ is H or methyl.

In one embodiment $R^6$ is H or methyl.

In one embodiment $R^7$ is H, methyl or $C_{1-6}$ alkylene-5-6-membered heterocycle, such as H or methyl.

In one embodiment $R^8$ represents H, halogen, $C_{1-6}$ alkyl optionally substituted by hydroxyl, $C_{1-6}$ alkoxy, $CO_2C_{1-3}$ alkyl, $C_{0-6}$ alkyleneNR$^{14}$R$^{15}$ or $C_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

In one embodiment $R^8$ represents H, $CO_2C_{1-3}$ alkyl, $C_{0-6}$ alkyleneNR$^{14}$R$^{15}$ or $C_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

In one embodiment $R^9$ is H or methyl.

In one embodiment $R^{10}$ is H or methyl.

In one embodiment $R^{11}$ is H or methyl, or morpholinoethyl, such as 4-morpholinoethyl.

In one embodiment $R^{12}$ represents H, halo, $C_{1-6}$ alkyl optionally substituted by hydroxyl, $C_{1-6}$ alkoxy, $CO_2C_{1-3}$ alkyl, $C_{0-6}$ alkyleneNR$^{14}$R$^{15}$ or $C_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

In one embodiment $R^{12}$ represents H, $CO_2C_{1-3}$ alkyl, $C_{0-6}$ alkyleneNR$^{14}$R$^{15}$ or $C_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

In one embodiment $R^{13}$ is H or methyl.

In one embodiment $R^{14}$ is H or methyl.

In one embodiment $R^{15}$ is H or methyl.

In one embodiment Q represents phenyl or pyridine substituted by 1 to 3 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle, and $C_{0-3}$ alkylene-O—$C_{1-6}$ alkylene-5-10 membered heterocycle, provided that at least one substituent is selected from $C_{1-6}$ alkyl, $C_{1-6}$ hydroxyalkyl, $C_{1-6}$ alkylene-5-10 membered heterocycle, and $C_{0-3}$ alkylene-O—$C_{1-6}$ alkylene-5-10 membered heterocycle.

In one embodiment Q represents phenyl, pyridine or pyridone, each substituted by 1 to 3 substituents independently selected from, $C_{4-6}$ alkoxy, $C_{4-6}$ haloalkoxy, $C_{1-6}$ hydroxyalkyl, O(CH$_2$)$_2$O(CH$_2$)$_2$OR$^A$, $C_{1-6}$ alkylene-5-10 membered heterocycle, and $C_{0-3}$ alkylene-O—$C_{1-6}$ alkylene-5-10 membered heterocycle.

In one embodiment Q represents phenyl, pyridine or pyridone.

In one embodiment Q represents pyridone.

In one embodiment Q represents phenyl substituted by 1, 2 or 3 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle, and $C_{0-3}$ alkylene-O—$C_{1-6}$ alkylene-5-10 membered heterocycle, for example 1 substituent, in particular wherein the substituent is selected from $C_{1-6}$ alkyl, $C_{1-6}$ hydroxyalkyl, $C_{1-6}$ alkylene-5-10 membered heterocycle, and $C_{0-3}$ alkylene-O—$C_{1-6}$ alkylene-5-10 membered heterocycle.

In one embodiment the substituent or substituents on phenyl are independently selected, from hydroxyl, methyl, methoxy, $C_{1-3}$ alkylene-5-10 membered heterocycle for example methylene, ethylene or propylene linked morpholinyl, pyridinyl, piperidinyl or pyrrolidonyl, such as morpholinyl or pyrrolidonyl, and $C_{0-3}$ alkylene-O—$C_{1-6}$ alkylene-5-10 membered heterocycle, for example methoxy, ethoxy or propoxy linked morpholinyl, pyridinyl, piperidinyl or pyrrolidonyl, such as morpholinyl or pyrrolidonyl, in particular where the heterocycle is linked through a carbon to the alkylene portion.

In one embodiment the substituent or at least one of the substituents is in the para-position of the phenyl ring.

In one embodiment the substituent or at least one of the substituents is in the meta-position of the phenyl ring.

In one embodiment the phenyl ring bears a substituent selected from methyl, methoxy, —CH$_2$N-pyrrolidinyl or —OCH$_2$CH$_2$N-morpholinyl, in particular in the para or meta position, such as at the para position.

In one embodiment Q represents pyridine substituted by 1, 2 or 3 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, 6 alkylene-5-10 membered heterocycle, and $C_{0-3}$ alkylene-O—$C_{1-6}$ alkylene-5-10 membered heterocycle, for example 1 substituent, in particular wherein the substituent is selected from $C_{1-6}$ alkyl, $C_{1-6}$ hydroxyalkyl, $C_{1-6}$ alkylene-5-10 membered heterocycle, and $C_{0-3}$ alkylene-O—$C_{1-6}$ alkylene-5-10 membered heterocycle.

In one embodiment the substituent or substituents on pyridine are independently selected from hydroxyl, methyl, methoxy, $C_{1-3}$ alkylene-5-10 membered heterocycle for example methylene, ethylene or propylene linked morpholinyl, pyridinyl, piperidinyl or pyrrolidinyl, such as morpholinyl or pyrrolidinyl, and $C_{0-3}$ alkylene-O—$C_{1-6}$ alkylene-5-10 membered heterocycle, for example methoxy, ethoxy or propoxy linked morpholinyl, pyridinyl, piperidinyl or pyrrolidinyl, such as morpholinyl or pyrrolidinyl, in particular where the heterocycle is linked through a carbon to the alkylene portion.

In one embodiment, wherein Q is pyridine, the ring nitrogen is in the meta-position relative to its point of attachment to the pyrazole nucleus in compounds of formula (I).

In one embodiment, wherein Q is pyridine, the substituent or at least one of the substituents is in the ortho-position, relative to the ring nitrogen.

In one embodiment, wherein Q is pyridine, the substituent or at least one of the substituents is in the meta-position, relative to the ring nitrogen.

In one embodiment the pyridinyl group bears a substituent selected from methyl, methoxy, —CH$_2$N-pyrrolidinyl or —OCH$_2$CH$_2$N-morpholinyl, in particular in the ortho- or meta-position, relative to the ring nitrogen, such as in the ortho-position.

In one embodiment, wherein Q comprises a pyridinone group, the ring nitrogen and the carbonyl substituent are disposed meta- and para-respectively relative to its point of attachment to the pyrazole nucleus in compounds of formula (I).

In one embodiment Q represents pyridinone substituted by 1 or 2 substituents independently selected from, $C_{1-6}$ alkyl, $C_{1-6}$ hydroxyalkyl and $C_{1-6}$ alkylene-5-10 membered heterocycle, for example 1 substituent.

In one embodiment Q represents a pyridinone substituted on the ring nitrogen.

In one embodiment Q represents a pyridinone substituted on the ring nitrogen by a substituent independently selected from, $C_{1-6}$ alkyl, $C_{1-6}$ hydroxyalkyl and $C_{1-6}$ alkylene-5-10 membered heterocycle, for example methyl, —CH$_2$CH$_2$OH or —CH$_2$CH$_2$N-morpholinyl.

In one embodiment V is CH or CR$^2$, wherein R$^2$ is Cl or methyl.

In one embodiment V is CR$^2$ wherein R$^2$ is Cl or CH$_3$.

In one embodiment V is N.

In one embodiment X is independently selected from S, N, O, CH$_2$, CH, CNH$_2$, CN(CH$_3$)$_2$, CCO$_3$CH$_3$, COCH$_2$CH$_2$morpholinyl, CC(O)NHCH$_2$CH$_2$morpholinyl, CC(O)morpholinyl, and CC(O)N(CH$_3$)$_2$.

In one embodiment Y is independently selected from N, C(O), O, SO$_2$, CH, CH$_2$ and CCH$_3$.

In one embodiment Z is independently selected from O, S, N, NH, N-tetrahydrofuranyl, NCH$_2$CH$_2$morpholinyl, CH, CH$_2$ and C(CH$_3$)$_2$.

In one embodiment X, Y and Z are respectively defined as:
CH, CH, NH
NH, C(O), CH$_2$,
CC(O)OCH$_3$, N, NH,
N, CH, NCH$_3$,
CNH$_2$, N, O,
OCH$_2$, CH$_2$, O,
O, CH$_2$, O,
CH$_2$, O, CH$_2$,
CH, N, NH
CH, N, NCH$_3$
CH, CH, NCH$_3$,
CH$_2$, C(O), NH,
CH$_2$, C(O), NCH$_3$,
CC(O)N(CH$_3$)$_2$, N, NH
NH, C(O), CH$_2$,
NH, C(O), C(CH$_3$)$_2$,
C(O), NH, CH$_2$,
NH, C(O), O,
O, C(O), NH,
NH, N, CH,
CH, N, N-tetrahydropyranyl, NCH$_2$CH$_2$N-morpholinyl, N, CH,
COCH$_2$CH$_2$N-morpholinyl, N, NH,
CC(O)N-morpholinyl, N, NH,
CH, N, NCH$_2$CH$_2$N-morpholinyl,
CC(O)NHCH$_2$CH$_2$N-morpholinyl, N, NH,
N, CH, NH,
N, N, NH,
NCH$_3$, CH, N,
N, CH, S,
CH$_2$, SO$_2$, CH$_2$,
CH, N, S,
N, CH, S,
S, CH, N,
CH$_2$, CH$_2$, CH$_2$,
CH, CCH$_3$, NH,
NH, N, CCH$_3$,
CCH$_3$, N, NH, or
N, CCH$_3$, NH.

In one embodiment there is provided a compound of formula (IA):

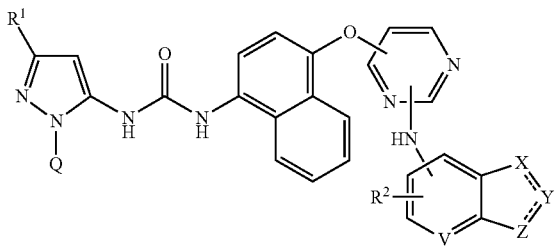

(IA)

wherein:
$R^1$, $R^2$, Q, V, X, Y and Z are defined as above, or a pharmaceutically acceptable salt thereof, including all stereoisomers and tautomers thereof.

In one embodiment there is provided a compound of formula (IB):

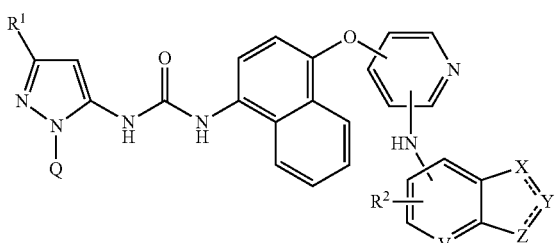

(IB)

wherein:
$R^1$, $R^2$, Q, V, X, Y and Z are defined as above, or a pharmaceutically acceptable salt thereof, including all stereoisomers and tautomers thereof.

In one embodiment there is provided a compound of formula (IC):

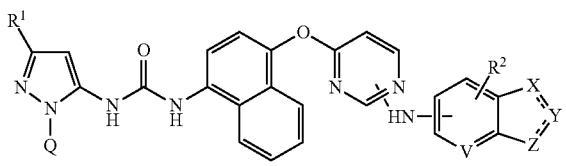

(IC)

wherein:
$R^1$, $R^2$, Q, V, X, Y and Z are defined as above, or a pharmaceutically acceptable salt thereof, including all stereoisomers and tautomers thereof.

In one embodiment there is provided a compound of formula (ID):

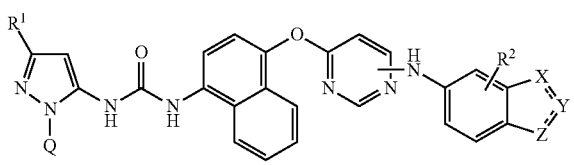

(ID)

wherein:
$R^1$, $R^2$, Q, X, Y and Z are as defined as above, or a pharmaceutically acceptable salt thereof, including all stereoisomers and tautomers thereof.

In one embodiment there is provided a compound of formula (IE):

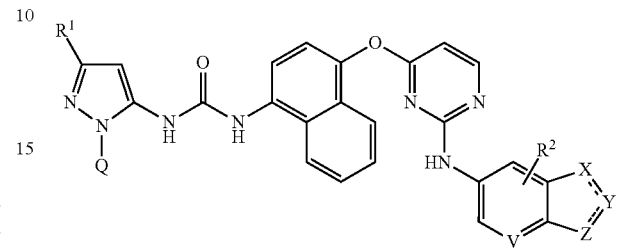

(IE)

wherein:
$R^1$, $R^2$, Q, V, X, Y and Z are as defined as above, or a pharmaceutically acceptable salt thereof, including all stereoisomers and tautomers thereof.

In one embodiment there is provided a compound of formula (IF)

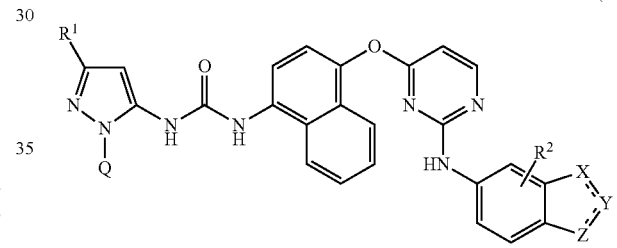

(IF)

wherein:
$R^1$, $R^2$, Q, X, Y and Z are as defined as above, or a pharmaceutically acceptable salt thereof, including all stereoisomers and tautomers thereof.

In one embodiment there is provided a compound of formula (IG)

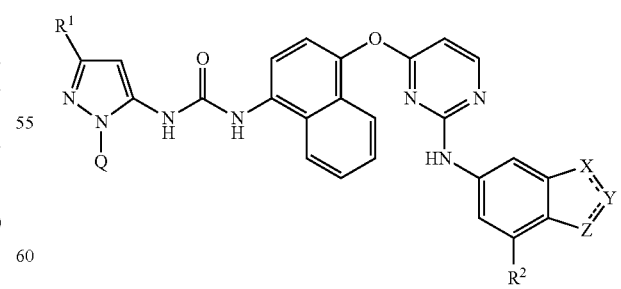

(IG)

wherein:
$R^1$, $R^2$, Q, X, Y and Z are as defined as above, or a pharmaceutically acceptable salt thereof, including all stereoisomers and tautomers thereof.

In one embodiment there is provided a compound of formula (IH):

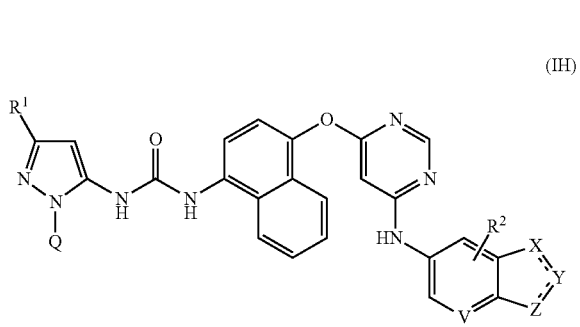

(IH)

wherein:

R¹, R², Q, V, X, Y and Z are as defined above, or a pharmaceutically acceptable salt thereof, including all stereoisomers and tautomers thereof.

In one embodiment there is provided a compound of formula (IJ):

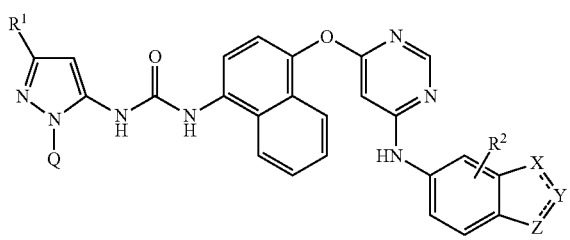

(IJ)

wherein:

R¹, R², Q, X, Y and Z are as defined above, or a pharmaceutically acceptable salt thereof, including all stereoisomers and tautomers thereof.

In one embodiment there is provided a compound of formula (IK):

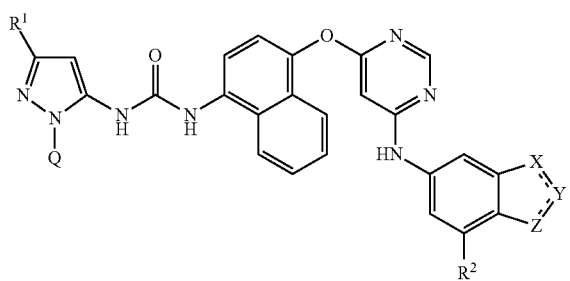

(IK)

wherein:

R¹, R², Q, X, Y and Z are as defined above, or a pharmaceutically acceptable salt thereof, including all stereoisomers and tautomers thereof.

In one embodiment there is provided a compound of formula (IL):

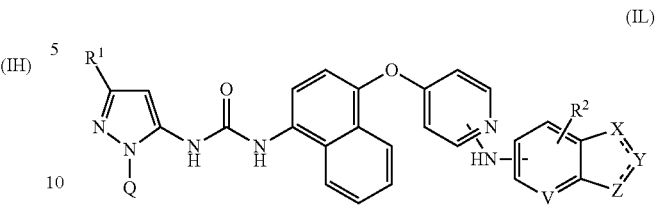

(IL)

wherein:

R¹, R², Q, V, X, Y and Z are as defined above, or a pharmaceutically acceptable salt thereof, including all stereoisomers and tautomers thereof.

In one embodiment there is provided a compound of formula (IM):

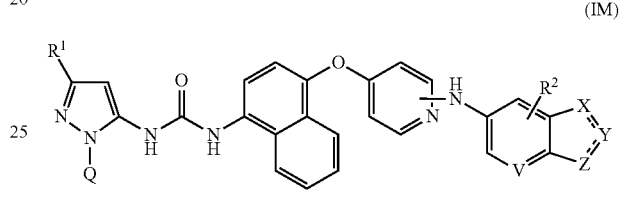

(IM)

wherein:

R¹, R², Q, V, X, Y and Z are as defined above, or a pharmaceutically acceptable salt thereof, including all stereoisomers and tautomers thereof.

In one embodiment there is provided a compound of formula (IN):

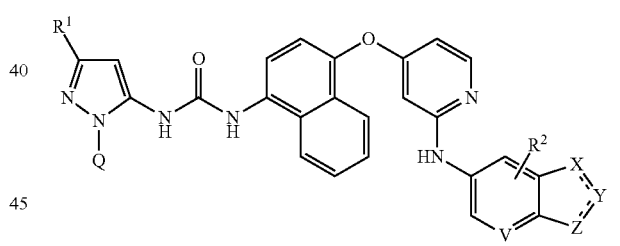

(IN)

wherein:

R¹, R², Q, V, X, Y and Z are as defined above, or a pharmaceutically acceptable salt thereof, including all stereoisomers and tautomers thereof.

In one embodiment there is provided a compound of formula (IP):

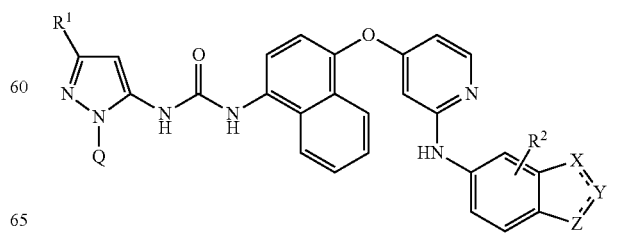

(IP)

wherein:

R$^1$, R$^2$, Q, X, Y and Z are as defined above, or a pharmaceutically acceptable salt thereof, including all stereoisomers and tautomers thereof.

In one embodiment there is provided a compound of formula (IQ):

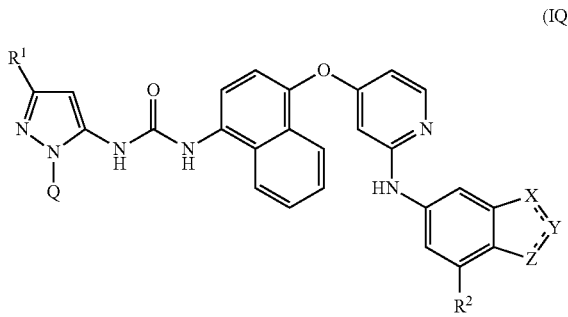

(IQ)

wherein:

R$^1$, R$^2$, Q, X, Y and Z are as defined above, or a pharmaceutically acceptable salt thereof, including all stereoisomers and tautomers thereof.

Preference described herein for compounds of formula (I) may apply equally to compounds of formula (IA), (IB), (IC), (ID), (IE), (IF), (IG), (IH), (IJ), (IK), (IL), (IM), (IN), (IP) and (IQ) as appropriate.

Particular embodiments of the invention include the following.

(1) A compound of formula (I), (IA), (IB), (IC), (ID), (IE), (IF), (IG), (IH), (IJ), (IK), (IL), (IM), (IN), (IP) or (IQ), as defined above, or a pharmaceutically acceptable salt thereof.

(2) A compound or salt according to Embodiment (1), wherein R$^1$ is C(CH$_3$)$_2$CH$_2$OH or CH(CH$_3$)CH$_2$OH.

(3) A compound or salt according to Embodiment (2), wherein R$^1$ is 1-hydroxy-2-methylpropan-2-yl.

(4) A compound or salt according to Embodiment (1), wherein R$^1$ is t-butyl.

(5) A compound or salt according to Embodiment (1), wherein R$^1$ is isopropyl.

(6) A compound or salt according to any one of Embodiments (1) to (5), wherein R$^2$ is H, C$_{1-6}$ alkyl or halo, for example H, methyl or chloro.

(7) A compound or salt according to any one of Embodiments (1) to (5), wherein R$^2$ is chloro, methyl or methoxy.

(8) A compound or salt according to any one of Embodiments (1) to (7), wherein R$^3$ is H, methyl or C$_{1-6}$ alkylene-5-6-membered heterocycle, such as H or methyl.

(9) A compound or salt according to any one of Embodiments (1) to (8), wherein R$^4$ represents H, halogen, C$_{1-6}$ alkyl optionally substituted by hydroxyl, C$_{1-6}$ alkoxy, CO$_2$C$_{1-3}$ alkyl, C$_{0-6}$ alkyleneNR$^{14}$R$^{15}$ or C$_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

(10) A compound or salt according to Embodiment (9), wherein R$^4$ represents H, CO$_2$C$_{1-3}$ alkyl, C$_{0-6}$ alkyleneNR$^{14}$R$^{15}$ or C$_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

(11) A compound or salt according to Embodiment (9), wherein R$^4$ is H, methyl, OCH$_2$CH$_2$morpholinyl, C(O)NHCH$_2$CH$_2$morpholinyl, C(O)morpholinyl or C(O)N(C$_{1-3}$ alkyl)$_2$.

(12) A compound or salt according to any one of Embodiments (1) to (11), wherein R$^5$ is H or methyl.

(13) A compound or salt according to any one of Embodiments (1) to (12), wherein R$^6$ is H or methyl.

(14) A compound or salt according to any one of Embodiments (1) to (13), wherein R$^7$ is H, methyl or C$_{1-6}$ alkylene-5-6-membered heterocycle, such as H or methyl.

(15) A compound or salt according to any one of Embodiments (1) to (14), wherein R$^8$ represents H, halogen, C$_{1-6}$ alkyl optionally substituted by hydroxyl, C$_{1-6}$ alkoxy, CO$_2$C$_{1-3}$ alkyl, C$_m$ alkyleneNR$^{14}$R$^{15}$ or C$_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

(16) A compound or salt according to Embodiment (15), wherein R$^8$ represents H, CO$_2$C$_{1-3}$ alkyl, C$_m$ alkyleneNR$^{14}$R$^{15}$ or C$_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

(17) A compound or salt according to any one of Embodiments (1) to (16), wherein R$^9$ is H or methyl.

(18) A compound or salt according to any one of Embodiments (1) to (17), wherein R$^{10}$ is H or methyl.

(19) A compound or salt according to any one of Embodiments (1) to (18), wherein R$^{11}$ is H or methyl, or morpholinoethyl, such as 4-morpholinoethyl.

(20) A compound or salt according to any one of Embodiments (1) to (19), wherein R$^{12}$ represents H, halo, C$_{1-6}$ alkyl optionally substituted by hydroxyl, C$_{1-6}$ alkoxy, CO$_2$C$_{1-3}$ alkyl, C$_{0-6}$ alkyleneNR$^{14}$R$^{15}$ or C$_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

(21) A compound or salt according to Embodiment (20), wherein R$^{12}$ represents H, CO$_2$C$_{1-3}$ alkyl, C$_{0-6}$ alkyleneNR$^{14}$R$^{15}$ or C$_{1-6}$ alkylene-5-10 membered heterocycle, wherein each alkylene group optionally bears 1 oxo substituent and optionally one or two carbons in the alkylene chain is replaced by a heteroatom selected from O, N, NR$^{14}$ or S(O)$_p$.

(22) A compound or salt according to any one of Embodiments (1) to (21), wherein R$^{13}$ is H or methyl.

(23) A compound or salt according to any one of Embodiments (1) to (22), wherein R$^{14}$ is H or methyl.

(24) A compound or salt according to any one of Embodiments (1) to (23), wherein R$^{15}$ is H or methyl.

(25) A compound or salt according to any one of Embodiments (1) to (24), wherein Q represents phenyl or pyridine substituted by 1 to 3 substituents independently selected from, hydroxyl, halogen, C$_{1-6}$ alkyl, C$_{1-6}$ alkoxy, C$_{1-6}$ haloalkoxy, C$_{1-6}$ hydroxyalkyl, C$_{1-6}$ alkylene-5-10 membered heterocycle, and C$_{0-3}$ alkylene-O—C$_{1-6}$ alkylene-5-10 membered heterocycle, provided that at least one substituent is selected from C$_{1-6}$ alkyl, C$_{1-6}$ hydroxyalkyl, C$_{1-6}$ alkylene-5-10 membered heterocycle, and C$_{0-3}$ alkylene-O—C$_{1-6}$ alkylene-5-10 membered heterocycle.

(26) A compound or salt according to any one of Embodiments (1) to (24), wherein Q represents phenyl, pyridine or pyridone, each substituted by 1 to 3 substituents independently selected from, $C_{4-6}$ alkoxy, $C_{4-6}$ haloalkoxy, $C_{1-6}$ hydroxyalkyl, $O(CH_2)_2O(CH_2)_2OR^4$, $C_{1-6}$ alkylene-5-10 membered heterocycle, and $C_{0-3}$ alkylene-O—$C_{1-6}$ alkylene-5-10 membered heterocycle.

(27) A compound or salt according to any one of Embodiments (1) to (24), wherein Q represents phenyl, pyridine or pyridone.

(28) A compound or salt according to Embodiment (27), wherein Q represents pyridone.

(29) A compound or salt according to any one of Embodiments (1) to (24), wherein Q represents phenyl substituted by 1, 2 or 3 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle, and $C_{0-3}$ alkylene-O—$C_{1-6}$ alkylene-5-10 membered heterocycle, for example 1 substituent, in particular wherein the substituent is selected from $C_{1-6}$ alkyl, $C_{1-6}$ hydroxyalkyl, $C_{1-6}$ alkylene-5-10 membered heterocycle, and $C_{0-3}$ alkylene-O—$C_{1-6}$ alkylene-5-10 membered heterocycle.

(30) A compound or salt according to Embodiment (29), wherein substituent or substituents on phenyl are independently selected, from hydroxyl, methyl, methoxy, $C_{1-3}$ alkylene-5-10 membered heterocyle for example methylene, ethylene or propylene linked morpholinyl, pyridinyl, piperidinyl or pyrrolidonyl, such as morpholinyl or pyrrolidonyl, and $C_{0-3}$ alkylene-O—$C_{1-6}$ alkylene-5-10 membered heterocycle, for example methoxy, ethoxy or propoxy linked morpholinyl, pyridinyl, piperidinyl or pyrrolidonyl, such as morpholinyl or pyrrolidonyl, in particular where the heterocycle is linked through a carbon to the alkylene portion.

(31) A compound or salt according to Embodiment (29) or (30), wherein the substituent or at least one of the substituents is in the para-position of the phenyl ring.

(32) A compound or salt according to Embodiment (29) or (30), wherein the substituent or at least one of the substituents is in the meta-position of the phenyl ring.

(33) A compound or salt according to Embodiment (29) or (30), wherein the phenyl ring bears a substituent selected from methyl, methoxy, —$CH_2$N-pyrrolidinyl or —$OCH_2CH_2$N-morpholinyl, in particular in the para or meta position, such as at the para position.

(34) A compound or salt according to any one of Embodiments (1) to (24), wherein Q represents pyridine substituted by 1, 2 or 3 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle, and $C_{0-3}$ alkylene-O—$C_{1-6}$ alkylene-5-10 membered heterocycle, for example 1 substituent, in particular wherein the substituent is selected from $C_{1-6}$ alkyl, $C_{1-6}$ hydroxyalkyl, $C_{1-6}$ alkylene-5-10 membered heterocycle, and $C_{0-3}$ alkylene-O—$C_{1-6}$ alkylene-5-10 membered heterocycle.

(35) A compound or salt according to Embodiment (34), wherein the substituent or substituents on pyridine are independently selected from hydroxyl, methyl, methoxy, $C_{1-3}$ alkylene-5-10 membered heterocyle for example methylene, ethylene or propylene linked morpholinyl, pyridinyl, piperidinyl or pyrrolidinyl, such as morpholinyl or pyrrolidinyl, and $C_{0-3}$ alkylene-O—$C_{1-6}$ alkylene-5-10 membered heterocycle, for example methoxy, ethoxy or propoxy linked morpholinyl, pyridinyl, piperidinyl or pyrrolidinyl, such as morpholinyl or pyrrolidinyl, in particular where the heterocycle is linked through a carbon to the alkylene portion.

(36) A compound or salt according to Embodiment (34) or (35), wherein Q is pyridine, the ring nitrogen is in the meta-position relative to its point of attachment to the pyrazole nucleus in compounds of formula (I).

(37) A compound or salt according to any one of Embodiments (34) to (36), wherein Q is pyridine, the substituent or at least one of the substituents is in the ortho-position, relative to the ring nitrogen.

(38) A compound or salt according to any one of Embodiments (34) to (36), wherein wherein Q is pyridine, the substituent or at least one of the substituents is in the meta-position, relative to the ring nitrogen.

(39) A compound or salt according to Embodiment (34) or (35), wherein the pyridinyl group bears a substituent selected from methyl, methoxy, —$CH_2$N-pyrrolidinyl or —$OCH_2CH_2$N-morpholinyl, in particular in the ortho- or meta-position, relative to the ring nitrogen, such as in the ortho-position.

(40) A compound or salt according to any one of Embodiments (1) to (24), wherein Q comprises a pyridinone group, the ring nitrogen and the carbonyl substituent are disposed meta- and para-respectively relative to its point of attachment to the pyrazole nucleus in compounds of formula (I).

(41) A compound or salt according to any one of Embodiments (1) to (24), wherein Q represents pyridinone substituted by 1 or 2 substituents independently selected from, $C_{1-6}$ alkyl, $C_{1-6}$ hydroxyalkyl and $C_{1-6}$ alkylene-5-10 membered heterocycle, for example 1 substituent.

(42) A compound or salt according to any one of Embodiments (1) to (24), wherein Q represents a pyridinone substituted on the ring nitrogen.

(43) A compound or salt according to any one of Embodiments (1) to (24), wherein Q represents a pyridinone substituted on the ring nitrogen by a substituent independently selected from, $C_{1-6}$ alkyl, $C_{1-6}$ hydroxyalkyl and $C_{1-6}$ alkylene-5-10 membered heterocycle, for example methyl, —$CH_2CH_2OH$ or —$CH_2CH_2$N-morpholinyl.

(44) A compound or salt according to any one Embodiments (1) to (43), wherein V is CH or $CR^2$, wherein $R^2$ is Cl or methyl.

(45) A compound or salt according to Embodiment (44), wherein V is $CR^2$ wherein $R^2$ is Cl or $CH_3$.

(46) A compound or salt according to any one of Embodiments (1) to (43), wherein V is N.

(47) A compound or salt according to any one of Embodiments (1) to (46), wherein X is independently selected from S, N, O, $CH_2$, CH, $CNH_2$, $CN(CH_3)_2$, $CCO_3CH_3$, $COCH_2CH_2$morpholinyl, CC(O)$NHCH_2CH_2$morpholinyl, CC(O)morpholinyl, and CC(O)$N(CH_3)_2$.

(48) A compound or salt according to any one of Embodiments (1) to (47), wherein Y is independently selected from N, C(O), O, $SO_2$, CH, $CH_2$ and $CCH_3$.

(49) A compound or salt according to any one of Embodiments (1) to (48), wherein Z is independently selected from O, S, N, NH, N-tetrahydrofuranyl, $NCH_2CH_2$morpholinyl, CH, $CH_2$ and $C(CH_3)_2$.

(50) A compound or salt according to any one of Embodiments (1) to (46), wherein X, Y and Z are respectively defined as:
CH, CH, NH
NH, C(O), $CH_2$,
$CC(O)OCH_3$, N, NH,
N, CH, $NCH_3$,
$CNH_2$, N, O,
$OCH_2$, $CH_2$, O,
O, $CH_2$, O, CH$_2$, O, CH$_2$,
CH, N, NH
CH, N, NCH$_3$
CH, CH, NCH$_3$,
CH$_2$, C(O), NH,
CH$_2$, C(O), NCH$_3$,
CC(O)N(CH$_3$)$_2$, N, NH
NH, C(O), CH$_2$,
NH, C(O), C(CH$_3$)$_2$,
C(O), NH, CH$_2$,
NH, C(O), O,
O, C(O), NH,
NH, N, CH,
CH, N, N-tetrahydropyranyl, NCH$_2$CH$_2$N-morpholinyl, N, CH,
COCH$_2$CH$_2$N-morpholinyl, N, NH,
CC(O)N-morpholinyl, N, NH,
CH, N, NCH$_2$CH$_2$N-morpholinyl,
CC(O)NHCH$_2$CH$_2$N-morpholinyl, N, NH,
N, CH, NH,
N, N, NH,
NCH$_3$, CH, N,
N, CH, S,
CH$_2$, SO$_2$, CH$_2$,
CH, N, S,
N, CH, S,
S, CH, N,
CH$_2$, CH$_2$, CH$_2$,
CH, CCH$_3$, NH,
NH, N, CCH$_3$,
CCH$_3$, N, NH, or
N, CCH$_3$, NH.

Exemplary compounds of formula (I) are selected from the group consisting of:

1-(4-((2-((1H-Indol-5-yl)amino)pyrimidin-4-yl)oxy)naphthalen-1-yl)-3-(3-(tert-butyl)-1-(p-tolyl)-1H-pyrazol-5-yl)urea;

1-(3-(tert-Butyl)-1-(p-tolyl)-1H-pyrazol-5-yl)-3-(4-((2-((2-oxoindolin-6-yl)amino)pyrimidin-4-yl)oxy)naphthalen-1-yl)urea;

5-((4-((4-(3-(3-(tert-Butyl)-1-(p-tolyl)-1H-pyrazol-5-yl)ureido)naphthalen-1-yl)oxy)pyrimidin-2-yl)amino)-N-(2-morpholinoethyl)-1H-indazole-3-carboxamide;

1-(3-(tert-Butyl)-1-(p-tolyl)-1H-pyrazol-5-yl)-3-(4-((2-((1-methyl-1H-benzo[d]imidazol-5-yl)amino)pyrimidin-4-yl)oxy)naphthalen-1-yl)urea, 1-(4-((2-((3-Aminobenzo[d]isoxazol-5-yl)amino)pyrimidin-4-yl)oxy)naphthalen-1-yl)-3-(3-(tert-butyl)-1-(p-tolyl)-1H-pyrazol-5-yl)urea;

1-(4-((2-((1H-Pyrazolo[3,4-b]pyridin-5-yl)amino)pyrimidin-4-yl)oxy)naphthalen-1-yl)-3-(3-(tert-butyl)-1-(p-tolyl)-1H-pyrazol-5-yl)urea;

1-(4-((2-((1H-Indazol-5-yl)amino)pyrimidin-4-yl)oxy)naphthalen-1-yl)-3-(3-(tert-butyl)-1-(4-hydroxyphenyl)-1H-pyrazol-5-yl)urea;

1-(4-((2-((1H-Indazol-5-yl)amino)pyrimidin-4-yl)oxy)naphthalen-1-yl)-3-(1-(4-methoxyphenyl)-3-(tetrahydrofuran-3-yl)-1H-pyrazol-5-yl)urea;

1-(3-Isopropyl-1-(4-methoxyphenyl)-1H-pyrazol-5-yl)-3-(4-((2-((7-methyl-1H-indazol-5-yl)amino)pyrimidin-4-yl)oxy)naphthalen-1-yl)urea;

1-(3-(tert-Butyl)-1-(3-((2-oxopyrrolidin-1-yl)methyl)phenyl)-1H-pyrazol-5-yl)-3-(4-((2-((7-methyl-1H-indazol-5-yl)amino)pyrimidin-4-yl)oxy)naphthalen-1-yl)urea;

1-(3-(tert-Butyl)-1-(4-(2-morpholinoethoxy)phenyl)-1H-pyrazol-5-yl)-3-(4-((2-((2,3-dihydrobenzo[b][1,4]dioxin-6-yl)amino)pyrimidin-4-yl)oxy)naphthalen-1-yl)urea;

1-(4-((2-((1H-Indazol-5-yl)amino)pyrimidin-4-yl)oxy)naphthalen-1-yl)-3-(3-(tert-butyl)-1-(4-(2-morpholinoethoxy)phenyl)-1H-pyrazol-5-yl)urea;

1-(4-((2-((1H-Indazol-5-yl)amino)pyrimidin-4-yl)oxy)naphthalen-1-yl)-3-(3-(tert-butyl)-1-(6-methoxypyridin-3-yl)-1H-pyrazol-5-yl)urea;

1-(4-((6-((1H-Indazol-5-yl)amino)pyrimidin-4-yl)oxy)naphthalen-1-yl)-3-(3-(tert-butyl)-1-(1-(2-hydroxyethyl)-6-oxo-1,6-dihydropyridin-3-yl)-1H-pyrazol-5-yl)urea;

1-(4-((2-((1H-Indazol-5-yl)amino)pyrimidin-4-yl)oxy)naphthalen-1-yl)-3-(3-(tert-butyl)-1-(6-(2-morpholinoethoxy)pyridin-3-yl)-1H-pyrazol-5-yl)urea;

1-(3-(tert-butyl)-1-(p-tolyl)-1H-pyrazol-5-yl)-3-(4-((2-((1-methyl-1H-indol-5-yl)amino)pyrimidin-4-yl)oxy)naphthalen-1-yl)urea;

1-(3-(tert-butyl)-1-(p-tolyl)-1H-pyrazol-5-yl)-3-(4-((2-((2-oxoindolin-5-yl)amino)pyrimidin-4-yl)oxy)naphthalen-1-yl)urea;

1-(3-(tert-butyl)-1-(p-tolyl)-1H-pyrazol-5-yl)-3-(4-((2-((1-methyl-2-oxoindolin-5-yl)amino) pyrimidin-4-yl)oxy)naphthalen-1-yl)urea;

1-(4-((2-((1H-indazol-5-yl)amino)pyrimidin-4-yl)oxy)naphthalen-1-yl)-3-(3-(tert-butyl)-1-(p-tolyl)-1H-pyrazol-5-yl)urea;

1-(4-((6-((1H-indazol-5-yl)amino)pyrimidin-4-yl)oxy)naphthalen-1-yl)-3-(3-(tert-butyl)-1-(p-tolyl)-1H-pyrazol-5-yl)urea;

1-(4-((2-((1H-indazol-6-yl)amino)pyrimidin-4-yl)oxy)naphthalen-1-yl)-3-(3-(tert-butyl)-1-(p-tolyl)-1H-pyrazol-5-yl)urea;

1-(3-(tert-butyl)-1-(p-tolyl)-1H-pyrazol-5-yl)-3-(4-((2-((1-methyl-1H-indazol-5-yl)amino) pyrimidin-4-yl)oxy)naphthalen-1-yl)urea;

1-(3-(tert-butyl)-1-(p-tolyl)-1H-pyrazol-5-yl)-3-(4-((2-((7-methyl-1H-indazol-5-yl)amino) pyrimidin-4-yl)oxy)naphthalen-1-yl)urea;

1-(3-(tert-butyl)-1-(p-tolyl)-1H-pyrazol-5-yl)-3-(4-((2-((7-chloro-1H-indazol-5-yl)amino) pyrimidin-4-yl)oxy)naphthalen-1-yl)urea;

1-(3-(tert-butyl)-1-(p-tolyl)-1H-pyrazol-5-yl)-3-(4-((2-((1-(2-morpholinoethyl)-1H-indazol-5-yl)amino)pyrimidin-4-yl)oxy)naphthalen-1-yl)urea;

1-(4-((2-((1H-benzo[d]imidazol-5-yl)amino)pyrimidin-4-yl)oxy)naphthalen-1-yl)-3-(3-(tert-butyl)-1-(p-tolyl)-1H-pyrazol-5-yl)urea;

1-(3-(tert-butyl)-1-(p-tolyl)-1H-pyrazol-5-yl)-3-(4-((2-((1-methyl-1H-benzo[d]imidazol-6-yl)amino)pyrimidin-4-yl)oxy)naphthalen-1-yl)urea;

1-(3-(tert-butyl)-1-(p-tolyl)-1H-pyrazol-5-yl)-3-(4-((2-((1-methyl-1H-benzo[d]imidazol-6-yl)amino)pyrimidin-4-yl)oxy)naphthalen-1-yl)urea;

1-(4-((2-((1H-pyrrolo[2,3-b]pyridin-5-yl)amino)pyrimidin-4-yl)oxy)naphthalen-1-yl)-3-(3-(tert-butyl)-1-(p-tolyl)-1H-pyrazol-5-yl)urea;

1-(4-((2-(benzo[d][1,3]dioxol-5-ylamino)pyrimidin-4-yl)oxy)naphthalen-1-yl)-3-(3-(tert-butyl)-1-(p-tolyl)-1H-pyrazol-5-yl)urea;

1-(4-((2-(benzo[d][1,3]dioxol-5-ylamino)pyrimidin-4-yl)oxy)naphthalen-1-yl)-3-(3-(tert-butyl)-1-(p-tolyl)-1H-pyrazol-5-yl)urea;

1-(4-((2-(benzo[d]thiazol-5-ylamino) pyrimidin-4-yl)oxy)naphthalen-1-yl)-3-(3-(tert-butyl)-1-(p-tolyl)-1H-pyrazol-5-yl)urea;

1-(4-((2-(benzo[d]thiazol-6-ylamino)pyrimidin-4-yl)oxy)naphthalen-1-yl)-3-(3-(tert-butyl)-1-(p-tolyl)-1H-pyrazol-5-yl)urea;

1-(4-((2-(((1H-benzo[d][1,2,3]triazol-5-yl)amino)pyrimidin-4-yl)oxy)naphthalen-1-yl)-3-(3-(tert-butyl)-1-(p-tolyl)-1H-pyrazol-5-yl)urea;

1-(4-((2-(((1H-indol-5-yl)amino)pyrimidin-4-yl)oxy)naphthalen-1-yl)-3-(3-(tert-butyl)-1-(4-hydroxyphenyl)-1H-pyrazol-5-yl)urea;

1-(4-((2-(((1H-indol-5-yl)amino)pyrimidin-4-yl)oxy)naphthalen-1-yl)-3-(3-(tert-butyl)-1-(4-methoxyphenyl)-1H-pyrazol-5-yl)urea;

1-(4-((6-((1H-indazol-5-yl)amino)pyrimidin-4-yl)oxy)naphthalen-1-yl)-3-(3-isopropyl-1-(4-methoxyphenyl)-1H-pyrazol-5-yl)urea;

1-(4-((2-((1H-indazol-5-yl)amino)pyrimidin-4-yl)oxy)naphthalen-1-yl)-3-(3-(tert-butyl)-1-(4-methoxyphenyl)-1H-pyrazol-5-yl)urea;

1-(3-(tert-butyl)-1-(4-methoxyphenyl)-1H-pyrazol-5-yl)-3-(4-((2-((1-methyl-1H-indazol-5-yl)amino)pyrimidin-4-yl)oxy)naphthalen-1-yl)urea;

1-(3-(tert-butyl)-1-(4-methoxyphenyl)-1H-pyrazol-5-yl)-3-(4-((2-((7-methyl-1H-indazol-5-yl)amino)pyrimidin-4-yl)oxy)naphthalen-1-yl)urea;

1-(3-(tert-butyl)-1-(4-methoxyphenyl)-1H-pyrazol-5-yl)-3-(4-((2-((1-(2-morpholinoethyl)-1H-indazol-5-yl)amino)pyrimidin-4-yl)oxy)naphthalen-1-yl)urea;

1-(3-isopropyl-1-(4-methoxyphenyl)-1H-pyrazol-5-yl)-3-(4-((2-((3-(2-morpholinoethoxy)-1H-indazol-5-yl)amino)pyrimidin-4-yl)oxy)naphthalen-1-yl)urea;

1-(3-(tert-butyl)-1-(4-methoxyphenyl)-1H-pyrazol-5-yl)-3-(4-((2-((3-(2-morpholinoethoxy)-1H-indazol-5-yl)amino)pyrimidin-4-yl)oxy)naphthalen-1-yl)urea;

5-((4-((4-(3-(3-isopropyl-1-(4-methoxyphenyl)-1H-pyrazol-5-yl)ureido)naphthalen-1-yl)oxy) pyrimidin-2-yl)amino)-N,N-dimethyl-1H-indazole-3-carboxamide;

5-((4-((4-(3-(3-(tert-butyl)-1-(4-methoxyphenyl)-1H-pyrazol-5-yl)ureido)naphthalen-1-yl)oxy) pyrimidin-2-yl)amino)-N,N-dimethyl-1H-indazole-3-carboxamide;

1-(4-((2-(((1H-indol-5-yl)amino)pyrimidin-4-yl)oxy)naphthalen-1-yl)-3-(3-(tert-butyl)-1-(3-((2-oxopyrrolidin-1-yl)methyl)phenyl)-1H-pyrazol-5-yl)urea;

1-(4-((2-(((1H-indazol-5-yl)amino)pyrimidin-4-yl)oxy)naphthalen-1-yl)-3-(3-(tert-butyl)-1-(3-((2-oxopyrrolidin-1-yl)methyl)phenyl)-1H-pyrazol-5-yl)urea;

1-(3-(tert-butyl)-1-(3-(2-morpholinoethoxy)phenyl)-1H-pyrazol-5-yl)-3-(4-((2-((2-oxoindolin-6-yl)amino)pyrimidin-4-yl)oxy)naphthalen-1-yl)urea;

1-(4-((2-(((1H-indazol-5-yl)amino)pyrimidin-4-yl)oxy)naphthalen-1-yl)-3-(3-isopropyl-1-(3-(2-morpholinoethoxy)phenyl)-1H-pyrazol-5-yl)urea;

1-(4-((2-(((1H-indazol-5-yl)amino)pyrimidin-4-yl)oxy)naphthalen-1-yl)-3-(3-(tert-butyl)-1-(3-(2-morpholinoethoxy)phenyl)-1H-pyrazol-5-yl)urea;

1-(3-isopropyl-1-(3-(2-morpholinoethoxy)phenyl)-1H-pyrazol-5-yl)-3-(4-((2-((7-methyl-1H-indazol-5-yl)amino)pyrimidin-4-yl)oxy)naphthalen-1-yl)urea;

1-(3-(tert-butyl)-1-(3-(2-morpholinoethoxy)phenyl)-1H-pyrazol-5-yl)-3-(4-((2-((7-methyl-1H-indazol-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((2,3-dihydro-1H-inden-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((1,3-dihydro isobenzofuran-5-yl)amino)pyrimidin-4-yl)oxy)naphthalen-1-yl)urea;

1-(3-isopropyl-1-(4-(2-morpholinoethoxy)phenyl)-1H-pyrazol-5-yl)-3-(4-((2-((2-oxoindolin-6-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((3,3-dimethyl-2-oxoindolin-6-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((3-oxoisoindolin-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((2,2-dioxido-1,3-dihydrobenzo[c]thiophen-5-yl)amino)pyrimidin-4-yl)oxy)naphthalen-1-yl)urea;

1-(4-((2-(benzo[d][1,3]dioxol-5-ylamino)pyrimidin-4-yl)oxy)naphthalen-1-yl)-3-(3-(tert-butyl)-1-(4-(2-morpholinoethoxy)phenyl)-1H-pyrazol-5-yl)urea;

1-(3-(tert-butyl)-1-(4-(2-morpholinoethoxy)phenyl)-1H-pyrazol-5-yl)-3-(4-((2-((2-methyl-1H-indol-5-yl)amino)pyrimidin-4-yl)oxy)naphthalen-1-yl)urea;

1-(4-((2-(((1H-indazol-5-yl)amino)pyrimidin-4-yl)oxy)naphthalen-1-yl)-3-(3-isopropyl-1-(4-(2-morpholinoethoxy)phenyl)-1H-pyrazol-5-yl)urea;

1-(4-((6-((1H-indazol-5-yl)amino)pyrimidin-4-yl)oxy)naphthalen-1-yl)-3-(3-(tert-butyl)-1-(4-(2-morpholinoethoxy)phenyl)-1H-pyrazol-5-yl)urea;

1-(3-(tert-butyl)-1-(4-(2-morpholinoethoxy)phenyl)-1H-pyrazol-5-yl)-3-(4-((2-((3-methyl-1H-indazol-6-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((7-methyl-1H-indazol-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((1-(2-morpholinoethyl)-1H-indazol-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((2-methyl-1H-benzo[d]imidazol-6-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((2-oxo-2,3-dihydrobenzo[d]oxazol-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((2-oxo-2,3-dihydrobenzo[d]oxazol-6-yl)amino)pyrimidin-4-yl)oxy)naphthalen-1-yl)urea;

1-(4-((2-(benzo[d]isothiazol-5-ylamino)pyrimidin-4-yl)oxy)naphthalen-1-yl)-3-(3-(tert-butyl)-1-(4-(2-morpholinoethoxy)phenyl)-1H-pyrazol-5-yl)urea;

1-(4-((2-(benzo[d]thiazol-5-ylamino)pyrimidin-4-yl)oxy)naphthalen-1-yl)-3-(3-(tert-butyl)-1-(4-(2-morpholinoethoxy)phenyl)-1H-pyrazol-5-yl)urea;

1-(4-((2-(benzo[d]thiazol-6-ylamino)pyrimidin-4-yl)oxy)naphthalen-1-yl)-3-(3-(tert-butyl)-1-(4-(2-morpholinoethoxy)phenyl)-1H-pyrazol-5-yl)urea;

1-(4-((2-(((1H-benzo[d][1,2,3]triazol-5-yl)amino)pyrimidin-4-yl)oxy)naphthalen-1-yl)-3-(3-(tert-butyl)-1-(4-(2-morpholinoethoxy)phenyl)-1H-pyrazol-5-yl)urea;

1-(4-((2-((1H-indol-5-yl)amino)pyrimidin-4-yl)oxy)naphthalen-1-yl)-3-(3-(tert-butyl)-1-(6-methoxypyridin-3-yl)-1H-pyrazol-5-yl)urea;

1-(3-(tert-butyl)-1-(6-methoxypyridin-3-yl)-1H-pyrazol-5-yl)-3-(4-((2-((3-(morpholine-4-carbonyl)-1H-indazol-5-yl)amino)pyrimidin-4-yl)oxy)naphthalen-1-yl)urea;

1-(4-((6-((1H-indazol-5-yl)amino)pyrimidin-4-yl)oxy)naphthalen-1-yl)-3-(1-(1-(2-hydroxyethyl)-6-oxo-1,6-dihydropyridin-3-yl)-3-isopropyl-1H-pyrazol-5-yl)urea;

1-(4-((2-((1H-indazol-5-yl)amino)pyrimidin-4-yl)oxy)naphthalen-1-yl)-3-(1-(1-(2-hydroxyethyl)-6-oxo-1,6-dihydropyridin-3-yl)-3-isopropyl-1H-pyrazol-5-yl)urea;

1-(4-((2-((1H-indazol-5-yl)amino)pyrimidin-4-yl)oxy)naphthalen-1-yl)-3-(3-(tert-butyl)-1-(1-(2-hydroxyethyl)-6-oxo-1,6-dihydropyridin-3-yl)-1H-pyrazol-5-yl)urea;

1-(3-(tert-butyl)-1-(1-(2-hydroxyethyl)-6-oxo-1,6-dihydropyridin-3-yl)-1H-pyrazol-5-yl)-3-(4-((2-((7-methyl-1H-indazol-5-yl)amino)pyrimidin-4-yl)oxy)naphthalen-1-yl)urea;

1-(4-((2-((1H-indazol-5-yl)amino)pyrimidin-4-yl)oxy)naphthalen-1-yl)-3-(3-(tert-butyl)-1-(1-(2-morpholinoethyl)-6-oxo-1,6-dihydropyridin-3-yl)-1H-pyrazol-5-yl)urea;

1-(3-(tert-butyl)-1-(1-(2-morpholinoethyl)-6-oxo-1,6-dihydropyridin-3-yl)-1H-pyrazol-5-yl)-3-(4-((2-((7-methyl-1H-indazol-5-yl)amino)pyrimidin-4-yl)oxy)naphthalen-1-yl)urea;

1-(3-(tert-butyl)-1-(6-(2-morpholinoethoxy)pyridin-3-yl)-1H-pyrazol-5-yl)-3-(4-((2-((2-oxo indolin-6-yl)amino)pyrimidin-4-yl)oxy)naphthalen-1-yl)urea;

1-(3-(tert-butyl)-1-(6-(2-morpholinoethoxy)pyridin-3-yl)-1H-pyrazol-5-yl)-3-(4-((2-((7-methyl-1H-indazol-5-yl)amino)pyrimidin-4-yl)oxy)naphthalen-1-yl)urea;

1-(3-(tert-butyl)-1-(6-(2-morpholinoethoxy)pyridin-3-yl)-1H-pyrazol-5-yl)-3-(4-((2-((1-(2-morpholinoethyl)-1H-indazol-5-yl)amino)pyrimidin-4-yl)oxy)naphthalen-1-yl)urea;

methyl 5-((4-((4-(3-(3-(tert-butyl)-1-(p-tolyl)-1H-pyrazol-5-yl)ureido)naphthalen-1-yl)oxy)pyrimidin-2-yl)amino)-1H-indazole-3-carboxylate;

1-(3-(tert-butyl)-1-(4-(2-morpholinoethoxy)phenyl)-1H-pyrazol-5-yl)-3-(4-((2-((1-(tetrahydro-2H-pyran-2-yl)-1H-indazol-5-yl)amino)pyrimidin-4-yl)oxy)naphthalen-1-yl)urea, and pharmaceutically acceptable salts thereof.

The pharmaceutically acceptable acid addition salts of compounds of formula (I) are meant to comprise the therapeutically active non-toxic acid addition salts that the compounds of formula (I) are able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like.

Conversely said salt forms can be converted by treatment with an appropriate base into the free base form.

Stereoisomers as employed herein refers to isomeric molecules that have the same molecular formula and sequence of bonded atoms (constitution), but that differ only in the three-dimensional orientations of their atoms in space. This contrasts with structural isomers, which share the same molecular formula, but the bond connections and/or their order differ(s) between different atoms/groups. In stereoisomers, the order and bond connections of the constituent atoms remain the same, but their orientation in space differs.

As employed herein below the definition of compounds of formula (I) is intended to include all tautomers of said compounds, and solvates of said compounds (including solvates of salts of said compounds) unless the context specifically indicates otherwise. Examples of solvates include hydrates.

The invention provided herein extends to prodrugs of the compound of formula (I), that is to say compounds which break down and/or are metabolised in vivo to provide an active compound of formula (I). General examples of prodrugs include simple esters, and other esters such as mixed carbonate esters, carbamates, glycosides, ethers, acetals and ketals.

In a further aspect of the invention there is provided one or more metabolites of the compound of formula (I), in particular a metabolite that retains one or more of the therapeutic activities of the compound of formula (I). A metabolite, as employed herein, is a compound that is produced in vivo from the metabolism of the compound of formula (I), such as, without limitation, oxidative metabolites and/or metabolites generated, for example, from O-dealkylation.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The disclosure also extends to all polymorphic forms of the compounds herein defined.

Generic routes by which compound examples of the invention may be conveniently prepared are summarised below. Thus compounds of formula (I) may be obtained by a general process, Route A (Scheme 1), whereby a naphthylamine precursor represented by Intermediate B is coupled with an activated, electrophilic derivative Intermediate A* prepared from the corresponding amine precursor, Intermediate A (G=H). The fragment $LG_1$ in Intermediate A* is a suitable leaving group such as an imidazolyl ($C_3H_3N_2$) or an aryloxy radical such as a phenoxy ($C_6H_5O$) group. It will be understood by persons skilled in the art that, in some instances, the compound represented by Intermediate A* may be isolated or in other cases may be a transient intermediate, that is not isolated, but generated in situ and used directly.

Scheme 1

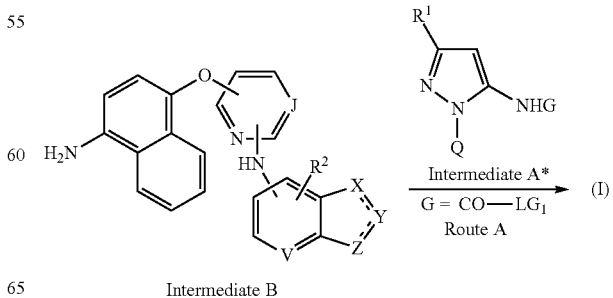

In the case wherein $LG_1$ is imidazoyl, compounds represented by Intermediate A* are obtained by reaction of the corresponding amine with an activating agent such as CDI in a non polar aprotic solvent, such as DCM and are conveniently generated in situ at RT and then reacted without isolation with compounds represented by Intermediate B.

In the case wherein $LG_1$ is aryloxy the required activated amine may be generated by treatment of the amine precursors with a suitable chloroformate, such as, for example, phenyl chloroformate, in the presence of a base. In some instances it is advantageous to conduct the activation process under Schotten Baumann type conditions, that is using an aqueous base, such as aq sodium carbonate and under biphasic conditions. The activated amine derivatives represented by Intermediate A* wherein $LG_1$ is aryloxy, for example phenoxy, may thereby be generated optionally in situ and then reacted without isolation with compounds represented by Intermediate B to provide compound examples of formula (I).

In other cases, depending upon the nature of the substituent Q, for example wherein Q contains a basic centre such as a tertiary amine group, the reaction may be conveniently carried out under homogeneous conditions in the absence of an external base. In such circumstances the electrophilic coupling partner represented by Intermediate A* may be isolated in the form of a salt which is usually formed when such conditions are employed, such as for example, a hydrochloride salt when an aryloxychloroformate has been used. In such cases the salt may be transformed into Intermediate A* by treatment with a suitable base such as aq $NaHCO_3$ in the presence of an a organic solvent such as DCM into which the Intermediate A* is thereby preferentially partitioned and subsequently isolated.

The coupling reaction to provide compounds of formula (I) may then be effected by exposing compounds represented by Intermediate B to compounds represented by Intermediate A* in a suitable aprotic solvent such as THF and in the presence of an appropriate base such as, for example, triethylamine.

Alternatively compounds of formula (I) may be generated by a synthetic process comprising Route B, (Scheme 2), employing a displacement reaction between a pyrimidine or pyridine compound represented by Intermediate C, wherein $LG_2$ is a suitable leaving group such as a halogen, for example, a chlorine atom, with an amine component represented by Intermediate D. The reaction proceeds under acidic conditions, in a suitable organic solvent for example in the presence of p-TSA and in THF and typically at elevated temperatures, such as 70° C.

Scheme 2

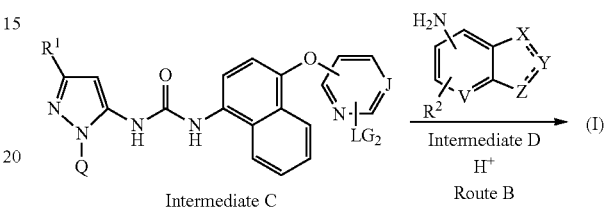

It will be understood that, in some instances, compounds of the present invention can be prepared by the conversion of a compound of formula (I) into another example of the same, by synthetic processes that are well established in the art. By way of example, a compound of formula (I) that comprises a carboxylic acid ester may be hydrolysed to the corresponding acid and subsequently reacted with a suitable primary or secondary amine under appropriate coupling conditions to provide amides that constitute additional examples of the invention. Compounds examples which may be subjected to this type of transformation include those of formula (I) in which the group X or the group Y or the group Z comprise of a carboxylic acid ester, for example those in which the group X comprises of an simple alkyl ester, for example a methyl ester (Scheme 3, wherein $R^a$, $R^b$ and $R^c$ represent the residue of substitutents permitted within the definition of X for compounds of formula (I) or a suitably protected derivative thereof).

Scheme 3

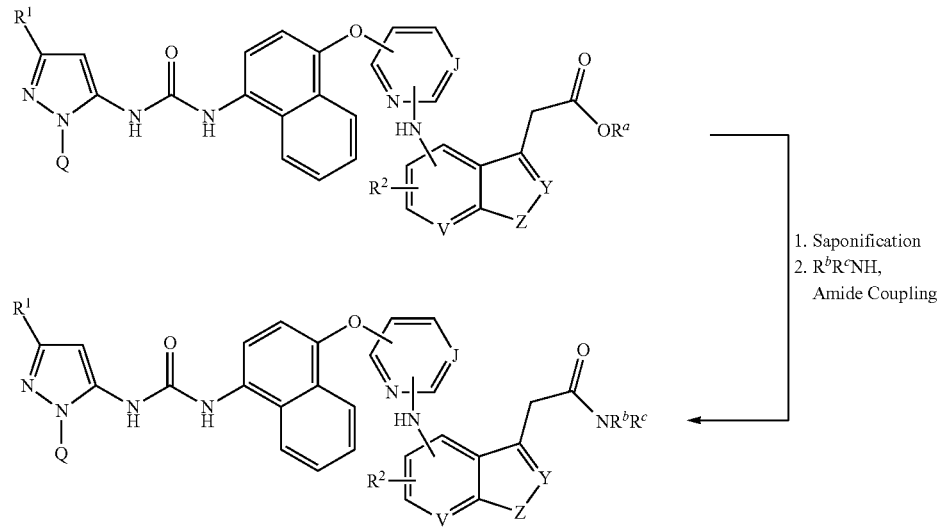

1. Saponification
2. $R^bR^cNH$, Amide Coupling

The ester may be hydrolysed under acidic conditions or alternatively, under basic conditions, that is by saponification; suitably by exposure to a base, such as lithium hydroxide, in a protic solvent or mixture of solvents, such as THF and water and at modestly elevated temperatures, typically RT to 40° C. The acid so formed, may be conveniently converted into amide examples of the invention by treatment with appropriate amines in the presence of an amide coupling reagent, such as HATU and a non nucleophilic base, such as DIPEA. The reaction is typically conducted in polar aprotic solvents such as THF and at ambient temperature.

Compounds represented by Intermediate A are either commercially available, or may be prepared by synthetic approaches that are well established in the art. For example compounds of this general structure may be prepared by the condensation of the appropriate hydrazine or a suitable salt thereof, such as a hydrochloride salt, or a compatible, protected derivative thereof, such as a bis-carbamate protected hydrazine for example the bis-Boc derivative, with the relevant ketonitrile (Scheme 4, wherein $R^d$ is selected to provide a carbamate protective group suitable for the transformation). The condensation/cyclisation

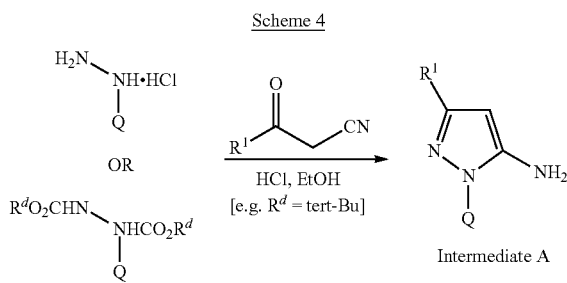

Scheme 4 reaction is suitably conducted in a polar protic solvent such as ethanol and in the presence of strong acid such concentrated hydrochloric acid and at elevated temperatures such as, at reflux.

In those cases where the desired hydrazine component, $QNHNH_2$ is not commercially available such compounds may be prepared by procedures that are well represented in the art. For example, a hydrazine derivative, wherein Q represents a substituted heteroaromatic nucleus as defined for compounds of formula (I), such an O-alkylated pyridone, may be generated starting from an appropriately functionalised pyridine (Scheme 5, wherein $R^f$ derives from a suitable commercially available diazene). Suitable pyridine precursors include dihalo pyridines, such as those in which $LG_3$ is an iodine atom and $LG_4$ is a fluorine atom, which may be transformed into 2-alkoxy pyridines by a chemoselective $S_NAr$ displacement reaction with a suitable alcohol under basic conditions. Appropriate reaction conditions are the use of a strong non-nucleophilic base, such as sodium hydride in a polar aprotic solvent such as THF and at elevated temperatures, for example at reflux.

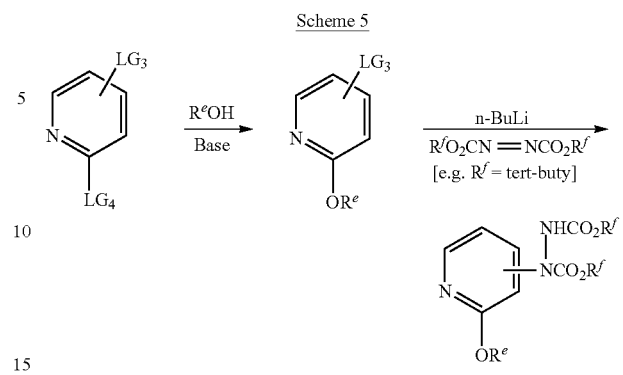

Scheme 5

The products so formed may be conveniently converted into protected derivatives of the desired hydrazines by metal halogen exchange, followed by treatment with a suitable diazene derivative. The metal halogen exchange can be effected with an akyl lithium, such n-butyllithium in a mixture of non protic solvents, for example, THF and hexanes and at reduced temperature, typically at −78° C. The resulting aryl lithium compounds are conveniently reacted in situ with an electrophilic diazene reagent such as, for example, a di-alkyl diazene-1,2-dicarboxylate, at more elevated temperatures, such as RT, resulting in the formation of the corresponding hydrazine as a bis carbamate derivative. A suitable diazene reagent is di-tert-butyl diazene-1,2-dicarboxylate since the hydrazine derivatives so formed may be used directly in the formation of compounds represented by Intermediate A, as described hereinabove, without the need for a discrete de-protection step.

In some instances it may be advantageous to prepare such intermediates by one or other alternative methodologies, as best suits the availability of starting materials and/or the functionality represented in the compounds and/or the need to protect one or more of them, during the synthetic processes in question or in subsequent transformations For example compounds represented by Intermediate A can also be accessed via a copper (I) mediated coupling reaction between a 1H-pyrazol-5-amine and a suitable arene Q-LG$_5$ in which Q is an optionally substituted aromatic nucleus as defined for compounds of formula (I) and LG$_5$ is a halide such as an iodine atom (Scheme 6). The reaction is conveniently conducted in an aprotic non-polar solvent such as toleune, employing a copper (I) salt as the

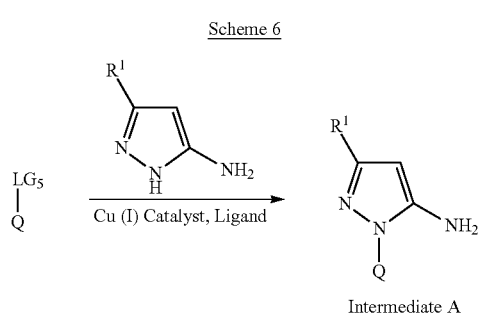

Scheme 6 catalyst, for example copper (I) iodide and in the presence of a copper co-ordinating ligand such as $N^1,N^2$-dimethylcyclohexane-1,2-diamine and in the presence of a base, for example potassium carbonate and typically at elevated temperature such as, at reflux.

It will be evident to those skilled in the art that it may be advantageous to convert one intermediate described herein into another example of the same by one or more transformations that are well known and precedented and thereby gain access to additional compounds of the invention. As an example of such a process those compounds represented by Intermediate A wherein Q is a phenyl ring substituted with an alkoxy group (OR$^g$ wherein R$^g$ is alkyl), such as a methoxy group, may be converted into the corresponding phenol by an O-dealkylation reaction (Scheme 7). Such a transformation may be effected with a boron trihalide such as boron tribromide in a non-polar, aprotic solvent such as DCM at reduced temperatures for example at −5 to 0° C.

Scheme 7

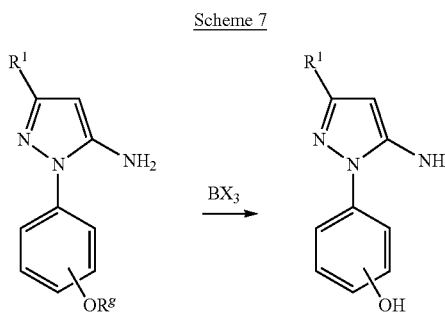

Similarly, compounds represented by Intermediate A wherein Q is a pyridine ring substituted with an ortho-alkoxy group (OR$^g$), such as a methoxy group, may be O-dealkylated by treatment with acid, such as aq. hydrochloric acid, to provide corresponding pyridone examples of Intermediate A (Scheme 8).

Scheme 8

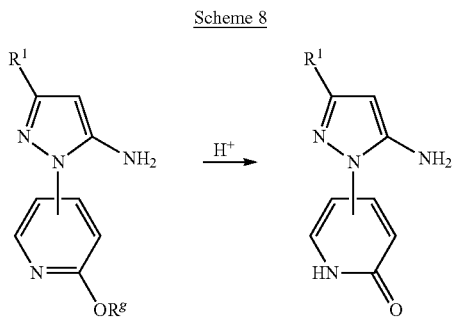

A further demonstration of the conversion of one intermediate, into another compound of the same generic type is provided by the functionalisation of the phenol examples of Intermediate A described hereinabove. For example intermediates of this composition can be conveniently alkylated on the phenolic oxygen by reaction with an alkyl halide, such as a simple alkyl bromide. Alternatively, the phenol products may be reacted with a functionalised alkyl halide, for example with a nitrogen mustard, that is, with a salt of a 2-haloethylamine of formula R$^h$(CH$_2$)$_2$LG$_6$, for example with 4-(2-chloroethyl)morpholine hydrochloride (Scheme 9 wherein R$^h$ and n1 are selected such that O(CH$_2$)$_{n1}$R$^h$ is allowable by the definition of Q in compounds of formula (I) or is a suitably protected derivative thereof). Such transformations Scheme 9

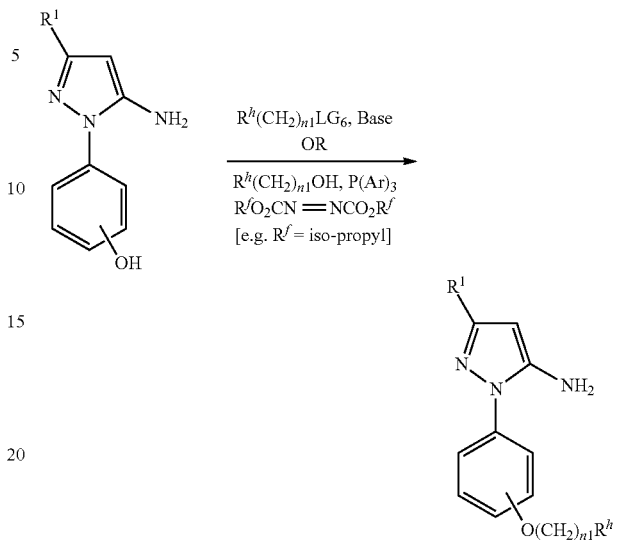

are usefully undertaken in polar non protic solvents such as acetonitrile or DMF and in the presence of a base such as potassium carbonate and with heating if necessary.

In some instances it may be advantageous to effect the O-alkylation under Mitsunobu conditions, by interaction of the phenol with the corresponding alcohol in the presence of a triaryl phosphine such as triphenyphosphine and a suitable diazodicarboxylate reagent, for example diisopropyl diazene-1,2-dicarboxylate and typically, carried out in non polar, aprotic solvents such as THF at reduced to ambient temperatures, for example at −50° C. to RT.

In a similar fashion, pyridone examples of Intermediate A described hereinabove, may also be functionalised by the same transformative processes (Scheme 10), on one or other of the ring heteroatoms (usually a mixture of both), to provide products of N- and/or O-alkylation.

Scheme 10

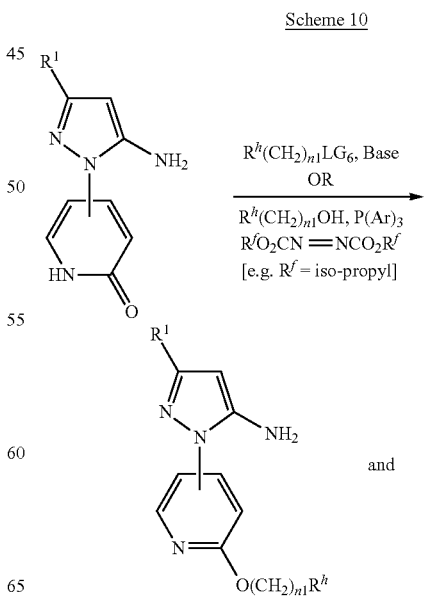

Compounds represented by Intermediate B may be obtained using the same transformative processes described hereinabove (Route B, Scheme 2) by reaction of a compound represented by Intermediate E ($P^1$=H) with a compound represented by Intermediate D (Scheme 11). It may be advantageous to use a protected derivative, of Intermediate E, such as Intermediate $E^P$ in this amination step, in order to maintain chemoselectivity, for example a carbamate derivative ($P^1$=$CO_2R'$) such as a Boc derivative ($P^1$=$CO_2{}^tBu$)

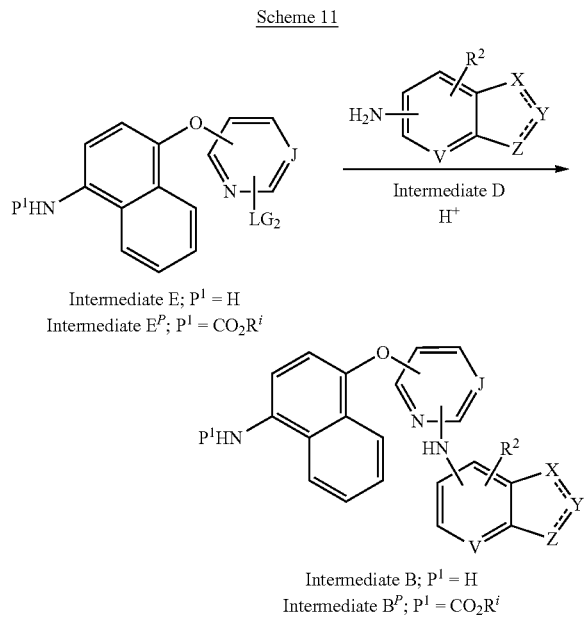

Compounds represented by Intermediate C may be prepared using the same transformative processes described hereinabove (Route A, Scheme 1) by the reaction of a compound represented by Intermediate E with a compound represented by Intermediate A* (Scheme 12).

The common precursors represented by Intermediate E are, in turn, readily prepared by an $S_NAr$ displacement reaction between a salt of 4-aminonaphthalen-1-ol or a suitable, protected derivative, readily generated therefrom, and an appropriately functionalised pyrimidine, for example wherein the leaving groups $LG_7$ and $LG_8$ are both halogen atoms, such as chlorine (Scheme 13). A suitable protective group for this transformation is a carbamate derivative ($P^1$=$CO_2R'$ wherein R' is alkyl such as $C_{1-6}$ alkyl) such as a tert-butyl carbamate ($P^1$=$CO_2{}^tBu$). The displacement reaction is conveniently carried out in a polar, aprotic solvent such as acetonitrile and in the presence of a base such as DBU, at reduced temperature, such as 0° C. It will be understood that, where employed, the protective group $P^1$ may be removed under standard conditions to reveal the compounds represented by Intermediate E. Alternatively, in some instances, it may be benficial to retain the protective group in one or more subsequent transformations (such as those typified in Scheme 11) and remove the same, later in the synthetic sequence.

It will be evident to those skilled in the art that the use of one or more orthogonal protective groups may be required to protect chemically sensitive groups during the reactions described above, to ensure that the process can be carried out and/or is efficient. Protective groups and the means for their removal are described in "Protective Groups in Organic Synthesis", by Theodora W. Greene and Peter G. M. Wuts, published by John Wiley & Sons Inc; 4th Rev Ed., 2006, ISBN-10: 0471697540.

Novel intermediates as described herein form an aspect of the invention.

Compounds of formula (I) are p38 MAP kinase inhibitors (especially of the alpha subtype) and in one aspect the compounds are useful in the treatment of inflammatory diseases, for example COPD and/or asthma.

Surprisingly, in at least some embodiments, the compounds of formula (I) exhibit a long duration of action and/or persistence of action in comparison to other previously disclosed allosteric p38 MAP kinase inhibitors such as, for example, BIRB796 (Pargellis, C et al., *Nature Struct. Biol.*, 2002, 9(4):268-272).

In one embodiment the compounds of formula (I) exhibit very low inhibitory activity against GSK 3α, for example they have an $IC_{50}$ value against GSK 3α of 1500 nM or greater; such as 2,000, 3,000, 4,000, 5,000, 6,000, 7,000, 8,000, 9,000 or 10,000 nM or greater.

Persistence of action as used herein is related to the dissociation rate or dissociation constant of the compound from the target (such as a receptor). A low dissociation rate may lead to persistence.

A low dissociation rate in combination with a high association rate tends to provide potent therapeutic entities.

The compounds of formula (I) are expected to be potent in vivo.

Typically, the prior art compounds developed to date have been intended for oral administration. This strategy involves optimizing the pharmacokinetic profile of drug substances in order to achieve an adequate duration of action. In this manner a sufficiently high drug concentration is established and maintained between doses to provide sustained clinical benefit. The inevitable consequence of this approach is that all bodily tissues, and especially the liver and the gut, are likely to be exposed to supra-therapeutically active concentrations of the drug, whether or not they are adversely affected by the disease being treated.

An alternative strategy is to design treatment paradigms in which the drug is dosed directly to the inflamed organ, that is, to exploit topical administration. Whilst this approach is not suitable for treating all chronic inflammatory diseases, it has been exploited in lung disorders, such as asthma and COPD; in skin diseases, for example against atopic dermatitis and psoriasis; for nasal conditions, typified by allergic rhinitis; and in gastrointestinal diseases, such as ulcerative colitis and Crohn's disease and inflammatory diseases of the eye, such as uveitis.

In topical therapy, one way in which efficacy can be achieved is by the use of a drug that has a sustained duration of action and is retained in the relevant organ, thereby minimizing the risk of systemic toxicity. Alternatively, in some cases, a formulation can be developed that generates a "reservoir" of the active drug which is available to sustain its desired effects. The first approach is exemplified by the anticholinergic drug tiotropium (Spiriva). This compound is administered topically to the lung as a treatment for COPD, and has an exceptionally high affinity for its target receptor resulting in a very slow off rate and consequently displays a sustained duration of action.

In one aspect of the disclosure the compounds of formula (I) is particularly suitable for topical delivery, such as topical delivery to the lungs, in particular for the treatment of respiratory disease, for example chronic respiratory diseases such as COPD and/or asthma.

In one embodiment the compounds of formula (I) is suitable for sensitizing patients to treatment with a corticosteroid who have become refractory to such treatment regimens.

The compounds of formula (I) may have antiviral properties, for example the ability to prevent the infection of cells (such as respiratory epithelial cells) with a picornavirus, in particular a rhinovirus, influenza or respiratory synctial virus.

Thus the compound is thought to be an antiviral agent, in particular suitable for the prevention, treatment or amelioration of picornavirus infections, such as rhinovirus infection, influenza or respiratory syncitial virus.

In one embodiment the compounds of formula (I) are able to reduce inflammation induced by viral infection, such as rhinovirus infection and in particular viral infections that result in the release of cytokines such as IL-8, especially in vivo. This activity may, for example, be tested in vitro employing a rhinovirus induced IL-8 assay as described in the Examples herein.

In one embodiment the compounds of formula (I) are able to reduce ICAM1 expression induced by rhinovirus, especially in vivo. ICAM1 is the receptor mechanism used by so-called major groove rhinovirus serotypes to infect cells. This activity may be measured, for example by a method described in the Examples herein.

It is expected that the above properties render the compounds of formula (I) particularly suitable for use in the treatment (including prophylaxis) of exacerbations of inflammatory diseases, in particular viral exacerbations, or in the treatment of viral infections, in patients with one or more chronic conditions such as congestive heart failure, COPD, asthma, diabetes, cancer and/or in immunosuppressed patients, for example post-organ transplant.

Such use may be in combination with anti-viral agents such as zanamivir, oseltamivir (for example oseltamivir phosphate) peramivir or laninamivir.

In general, the compounds of formula (I) may be useful in the treatment of one or more conditions having an inflammatory component which, suitably, may be treated by topical or local therapy.

In particular, the compounds of formula (I) may be useful in the treatment of one or more respiratory disorders including COPD (including chronic bronchitis and emphysema), asthma, paediatric asthma, cystic fibrosis, sarcoidosis, idiopathic pulmonary fibrosis, allergic rhinitis, rhinitis and sinusitis, especially asthma, or COPD (including chronic bronchitis and emphysema).

The compounds of formula (I) may be useful in the treatment of eye diseases or disorders including allergic conjunctivitis, conjunctivitis, diabetic retinopathy, macular oedema (including wet macular oedema and dry macular oedema), post-operative cataract inflammation or, particularly, uveitis (including posterior, anterior and pan uveitis).

The compounds of formula (I) may be useful in the treatment of skin diseases or disorders including allergic dermatitis, contact dermatitis, atopic dermatitis or psoriasis.

The compounds of formula (I) may be useful in the treatment of gastrointestinal diseases or disorders including ulcerative colitis or Crohn's disease.

The compounds of formula (I) may be useful in the treatment of joint diseases or disorders including rheumatoid arthritis or osteoarthritis and particularly inflamed joints secondary to such conditions.

The compounds of formula (I) may be useful in the treatment of cancers including cancer of the stomach and in the inhibition of the growth and metastasis of tumours including non-small cell lung carcinoma, gastric carcinoma, colorectal carcinomas and malignant melanoma.

It is also expected that the compounds of formula (I) may be useful in the treatment of certain other conditions including periodontitis, gingivitis and pharyngitis.

Compounds of formula (I) may also re-sensitise the patient's condition to treatment with a corticosteroid, when the patient's condition has become refractory to the same.

Furthermore, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

The present invention also provides a process for preparing such a pharmaceutical composition (for example a pharmaceutical composition for parenteral, oral, topical, mucosal or rectal administration) which comprising mixing the ingredients.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably a compound of formula (I) is administered topically to the lung, eye or bowel. Hence we provide according to the invention a pharmaceutical composition comprising a compound of the disclosure optionally in combination with one or more topically acceptable diluents or carriers.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoro methane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean aerodynamic diameter (MMAD) of 1-10 μm. The formulation will typically contain a topically acceptable diluent such as lactose, usually of large particle size e.g. an MMAD of 100 μm or more. Examples of dry powder delivery systems include SPINHALER, DISKHALER, TURBOHALER, DISKUS and CLICKHALER.

The compounds of the present invention (i.e. compounds of formula (I), (IA), (IB), (IC), (ID), (IE), (IF), (IG), (IH), (IJ), (IK), (IL), (IM), (IN), (IP) and (IQ) as defined above, or pharmaceutically acceptable salts thereof) may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

A compound of formula (I) has therapeutic activity. In a further aspect, the present invention provides a compound of the disclosure for use as a medicament. Thus, in a further aspect, the present invention provides a compound as described herein for use in the treatment of one or more of the above mentioned conditions.

In one embodiment a dry powder formulation according the present disclosure comprises magnesium or calcium stearate. Such formulations may have superior chemical and/or physical stability especially when such formulations also contain lactose.

In a further aspect, the present invention provides use of a compound as described herein for the manufacture of a medicament for the treatment of one or more of the above mentioned conditions.

In a further aspect, the present invention provides a method of treatment of one or more of the above mentioned conditions which comprises administering to a subject an effective amount of a compound of the disclosure or a pharmaceutical composition comprising the compound.

The word "treatment" is intended to embrace prophylaxis as well as therapeutic treatment. Treatment of conditions or disorders also embraces treatment of exacerbations thereof.

A compound of the disclosure may also be administered in combination with one or more other active ingredients e.g. active ingredients suitable for treating the above mentioned conditions.

For example, possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol), xanthines (e.g. theophylline), anticholinergics (e.g. ipratropium or tiotropium, for example as the bromide) and antiviral agents (e.g. zanamivir, oseltamivir, for example as the phosphate, peramivir and laninamivir).

Further, for the treatment of gastrointestinal disorders (such as Crohn's disease or ulcerative colitis), possible combinations include combinations with, for example, one or more agents selected from the list comprising:

5-aminosalicylic acid, or a prodrug thereof (such as sulfasalazine, olsalazine or bisalazide);
corticosteroids (e.g. prednisolone, methylprednisolone, or budesonide);
immunosuppressants (e.g. cyclosporin, tacrolimus, methotrexate, azathioprine or 6-mercaptopurine);
anti-TNFα antibodies (e.g., infliximab, adalimumab, certolizumab pegol or golimumab);
anti-IL12/IL23 antibodies (e.g., ustekinumab) or small molecule IL12/IL23 inhibitors (e.g., apilimod);
Anti-α4β7 antibodies (e.g., vedolizumab);
MAdCAM-1 blockers (e.g., PF-00547659);
antibodies against the cell adhesion molecule a4-integrin (e.g., natalizumab);
antibodies against the IL2 receptor a subunit (e.g., daclizumab or basiliximab);
JAK3 inhibitors (e.g., tofacitinib or R348);
Syk inhibitors and prodrugs thereof (e.g., fostamatinib and R-406);
Phosphodiesterase-4 inhibitors (e.g., tetomilast);
HMPL-004;
probiotics;
Dersalazine;
semapimod/CPSI-2364; and
protein kinase C inhibitors (e.g. AEB-071).

For the treatment of eye disorders (such as uveitis), possible combinations include combinations with, for example, one or more agents selected from the list comprising:

corticosteroids (e.g. dexamethasone, prednisolone, triamcinolone acetonide, difluprednate or fluocinolone acetonide);

immunosuppressants (e.g. cyclosporin, voclosporin, azathioprine, methotrexate, mycophenolate mofetil or tacrolimus);

anti-TNFα antibodies (e.g., infliximab, adalimumab, certolizumab pegol, ESBA-105 or golimumab);

anti-IL-17A antibodies (e.g., secukinumab);

mTOR inhibitors (e.g., sirolimus);

VGX-1027;

JAK3 inhibitors (e.g., tofacitinib or R348); and protein kinase C inhibitors (e.g. AEB-071).

Hence another aspect of the invention provides a compound of formula (I) in combination with one or more further active ingredients, for example one or more active ingredients described above.

Similarly, another aspect of the invention provides a combination product comprising:

(A) a compound of the present invention (i.e. a compound of formula (I), (IA), (IB), (IC), (ID), (IE), (IF), (IG), (IH), (IJ), (IK), (IL), (IM), (IN), (IP) and (IQ), as defined above, or a pharmaceutically acceptable salt thereof); and (B) another therapeutic agent, wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of the present invention and another therapeutic agent, in admixture with a pharmaceutically acceptable adjuvant, diluent or carrier (which formulation is hereinafter referred to as a "combined preparation").

It also encompasses a kit of parts comprising components:

(i) a pharmaceutical formulation including a compound of the present invention in admixture with a pharmaceutically acceptable adjuvant, diluent or carrier; and (ii) a pharmaceutical formulation including another therapeutic agent, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

The other therapeutic agent (i.e. component (B) above) may be, for example, any of the agents mentioned above in connection with the treatment of respiratory, gastrointestinal and eye disorders.

The combination product (either a combined preparation or kit-of-parts) of this aspect of the invention may be used in the treatment or prevention of an inflammatory disease (e.g. the inflammatory diseases mentioned above, such as:

respiratory disorders including COPD (including chronic bronchitis and emphysema), asthma, paediatric asthma, cystic fibrosis, sarcoidosis, idiopathic pulmonary fibrosis, allergic rhinitis, rhinitis and sinusitis, especially asthma, or COPD (including chronic bronchitis and emphysema);

eye diseases or disorders including allergic conjunctivitis, conjunctivitis, diabetic retinopathy, macular oedema (including wet macular oedema and dry macular oedema), post-operative cataract inflammation or, particularly, uveitis (including posterior, anterior and pan uveitis);

skin diseases or disorders including allergic dermatitis, contact dermatitis, atopic dermatitis or psoriasis; and gastrointestinal diseases or disorders including ulcerative colitis or Crohn's disease.

EXPERIMENTAL SECTION

Abbreviations used herein are defined below (Table 1). Any abbreviations not defined are intended to convey their generally accepted meaning.

TABLE 1

| | Abbreviations |
|---|---|
| AcOH | glacial acetic acid |
| aq | aqueous |
| ATP | adenosine-5'-triphosphate |
| BALF | bronchoalveolae lavage fluid |
| br | broad |
| BSA | bovine serum albumin |
| CatCart ® | catalytic cartridge |
| CDI | 1,1-carbonyl-diimidazole |
| COPD | chronic obstructive pulmonary disease |
| c-Src | cellular sarc(oma) kinase |
| d | doublet |
| DCM | dichloromethane |
| DMEM | Dulbecco's Modified Eagle Medium |
| DMSO | dimethyl sulfoxide |
| DSS | dextran sodium sulphate |
| d-U937 cells | PMA differentiated U-937 cells |
| (ES+) | electrospray ionization, positive mode |
| Et | ethyl |
| EtOAc | ethyl acetate |
| FCS | foetal calf serum |
| FRET | fluorescence resonance energy transfer |
| GR | glucocorticoid receptor |
| GSK3α | glycogen synthase kinase 3α |
| HBEC | primary human bronchial epithelial cells |
| hr | hour(s) |
| HRP | horseradish peroxidise |
| HRV | human rhinovirus |
| IBD | inflammatory bowel disease |
| ICAM-1 | inter-cellular adhesion molecule 1 |
| IL-8 | interleukin 8 |
| JNK | c-Jun N-terminal kinase |
| LPS | lipopolysaccharide |
| $(M + H)^+$ | protonated molecular ion |
| MAPK | mitogen protein activated protein kinase |
| MAPKAP-K2 | mitogen-activated protein kinase-activated protein kinase-2 |
| Me | methyl |
| MeCN | acetonitrile |
| MeOH | methanol |
| MHz | megahertz |
| MMAD | mass median aerodynamic diameter |
| MOI | multiplicity of infection |
| min | minute(s) |
| MPO | myeloperoxidase |
| MTT | 3-(4,5-dimethylthiazol-2-yl)-2,5-diphenyltetrazolium bromide |
| m/z: | mass-to-charge ratio |
| NMR | nuclear magnetic resonance (spectroscopy) |
| PBMC | peripheral blood mononuclear cell |
| PBS | phosphate buffered saline |
| Ph | phenyl |
| PHA | phytohaemagglutinin |
| PMA | phorbol myristate acetate |
| pTSA | 4-methylbenzenesulfonic acid |
| q | quartet |
| RT | room temperature |
| RP HPLC | reverse phase high performance liquid chromatography |
| RSV | respiratory syncytial virus |
| s | singlet |
| sat | saturated |

TABLE 1-continued

Abbreviations

| | |
|---|---|
| SCX | solid supported cation exchange (resin) |
| SDS | sodium dodecyl sulphate |
| $S_NAr$ | nucleophilic aromatic substitution |
| Syk | spleen tyrosine kinase |
| t | triplet |
| TBDMS | tert-butyldimethylsilyl |
| $TCID_{50}$ | 50% tissue culture infectious dose |
| THF | tetrahydrofuran |
| TMB | 3,3',5,5'-tetramethylbenzidine |
| TNBS | 2,4,6-trinitrobenzenesulfonic acid |
| TNFα | tumor necrosis factor alpha |
| WB | washing buffer |

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 µm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Preparative Reverse Phase High Performance Liquid Chromatography

Agilent Scalar column C18, 5 µm (21.2×50 mm), flow rate 28 mL $min^{-1}$ eluting with a $H_2O$-MeCN gradient containing 0.1% v/v formic acid over 10 min using UV detection at 215 and 254 nm. Gradient information: 0.0-0.5 min; 95% $H_2O$-5% MeCN; 0.5-7.0 min; ramped from 95% $H_2O$-5% MeCN to 5% $H_2O$-95% MeCN; 7.0-7.9 min; held at 5% $H_2O$-95% MeCN; 7.9-8.0 min; returned to 95% $H_2O$-5% MeCN; 8.0-10.0 min; held at 95% $H_2O$-5% MeCN.

Analytical Methods

Reverse Phase High Performance Liquid Chromatography

Method 1: Agilent Scalar column C18, 5 µm (4.6×50 mm) or Waters XBridge C18, 5 µm (4.6×50 mm) flow rate 2.5 mL $min^{-1}$ eluted with a $H_2O$-MeCN gradient containing either 0.1% v/v formic acid (Method 1 acidic) or $NH_3$ (Method 1 basic) over 7 min employing UV detection at 215 and 254 nm. Gradient information: 0.0-0.1 min, 95% $H_2O$-5% MeCN; 0.1-5.0 min, ramped from 95% $H_2O$-5% MeCN to 5% $H_2O$-95% MeCN; 5.0-5.5 min, held at 5% $H_2O$-95% MeCN; 5.5-5.6 min, held at 5% $H_2O$-95% MeCN, flow rate increased to 3.5 mL $min^{-1}$; 5.6-6.6 min, held at 5% $H_2O$-95% MeCN, flow rate 3.5 mL $min^{-1}$; 6.6-6.75 min, returned to 95% $H_2O$-5% MeCN, flow rate 3.5 mL $min^{-1}$; 6.75-6.9 min, held at 95% $H_2O$-5% MeCN, flow rate 3.5 mL·$min^{-1}$; 6.9-7.0 min, held at 95% $H_2O$-5% MeCN, flow rate reduced to 2.5 mL $min^{-1}$.

Method 2: Agilent Extend C18 column, 1.8 µm (4.6×30 mm) at 40° C.; flow rate 2.5-4.5 mL $min^{-1}$ eluted with a $H_2O$-MeCN gradient containing 0.1% v/v formic acid over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL $min^{-1}$; 3.01 3.50 min, held at 5% $H_2O$-95% MeCN; 3.50-3.60 min, returned to 95% $H_2O$-5% MeCN, flow rate reduced to 3.50 mL $min^{-1}$; 3.60-3.90 min, held at 95% $H_2O$-5% MeCN; 3.90-4.00 min, held at 95% $H_2O$-5% MeCN, flow rate reduced to 2.5 mL $min^{-1}$.

Method 3: Waters Xselect CSH C18 3.5 µm (4.6×50 mm) flow rate 2.5 mL $min^{-1}$ eluted with a $H_2O$-MeCN gradient containing 0.1% v/v formic acid over 7 min employing UV detection at 215 and 254 nm. Gradient information: 0.0-0.1 min, 95% $H_2O$-5% MeCN; 0.1-5.0 min, ramped from 95% $H_2O$-5% MeCN to 5% $H_2O$-95% MeCN; 5.0-5.5 min, held at 5% $H_2O$-95% MeCN; 5.5-5.6 min, held at 5% $H_2O$-95% MeCN, flow rate increased to 3.5 mL $min^{-1}$; 5.6-6.6 min, held at 5% $H_2O$-95% MeCN, flow rate 3.5 mL $min^{-1}$; 6.6-6.75 min, returned to 95% $H_2O$-5% MeCN, flow rate 3.5 mL $min^{-1}$; 6.75-6.9 min, held at 95% $H_2O$-5% MeCN, flow rate 3.5 mL·$min^{-1}$; 6.9-7.0 min, held at 95% $H_2O$-5% MeCN, flow rate reduced to 2.5 mL $min^{-1}$.

$^1H$ NMR Spectroscopy $^1H$ NMR spectra were acquired on a Bruker Avance III spectrometer at 400 MHz using residual undeuterated solvent as reference and unless specified otherwise were run in DMSO-$d_6$.

Those intermediates, used to prepare compound examples of the invention, that have been previously disclosed were obtained using the procedures contained in the references cited below (Table 2). Additional intermediates were prepared by the synthetic processes described herein.

TABLE 2

Compound Intermediates

| No. | Structure | Name, LCMS Data and Reference |
|---|---|---|
| A1 | $^tBu$ pyrazole with p-tolyl and $NH_2$ | 3-tert-butyl-1-p-tolyl-1H-pyrazol-5-amine. $R^t$ 2.46 min (Method 1 basic); m/z 230 $(M + H)^+$, $(ES^+)$. Cirillo, P. F. et al., WO 2000/43384, 27 Jul. 2000. |

TABLE 2-continued

Compound Intermediates

| No. | Structure | Name, LCMS Data and Reference |
|---|---|---|
| A2 | 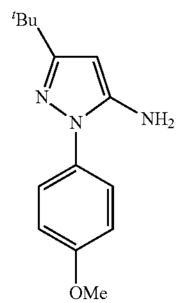 [SMILES: COc1ccc(-n2nc(C(C)(C)C)cc2N)cc1] | 3-tert-butyl-1-(4-methoxyphenyl)-1H-pyrazol-5-amine.<br>$R^t$ 1.32 min (Method 2); m/z 246 (M + H)$^+$, (ES$^+$).<br>Mathias, J. P. et al., US 2006/0035922, 10 Aug. 2005. |
| A3 | 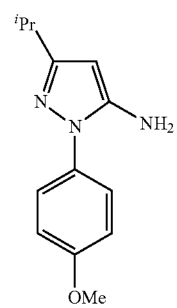 [SMILES: COc1ccc(-n2nc(C(C)C)cc2N)cc1] | 3-isopropyl-1-(4-methoxyphenyl)-1H-pyrazol-5-amine.<br>$R^t$ 1.10 min (Method 2); m/z 232 (M + H)$^+$, (ES$^+$).<br>Abraham, S. et al., WO 2009/117080, 24 Sep. 2009 |
| A4 | 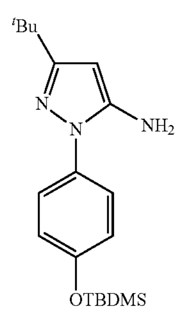 [SMILES: CC(C)(C)c1cc(N)n(-c2ccc(O[Si](C)(C)C(C)(C)C)cc2)n1] | 3-tert-butyl-1-(4-(tert-butyldimethylsilyloxy)phenyl)-1H-pyrazol-5-amine.<br>$R^t$ 2.80 min (Method 2); m/z 346 (M + H)$^+$, (ES$^+$).<br>Mathias, J. P. et al., US 2006/0035922, 10 Aug. 2005. |
| A5 | 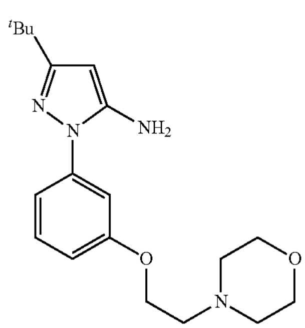 [SMILES: CC(C)(C)c1cc(N)n(-c2cccc(OCCN3CCOCC3)c2)n1] | 3-tert-butyl-1-(3-(2-morpholinoethoxy)phenyl)-1H-pyrazol-5-amine.<br>$R^t$ 1.04 min (Method 2, Acidic); m/z 345 (M + H)$^+$, (ES$^+$).<br>Prepared by analogous procedures to those used for Intermediate A13. |

TABLE 2-continued

Compound Intermediates

| No. | Structure | Name, LCMS Data and Reference |
|---|---|---|
| A6 | 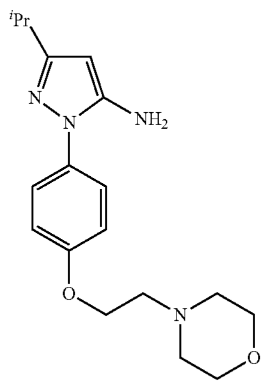 [SMILES: CC(C)c1cc(N)n(-c2ccc(OCCN3CCOCC3)cc2)n1] | 3-isopropyl-1-(4-(2-morpholinoethoxy) phenyl)-1H-pyrazol-5-amine. R$^t$ 1.60 min (Method 2, Basic); m/z 331 (M + H)$^+$, (ES$^+$). Prepared by analogous procedures to those used for Intermediate A7. |
| A7 | 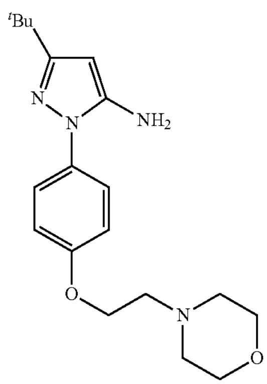 | 3-tert-butyl-1-(4-(2-morpholinoethoxy) phenyl)-1H-pyrazol-5-amine. R$^t$ 0.75 min (Method 2); m/z 345 (M + H)$^+$, (ES$^+$). Finch, H. et al., WO 2010/094956, 26 Aug. 2010. Also prepared by analogous procedures to those used for Intermediate A13. |
| A8 | 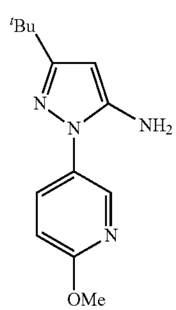 [SMILES: COc1ccc(-n2nc(C(C)(C)C)cc2N)cn1] | 3-tert-butyl-1-(6-methoxypyridin-3-yl)-1H-pyrazol-5-amine. R$^t$ 1.38 min (Method 2); m/z 247 (M + H)$^+$, (ES$^+$). Abraham, S. et al., WO 2009/117080, 24 Sep. 2009. |
| A9 | 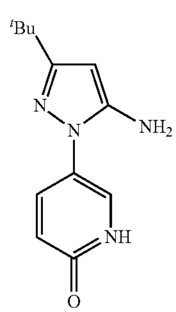 | 5-(5-amino-3-(tert-butyl)-1H-pyrazol-1-yl) pyridin-2-ol. Abraham, S. et al., WO 2009/117080, 24 Sep. 2009. |

TABLE 2-continued

Compound Intermediates

| No. | Structure | Name, LCMS Data and Reference |
|---|---|---|
| A10 | 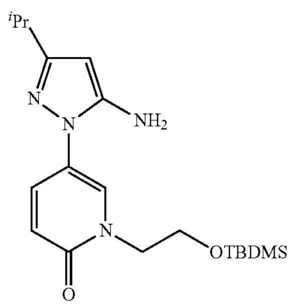 [SMILES: CC(C)c1cc(N)n(-c2ccc(=O)n(CCO[Si](C)(C)C(C)(C)C)c2)n1] | 5-(5-amino-3-isopropyl-1H-pyrazol-1-yl)-1-(2-(tert-butyldimethylsilyloxy)ethyl)pyridin-2(1H)-one.<br>R$^t$ 2.09 min (Method 2, Acidic); m/z 377 (M + H)$^+$, (ES$^+$).<br>Prepared by analogous procedures to those used for Intermediate A11. |
| B1 | 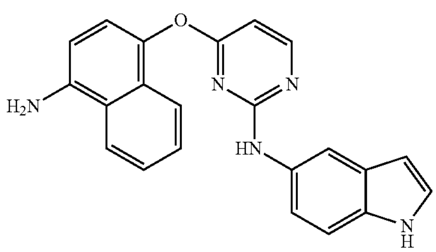 [SMILES: Nc1ccc(Oc2ccnc(Nc3ccc4[nH]ccc4c3)n2)c2ccccc12] | N-(4-((4-aminonaphthalen-1-yl)oxy)pyrimidin-2-yl)-1H-indol-5-amine.<br>R$^t$ 1.63 min (Method 2; acidic); m/z 368 (M + H)$^+$, (ES$^+$).<br>Prepared by analogous procedures to those used for Intermediate B 12. |
| B2 | 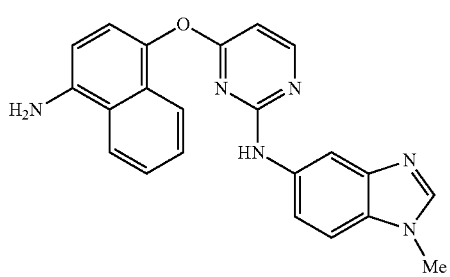 [SMILES: Cn1cnc2cc(Nc3nccc(Oc4ccc(N)c5ccccc45)n3)ccc21] | N-(4-((4-aminonaphthalen-1-yl)oxy)pyrimidin-2-yl)-1-methyl-1H-benzo[d]imidazol-5-amine.<br>R$^t$ 1.31 min (Method 2, acidic); m/z 383 (M + H)$^+$, (ES$^+$).<br>Prepared by analogous procedures to those used for Intermediate B 13. |
| B3 | 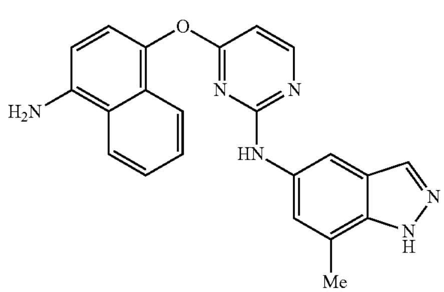 [SMILES: Cc1cc(Nc2nccc(Oc3ccc(N)c4ccccc34)n2)cc2cn[nH]c12] | N-(4-((4-aminonaphthalen-1-yl)oxy)pyrimidin-2-yl)-7-methyl-1H-indazol-5-amine.<br>R$^t$ 1.65 min (Method 2, acidic); m/z 383 (M + H)$^+$, (ES$^+$).<br>Prepared by analogous procedures to those used for Intermediate B 12. |
| B4 | 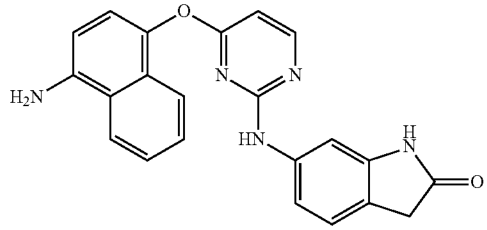 [SMILES: Nc1ccc(Oc2ccnc(Nc3ccc4c(c3)NC(=O)C4)n2)c2ccccc12] | 6-((4-((4-aminonaphthalen-1-yl)oxy)pyrimidin-2-yl)amino)indolin-2-one.<br>R$^t$ 1.65 min (Method 2, acidic); m/z 384 (M + H)$^+$, (ES$^+$).<br>Prepared by analogous procedures to those used for Intermediate B 13. |

TABLE 2-continued

Compound Intermediates

| No. | Structure | Name, LCMS Data and Reference |
|---|---|---|
| B5 | 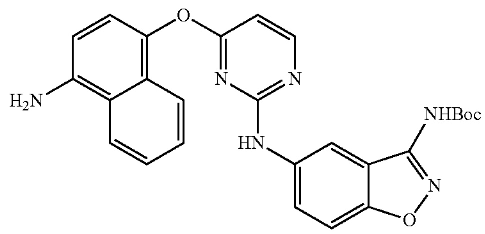 [SMILES: CC(C)(C)OC(=O)Nc1noc2ccc(Nc3nccc(Oc4ccc(N)c5ccccc45)n3)cc12] | tert-butyl (5-((4-((4-aminonaphthalen-1-yl)oxy)pyrimidin-2-yl)amino)benzo[d]isoxazol-3-yl)carbamate.<br>R$^t$ 2.11 min (Method 2, acidic); m/z 485 (M + H)$^+$, (ES$^+$).<br>Prepared by analogous procedures to those used for Intermediate B 12. |
| B6 | 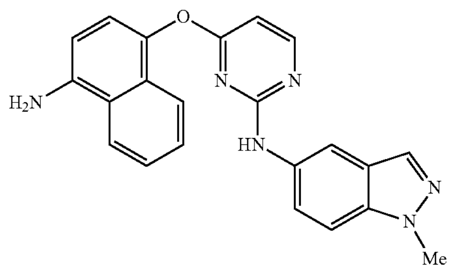 [SMILES: Cn1ncc2cc(Nc3nccc(Oc4ccc(N)c5ccccc45)n3)ccc21] | N-(4-((4-aminonaphthalen-1-yl)oxy)pyrimidin-2-yl)-1-methyl-1H-indazol-5-amine.<br>R$^t$ 1.74 min (Method 2, acidic); m/z 383 (M + H)$^+$, (ES$^+$).<br>Prepared by analogous procedures to those used for Intermediate B 12. |
| B7 | 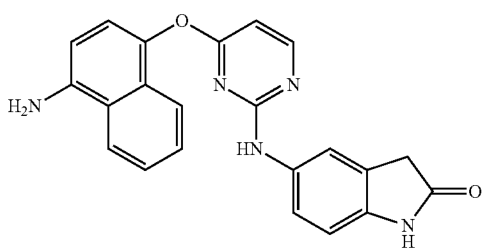 [SMILES: Nc1ccc(Oc2ccnc(Nc3ccc4c(c3)CC(=O)N4)n2)c2ccccc12] | 5-((4-((4-aminonaphthalen-1-yl)oxy)pyrimidin-2-yl)amino)indolin-2-one.<br>R$^t$ 1.53 min (Method 2, acidic); m/z 384 (M + H)$^+$, (ES$^+$).<br>Prepared by analogous procedures to those used for Intermediate B 12. |
| B8 | 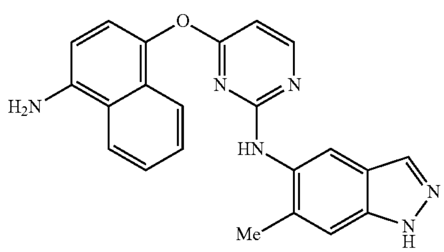 [SMILES: Cc1cc2[nH]ncc2cc1Nc1nccc(Oc2ccc(N)c3ccccc23)n1] | N-(4-((4-aminonaphthalen-1-yl)oxy)pyrimidin-2-yl)-6-methyl-1H-indazol-5-amine.<br>R$^t$ 1.56 min (Method 2, acidic); m/z 383 (M + H)$^+$, (ES$^+$).<br>Prepared by analogous procedures to those used for Intermediate B 12. |
| B9 | 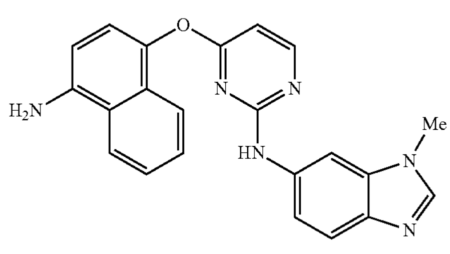 [SMILES: Cn1cnc2ccc(Nc3nccc(Oc4ccc(N)c5ccccc45)n3)cc21] | N-(4-((4-aminonaphthalen-1-yl)oxy)pyrimidin-2-yl)-1-methyl-1H-benzo[d]imidazol-6-amine.<br>R$^t$ 1.32 min (Method 2, acidic); m/z 383 (M + H)$^+$, (ES$^+$).<br>Prepared by analogous procedures to those used for Intermediate B 13. |
| E1 | 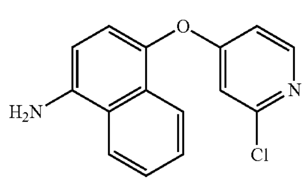 [SMILES: Nc1ccc(Oc2ccnc(Cl)c2)c2ccccc12] | 4-((2-chloropyridin-4-yl)oxy)naphthalen-1-amine.<br>R$^t$ 3.13 min (Method 3); m/z 271/273 (M + H)$^+$, (ES$^+$).<br>Ito, K. et al., WO 2010/112936, 07 Oct. 2010 |

| No. | Structure | Name, LCMS Data and Reference |
|---|---|---|
| E2 | 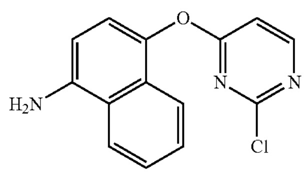 [SMILES: Nc1ccc(Oc2ccnc(Cl)n2)c2ccccc12] | 4-((2-chloropyrimidin-4-yl)oxy)naphthalen-1-amine. $R^t$ 1.80 min (Method 2); m/z 272/274 $(M + H)^+$, $(ES^+)$. Cirillo, P. F. et al., WO 2002/92576, 21 Nov. 2000. |

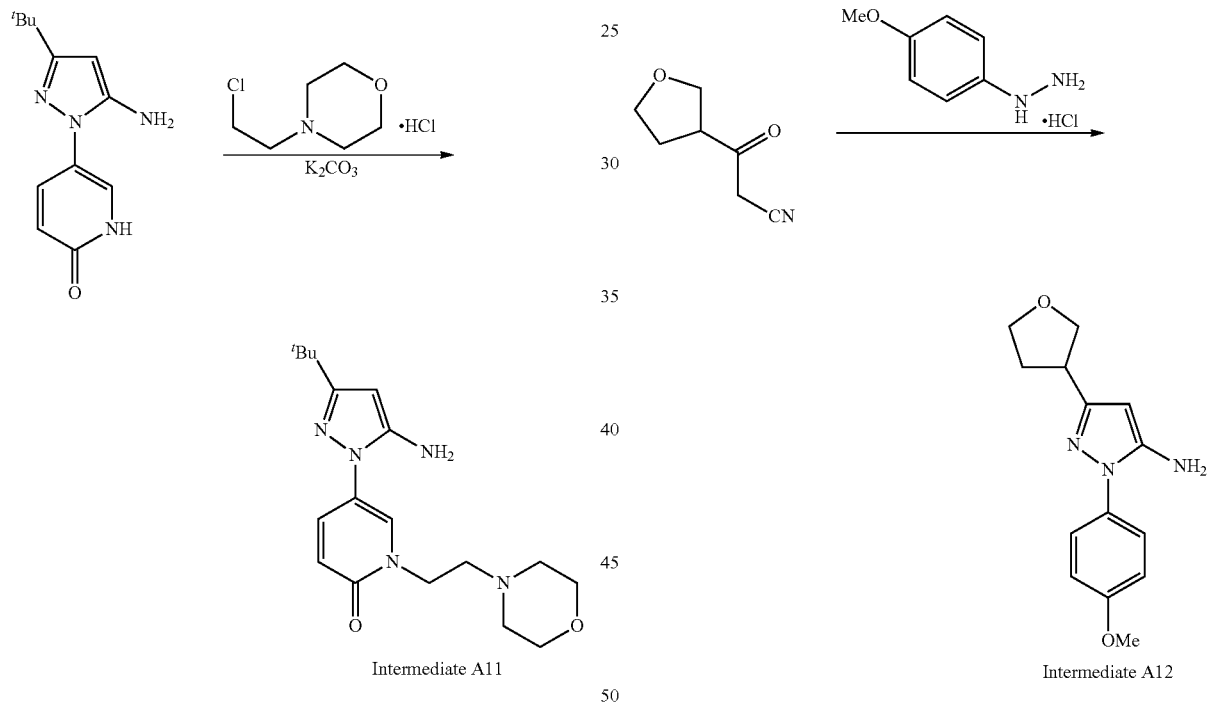

Intermediate A11

5-(5-Amino-3-tert-butyl-1H-pyrazol-1-yl)-1-(2-morpholinoethyl)pyridin-2(1H)-one

Intermediate A12

1-(4-Methoxyphenyl)-3-(tetrahydrofuran-3-yl)-1H-pyrazol-5-amine

To a solution of 5-(5-amino-3-(tert-butyl)-1H-pyrazol-1-yl)pyridin-2-ol (Abraham, S. et al., WO 2009/117080, 24 Sep. 2009) (4.04 g, 17.4 mmol) in MeCN (50 mL) was added 4-(2-chloroethyl)morpholine hydrochloride (3.88 g, 20.9 mmol) and $K_2CO_3$ (5.29 g, 38.3 mmol)

The mixture was heated to reflux for 16 hr and then diluted with DMF (50 mL) and heated to 120° C. for a further 4 hr. The reaction mixture was cooled to RT and partitioned between EtOAc (150 mL) and water (150 mL). The aq phase was extracted with EtOAc (150 mL) and the organic extracts were combined, washed with water (2×50 mL), dried and concentrated in vacuo, during which process a precipitate formed. The solid was collected by filtration to afford the title compound, Intermediate A11, as a yellow crystalline solid; $R^t$ 0.95 min (Method 2, Acidic); m/z 346 $(M+H)^+$, $(ES^+)$.

To a solution of 3-oxo-3-(tetrahydrofuran-3-yl)propanenitrile (718 mg, 4.64 mmol) in EtOH (20 mL) was added conc. hydrochloric acid (0.387 mL, 4.64 mmol) and (4-methoxyphenyl)hydrazine hydrochloride (737 mg, 4.22 mmol). The reaction mixture was heated to 80° C. for 4 hr and was then cooled to RT and adjusted to pH8 by the addition of aq NaOH (2M, <5 mL). The resulting mixture was partitioned between water (20 mL) and $Et_2O$ (25 mL) and the aq layer was separated and extracted with ether (25 mL). The combined organic extracts were dried and evaporated in vacuo and the residue was purified by flash column chromatography ($SiO_2$, 40 g, 0-5% MeOH in DCM, gradient elution) to afford the title compound, Intermediate A12, as a pale orange solid (503 mg, 45%); $R^t$ 1.04 min (Method 2); m/z 260 $(M+H)^+$, $(ES^+)$.

Intermediate A13

3-Isopropyl-1-(3-(2-morpholinoethoxy)phenyl)-1H-pyrazol-5-amine

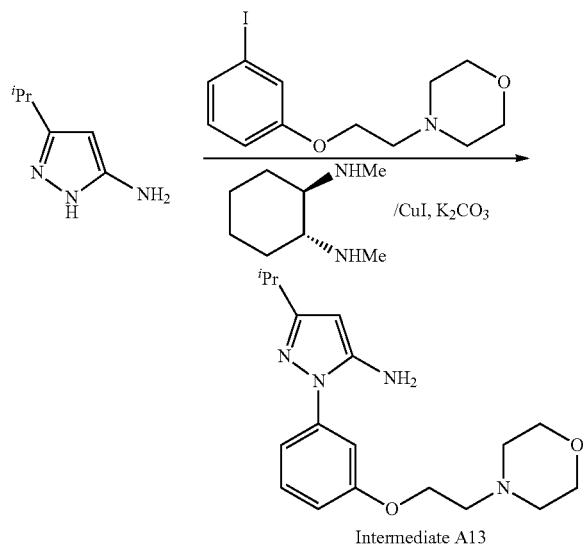

Intermediate A13

To a solution of 4-(2-(3-iodophenoxy)ethyl)morpholine (1.0 g, 2.9 mmol) in anhydrous toluene (20 mL) was added 3-isopropyl-1H-pyrazol-5-amine (397 mg, 3.17 mmol) followed by (1R,2R)—$N^1,N^2$-dimethylcyclohexane-1,2-diamine (227 μL, 1.44 mmol) and potassium carbonate (1.99 g, 14.4 mmol). The mixture was purged with $N_2$, copper(I) iodide (82 mg, 0.43 mmol) was added and the reaction mixture was heated at reflux under $N_2$ for 64 hr. The resulting mixture was cooled to RT and was partitioned between EtOAc and water (100 mL). The organic layer was separated and washed with brine (2×100 mL) and was then dried and evaporated in vacuo. The residue was purified by flash column chromatography ($SiO_2$, 40 g, 0-20% MeOH in DCM, gradient elution) to afford the title compound, Intermediate A13, as a brown oil (325 mg, 33%); $R^t$ 1.66 min (Method 2, basic); m/z 329 $(M+H)^+$ $(ES^+)$.

Intermediate A14

3-(tert-Butyl)-1-(6-(2-morpholinoethoxy)pyridin-3-yl)-1H-pyrazol-5-amine

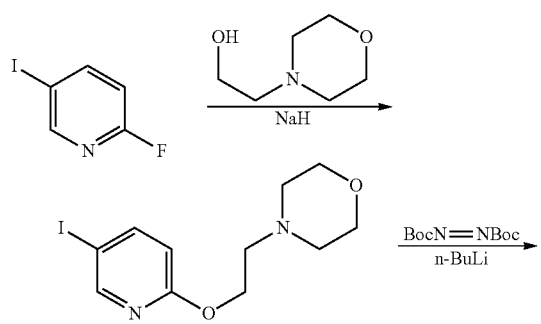

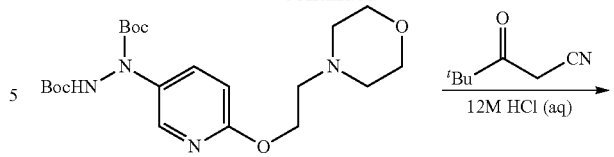

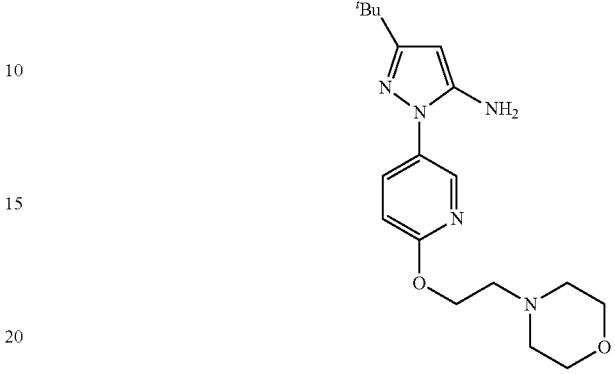

Intermediate A14

To a suspension of sodium hydride (2.15 g, 60% dispersion in mineral oil, 54.0 mmol) in THF (100 mL) at 0° C. was added 2-morpholinoethanol (5.43 mL, 44.8 mL). After 30 min 2-fluoro-5-iodopyridine (10.0 g, 44.8 mmol) was added and the reaction mixture was heated to 60° C. for 16 hr and was then cooled and diluted with water (75 mL). The resulting mixture was extracted with EtOAc (2×75 mL) and the combined organic extracts were dried and evaporated in vacuo and the residue was purified by flash column chromatography ($SiO_2$, 120 g, 20-60% EtOAc in isohexane, gradient elution) to afford 4-(2-(5-iodopyridin-2-yloxy)ethyl)morpholine as a yellow oil (9.35 g, 60%); $R^t$ 0.94 min (Method 2, acidic); m/z 335 $(M+H)^+$, $(ES^+)$.

To a solution of the aryl ether, obtained above, (8.78 g, 26.3 mmol) in anhydrous THF (10 mL) at −78° C. and under nitrogen was added, drop-wise, a solution of n-butyllithium (1.1 M in hexanes, 26.0 mL, 29.0 mmol). The mixture was maintained at −78° C. for 10 min and was then treated portion-wise over 15 min with (E)-di-tert-butyl diazene-1,2-dicarboxylate (6.66 g, 28.9 mmol). The reaction mixture was warmed to RT and after 3 days was diluted with saturated aq. $NH_4Cl$ and extracted with EtOAc (2×100 mL). The combined organic extracts were dried, and evaporated in vacuo to afford di-tert-butyl 1-(6-(2-morpholinoethoxy)pyridin-3-yl)hydrazine-1,2-dicarboxylate as an orange oil (11.75 g, 61% purity by HPLC, 62%); $R^t$ 1.28 min (Method 2, acidic, 61% pure); m/z 439 $(M+H)^+$, $(ES^+)$.

The compound was used in the subsequent step without purification.

To a stirred solution of the hydrazine di-tert-butylcarboxylate, obtained above (11.75 g, 61% pure, 16.34 mmol) and 4,4-dimethyl-3-oxopentanenitrile (2.25 g, 18.0 mmol) in EtOH (150 mL) was added 12 M hydrochloric acid (16.0 mL, 192 mmol). The reaction mixture was heated at reflux for 16 hr and was then cooled to RT and diluted with saturated aq. $NaHCO_3$ (100 mL). The mixture was extracted with DCM (2×75 mL) and the combined organic layers were dried and evaporated in vacuo. The residue was purified by flash column chromatography ($SiO_2$, 330 g, 0-10% MeOH in DCM, gradient elution) to afford the title compound, Intermediate A14, as an orange solid (3.78 g, 64%); R$^t$ 0.99 min (Method 2, acidic); m/z 346 (M+H)$^+$, (ES$^+$).

Intermediate A15

5-(5-Amino-3-(tert-butyl)-1H-pyrazol-1-yl)-1-(2-((tert-butyldimethylsilyl)oxy)ethyl)pyridin-2(1H)-one

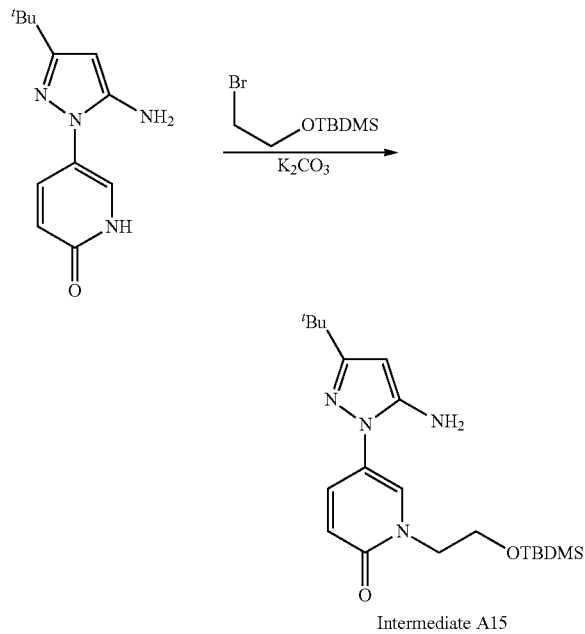

Intermediate A15

To a solution of 5-(5-amino-3-(tert-butyl)-1H-pyrazol-1-yl)pyridin-2-ol (1.10 g, 4.74 mmol) in MeCN (10.0 mL) was added (2-bromoethoxy)(tert-butyl)dimethylsilane (1.28 mL, 5.68 mmol) and K$_2$CO$_3$ (0.785 g, 5.68 mmol) and the mixture heated to reflux for 6 hr. The resulting mixture was cooled and was loaded directly onto silica and purified by flash column chromatography (SiO$_2$, 40 g, 0-100% EtOAc in isohexane, gradient elution) to afford the title compound, Intermediate A15, as a pale yellow solid (1.11 g, 60%); R$^t$ 2.61 min (Method 2, acidic); m/z 391 (M+H)$^+$, (ES$^+$).

Intermediate A16

1-(3-(5-amino-3-(tert-butyl)-1H-pyrazol-1-yl)benzyl)pyrrolidin-2-one

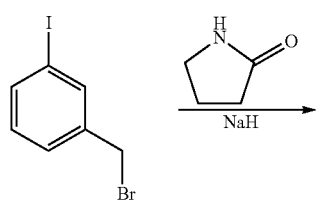

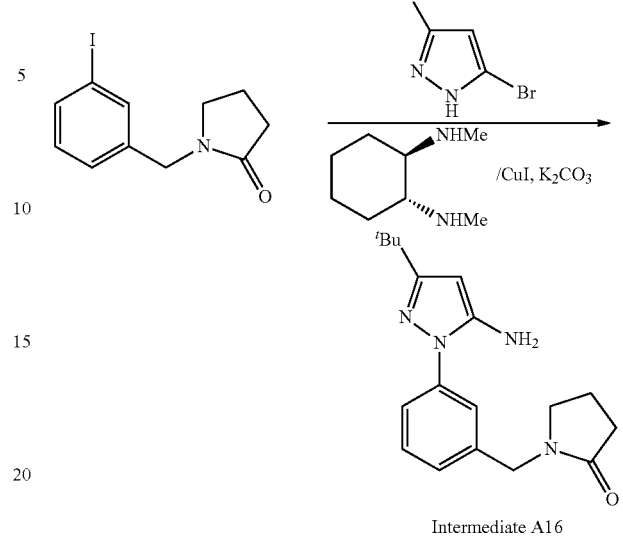

Intermediate A16

To a stirred solution of pyrrolidin-2-one (1.55 mL, 20.2 mmol) in DMF (25 mL) at 0° C. under N$_2$ was added NaH (60% dispersion in mineral oil, 808 mg, 20.2 mmol) portionwise over 10 min. The reaction mixture was maintained at 0° C. for 30 min and was then treated with 1-(bromomethyl)-3-iodobenzene (5.00 g, 17.0 mmol) over 10 min and afterwards was warmed to RT for 2 hr. The resulting mixture was diluted with water (100 mL) and extracted with DCM (2×100 mL). The combined organic extracts were washed with water (100 mL) and with brine (100 mL) and evaporated in vacuo to afford 1-(3-iodobenzyl)pyrrolidin-2-one as a yellow oil (5.49 g, 100%); R$^t$ 1.85 min (Method 2, acidic); m/z 302 (M+H)$^+$, (ES$^+$).

To a solution of 1-(3-iodobenzyl)pyrrolidin-2-one (5.49 g, 16.8 mmol) in toluene (20 mL) was added N$^1$,N$^2$-dimethylcyclohexane-1,2-diamine (530 μL, 3.40 mmol), 3-(tert-butyl)-1H-pyrazol-5-amine (2.57 g, 18.5 mmol), potassium carbonate (4.64 g, 33.5 mmol) and copper(I) iodide (160 mg, 0.839 mmol), and the reaction mixture was heated to 110° C. for 3 days. The mixture was cooled to RT and was partitioned between water (50 mL) and EtOAc (100 mL). The organic phase was separated and was washed with water (4×50 mL) and then dried and evaporated in vacuo. The residue was purified by flash column chromatography (SiO$_2$, 120 g, 0-50% EtOAc in isohexane, gradient elution) to afford the title compound, Intermediate A16, as a black gum (1.64 g, 30%); R$^t$ 1.43 min (Method 2, acidic); m/z 313 (M+H)$^+$, (ES$^+$).

Intermediate B10

N-(4-((4-Aminonaphthalen-1-yl)oxy)pyridin-2-yl)-1H-indazol-5-amine

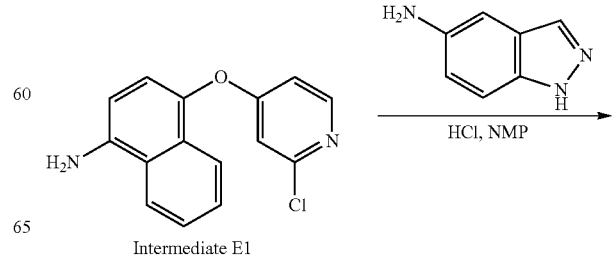

Intermediate E1

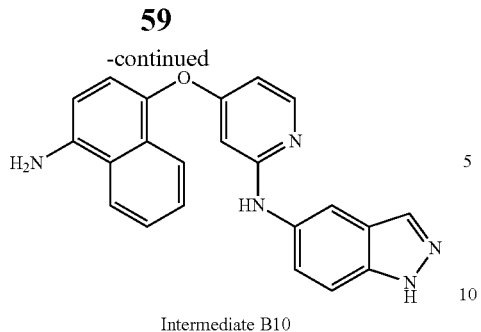

Intermediate B10

To solution of Intermediate E1 (608 mg, 2.25 mmol) and 1H-indazol-5-amine (897 mg, 6.74 mmol) in NMP (5.0 mL) was added a solution of hydrogen chloride in dioxane (4 M, 1.7 mL, 6.8 mmol) and mixture heated to 110° C. in a sealed tube for 7 hr. After cooling to RT for 64 hr.

the mixture was re-heated to 110° C. for 7 hr, kept at RT for 18 hr and finally heated for a third time to 110° C. for an additional 8 hr. The resulting mixture was cooled to RT and was combined with the crude product from a reaction performed in a similar manner on a 0.19 mmol scale. The combined material was subjected to purification by SCX capture and release and the crude product so obtained was purified by flash column chromatography (SiO$_2$, 120 g, 0-100% EtOAc in isohexane, gradient elution) to afford the title compound, Intermediate B10, as a dark pink solid (581 mg, 57%) which contained 12 wt % EtOAc as determined by $^1$H-NMR; R$^t$ 1.93 min (Method 4); m/z 368 (M+H)$^+$, (ES$^+$).

Intermediate B11

N-(4-((4-Aminonaphthalen-1-yl)oxy)pyridin-2-yl)-7-methyl-1H-indazol-5-amine

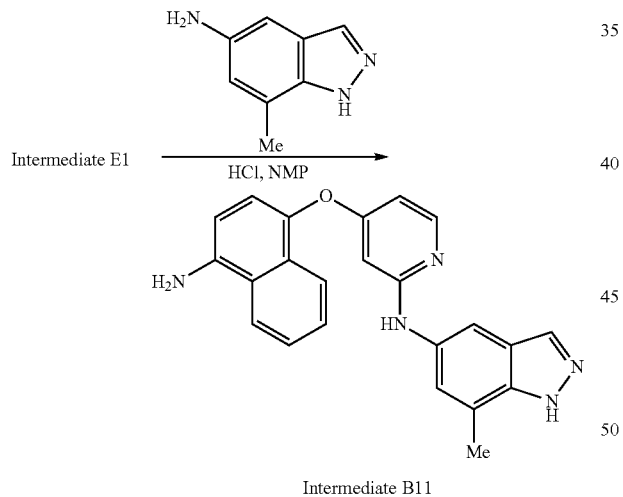

Intermediate B11

To a solution of Intermediate E1 (460 mg, 1.70 mmol) and 7-methyl-1H-indazol-5-amine (250 mg, 1.70 mmol) in NMP (2.5 mL) was added a solution of hydrogen chloride in dioxane (4 M, 430 µL, 1.7 mmol) and the mixture heated to 120° C. in a sealed tube for 18 hr. After cooling to RT the mixture was combined with the crude product from a reaction performed in a similar manner on a 0.34 mmol scale and the combined material was subjected to purification by SCX capture and release. The crude product so obtained was purified by flash column chromatography (SiO$_2$, 120 g, 0-10% [0.7M NH$_3$ in MeOH] in DCM, gradient elution) to afford the title compound, Intermediate B11, as a pale brown solid (342 mg, 43%); R$^t$ 1.92 min (Method 2, basic); m/z 382 (M+H)$^+$, (ES$^+$).

Intermediate B12

N-(4-((4-Aminonaphthalen-1-yl)oxy)pyrimidin-2-yl)-1H-indazol-5-amine

Intermediate E2 $\xrightarrow{\text{pTSA, DMF}}$

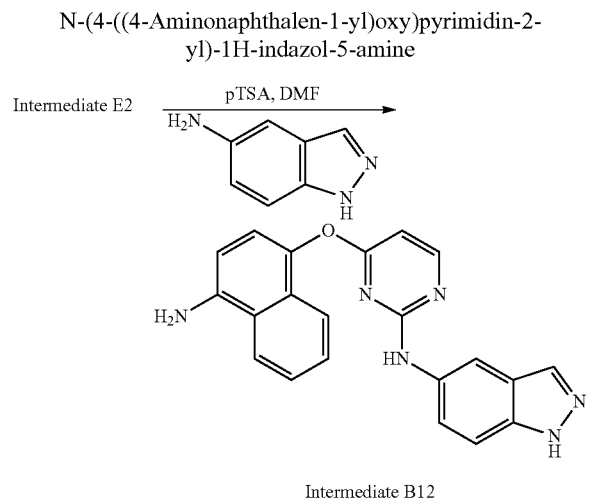

Intermediate B12

A solution of Intermediate E2 (8.00 g, 25.6 mmol), 1H-indazol-5-amine (7.02 g, 52.7 mmol) and p-TSA (10.07 g, 52.9 mmol) in DMF (128 mL) was stirred at 60° C. for 16 hr. The reaction mixture was cooled to RT and was poured onto a mixture of sat. aq. NaHCO$_3$ (200 mL) and EtOAc (200 mL). The layers were separated and the organic extract was washed with water (3×100 mL) and brine (3×100 mL) and then dried and concentrated in vacuo to afford a dark/brown solid. The compound was preloaded onto silica and purified by chromatography (SiO$_2$, 80 g, eluted with 0-100% EtOAc in isohexane, product eluted at 85%) to give the title compound Intermediate B12 as a light brown solid (2.34 g, 6.22 mmol, 24% yield); R$^t$ 1.51 min; m/z 369 (M+H)+(ES+); 1H NMR (400 MHz, DMSO-d6) δ: 5.89 (2H, s), 6.48 (1H, d), 6.79 (1H, d), 7.13 (1H, d), 7.23 (2H, s), 7.35-7.46 (2H, over-lapping m), 7.62-7.66 (2H, over-lapping m), 7.72 (1H, s), 8.20 (1H, m), 8.33 (1H, d), 9.49 (1H, s), 12.72 (1H, s).

Intermediate B13

N-(4-((4-Aminonaphthalen-1-yl)oxy)pyrimidin-2-yl)-1-(tetrahydro-2H-pyran-2-yl)-1H-indazol-5-amine Intermediate E2 $\xrightarrow{\text{Intermediate D1}}_{\text{p-TSA, THF}}$

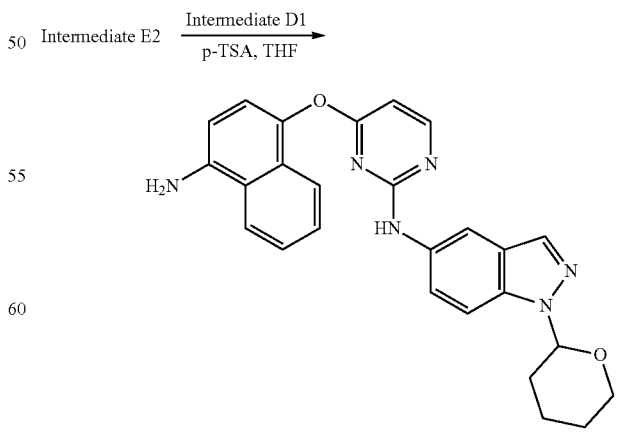

Intermediate B13

To a degassed solution of Intermediate E2 (450 mg, 1.656 mmol) in THF (6.0 mL) was added 1-(tetrahydro-2H-pyran-2-yl)-1H-indazol-5-amine Intermediate D1 (404 mg, 1.822 mmol) and p-TSA (63.0 mg, 0.331 mmol). The resulting mixture was heated to 60° C. for 18 hr, then cooled to RT and partitioned between DCM (50 mL) and sat. aq. NaHCO$_3$ (50 mL). The layers were separated and the organic phase was washed with brine (2×50 mL) and then dried and concentrated in vacuo to afford a dark reddish brown solid. The crude product was purified by column chromatography (40 g SiO$_2$, eluted with 0-30% acetonitrile in DCM, product eluted at 20%) to yield the title compound, Intermediate B13 as a pink solid (314 mg, 0.659 mmol, 40% yield); R$^t$ 2.00 min, m/z 453.0(M+H)$^+$ (ES$^+$); $^1$H NMR (400 MHz, DMSO-d$_6$) δ: 1.53-1.58 (3H, over-lapping m), 1.87-2.03 (2H, over-lapping m), 2.33 (1H, m), 3.67 (1H, m), 3.83 (1H, d), 5.68 (1H, dd), 5.93 (2H, s), 6.51 (1H, d), 6.77 (1H, d), 7.13 (1H, d), 7.25 (1H, d), 7.39-7.43 (3H, over-lapping m), 7.62-7.73 (3H, over-lapping m), 8.20 (1H, m), 8.34 (1H, d), 9.56 (1H, s).

Intermediate B14

N-(6-((4-Aminonaphthalen-1-yl)oxy)pyrimidin-4-yl)-1H-indazol-5-amine

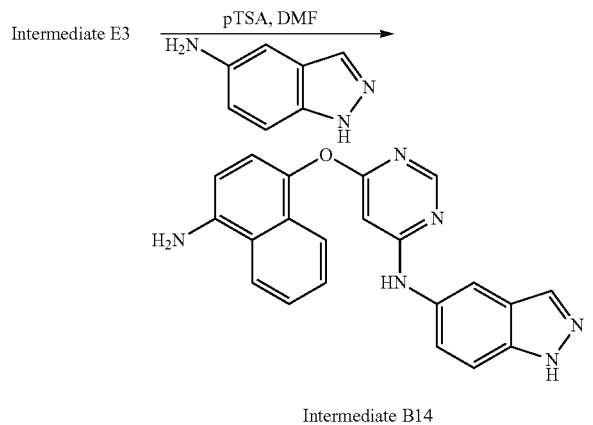

Intermediate B14

A solution of Intermediate E3 (1.50 g, 5.50 mmol), 1H-indazol-5-amine (735 mg, 5.52 mmol) and p-TSA (525 mg, 2.76 mmol) in DMF (14.0 mL) was degassed with nitrogen and was then heated to 60° C. for 16 hr. Additional p-TSA (525 mg, 2.76 mmol) and 1H-indazol-5-amine (368 mg, 2.76 mmol) was added and the reaction maintained at 60° C. for a further 3 hr and then cooled to RT. The resulting mixture was diluted with EtOAc (250 mL) and was washed sequentially with saturated aq. NaHCO$_3$ (2×50 mL), water (2×50 mL) and brine (2×50 mL) and then dried and evaporated in vacuo. The residue was purified by flash column chromatography (SiO$_2$, 120 g, 0-10% [1% NH$_3$ in MeOH] in DCM, gradient elution) to afford the title compound, Intermediate B14, as a dark purple solid (536 mg, 26%); R$^t$ 1.59 min (Method 2, acidic); m/z 369 (M+H)$^+$, (ES$^+$).

Intermediate B15

N-(4-((4-Aminonaphthalen-1-yl)oxy)pyrimidin-2-yl)-1-(2-morpholinoethyl)-1H-indazol-5-amine

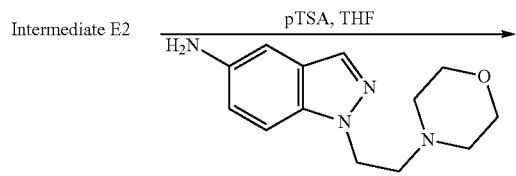

-continued

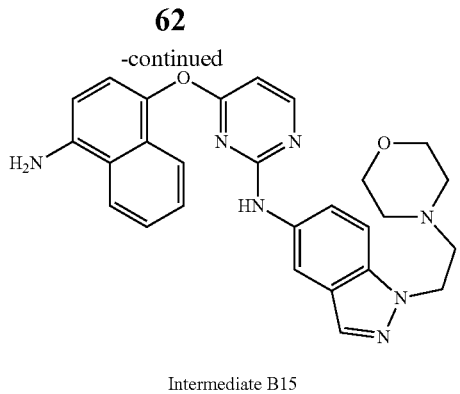

Intermediate B15

A solution of Intermediate E2 (5.08 g, 80% purity, 15.0 mmol), 1-(2-morpholinoethyl)-1H-indazol-5-amine (Breslin, H. J. et al., WO 2010/071885, 24 Jun. 2010) (4.42 g, 17.9 mmol) and p-TSA (2.84 g, 15.0 mmol) in THF (30 mL) was stirred at 60° C. for 48 hr. The reaction mixture was cooled to RT and was partitioned between EtOAc (100 mL) and saturated aq. NaHCO$_3$ (50 mL). The organic layer was separated and then dried and evaporated in vacuo.

The residue was purified by flash column chromatography (SiO$_2$, 120 g, 0-100%, EtOAc in isohexane, gradient elution, then 10% MeOH in DCM, isocratic elution) to afford the title compound Intermediate B15 as a dark purple solid (2.08 g, 26%); R$^t$ 1.39 min (Method 2, acidic); m/z 482 (M+H)$^+$ (ES$^+$).

Intermediate B16

Methyl 5-((4-((4-aminonaphthalen-1-yl)oxy)pyrimidin-2-yl)amino)-1H-indazole-3-carboxylate

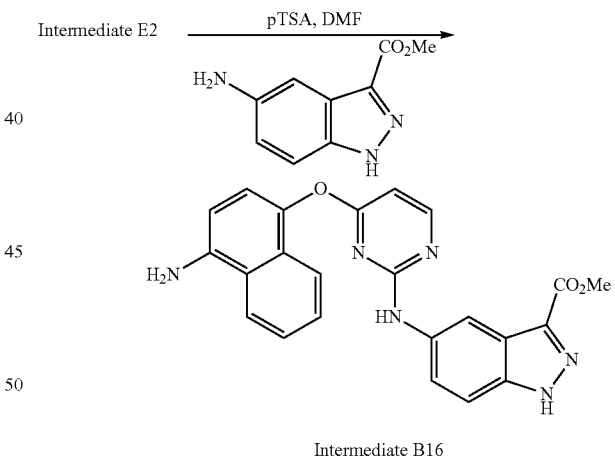

Intermediate B16

A solution of Intermediate E2 (1.60 g, 5.90 mmol), methyl 5-amino-1H-indazole-3-carboxylate (1.35 g, 7.07 mmol) and p-TSA (2.24 g, 11.8 mmol) in DMF (30 mL) was stirred at 60° C. for 16 hr. The reaction mixture was cooled to RT and was partitioned between EtOAc (100 mL) and saturated aq. NaHCO$_3$ (100 mL). The layers were separated and the organic extract was washed with water (2×100 mL) and brine (2×100 mL) and then dried and evaporated in vacuo. The residue was purified by trituration with acetonitrile to afford the title compound Intermediate B16 as a brown solid (0.937 g, 87% pure by HPLC, 33%); R$^t$ 1.67 min (Method 2, acidic); m/z 427 (M+H)$^+$ (ES$^+$). The material was used in subsequent steps without additional purification.

Intermediate B17

N-(4-((4-Aminonaphthalen-1-yl)oxy)pyrimidin-2-yl)-3-(2-morpholinoethoxy)-1H-indazol-5-amine

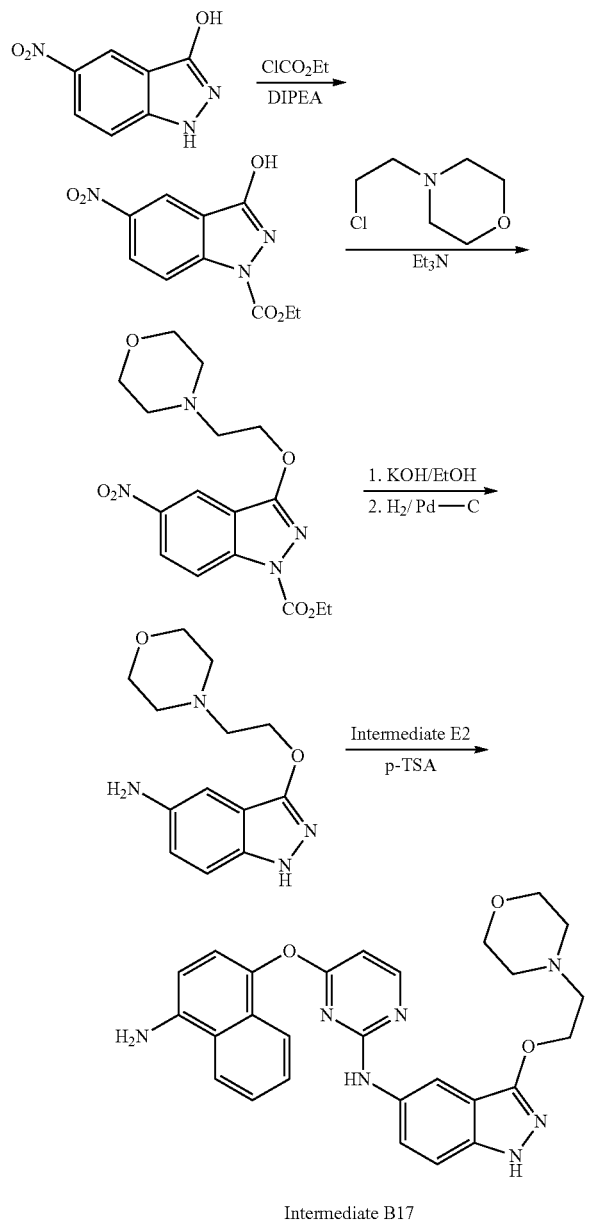

Intermediate B17

To a solution of 5-nitro-1H-indazol-3-ol (1.00 g, 5.60 mmol) in pyridine (6.0 mL) was added ethyl carbonochloridate (0.590 μL, 6.14 mmol) and the reaction mixture was heated to 70° C. After 3 hr the reaction mixture was cooled to RT and evaporated in vacuo. The residue was triturated with water (50 mL) to afford ethyl 3-hydroxy-5-nitro-1H-indazole-1-carboxylate as a yellow solid (1.26 g, 85%); $R^t$ 1.70 min (Method 2, acidic); m/z 252 (M+H)$^+$ (ES$^+$).

To a solution of 4-(2-chloroethyl)morpholine hydrochloride (390 mg, 2.10 mmol) in acetonitrile (25 mL) was added triethylamine (0.56 mL, 4.0 mmol) and ethyl 3-hydroxy-5-nitro-1H-indazole-1-carboxylate (563 mg, 1.91 mmol) and the mixture heated to reflux for 2 days. Additional portions of 4-(2-chloroethyl)morpholine hydrochloride (178 mg, 0.955 mmol) and triethylamine (130 μL, 0.95 mmol) were added and the reaction mixture was heated at reflux for a further 3 hr and then cooled to RT. Saturated aq. NaHCO$_3$ (50 mL) was added and the mixture was extracted with EtOAc (2×100 mL). The organic extracts were combined, dried and evaporated in vacuo and the residue was purified by flash column chromatography (SiO$_2$, 40 g, 0-100% EtOAc in isohexane, gradient elution) to afford ethyl 3-(2-morpholinoethoxy)-5-nitro-1H-indazole-1-carboxylate as a yellow solid (294 mg, 41%); $R^t$ 1.26 min (Method 2, acidic); m/z 365 (M+H)$^+$ (ES$^+$).

To a solution of the morpholinoethoxy indazole described above (combined with a previous batch made in an identical manner) (309 mg, 0.848 mmol) in EtOH (2.0 mL) was added a solution of KOH (48 mg, 0.848 mmol) in water (1.0 mL) and the reaction mixture maintained at RT for 16 hr. The reaction mixture was then purified directly, without work-up, by SCX capture and release to afford 4-(2-((5-nitro-1H-indazol-3-yl)oxy)ethyl)morpholine as a bright yellow solid (221 mg, 86%); $R^t$ 0.94 min (Method 2, acidic); m/z 293 (M+H)$^+$ (ES$^+$).

To a solution of the deprotected indazole described above (221 mg, 0.756 mmol) in MeOH (10 mL) and THF (10 mL) containing a drop of water was added palladium on carbon (10% Pd w/w, 80 mg, 0.076 mmol) and the mixture maintained at RT under an atmosphere of hydrogen for 16 hr. The reaction mixture was filtered through a celite pad and the pad was washed with THF (20 mL). The combined filtrate and washings were evaporated in vacuo to afford 3-(2-morpholinoethoxy)-1H-indazol-5-amine (215 mg, ~100%) as a pale pink solid; $R^t$ 0.16 min (Method 2, acidic); m/z 263 (M+H)$^+$ (ES$^+$).

A solution of Intermediate E2 (223 mg, 0.738 mmol), 3-(2-morpholinoethoxy)-1H-indazol-5-amine (215 mg, 0.738 mmol) and p-TSA (140 mg, 0.738 mmol) in a mixture of DMF and THF (1:1 v/v, 20 mL) was heated to 90° C. for 6 h and then cooled to RT and maintained at that temperature for a further 64 hr. The reaction mixture was partitioned between saturated aq. NaHCO$_3$ (50 mL) and EtOAc (50 mL). The aq layer was separated and extracted with EtOAc (50 mL) and the combined organic extracts were dried and evaporated in vacuo. The residue was purified by flash column chromatography (SiO$_2$, 40 g, 0-10% [0.1% NH$_3$ in MeOH] in DCM, gradient elution) to afford the title compound, Intermediate B17, as a black solid (201 mg, 49%); $R^t$ 1.32 min (Method 2, acidic); m/z 498 (M+H)$^+$ (ES$^+$).

Intermediate B18

(5-((4-((4-Aminonaphthalen-1-yl)oxy)pyrimidin-2-yl)amino)-1H-indazol-3-yl)(morpholino)methanone

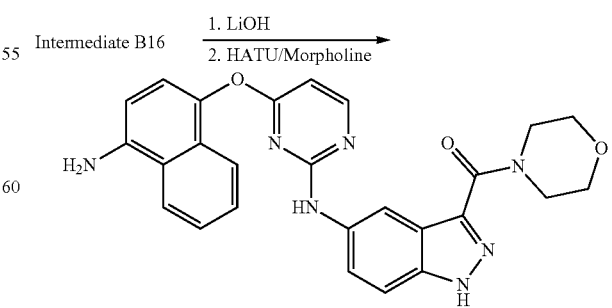

Intermediate B18

To a solution of Intermediate B16 (750 mg, 1.53 mmol) in THF (6.0 mL) at RT was added a solution of LiOH (55.0 mg, 2.30 mmol) in a 1:1 mixture of water and ethanol (2.0 mL) and the reaction mixture maintained at RT for 1 hr and then heated to 40° C. for 6 hr. An additional portion of LiOH (36 mg, 1.5 mmo) was added and the mixture was maintained at 40° C. for 2 days and then cooled to RT and concentrated to approximately half of its original volume in vacuo. The resulting mixture was added to 1 M hydrochloric acid (30 mL) and was then neutralised by the addition of aq. NaOH (2.0 M), at which point a white precipitate formed. The solid was collected by filtration and washed with water and Et$_2$O and then dried to afford 5-((4-((4-aminonaphthalen-1-yl)oxy)pyrimidin-2-yl)amino)-1H-indazole-3-carboxylic acid as a white solid (520 mg, 80% pure by HPLC, 66%); R$^t$ 1.44 min (Method 2, acidic); m/z 413 (M+H)$^+$ (ES$^+$).

The material was used in subsequent transformations without additional purification.

To a solution of the carboxylic acid described above (460 mg, 80% pure, 0.90 mmol) in THF (6.0 mL) at RT was added HATU (613 mg, 1.61 mmol) and DIPEA (0.340 µL, 1.97 mmol). After 10 min the resulting mixture was treated with morpholine (0.141 mL, 1.61 mmol) and after a further 16 hr at RT additional portions of HATU (170 mg, 0.45 mmol), DIPEA (80 µL, 0.45 mmol) and morpholine (39 µL, 0.45 mmol) were added. The resulting mixture was maintained at RT for a further 24 hr and was then partitioned between saturated aq. NaHCO$_3$ (20 mL) and EtOAc (20 mL). The organic phase was separated and was washed sequentially with 1M hydrochloric acid (20 mL), water (2×30 mL) and brine (2×30 mL) and was then dried and evaporated in vacuo. The residue was purified by flash column chromatography (SiO$_2$, 40 g, 0-100% [10% MeOH in EtOAc] in isohexane, gradient elution) to afford the title compound, Intermediate B18, as a dark purple solid (165 mg, 82% pure, 24%); R$^t$ 1.55 min (Method 2, acidic); m/z 482 (M+H)$^+$ (ES$^+$). The material was used in subsequent reactions without additional purification.

Intermediate B19

5-((4-((4-Aminonaphthalen-1-yl)oxy)pyrimidin-2-yl)amino)-N,N-dimethyl-1H-indazole-3-carboxamide

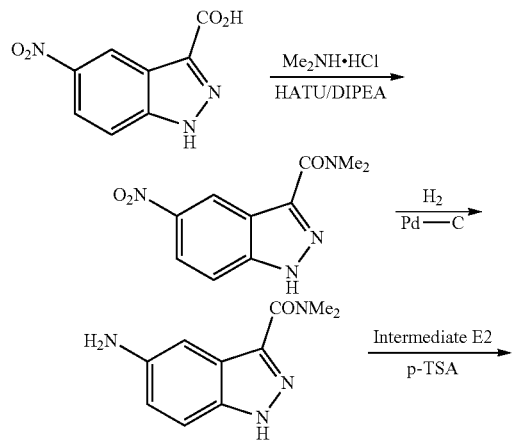

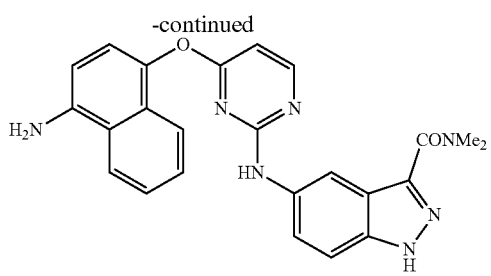

Intermediate B19

To a solution of 5-nitro-1H-indazole-3-carboxylic acid (1.01 g, 4.88 mmol), dimethylamine hydrochloride (1.99 g, 24.4 mmol) and HATU (2.78 g, 7.31 mmol) in DMF at RT was added DIPEA (4.3 mL, 24 mmol) and the reaction mixture kept at RT for 18 hr and then diluted with water (150 mL). The resulting precipitate was collected by filtration and was dried in vacuo to afford N,N-dimethyl-5-nitro-1H-indazole-3-carboxamide as a pale yellow solid (1.10 g, 92%); R$^t$ 0.26 min (Method 2, acidic); m/z 235 (M+H)$^+$ (ES$^+$).

A suspension of the nitroindazole product described above (1.01 g, 4.31 mmol) and palladium on carbon (10% Pd w/w, 0.46 g, 0.43 mmol) in MeOH (50 mL) was maintained at RT under an atmosphere of hydrogen for 16 hr. The mixture was then filtered through a pad of celite and the filtrate was evaporated in vacuo to afford 5-amino-N,N-dimethyl-1H-indazole-3-carboxamide as a beige solid (865 mg, 91%); R$^t$ 0.26 min (Method 2, acidic); m/z 205 (M+H)$^+$ (ES$^+$).

A solution of the aminoindazole described above (759 mg, 3.46 mmol), Intermediate E2 (600 mg, 1.90 mmol) and pTSA (731 mg, 3.84 mmol) in DMF (12.0 mL) was heated at 60° C. for 16 hr. The reaction mixture was then cooled to RT and was partitioned between EtOAc (50 mL) and saturated aq. NaHCO$_3$ (50 mL). The organic layer was separated and was washed with water (2×100 mL) and brine (2×100 mL) and then dried and evaporated in vacuo. The residue was purified by flash column chromatography (SiO$_2$, 40 g, 0-5% MeOH in DCM, gradient elution) to afford the title compound, Intermediate B19, as a dark purple solid (216 mg, 86% pure, 22%); R$^t$ 1.55 min (Method 2, acidic, 86% pure); m/z 440 (M+H)$^+$ (ES$^+$). The material was used in subsequent transformations without additional purification.

Intermediate C1

1-(3-(tert-Butyl)-1-(p-tolyl)-1H-pyrazol-5-yl)-3-(4-((2-chloropyrimidin-4-yl)oxy)naphthalen-1-yl)urea

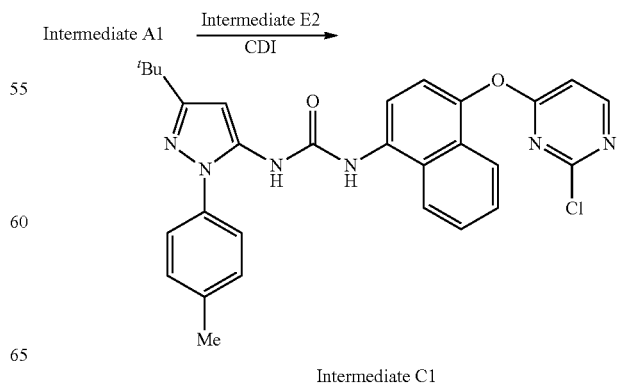

Intermediate C1

To a suspension of CDI (4.81 g, 29.7 mmol) in DCM (60 mL) was added Intermediate A1 (8.50 g, 29.7 mmol) portionwise. After 3 hr an aliquot of this solution containing the activated CDI adduct (30 mL, 15 mmol) was added to a solution of Intermediate E2 (3.01 g, 9.97 mmol) in DCM (60 mL) and the reaction mixture maintained at RT. After 2 hr a second aliquot of the CDI adduct solution (6.0 mL, 6.0 mmol) was added and the reaction mixture kept at RT for a further 16 hr. The resulting mixture was diluted with DCM (100 mL) and washed with saturated aq. NaHCO$_3$ (100 mL) and water (2×100 mLl) and then dried and evaporated in vacuo. The residue was purified by flash column chromatography (SiO$_2$, [10% MeOH in DCM] in DCM, 0-100%, gradient elution then SiO$_2$, EtOAc in isohexane 0-100%, gradient elution) to afford the title compound, Intermediate C1 as a yellow solid (3.07 g, 55%); R$^t$ 2.59 min (Method 2); m/z 527/529 (M+H)$^+$ (ES$^+$).

Intermediate C2

1-(3-tert-Butyl-1-(4-(2-morpholinoethoxy)phenyl)-1H-pyrazol-5-yl)-3-(4-(2-chloropyrimidin-4-yloxy)naphthalen-1-yl)urea

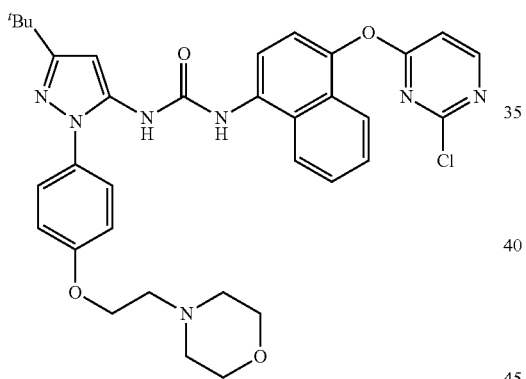

Intermediate C2

Phenyl carbonochloridate (4.41 mL, 35.1 mmol) was added to a solution of 3-(tert-butyl)-1-(4-(2-morpholinoethoxy)phenyl)-1H-pyrazol-5-amine Intermediate A7 (10.98 g, 31.9 mmol) in DCM (55 mL) and the resulting mixture was stirred for 1 hr and then partitioned between DCM (30 mL) and sat. aq. NaHCO$_3$ (50 mL). The organic layer was separated and concentrated in vacuo and the residue was dissolved in THF (20 mL) and added to a solution of Intermediate E2 (7.00 g, 25.8 mmol) in THF (20 mL). Triethylamine (3.61 mL, 25.8 mmol) was added and the resulting mixture was heated at 50° C. for 6 hr and then cooled and poured onto water (50 mL). The mixture was extracted with DCM (2×70 mL) and the combined DCM extracts concentrated in vacuo. The residue was treated with EtOAc (100 mL), filtered (to remove solid impurities) and the filtrate washed with water (2×50 mL).

The EtOAc extracts were dried over MgSO$_4$ and concentrated in vacuo. The residue was preloaded onto silica and was purified by column chromatography (SiO$_2$, 120 g, eluted with 0-3% [1% NH$_3$ in MeOH] in DCM) to yield the title compound, Intermediate C2 as a light brown crystalline solid (10.40 g, 16.03 mmol, 62% yield); R$^t$ 2.69 min, X-select method, m/z 643 (M+H)$^+$ (ES$^+$); $^1$H NMR (400 MHz, DMSO-d$_6$) δ: 1.28 (9H, s), 2.48-2.50 (4H, over-lapping m), 2.73 (2H, t), 3.58-3.60 (4H, over-lapping m), 4.17 (2H, t), 6.39 (1H, s), 7.12-7.14 (2H, over-lapping m), 7.28 (1H, d), 7.42-7.48 (3H, over-lapping m), 7.56-7.68 (2H, over-lapping m), 7.79 (1H, m), 7.95 (1H, d), 8.08 (1H, d), 8.67 (1H, d), 8.75 (1H, s), 9.14 (1H, s).

Intermediate D1

1-(Tetrahydro-2H-pyran-2-yl)-1H-indazol-5-amine

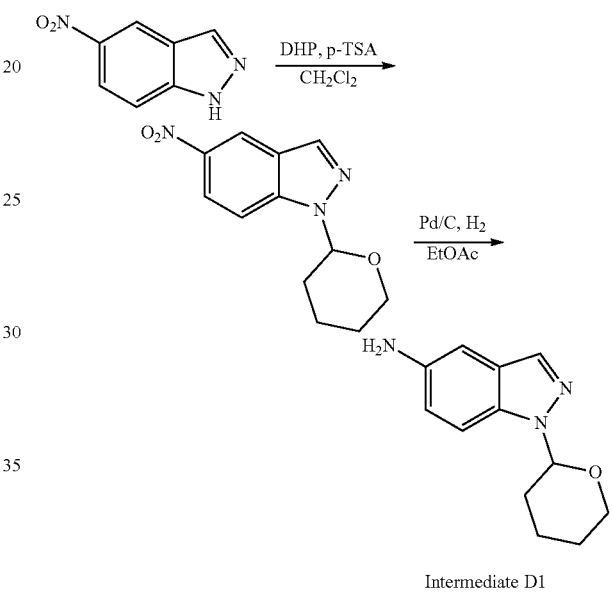

Intermediate D1

A suspension of 5-nitro-1H-indazole (24.4 g, 150 mmol) and p-TSA (2.58 g, 14.98 mmol) in DCM (1000 mL) was treated with 3,4-dihydro-2H-pyran (41.0 mL, 449 mmol) over 5 min to provide a solution that was stirred at RT for 6 hr. The resulting dark reaction mixture was added to 2 M NaOH (250 mL) and the organic layer was separated, dried and then concentrated in vacuo to afford a black oil. This material was purified by filtering through a plug of silica (~700 g), loading and eluting with DCM (>12 L) to yield 5-nitro-1-(tetrahydro-2H-pyran-2-yl)-1H-indazole as a pale yellow solid (34.02 g, 133 mmol, 89% yield); R$^t$ 2.06 min, no ionisation observed; $^1$H NMR (400 MHz, CDCl$_3$) δ: 1.70-1.78 (3H, over-lapping m), 2.14 (2H, m), 2.51 (1H, m), 3.76 (1H, ddd), 4.01 (1H, m), 5.77 (1H, dd), 7.69 (1H, d), 8.21 (1H, d), 8.27 (1H, dd), 8.71 (1H, dd).

A stirred solution of 5-nitro-1-(tetrahydro-2H-pyran-2-yl)-1H-indazole (1.00 g, 4.04 mmol) in EtOAc (10 mL) was degassed for 10 min and then placed under vacuum and filled with nitrogen. The reaction mixture was placed under vacuum again, palladium on carbon (10% wt./wt, 272 mg, 0.256 mmol) was added and the resulting mixture was stirred under an atmosphere of hydrogen at RT for 20 hr. The reaction mixture was filtered through a pad of celite and the filtrate was concentrated in vacuo to yield the title compound, Intermediate D1 as a pale yellow solid (553 mg, 2.47 mmol, 61% yield); R$^t$ 1.38 min, Basic method, m/z 218.3 (M+H)$^+$ (ES$^+$);

¹H NMR (400 MHz, DMSO-d₆) δ: 1.52-1.58 (2H, overlapping m), 1.71 (1H, m), 1.90 (1H, m), 2.01 (1H, m), 2.36 (1H, m), 3.68 (1H, m), 3.86 (1H, m), 4.85 (2H, s), 5.67 (1H, dd), 6.74 (1H, m), 6.81 (1H, dd), 7.40 (1H, m), 7.75 (1H, d).

Intermediate E3

4-((6-Chloropyrimidin-4-yl)oxy)naphthalen-1-amine

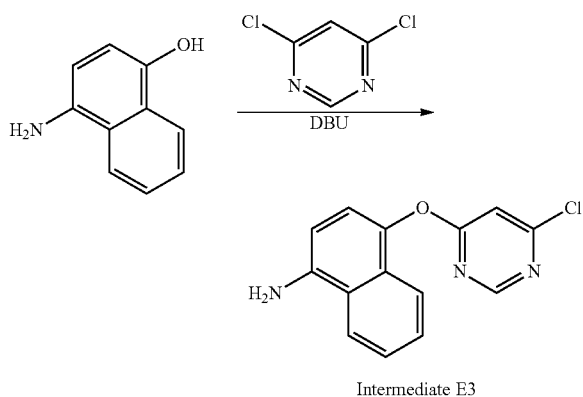

Intermediate E3

To a solution of 4-aminonaphthalen-1-ol hydrochloride (6.82 g, 31.4 mmol) in acetonitrile (80 mL) at 0° C. was added drop-wise DBU (11.0 mL, 75.0 mmol). After 10 min 4,6-dichloropyrimidine (5.00 g, 34.0 mmol) was added portion-wise over 5 min and the reaction mixture warmed to RT for 3 hr and then evaporated in vacuo. The residue was diluted with water (250 mL) and sonicated for 15 min and then stirred at RT for 16 hr. The resulting precipitate was isolated by filtration, washed with water (3×100 mL) and dried in vacuo to afford the title compound, Intermediate E3, as a grey solid (8.27 g, 97%); R^t 1.85 min (Method 2, acidic); m/z 272 (M+H)⁺, (ES⁺).

Example 1

1-(4-((2-((1H-Indol-5-yl)amino)pyrimidin-4-yl)oxy)naphthalen-1-yl)-3-(3-(tert-butyl)-1-(p-tolyl)-1H-pyrazol-5-yl)urea

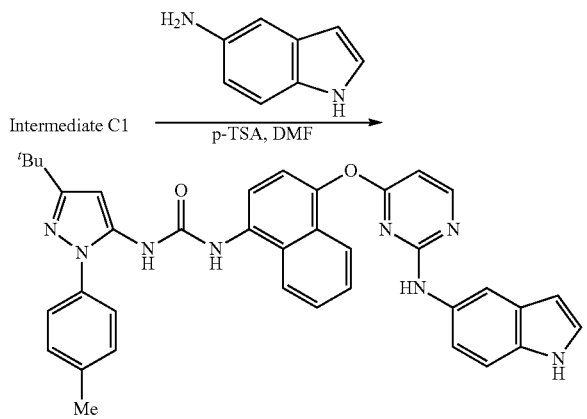

Example 1

To a solution of Intermediate C1 (151 mg, 0.287 mmol) in DMF (2.0 mL) was added p-TSA.H₂O (109 mg, 0.573 mmol) and 1H-indol-5-amine (45.4 mg, 0.344 mmol). The resulting mixture was heated at 60° C. for 16 hr and then treated with additional portions of 1H-indol-5-amine (19 mg, 0.14 mmol) and p-TSA.H₂O (27 mg, 0.14 mmol). The reaction mixture was maintained at 60° C. for a further 24 hr and then cooled to RT and partitioned between saturated aq. NaHCO₃ (40 mL) and EtOAc (25 mL). The organic layer was separated and was washed with water (2×50 mL) and brine (50 mL) and then dried and evaporated in vacuo. The residue was purified by flash column chromatography (SiO₂, 40 g, 0-100% EtOAc in isohexane, gradient elution) and finally by preparative HPLC to afford the title compound, Example 1, as a white solid (49 mg, 26%); R^t 2.47 min (Method 2, acidic); m/z 621 (M−H)⁻, (ES⁻); ¹H NMR δ: 1.29 (9H, s), 2.40 (3H, s), 6.09 (1H, br s), 6.42 (1H, s), 6.45 (1H, d), 7.02-7.10 (2H, overlapping m), 7.15 (1H, s), 7.37-7.41 (3H, overlapping m), 7.48 (2H, d), 7.49-7.64 (3H, overlapping m), 7.83 (1H, d), 8.01 (1H, d), 8.10 (1H, d), 8.33 (1H, d), 8.85 (1H, s), 9.19 (1H, s), 9.26 (1H, s), 10.79 (1H, s).

Example 2

1-(3-(tert-Butyl)-1-(p-tolyl)-1H-pyrazol-5-yl)-3-(4-((2-((2-oxoindolin-6-yl)amino)pyrimidin-4-yl)oxy)naphthalen-1-yl)urea

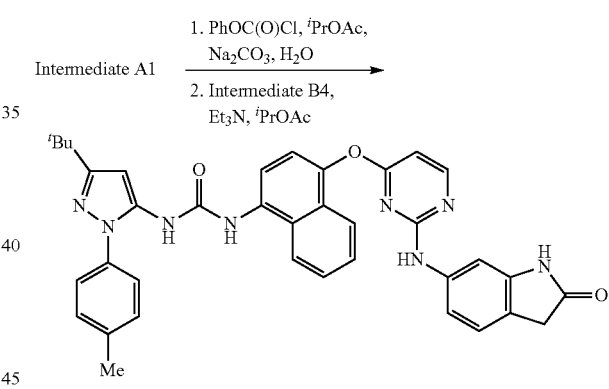

Example 2

To a solution of Intermediate A1 (1.01 g, 4.30 mmol) in isopropyl acetate (40 mL) at RT was added a solution of Na₂CO₃ (552 mg, 5.21 mmol) in water (10 mL). After 5 min phenyl chloroformate (550 µL, 4.36 mmol) was added and the resulting biphasic reaction mixture was maintained at RT for 3 days. The layers were separated and the organic phase was washed with water (30 mL) and then dried and evaporated in vacuo to afford phenyl 3-tert-butyl-1-p-tolyl-1H-pyrazol-5-ylcarbamate as an off-white solid (1.36 g, 70% pure by HPLC, 63%); R^t 2.68 min (Method 2, acidic); m/z 350 (M+H)⁺, (ES⁺). This material was used directly in the subsequent synthetic step without additional purification.

To a suspension of Intermediate B4 (61 mg, 0.127 mmol) in isopropyl acetate (6.0 mL) was added the pyrazole carbamate, prepared above, (103 mg, 70% pure, 0.206 mmol) and Et₃N (50 µL, 0.36 mmol). The resulting suspension was heated to 40° C. for 45 min and was then cooled to RT for 16 hr. The reaction mixture was evaporated onto silica gel and purified by flash column chromatography (SiO₂, 12 g, 0-30% MeOH in DCM, gradient elution then SiO$_2$, 12 g, 0-100% EtOAc in isohexane, gradient elution followed by 0-30% MeOH in DCM, gradient elution). The crude product so obtained was triturated with a mixture of IPA, MeOH and DCM to afford the title compound, Example 2, as an off white solid (10 mg, 12%); R$^t$ 2.37 min (Method 2, basic); m/z 639 (M+H)$^+$ (ES$^+$); m/z 637 (M–H)$^-$ (ES$^-$); $^1$H NMR δ: 1.29 (9H, s), 2.40 (3H, s), 3.30 (2H, s), 6.44 (1H, s), 6.49 (1H, d), 6.79 (1H, d), 6.94 (1H, d), 7.14 (1H, br s), 7.37-7.48 (5H, over-lapping m), 7.54-7.65 (2H, over-lapping m), 7.82 (1H, dd), 7.92 (1H, d), 8.07 (1H, d), 8.37 (1H, d), 8.76 (1H, s), 9.14 (1H, s), 9.50 (1H, s), 10.20 (1H, s).

Example 3

5-((4-((4-(3-(3-(tert-Butyl)-1-(p-tolyl)-1H-pyrazol-5-yl)ureido)naphthalen-1-yl)oxy)pyrimidin-2-yl)amino)-N-(2-morpholinoethyl)-1H-indazole-3-carboxamide

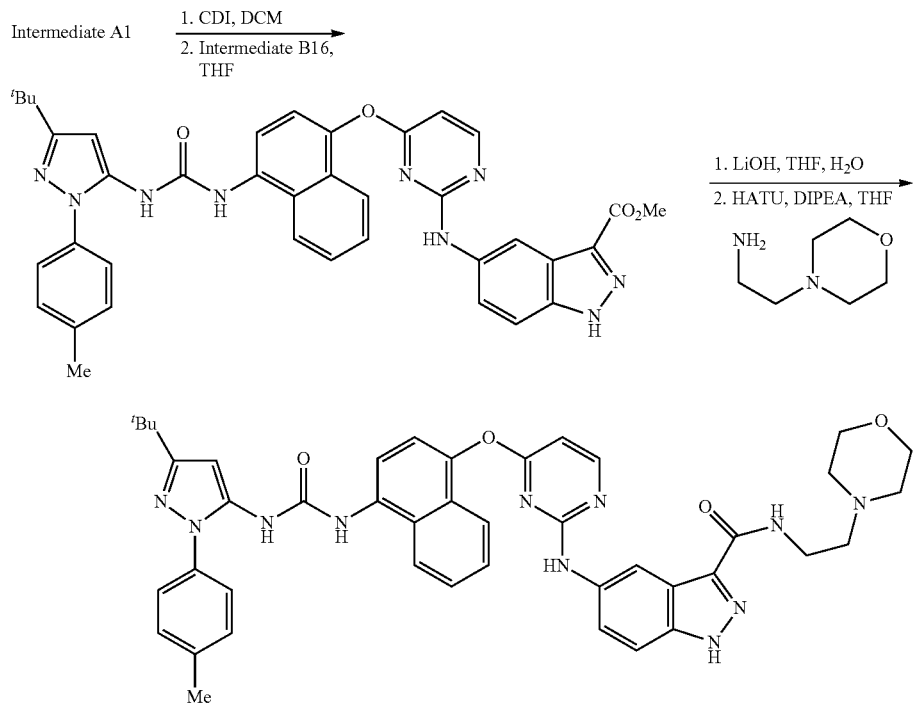

Example 3

To a solution of CDI (91 mg, 0.56 mmol) in DCM (1.0 mL) was added Intermediate A1 (129 mg, 0.563 mmol) and the reaction mixture maintained at RT for 2 hr. A portion of this solution (500 μL, 0.28 mmol) was added to a solution of Intermediate B16 (80 mg, 0.19 mmol) in THF (2.0 mL) and the reaction mixture kept at RT for 3 hr and then quenched with the addition of MeOH (2.0 mL). The resulting mixture was evaporated in vacuo and the residue was purified by flash column chromatography (SiO$_2$, 12 g, 0-100% [10% MeOH in EtOAc] in isohexane, gradient elution) to afford methyl 5-((4-((4-(3-(3-(tert-butyl)-1-(p-tolyl)-1H-pyrazol-5-yl)ureido)naphthalen-1-yl)oxy)pyrimidin-2-yl)amino)-1H-indazole-3-carboxylate as a pale tan solid (77 mg, 57%); R$^t$ 2.50 min (Method 2, acidic); m/z 680 (M–H)$^-$, (ES$^-$).

To a solution of the methyl ester, described above, (72 mg, 0.106 mmol) in THF (2.0 mL) at RT was added a solution of LiOH (4 mg, 0.2 mmol) in water (0.25 mL) and the reaction mixture maintained at RT for 1.5 hr and then heated to 40° C. for a further 24 hr. The mixture was cooled to RT and was treated with aq. citric acid (10% w/v) drop-wise until a precipitate formed. The resulting mixture was diluted with EtOAc (2.0 mL) and then sonicated and the precipitate was collected and dried in vacuo to afford 5-((4-((4-(3-(3-(tert-butyl)-1-(p-tolyl)-1H-pyrazol-5-yl)ureido)naphthalen-1-yl)oxy)pyrimidin-2-yl)amino)-1H-indazole-3-carboxylic acid as a peach coloured solid (26 mg, 35%); R$^t$ 2.21 min (Method 2, acidic); m/z 668 (M+H)$^+$, (ES$^+$).

To a solution of the acid described above (24 mg, 0.036 mmol) in THF (1.0 mL) was added HATU (19 mg, 0.050 mmol) and DIPEA (13 μL, 0.072 mmol). The resulting mixture was maintained at RT for 10 min and was then treated with 2-morpholinoethanamine (7.1 μL, 0.054 mmol). Additional portions of HATU were added after 4 hr (14 mg, 0.036 mmol) and 21 hr (7 mg, 0.02 mmol) and after a further 3 hr the reaction mixture was partitioned between EtOAc (5.0 mL) and saturated aq. NaHCO$_3$ (5.0 mL). The organic layer was separated and washed with half-saturated brine (brine/water 1:1 v/v, 2×20 mL) and then dried and evaporated in vacuo. The residue was purified by flash column chromatography (SiO$_2$, 4.0 g, 0-5% MeOH in DCM, gradient elution) to afford the title compound, Example 3, as a pale yellow solid (6 mg, 21%); R$^t$ 1.80 min (Method 2); m/z 780 (M+H)$^+$ (ES$^+$); $^1$H NMR δ: 1.29 (9H, s), 2.40-2.42 (7H, over-lapping m), 3.30 (2H, m), 3.42 (2H, m), 3.57 (4H, m), 6.42 (1H, s), 6.44 (1H, d), 7.30 (1H, d), 7.38 (2H, m), 7.42-7.50 (4H, over-lapping m), 7.57-7.63 (2H, over-lapping m), 7.84 (1H, m), 7.92 (1H, d), 8.07-8.11 (2H, over-lapping m), 8.38 (1H, d), 8.42 (1H, s), 8.75 (1H, s), 9.11 (1H, s), 9.52 (1H, s), 13.36 (1H, s).

Example 4

1-(3-(tert-Butyl)-1-(p-tolyl)-1H-pyrazol-5-yl)-3-(4-((2-((1-methyl-1H-benzo[d]imidazol-5-yl)amino)pyrimidin-4-yl)oxy)naphthalen-1-yl)urea

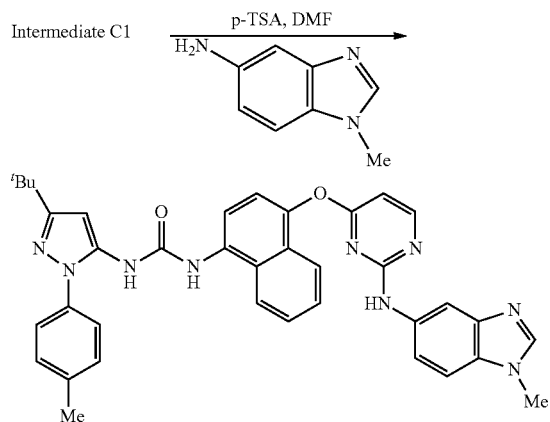

Example 4

To a solution of Intermediate C1 (155 mg, 80% purity, 0.236 mmol) in DMF (2.0 mL) was added p-TSA.H₂O (90 mg, 0.47 mmol) and 1-methyl-1H-benzo[d]imidazol-5-amine (49 mg, 0.33 mmol). The resulting mixture was heated at 60° C. for 16 hr and was then cooled to RT and partitioned between saturated aq. NaHCO₃ (40 mL) and EtOAc (25 mL). The organic layer was separated and washed with water (2×50 mL) and brine (50 mL) and then dried and evaporated in vacuo. The residue was purified by flash column chromatography (SiO₂, 40 g, 0-30% MeOH in DCM, gradient elution) and by preparative HPLC to afford the title compound, Example 4, as a pale pink solid (15 mg, 9%); R$^t$ 1.96 min (Method 2, acidic); m/z 638 (M+H)$^+$, (ES$^+$); $^1$H NMR δ: 1.30 (9H, s), 2.39 (3H, s), 3.74 (3H, s), 6.42 (1H, s), 6.46 (1H, d), 7.23-7.31 (2H, over-lapping m), 7.37 (2H, d), 7.40 (1H, d), 7.47 (2H, d), 7.55 (1H, dd), 7.61 (1H, dd), 7.77 (1H, br s), 7.83 (1H, d), 7.88 (1H, d), 8.00 (1H, s), 8.07 (1H, d), 8.36 (1H, d), 8.86 (1H, s), 9.18 (1H, s), 9.42 (1H, s).

Example 5

1-(4-((2-((3-Aminobenzo[d]isoxazol-5-yl)amino)pyrimidin-4-yl)oxy)naphthalen-1-yl)-3-(3-(tert-butyl)-1-(p-tolyl)-1H-pyrazol-5-yl)urea

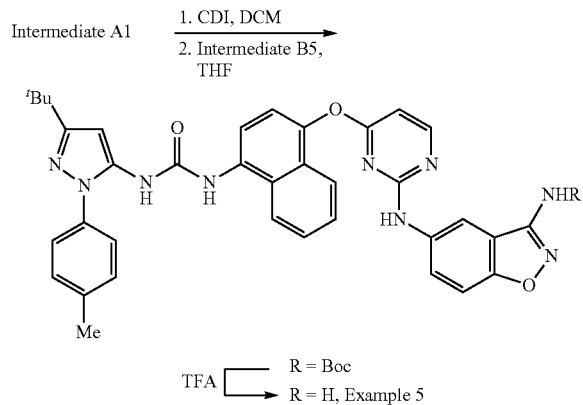

To a solution of CDI (56 mg, 0.35 mmol) in DCM (3.0 mL) was added Intermediate A1 (68 mg, 0.24 mmol) and the reaction mixture maintained at RT for 23 hr. The resulting solution was added to a solution of Intermediate B5 (50 mg, 0.098 mmol) in THF (3.0 mL) and the reaction mixture was kept at RT for 2 hr and was then partitioned between EtOAc (30 mL) and saturated aq. NaHCO₃ (30 mL). The organic phase was separated and washed with saturated aq. NaHCO₃ (30 mL), water (2×30 mL) and brine (2×30 mL), and then dried and evaporated in vacuo. The residue was purified by flash column chromatography (SiO₂, 12 g, 0-100% EtOAc in isohexane, gradient elution) to afford tert-butyl (5-((4-((4-(3-(3-(tert-butyl)-1-(p-tolyl)-1H-pyrazol-5-yl)ureido)naphthalen-1-yl)oxy)pyrimidin-2-yl)amino)benzo[d]isoxazol-3-yl)carbamate (62 mg, 81%); R$^t$ 2.88 min (Method 2, acidic); m/z 740 (M+H)$^+$, (ES$^+$).

To a solution of the Boc-protected amine described above (62 mg, 0.080 mmol) in DCM (1.0 mL) at RT was added TFA (200 μL, 2.6 mmol) and the reaction mixture maintained at RT for 2 hr and then diluted with EtOAc (30 mL) and water (30 mL). Saturated aq. NaHCO₃ (5.0 mL) was added to the biphasic mixture and the layers were then separated. The organic phase was washed with saturated aq. NaHCO₃ (30 mL), water (2×30 mL) and brine (2×30 mL) and then dried and evaporated in vacuo. The residue was purified by flash column chromatography (SiO₂, 12 g, 0-100% EtOAc in isohexane, gradient elution) to afford the title compound, Example 5, as a pale pink solid (23 mg, 44%); R$^t$ 2.40 min (Method 2); m/z 640 (M+H)$^+$ (ES$^+$); m/z 638 (M−H)$^−$ (ES$^−$); $^1$H NMR δ: 1.29 (9H, s), 2.40 (3H, s), 6.20 (2H, br s), 6.42 (1H, s), 6.49 (1H, d), 7.11 (1H, br d), 7.37-7.42 (4H, over-lapping m), 7.47 (2H, m), 7.55-7.65 (2H, over-lapping m), 7.82 (1H, m), 7.90 (2H, br d), 8.06 (1H, m), 8.36 (1H, d), 8.74 (1H, s), 9.11 (1H, s), 9.55 (1H, s).

Example 6

1-(4-((2-((1H-Pyrazolo[3,4-b]pyridin-5-yl)amino)pyrimidin-4-yl)oxy)naphthalen-1-yl)-3-(3-(tert-butyl)-1-(p-tolyl)-1H-pyrazol-5-yl)urea

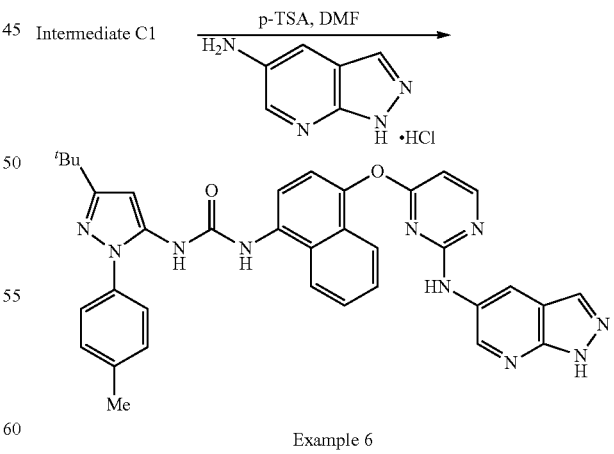

Example 6

To a solution of Intermediate C1 (105 mg, 80% purity, 0.236 mmol) in DMF (2.0 mL) was added p-TSA.H₂O (61 mg, 0.32 mmol) and 1H-pyrazolo[3,4-b]pyridin-5-amine hydrochloride (38 mg, 0.22 mmol). The mixture was heated at 60° C. for 16 hr and then cooled to RT and partitioned between saturated aq. NaHCO₃ (40 mL) and EtOAc (25 mL). The layers were separated and the organic layer was washed with water (2×50 mL) and with brine (50 mL) and then dried and evaporated in vacuo. The residue was purified by flash column chromatography (SiO₂, 40 g, 0-100% EtOAc in isohexane, gradient elution) and then by preparative HPLC to give the title compound, Example 6, as a pale red solid (8 mg, 7%); R$^t$ 2.24 min (Method 2, acidic); m/z 625 (M+H)⁺, (ES⁺); ¹H NMR δ: 1.29 (9H, s), 2.39 (3H, s), 6.42 (1H, s), 6.65 (1H, d), 7.38 (2H, d), 7.43 (1H, d), 7.50 (2H, d), 7.55 (1H, dd), 7.62 (1H, dd), 7.70 (1H, br s), 7.82 (1H, d), 7.84-8.03 (2H, overlapping m), 8.15 (1H, d), 8.40-8.44 (2H, over-lapping m), 9.06 (1H, s), 9.40 (1H, s), 9.78 (1H, br s), 13.40 (1H, s).

Example 7

1-(4-((2-((1H-Indazol-5-yl)amino)pyrimidin-4-yl)oxy)naphthalen-1-yl)-3-(3-(tert-butyl)-1-(4-hydroxyphenyl)-1H-pyrazol-5-yl)urea

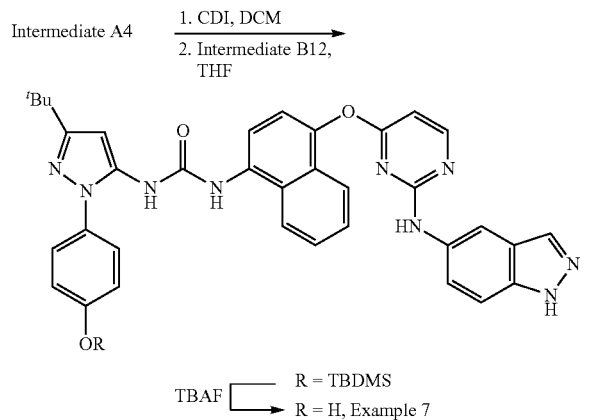

To a solution of CDI (132 mg, 0.814 mmol) in DCM (2.0 mL) was added Intermediate A4 (281 mg, 0.814 mmol) and the reaction mixture maintained at RT for 3 hr. A portion of the resulting solution (1.0 mL, 0.41 mmol) was added to a solution of Intermediate B12 (100 mg, 0.27 mmol) in THF (2.0 mL) and the reaction mixture kept at RT for 2 hr and then treated with an additional aliquot of the CDI adduct (400 μL, 0.2 mmol). The resulting mixture was maintained at RT for a further 16 hr and was then partitioned between EtOAc (15 mL) and water (15 mL). The organic phase was separated and was washed with saturated aq. NaHCO₃ (2×20 mL), water (2×20 mL) and brine (2×20 mL) and then dried and evaporated in vacuo. The residue was purified by flash column chromatography (SiO₂, 40 g, 0-100% EtOAc in isohexane, gradient elution) to afford 1-(4-((2-((1H-indazol-5-yl)amino)pyrimidin-4-yl)oxy)naphthalen-1-yl)-3-(3-(tert-butyl)-1-(4-((tert-butyldimethylsilyl)oxy)phenyl)-1H-pyrazol-5-yl)urea as a pale pink solid (80 mg, 38%); R$^t$ 2.89 min (Method 2, acidic); m/z 741 (M+H)⁺, (ES⁺).

To a solution of the TBDMS-protected intermediate described above (80 mg, 0.10 mmol) in THF (2.0 mL) at RT was added a solution of TBAF (1 M in THF, 150 μL, 0.150 mmol) and the reaction mixture kept at RT for 0.5 hr and then diluted with DCM (10 mL) and saturated aq. NaHCO₃ (10 mL). Water (10 mL) was added which caused a white suspension to be formed. The resulting triphasic mixture was filtered and the filtrand was suspended in MeOH (1.5 mL) and then sonicated. The supernatant liquor was decanted and the process was repeated twice to provide a solid that was collected by filtration to afford the title compound, Example 7, as a pale pink solid (15 mg, 22%); R$^t$ 2.09 min (Method 2); m/z 626 (M+H)⁺ (ES⁺); ¹H NMR δ: 1.28 (9H, s), 6.35 (1H, s), 6.56 (1H, d), 6.92 (2H, m), 7.25 (2H, br s), 7.37-7.41 (3H, overlapping m), 7.54-7.65 (4H, over-lapping m), 7.82 (1H, dd), 8.04 (1H, m), 8.33 (1H, d), 8.36 (1H, d), 9.27 (1H, s), 9.50 (1H, s), 9.62 (1H, s), 9.85 (1H, s), 12.83 (1H, s).

Example 8

1-(4-((2-((1H-Indazol-5-yl)amino)pyrimidin-4-yl)oxy)naphthalen-1-yl)-3-(1-(4-methoxyphenyl)-3-(tetrahydrofuran-3-yl)-1H-pyrazol-5-yl)urea

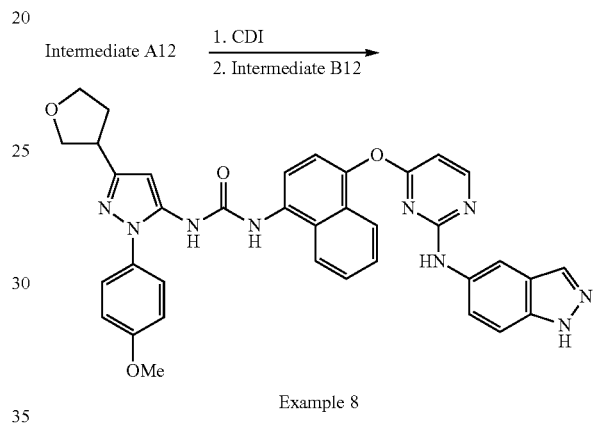

To a solution of CDI (103 mg, 0.636 mmol) in DCM (1.5 mL) was added Intermediate A12 (150 mg, 0.578 mmol) and the reaction mixture was kept at RT for 16 hr. An aliquot of the resulting solution (1.2 mL, 0.46 mmol) was added to a solution of Intermediate B12 (60 mg, 0.16 mmol) in THF (1.0 mL) and the reaction mixture was maintained at RT for 2 hr, during which time a white precipitate formed. The reaction mixture was diluted with MeOH (3.0 mL) and the solid was collected by filtration to afford the title compound, Example 8, as a cream solid (32 mg, 29%); R$^t$ 1.88 min (Method 2, acidic); m/z 654 (M+H)⁺ (ES⁺); ¹H NMR δ: 2.07 (1H, m), 2.26 (1H, m), 3.40 (1H, t), 3.69 (1H, t), 3.76-3.91 (2H, over-lapping m), 3.85 (3H, s), 4.03 (1H, t), 6.44 (1H, s), 6.60 (1H, d), 7.14 (2H, m), 7.24 (2H, m), 7.44 (1H, d), 7.52-7.65 (6H, over-lapping m), 7.83 (1H, m), 8.06-8.13 (2H, over-lapping m), 8.40 (1H, d), 8.88 (1H, br s), 9.24 (1H, s), 9.57 (1H, s), 12.80 (1H, br s)

Example 9

1-(3-Isopropyl-1-(4-methoxyphenyl)-1H-pyrazol-5-yl)-3-(4-((2-((7-methyl-1H-indazol-5-yl)amino)pyrimidin-4-yl)oxy)naphthalen-1-yl)urea

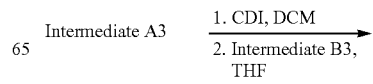

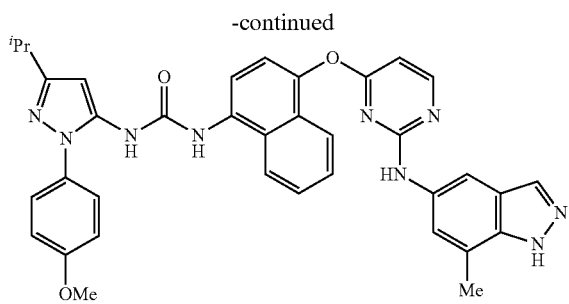

Example 9

To a solution of CDI (83 mg, 0.510 mmol) in DCM (1.0 mL) was added Intermediate A3 (118 mg, 0.510 mmol) and the reaction mixture heated to 40° C. for 1 hr. A portion of the resulting solution (0.630 μL, 0.32 mmol) was added to a solution of Intermediate B3 (65 mg, 0.17 mmol) in THF (1.0 mL) and the reaction mixture kept at RT for 18 hr and then partitioned between EtOAc (50 mL) and saturated aq. NaHCO₃ (50 mL). The layers were separated and the organic phase was washed with saturated aq. NaHCO₃ (50 mL), water (2×50 mL) and brine (2×50 mL) and then dried and evaporated in vacuo. The residue was purified by flash column chromatography (SiO₂, 12 g, 0-10% [0.07 M NH₃ in MeOH] in DCM, gradient elution) and then by preparative HPLC to afford the title compound, Example 9, as a beige solid (5 mg, 4%); R$^t$ 2.23 min (Method 2, basic); m/z 640 (M+H)$^+$ (ES$^+$); m/z 638 (M−H)$^−$ (ES$^−$); $^1$H NMR δ: 1.24 (6H, d), 2.29 (3H, s), 2.89 (1H, m), 3.83 (3H, s), 6.37 (1H, s), 6.58 (1H, d), 7.01 (1H, br s), 7.14 (2H, m), 7.42 (2H, d), 7.50-7.61 (5H, over-lapping m), 7.82 (1H, d), 8.07 (1H, d), 8.12 (1H, d), 8.38 (1H, d), 8.92 (1H, s), 9.29 (1H, s), 9.47 (1H, s), 12.86 (1H, br s).

Example 10

1-(3-(tert-Butyl)-1-(3-((2-oxopyrrolidin-1-yl)methyl)phenyl)-1H-pyrazol-5-yl)-3-(4-((2-((7-methyl-1H-indazol-5-yl)amino)pyrimidin-4-yl)oxy)naphthalen-1-yl)urea

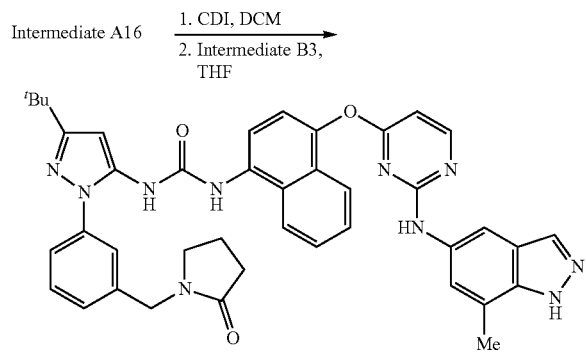

Example 10

To a solution of CDI (83 mg, 0.510 mmol) in DCM (1.0 mL) was added Intermediate A16 (118 mg, 0.510 mmol) and the reaction mixture heated to 40° C. for 1 hr. An aliquot of this solution (400 μL, 0.20 mmol) was added to a solution of Intermediate B3 (65 mg, 0.17 mmol) in THF (1.0 mL) and the reaction mixture was kept at RT for 18 hr. The resulting mixture was treated with CDI (83 mg, 0.51 mmol) and was heated to 40° C. for 3 hr and then cooled to RT. After a further 18 hr the reaction mixture was partitioned between EtOAc (30 mL) and saturated aq. NaHCO₃ (30 mL). The organic phase was separated and was washed with saturated aq. NaHCO₃ (30 mL), water (2×30 mL) and with brine (2×30 mL) and then dried and evaporated in vacuo. The residue was purified by flash column chromatography (SiO₂, 12 g, 0-10% [0.07 M NH₃ in MeOH] in DCM, gradient elution) and then by preparative HPLC to afford the title compound, Example 10, as a pale brown solid (27 mg, 21%); R$^t$ 2.24 min (Method 2, basic); m/z 721 (M+H)$^+$ (ES$^+$); $^1$H NMR δ: 1.30 (9H, s), 1.84 (2H, m), 2.25 (2H, t), 2.29 (3H, s), 3.29 (2H, t), 4.47 (2H, s), 6.46 (1H, s), 6.58 (1H, d), 7.02 (1H, br s), 7.29 (1H, d), 7.42 (1H, d), 7.46 (1H, s), 7.53-7.64 (6H, over-lapping m), 7.83 (1H, d), 8.07 (1H, d), 8.13 (1H, d), 8.38 (1H, d), 8.93 (1H, s), 9.19 (1H, s), 9.47 (1H, s), 12.86 (1H, br s).

Example 11

1-(3-(tert-Butyl)-1-(4-(2-morpholinoethoxy)phenyl)-1H-pyrazol-5-yl)-3-(4-((2-((2,3-dihydrobenzo[b][1,4]dioxin-6-yl)amino)pyrimidin-4-yl)oxy)naphthalen-1-yl)urea

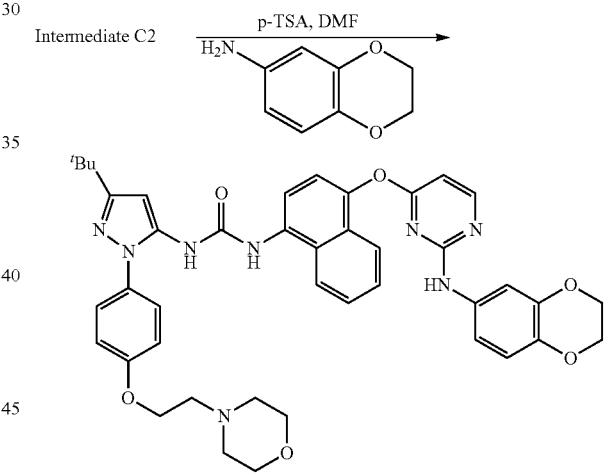

Example 11

To a suspension of Intermediate C2 (95 mg, 0.15 mmol) in THF (1.0 mL) was added p-TSA.H₂O (59 mg, 0.31 mmol) and 2,3-dihydrobenzo[b][1,4]dioxin-6-amine (30 μL, 0.24 mmol) and the resulting mixture heated at 60° C. for 16 hr and then cooled to RT. The resulting, unwanted precipitate was removed by filtration and the filtrate was evaporated in vacuo. The residue was purified by preparative HPLC to afford the title compound as a mixture of its formate and pTSA salts. This material was purified by SCX capture and release to furnish title compound Example 11, as a pale pink solid (10 mg, 9%); R$^t$ 2.11 min (Method 2, basic); m/z 757 (M+H)$^+$ (ES$^+$); m/z 755 (M−H)$^−$ (ES$^−$); $^1$H NMR δ: 1.28 (9H, s), 2.47-2.50 (4H, over-lapping m), 2.73 (2H, m), 3.57-3.59 (4H, over-lapping m), 4.10 (4H, br s), 4.15 (2H, m), 6.40 (1H, s), 6.45 (1H, m), 6.49 (1H, d), 6.74 (1H, br s), 6.95 (1H, br s), 7.12 (2H, m), 7.37 (1H, d), 7.47 (2H, m), 7.52-7.63 (2H, over-lapping m), 7.79 (1H, m), 7.92 (1H, d), 8.06 (1H, d), 8.33 (1H, d), 8.72 (1H, s), 9.11 (1H, s), 9.31 (1H, br s).

Example 12

1-(4-((2-((1H-Indazol-5-yl)amino)pyrimidin-4-yl)oxy)naphthalen-1-yl)-3-(3-(tert-butyl)-1-(4-(2-morpholinoethoxy)phenyl)-1H-pyrazol-5-yl)urea; Route 1

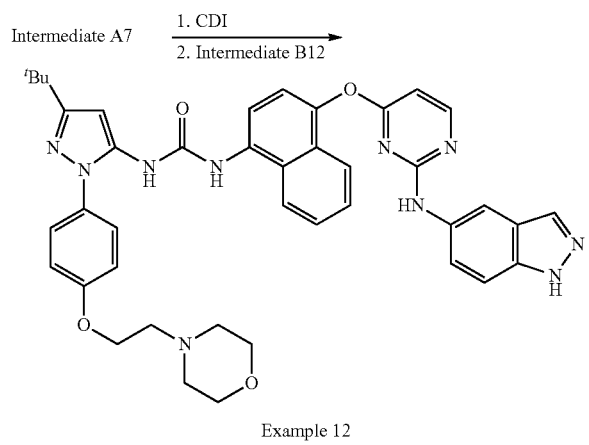

Example 12

To a solution of CDI (925 mg, 5.71 mmol) in DCM (12.0 mL) was added Intermediate A7, (2.01 g, 5.71 mmol) and the resulting mixture heated to 40° C. for 30 min and then cooled to RT for 4 hr. The resulting solution was added to a solution of Intermediate B12 (1.43 g, 3.80 mmol) in THF (15.0 mL) and the resulting mixture was maintained at RT for 1.5 hr. The reaction was quenched by the addition of methanol (10 mL) and the mixture was concentrated in vacuo to afford a purple/brown solid. The solid was taken up in a 1:1 mixture of MeOH/DCM, preloaded onto silica and purified by column chromatography (SiO$_2$, 120 g, 0-10% [1% NH$_3$ in MeOH] in DCM, gradient elution) to afford a crude product. This material was triturated with MeOH (10 mL) and the solid so obtained taken up in DMSO (approximately 100 mg/mL) and purified by preparative HPLC to yield the formate salt of the title compound as a beige solid (645 mg, 21%); R$^t$ 2.2 min, basic method; m/z 739 (M+H)$^+$ (ES$^+$).

The formate salt described above was combined with a second batch that was prepared on a similar scale in an identical manner. The combined material (1.09 g, 1.39 mmol) in a mixture of MeOH (40 mL), THF (8.0 mL) and AcOH (1.0 mL) was loaded by gravity onto SCX resin (20.00 g), prewashed with MeOH (200 mL). The resin was washed with MeOH (200 mL) and the product then eluted with 1% NH$_3$ in MeOH (300 mL). To recover more material the resin was stirred in DCM (50 mL) and 1% NH$_3$ in MeOH (100 mL), filtered and the combined ammoniacal washings concentrated in vacuo to yield the title compound, Example 12, as a white solid (934 mg, 89%); R$^t$ 2.16 min, basic method; m/z 739 (M+H)$^+$ (ES$^+$); $^1$H NMR δ: 1.29 (9H, s), 2.46-2.48 (4H, over-lapping m), 2.72 (2H, m), 3.59-3.65 (4H, over-lapping m), 4.15 (2H, m), 6.41 (1H, s), 6.58 (1H, d), 7.13 (2H, d), 7.24 (1H, s), 7.42 (1H, d), 7.49-7.62 (6H, over-lapping m), 7.83 (2H, d), 8.04 (1H, d), 8.11 (1H, d), 8.39 (1H, d), 8.80 (1H, s), 9.21 (1H, s), 9.53 (1H, s), 12.77 (1H, s).

Example 12

Route 2

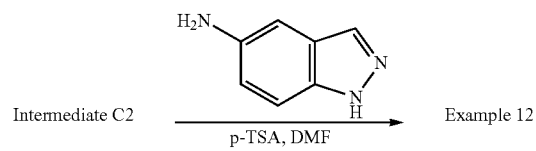

To a solution of Intermediate C2 (6.63 g, 10.32 mmol) in DMF (30 mL) was added p-TSA (3.93 g, 20.65 mmol) and 1H-indazol-5-amine (2.06 g, 15.49 mmol) and the resulting mixture heated at 65° C. for 5 hr and then cooled to RT and poured onto sat. aq. NaHCO$_3$ (100 mL). The mixture was extracted with EtOAc (2×150 mL) and the combined organic extracts were washed with brine (2×50 mL) and then dried and concentrated in vacuo to approximately ~50 mL. Upon standing for 20 hr a solid formed that was collected by filtration, taken up in a 1:1 mixture of MeOH/DCM, and then preloaded onto silica and purified by column chromatography (SiO$_2$, 80 g, 0-5% [1% NH$_3$ in MeOH] in DCM, gradient elution) to afford a crude product. The EtOAc filtrate was also purified by column chromatography (SiO$_2$, 80 g, 0-5% [1% NH$_3$ in MeOH] in DCM, gradient elution) to afford a second batch of product. Both batches of material were combined and subjected to further purification by column chromatography (SiO$_2$, 80 g, 0-5% [1% NH$_3$ in MeOH] in EtOAc, gradient elution) to provide the title compound, Example 12, as a light orange solid (2.46 g, 3.23 mmol, 31.3% yield).

Example 12

Route 3

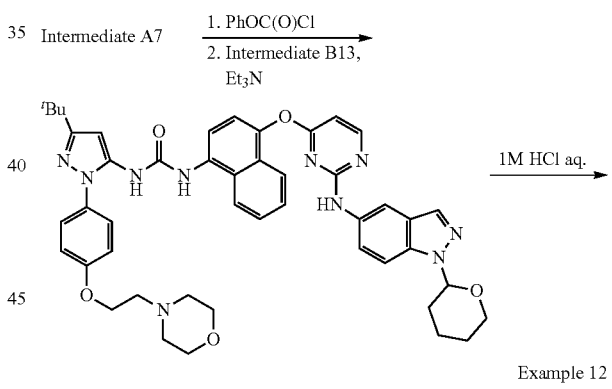

Example 12

Phenyl carbonochloridate (3.62 mL, 28.8 mmol) was added to a stirred suspension of Intermediate A7 (9.02 g, 26 mmol) in DCM (56 mL) and the resulting mixture stirred at RT for 1 hr and then partitioned between saturated aq. NaHCO$_3$ (150 mL) and DCM (100 mL). The organic layer was separated and dried and evaporated in vacuo to afford phenyl(3-(tert-butyl)-1-(4-(2-morpholinoethoxy)phenyl)-1H-pyrazol-5-yl)carbamate, as a foam, which was taken up into isopropyl acetate (200 mL). The resulting solution was added as a steady stream to a suspension of Intermediate B13 (9.5 g, 21 mmol) in isopropyl acetate (400 mL) and the mixture was treated with Et$_3$N (4.0 mL, 29 mmol) and then heated at 50° C. for 2 hr. The resulting mixture was cooled to RT for 2 hr to afford a precipitate in two crops. The solids were collected by filtration, washed with isopropyl acetate (250 mL) and dried in vacuo. The combined crops were purified by flash column chromatography (SiO$_2$, 330 g, 0-6% [0.07 M NH$_3$ in MeOH] in DCM, gradient elution).

The material so obtained was dissolved in DCM/MeOH (4:1 v/v, 150 mL) and ether was added until a precipitate was formed. The solid was collected by filtration, washed with a mixture of DCM, MeOH and Et$_2$O (40:5:55 v/v/v) and then dried in vacuo to afford 1-(3-(tert-butyl)-1-(4-(2-morpholinoethoxy)phenyl)-1H-pyrazol-5-yl)-3-(4-((2-((1-(tetrahydro-2H-pyran-2-yl)-1H-indazol-5-yl)amino)pyrimidin-4-yl)oxy)naphthalen-1-yl)urea, as a white solid (6.94 g, 39%). R$^t$ 2.94 min (Method 1, acidic); m/z 823 (M+H)$^+$ (ES$^+$); $^1$H NMR (400 MHz, DMSO-d$_6$) δ: 1.29 (9H, s), 1.45-1.67 (3H, over-lapping m), 1.86-1.96 (3H, over-lapping m), 2.33 (1H, m), 2.46-2.49 (4H, over-lapping m), 2.71 (2H, t), 3.56-3.58 (4H, over-lapping m), 3.65 (1H, m), 3.82 (1H, m), 4.14 (2H, t), 5.66 (1H, dd), 6.43 (1H, s), 6.64 (1H, d), 7.14 (2H, d), 7.27 (1H, m), 7.45-7.61 (8H, over-lapping m), 7.82 (1H, m), 8.07-8.14 (2H, over-lapping m), 8.41 (1H, d), 8.86 (1H, s), 9.25 (1H, s), 9.61 (1H, s). The filtrate and washings were evaporated in vacuo and the residue (1.73 g) was combined with a similar residue from a previous reaction (1.0 g) and triturated with MeOH to afford a second crop (1.55 g).

To a solution of the combined THP protected product obtained above (7.97 g, 9.68 mmol) in dioxane (500 mL) at 60° C. was added, drop-wise, a solution of hydrochloric acid (4 M in dioxane, 40 mL, 160 mmol) The reaction mixture was heated at 60° C. for 1 hr, during which time a white precipitate formed and was then treated with water (8 mL). After a further 2.5 hr at 60° C. an additional portion of water (8 mL) was added and the reaction mixture was heated to 65° C. for 1.5 hr and then was cooled to RT. The resulting mixture was diluted with sufficient water (2 L) to dissolve the precipitate. Saturated aq. NaHCO$_3$ (800 mL) was added and the resulting precipitate was collected by filtration, washed with copious quantities of water and dried in vacuo over CaCl$_2$. The material was then taken up into a mixture of DCM/MeOH (3×250 mL) and re-evaporated to remove residual dioxane to afford the title compound, Example 12, as a white solid (6.86 g, 95%).

Example 13

1-(4-((2-((1H-Indazol-5-yl)amino)pyrimidin-4-yl)oxy)naphthalen-1-yl)-3-(3-(tert-butyl)-1-(6-methoxypyridin-3-yl)-1H-pyrazol-5-yl)urea Intermediate A8 →(1. CDI / 2. Intermediate B12)→

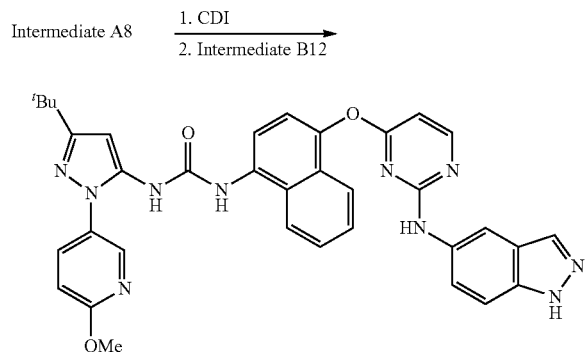

Example 13

To a solution of CDI (79 mg, 0.49 mmol) in DCM (1.2 mL) was added Intermediate A8 (120 mg, 0.489 mmol) and the reaction mixture maintained at RT for 18 hr. The resulting solution was added to a solution of Intermediate B12 (60 mg, 0.16 mmol) in THF (2.0 mL) and the reaction mixture was kept at RT for 24 hr and was then partitioned between EtOAc (10 mL) and water (10 mL). The organic phase was separated and was washed with saturated aq. NaHCO$_3$ (2×15 mL), water (2×15 mL) and brine (2×15 mL) and then dried and evaporated in vacuo. The residue was purified by flash column chromatography (SiO$_2$, 40 g, 0-100% EtOAc in isohexane, gradient elution) and then by preparative HPLC to furnish the title compound, Example 13, as a white solid (8 mg, 8%); R$^t$ 2.18 min (Method 2); m/z 641 (M+H)$^+$ (ES$^+$); $^1$H NMR δ: 1.29 (9H, s), 3.94 (3H, s), 6.45 (1H, s), 6.56 (1H, d), 7.03 (1H, d), 7.24 (2H, s), 7.42 (1H, d), 7.53-7.64 (4H, over-lapping m), 7.83 (1H, m), 7.93 (1H, dd), 8.02 (1H, d), 8.11 (1H, d), 8.38 (1H, d), 8.42 (1H, d), 8.92 (1H, s), 9.21 (1H, s), 9.52 (1H, s), 12.76 (1H, s).

Example 14

1-(4-((6-((1H-Indazol-5-yl)amino)pyrimidin-4-yl)oxy)naphthalen-1-yl)-3-(3-(tert-butyl)-1-(1-(2-hydroxyethyl)-6-oxo-1,6-dihydropyridin-3-yl)-1H-pyrazol-5-yl)urea Intermediate A15 →(1. CDI / 2. Intermediate B14)→

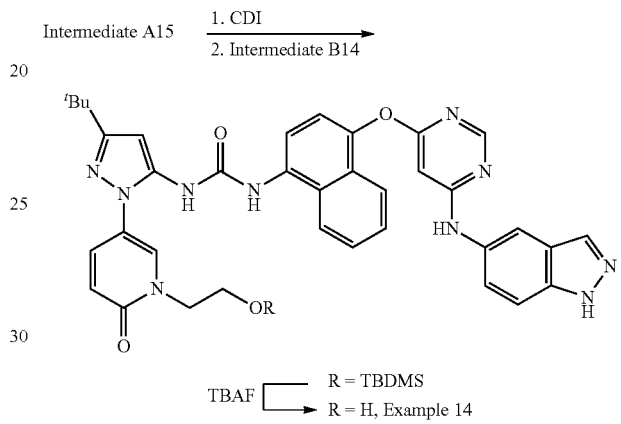

TBAF: R = TBDMS → R = H, Example 14

To a solution of CD (122 mg, 0.753 mmol) in DCM (2.0 mL) was added Intermediate A15 (284 mg, 0.726 mmol) and the reaction mixture heated to 40° C. for 4 hr. An aliquot of the resulting solution (1.0 mL, 0.36 mmol) was added to a solution of Intermediate B14 (108 mg, 0.294 mmol) in THF (1.5 mL) and the reaction mixture maintained at RT for 24 hr and then partitioned between EtOAc (50 mL) and saturated aq. NaHCO$_3$ (50 mL). The organic phase was separated and was washed with saturated aq. NaHCO$_3$ (50 mL), water (2×50 mL) and brine (2×50 mL) and then dried and evaporated in vacuo. The residue was purified by flash column chromatography (SiO$_2$, 12 g, 0-10% [0.07 M NH$_3$ in MeOH] in DCM, gradient elution) to afford 1-(4-((6-((1H-indazol-5-yl)amino)pyrimidin-4-yl)oxy)naphthalen-1-yl)-3-(3-(tert-butyl)-1-(1-(2-((tert-butyldimethylsilyl)oxy)ethyl)-6-oxo-1,6-dihydropyridin-3-yl)-1H-pyrazol-5-yl)urea as a pale pink solid (60 mg, 26%); R$^t$ 2.46 min (Method 2, basic); m/z 783 (M−H)$^−$ (ES$^−$).

To a suspension of the TBDMS protected intermediate described above (30 mg, 0.038 mmol) in THF (0.5 mL) was added a solution of TBAF (1 M in THF, 38 μL, 0.038 mmol) and the reaction mixture maintained at RT for 2 hr and then partitioned between DCM (10. mL) and saturated aq. NaHCO$_3$ (10 mL). The organic phase was separated and evaporated in vacuo and the residue was purified by SCX capture and release to afford the title compound, Example 14, as an off white solid (12 mg, 46%); R$^t$ 1.71 min (Method 2, basic); m/z 671 (M+H)$^+$ (ES$^+$); m/z 669 (M−H)$^−$ (ES); $^1$H NMR δ: 1.27 (9H, s), 3.70 (2H, m), 4.04 (2H, t), 4.93 (1H, t), 6.09 (1H, s), 6.38 (1H, s), 6.55 (1H, d), 7.35 (1H, d), 7.37 (1H, dd), 7.49 (1H, d), 7.56-7.67 (3H, over-lapping m), 7.83 (1H, dd), 7.91 (1H, d), 8.01-8.08 (4H, over-lapping m), 8.28 (1H, s), 8.80 (1H, br s), 9.02 (1H, br s), 9.51 (1H, br s), 12.97 (1H, br s)

Example 15

1-(4-((2-((1H-Indazol-5-yl)amino)pyrimidin-4-yl)oxy)naphthalen-1-yl)-3-(3-(tert-butyl)-1-(6-(2-morpholinoethoxy)pyridin-3-yl)-1H-pyrazol-5-yl)urea Intermediate A14 $\xrightarrow{\text{1. CDI}}_{\text{2. Intermediate B12}}$

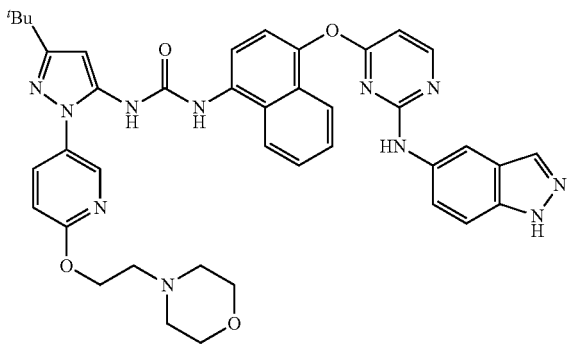

Example 15

To a solution of CDI (79 mg, 0.49 mmol) in DCM (1.5 mL) was added Intermediate A14 (176 mg, 0.489 mmol) and the reaction mixture kept at RT for 4 hr. A portion of this solution (0.75 mL, 0.25 mmol) was added to a solution of Intermediate B12 (60 mg, 0.163 mmol) in THF (1.5 mL) and the reaction mixture maintained at RT for 2.5 hr and then treated with a second aliquot of the CDI adduct (300 µL, 0.10 mmol). After 18 hr the reaction mixture was evaporated in vacuo and the residue was purified by flash column chromatography (SiO$_2$, 12 g, 0-100% [10% MeOH in EtOAc] in isohexane, gradient elution) to afford the title compound, Example 15, as a pale pink solid (45 mg, 37%); R$^t$ 1.79 min (Method 2, acidic); m/z 740 (M+H)$^+$ (ES$^+$); $^1$H NMR δ: 1.29 (9H, s), 2.45-2.48 (4H, over-lapping m), 2.72 (2H, t), 3.56-3.58 (4H, over-lapping m), 4.45 (2H, t), 6.45 (1H, s), 6.57 (1H, d), 7.02 (1H, d), 7.25 (2H, br s), 7.42 (1H, d), 7.54-7.64 (4H, over-lapping m), 7.83 (1H, m), 7.93 (1H, dd), 8.01 (1H, d), 8.10 (1H, d), 8.38-8.40 (2H, over-lapping m), 8.85 (1H, s), 9.16 (1H, s), 9.52 (1H, s), 12.77 (1H, s).

TABLE 3

Additional Compound Examples of the Invention

| Structure, Example No. and Name | Analytical Data [Generic Route] |
|---|---|
| 16: 1-(4-((2-((1H-indol-4-yl)amino)pyrimidin-4-yl)oxy)naphthalen-1-yl)-3-(3-(tert-butyl)-1-(p-tolyl)-1H-pyrazol-5-yl)urea. | R$^t$ 2.59 min (Method 2, acidic); m/z 623 (M + H)$^+$ (ES$^+$); $^1$H NMR δ: 1.29 (9H, s), 2.40 (3H, s), 6.42 (1H, s), 6.46 (1H, d), 6.59 (1H, t), 6.71 (1H, m), 6.92 (1H, d), 7.03 (1H, d), 7.15 (1H, t), 7.37-7.41 (3H, over-lapping m), 7.48 (2H, d), 7.56 (1H, dd), 7.62 (1H, dd), 7.84 (1H, d), 7.94 (1H, d), 8.10 (1H, d), 8.36 (1H, d), 8.82 (1H, s), 9.14 (1H, s), 9.19 (1H, s), 10.93 (1H, s). [Route 2] |
| 17: 1-(4-((2-((1H-indol-7-yl)amino)pyrimidin-4-yl)oxy)naphthalen-1-yl)-3-(3-(tert-butyl)-1-(p-tolyl)-1H-pyrazol-5-yl)urea. | R$^t$ 2.67 min (Method 2, acidic); m/z 623 (M + H)$^+$ (ES$^+$); $^1$H NMR δ: 1.29 (9H, s), 2.40 (3H, s), 6.35 (1H, dd), 6.42 (1H, s), 6.52 (1H, d), 6.58 (1H, br s), 7.11 (1H, d), 7.15 (1H, br s), 7.23 (1H, t), 7.37-7.41 (3H, over-lapping m), 7.48 (2H, d), 7.57 (1H, dd), 7.62 (1H, dd), 7.84 (1H, d), 7.93 (1H, d), 8.09 (1H, d), 8.36 (1H, d), 8.80 (1H, s), 9.18 (2H, over-lapping m), 10.87 (1H, s). [Route 2] |

TABLE 3-continued

Additional Compound Examples of the Invention

| Structure, Example No. and Name | Analytical Data [Generic Route] |
|---|---|
| 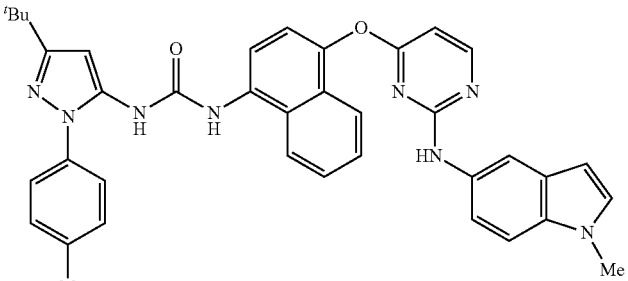<br>18: 1-(3-(tert-butyl)-1-(p-tolyl)-1H-pyrazol-5-yl)-3-(4-((2-((1-methyl-1H-indol-5-yl)amino)pyrimidin-4-yl)oxy)naphthalen-1-yl)urea. | $R^t$ 2.63 min (Method 2, acidic); m/z 637 (M + H)$^+$ (ES$^+$); $^1$H NMR δ: 1.29 (9H, s), 2.40 (3H, s), 3.67 (3H, s), 6.06 (1H, br s), 6.43 (1H, s), 6.48 (1H, d), 7.07-7.12 (3H, over-lapping m), 7.36-7.50 (6H, over-lapping m), 7.55 (1H, dd), 7.62 (1H, dd), 7.83 (1H, d), 8.00 (1H, d), 8.10 (1H, d), 8.34 (1H, d), 8.83 (1H, s), 9.18 (1H, s), 9.32 (1H, br s).<br>[Route 2] |
| 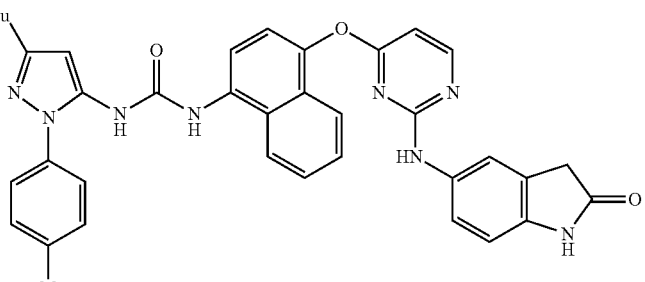<br>19: 1-(3-(tert-butyl)-1-(p-tolyl)-1H-pyrazol-5-yl)-3-(4-((2-((2-oxoindolin-5-yl)amino) pyrimidin-4-yl)oxy)naphthalen-1-yl)urea. | $R^t$ 2.28 min (Method 2, acidic); m/z 639 (M + H)$^+$ (ES$^+$); m/z 637 (M − H)$^-$ (ES$^-$); $^1$H NMR δ: 1.29 (9H, s), 2.40 (3H, s), 3.14 (2H, br s), 6.44 (1H, s), 6.49-6.53 (2H, over-lapping m), 7.12 (2H, br d), 7.37-7.39 (3H, over-lapping m), 7.48 (2H, m), 7.54-7.65 (2H, over-lapping m), 7.81 (1H, m), 7.99 (1H, d), 8.10 (1H, d), 8.34 (1H, d), 8.79 (1H, s), 9.15 (1H, s), 9.38 (1H, s), 10.12 (1H, s). [Route 1, CDI] |
| 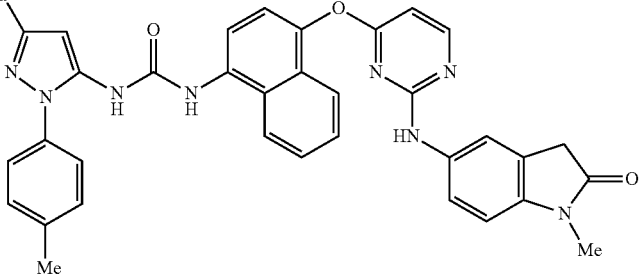<br>20: 1-(3-(tert-butyl)-1-(p-tolyl)-1H-pyrazol-5-yl)-3-(4-((2-((1-methyl-2-oxoindolin-5-yl) amino) pyrimidin-4-yl)oxy)naphthalen-1-yl)urea. | $R^t$ 2.41 min (Method 2 acidic); m/z 653 (M + H)$^+$ (ES$^+$); m/z 651 (M − H)$^-$ (ES$^-$); $^1$H NMR δ: 1.29 (9H, s), 2.40 (3H, s), 3.00 (3H, s), 3.23 (2H, br s), 6.43 (1H, s), 6.56 (1H, d), 6.66 (1H, d), 7.15 (2H, br s), 7.37-7.40 (3H, over-lapping m), 7.48 (2H, m), 7.55 (1H, m), 7.62 (1H, m), 7.81 (1H, m), 7.95 (1H, d), 8.09 (1H, d), 8.36 (1H, d), 8.79 (1H, s), 9.15 (1H, s), 9.45 (1H, br s).<br>[Route 2] |
| 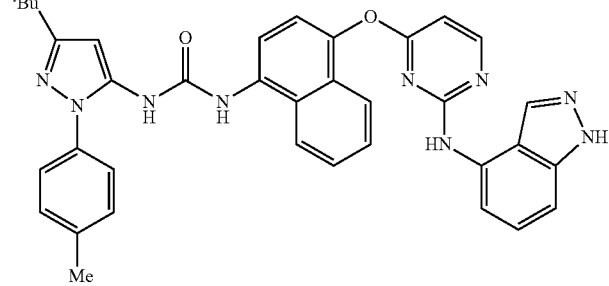<br>21: 1-(4-((2-(1H-indazol-4-yl)amino)pyrimidin-4-yl)oxy)naphthalen-1-yl)-3-(3-(tert-butyl)-1-(p-tolyl)-1H-pyrazol-5-yl)urea. | $R^t$ 2.51 min (Method 2 acidic); m/z 622 (M − H)$^-$ (ES$^-$); $^1$H NMR δ: 1.30 (9H, s), 2.39 (3H, s), 6.41 (1H, s), 6.59 (1H, s), 6.80 (1H, t), 6.96 (1H, d), 7.12 (1H, d), 7.37 (2H, d), 7.41 (1H, d), 7.48 (2H, d), 7.55 (1H, dd), 7.61 (1H, dd), 7.84 (1H, d), 7.94 (1H, d), 8.12 (1H, d), 8.36 (1H, s), 8.43 (1H, d), 9.00 (1H, s), 9.36 (1H, s), 9.73 (1H, s), 12.85 (1H, s).<br>[Route 2] |

TABLE 3-continued

Additional Compound Examples of the Invention

| Structure, Example No. and Name | Analytical Data [Generic Route] |
|---|---|
| 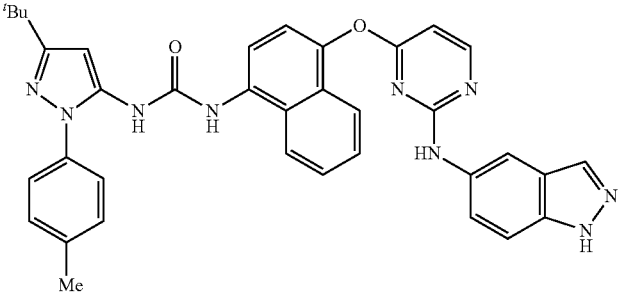<br>22: 1-(4-((2-(1H-indazol-5-yl)amino)pyrimidin-4-yl)oxy)naphthalen-1-yl)-3-(3-(tert-butyl)-1-(p-tolyl)-1H-pyrazol-5-yl)urea. | $R^t$ 2.41 min (Method 2 acidic); m/z 622 (M − H)⁻ (ES⁻); ¹H NMR δ: 1.29 (9H, s), 2.39 (3H, s), 6.43 (1H, s), 6.58 (1H, d), 7.25 (2H, br s), 7.38 (2H, d), 7.42 (1H, d), 7.50 (2H, d), 7.51-7.65 (4H, over-lapping m), 7.83 (1H, d), 8.04 (1H, d), 8.15 (1H, d), 8.39 (1H, d), 9.01 (1H, s), 9.36 (1H, s), 9.52 (1H, s), 12.78 (1H, s).<br>[Route 2] |
| 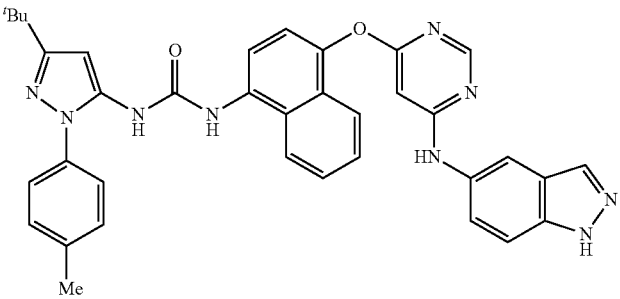<br>23: 1-(4-((6-(1H-indazol-5-yl)amino)pyrimidin-4-yl)oxy)naphthalen-1-yl)-3-(3-(tert-butyl)-1-(p-tolyl)-1H-pyrazol-5-yl)urea. | $R^t$ 2.21 min (Method 2 acidic); m/z 624 (M + H)⁺ (ES⁺); ¹H NMR δ: 1.29 (9H, s), 2.41 (3H, s), 6.08 (1H, d), 6.42 (1H, s), 7.34-7.40 (4H, over-lapping m), 7.46-7.48 (3H, over-lapping m), 7.57-7.64 (2H, over-lapping m), 7.82 (1H, m), 7.91 (1H, d), 8.01-8.08 (3H, over-lapping m), 8.29 (1H, s), 8.76 (1H, br s), 9.10 (1H, br s), 9.51 (1H, br s), 12.98 (1H, br s).<br>[Route 1, CDI] |
| 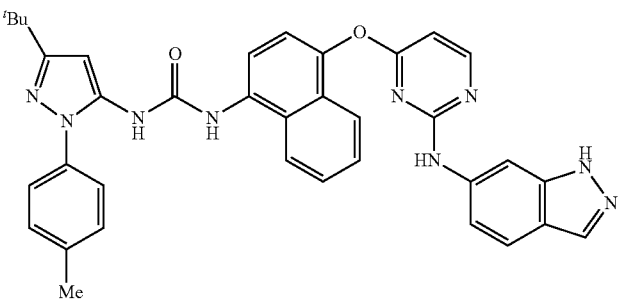<br>24: 1-(4-((2-(1H-indazol-6-yl)amino)pyrimidin-4-yl)oxy)naphthalen-1-yl)-3-(3-(tert-butyl)-1-(p-tolyl)-1H-pyrazol-5-yl)urea. | $R^t$ 2.67 min (Method 2 acidic); m/z 624 (M + H)⁺ (ES⁺); ¹H NMR δ: 1.30 (9H, s), 2.40 (3H, s), 6.51 (1H, s), 6.55 (1H, d), 7.11 (1H, d), 7.38-7.49 (5H, over-lapping m), 7.57 (1H, dd), 7.63 (1H, dd), 7.82-7.85 (2H, over-lapping m), 7.92 (2H, over-lapping m), 7.93 (1H, br s), 8.06 (1H, d), 8.43 (1H, d), 8.82 (1H, s), 9.18 (1H, s), 9.71 (1H, s), 12.57 (1H, s).<br>[Route 2] |
| 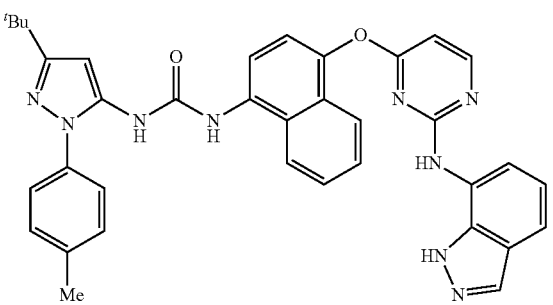<br>25: 1-(4-((2-(1H-indazol-7-yl)amino)pyrimidin-4-yl)oxy)naphthalen-1-yl)-3-(3-(tert-butyl)-1-(p-tolyl)-1H-pyrazol-5-yl)urea. | $R^t$ 2.57 min (Method 2 acidic); m/z 624 (M + H)⁺ (ES⁺); ¹H NMR δ: 1.29 (9H, s), 2.40 (3H, s), 6.41 (1H, s), 6.60 (1H, d), 6.68 (1H, br s), 7.28 (1H, d), 7.37-7.41 (4H, over-lapping m), 7.48 (2H, d), 7.56 (1H, dd), 7.62 (1H, dd), 7.84 (1H, d), 7.92 (1H, d), 7.98 (1H, s), 8.10 (1H, d), 8.42 (1H, d), 8.84 (1H, br s), 9.22 (1H, br s), 9.38 (1H, s), 12.73 (1H, s).<br>[Route 2] |

TABLE 3-continued

Additional Compound Examples of the Invention

| Structure, Example No. and Name | Analytical Data [Generic Route] |
|---|---|
| 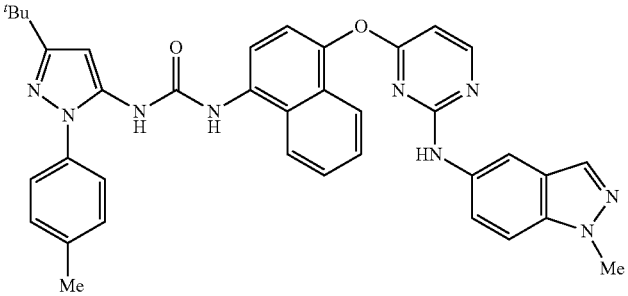<br>26: 1-(3-(tert-butyl)-1-(p-tolyl)-1H-pyrazol-5-yl)-3-(4-((2-((1-methyl-1H-indazol-5-yl)amino)pyrimidin-4-yl)oxy)naphthalen-1-yl)urea. | $R^t$ 2.45 min (Method 2 acidic); m/z 638 $(M + H)^+$ $(ES^+)$; $^1H$ NMR δ: 1.29 (9H, s), 2.40 (3H, s) 3.91 (3H, s), 6.45 (1H, s), 6.61 (1H, d), 7.22 (1H, br s), 7.34 (1H, d), 7.40-7.43 (3H, over-lapping m), 7.50 (2H, m), 7.55 (2H, m), 7.62 (2H, m), 7.82 (1H, dd), 8.05 (1H, d), 8.12 (1H, d), 8.40 (1H, d), 8.85 (1H, br s), 9.22 (1H, br s), 9.57 (1H, br s).<br>[Route 1, CDI] |
| 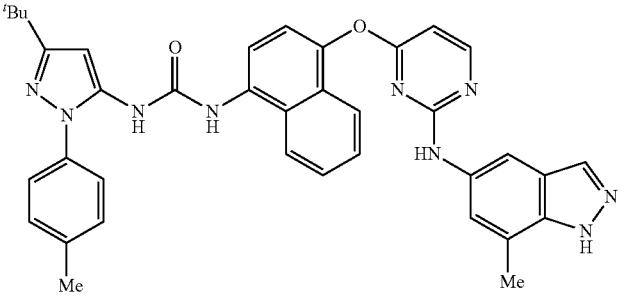<br>27: 1-(3-(tert-butyl)-1-(p-tolyl)-1H-pyrazol-5-yl)-3-(4-((2-((7-methyl-1H-indazol-5-yl)amino)pyrimidin-4-yl)oxy)naphthalen-1-yl)urea. | $R^t$ 2.36 min (Method 2 acidic); m/z 638 $(M + H)^+$ $(ES^+)$; $^1H$ NMR δ: 1.30 (9H, s), 2.29 (3H, s), 2.40 (3H, s), 6.44 (1H, s), 6.57 (1H, d), 7.02 (1H, br s), 7.39-7.43 (3H, over-lapping m), 7.48-7.64 (6H, over-lapping m), 7.83 (1H, d), 8.07 (1H, d), 8.13 (1H, d), 8.38 (1H, d), 8.85 (1H, s), 9.20 (1H, s), 9.44 (1H, br s), 12.84 (1H, s).<br>[Route 1, CDI] |
| 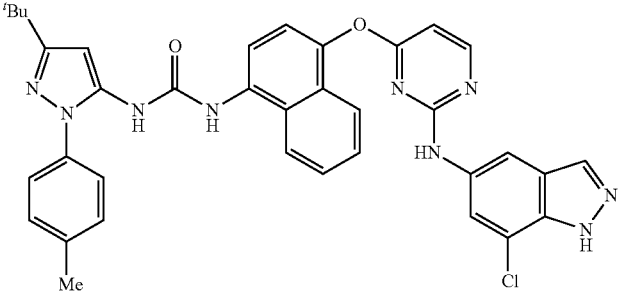<br>28: 1-(3-(tert-butyl)-1-(p-tolyl)-1H-pyrazol-5-yl)-3-(4-((2-((7-chloro-1H-indazol-5-yl)amino)pyrimidin-4-yl)oxy)naphthalen-1-yl)urea. | $R^t$ 2.62 min (Method 2 acidic); m/z 658 $(M + H)^+$ $(ES^+)$; $^1H$ NMR δ: 1.29 (9H, s), 2.40 (3H, s), 6.44 (1H, s), 6.64 (1H, d), 7.38-7.44 (4H, over-lapping m), 7.48-7.50 (2H, over-lapping m), 7.52-7.62 (3H, over-lapping m), 7.75 (1H, m), 7.82 (1H, m), 8.05 (1H, m), 8.12 (1H, m), 8.43 (1H, d), 8.83 (1H, br s), 9.20 (1H, br s), 9.65 (1H, br s), 13.29 (1H, br s).<br>[Route 2] |
| 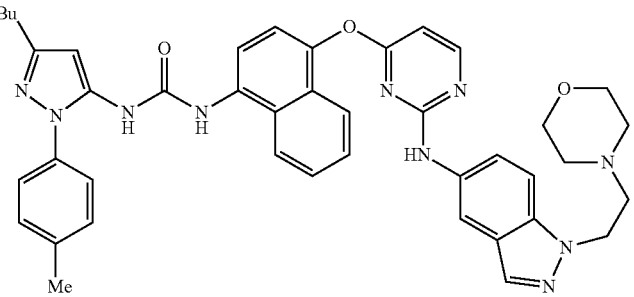<br>29: 1-(3-(tert-butyl)-1-(p-tolyl)-1H-pyrazol-5-yl)-3-(4-((2-((1-(2-morpholinoethyl)-1H-indazol-5-yl)amino)pyrimidin-4-yl)oxy)naphthalen-1-yl)urea. | $R^t$ 1.94 min (Method 2 acidic); m/z 737 $(M + H)^+$ $(ES^+)$; $^1H$ NMR δ: 1.30 (9H, s), 2.35-2.37 (4H, over-lapping m), 2.40 (3H, s), 2.66 (2H, t), 3.43-3.45 (4H, over-lapping m), 4.37 (2H, t), 6.45 (1H, s), 6.60 (1H, d), 7.25 (1H, m), 7.34-7.44 (4H, over-lapping m), 7.51-7.63 (6H, over-lapping m), 7.81 (1H, m), 8.05 (1H, d), 8.13 (1H, d), 8.39 (1H, d), 8.87 (1H, br s), 9.23 (1H, br s), 9.54 (1H, br s).<br>[Route 1, CDI] |

TABLE 3-continued

Additional Compound Examples of the Invention

| Structure, Example No. and Name | Analytical Data [Generic Route] |
|---|---|
| 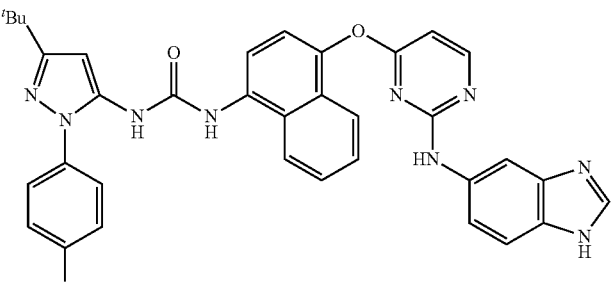<br>30: 1-(4-((2-(1H-benzo[d]imidazol-5-yl)amino)pyrimidin-4-yl)oxy)naphthalen-1-yl)-3-(3-(tert-butyl)-1-(p-tolyl)-1H-pyrazol-5-yl)urea. | $R^t$ 1.83 min (Method 2 acidic); m/z 624 (M + H)$^+$ (ES$^+$); $^1$H NMR δ: 1.29 (9H, s), 2.40 (3H, s), 6.44 (1H, s), 6.49 (1H, br s), 7.15-7.27 (2H, over-lapping m), 7.38 (2H, d), 7.43 (1H, d), 7.48 (2H, d), 7.57 (1H, dd), 7.62 (1H, dd), 7.83 (2H, over-lapping m), 7.91 (1H, d), 7.95 (1H, br s), 8.06 (1H, d), 8.38 (1H, d), 8.84 (1H, s), 9.18 (1H, br s), 9.45 (1H, br s), 12.10 (1H, br s).<br>[Route 2] |
| 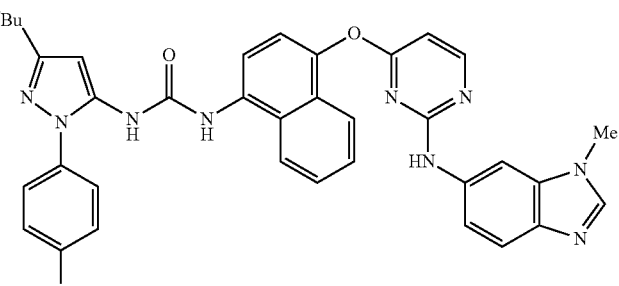<br>31: 1-(3-(tert-butyl)-1-(p-tolyl)-1H-pyrazol-5-yl)-3-(4-((2-((1-methyl-1H-benzo[d]imidazol-6-yl)amino)pyrimidin-4-yl)oxy)naphthalen-1-yl)urea. | $R^t$ 1.83 min (Method 2 acidic); m/z 638 (M + H)$^+$ (ES$^+$); $^1$H NMR δ: 1.29 (9H, s), 2.40 (3H, s), 3.41 (3H, br s), 6.43 (1H, s), 6.58 (1H, d), 7.13 (1H, br d), 7.30 (1H, d), 7.39 (2H, d), 7.43 (1H, d), 7.48 (2H, d), 7.57 (1H, dd), 7.61-7.65 (2H, over-lapping m), 7.84 (1H, d), 7.95 (1H, s), 7.98 (1H, d), 8.08 (1H, d), 8.41 (1H, d), 8.86 (1H, s), 9.19 (1H, s), 9.63 (1H, s).<br>[Route 2] |
| 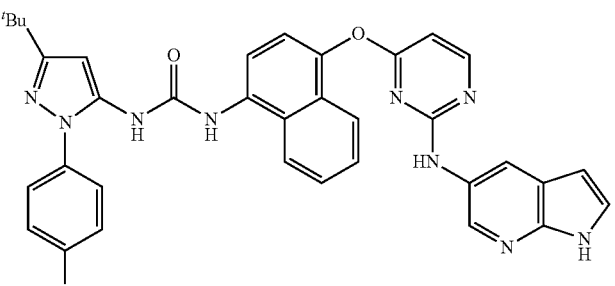<br>32: 1-(4-((2-((1H-pyrrolo[2,3-b]pyridin-5-yl)amino)pyrimidin-4-yl)oxy)naphthalen-1-yl)-3-(3-(tert-butyl)-1-(p-tolyl)-1H-pyrazol-5-yl)urea. | $R^t$ 2.24 min (Method 2 acidic); m/z 624 (M + H)$^+$ (ES$^+$); m/z 622 (M − H)$^-$ (ES$^-$); $^1$H NMR δ: 1.29 (9H, s), 2.40 (3H, s), 6.11 (1H, br s), 6.42 (1H, s), 6.53 (1H, d), 7.27 (1H, br s), 7.37-7.43 (3H, over-lapping m), 7.48 (2H, m), 7.54-7.65 (2H, over-lapping m), 7.83-7.91 (2H, over-lapping m), 8.01 (1H, br d), 8.10 (1H, d), 8.15 (1H, br s), 8.36 (1H, d), 8.81 (1H, s), 9.15 (1H, s), 9.47 (1H, br s), 11.36 (1H, s).<br>[Route 2] |
| 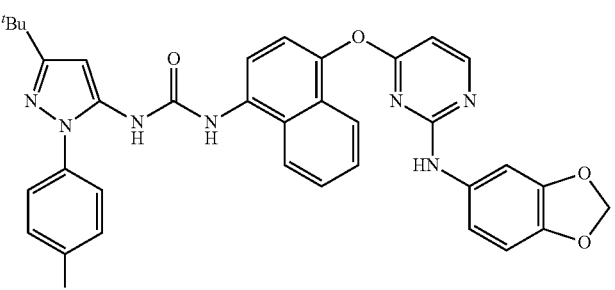<br>33: 1-(4-((2-((benzo[d][1,3]dioxol-5-ylamino)pyrimidin-4-yl)oxy)naphthalen-1-yl)-3-(3-(tert-butyl)-1-(p-tolyl)-1H-pyrazol-5-yl)urea. | $R^t$ 2.61 min (Method 2 acidic); m/z 628 (M + H)$^+$ (ES$^+$); $^1$H NMR δ: 1.29 (9H, s), 2.39 (3H, s), 5.86 (2H, s), 6.42 (1H, s), 6.52 (1H, d), 6.56 (1H, m), 6.77 (1H, m), 6.99 (1H, m), 7.37-7.39 (3H, over-lapping m), 7.48 (2H, m), 7.54-7.64 (2H, over-lapping m), 7.79 (1H, m), 7.92 (1H, d), 8.07 (1H, d), 8.35 (1H, d), 8.83 (1H, s), 9.15 (1H, s), 9.38 (1H, br s).<br>[Route 2] |

TABLE 3-continued

Additional Compound Examples of the Invention

| Structure, Example No. and Name | Analytical Data [Generic Route] |
|---|---|
| 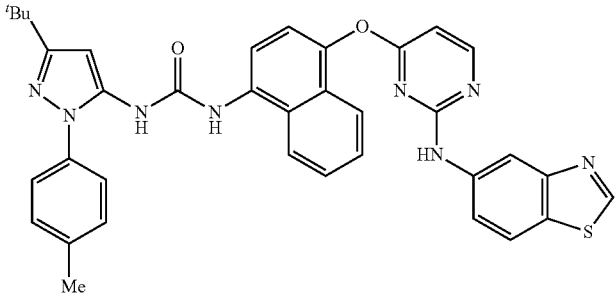<br>34: 1-(4-((2-((benzo[d]thiazol-5-ylamino)pyrimidin-4-yl)oxy)naphthalen-1-yl)-3-(3-(tert-butyl)-1-(p-tolyl)-1H-pyrazol-5-yl)urea. | $R^t$ 2.66 min (Method 2 acidic); m/z 641 $(M + H)^+$ $(ES^+)$; $^1$H NMR δ: 1.29 (9H, s), 2.39 (3H, s), 6.42 (1H, s), 6.58 (1H, d), 7.37 (2H, d), 7.42 (1H, d), 7.48 (2H, d), 7.52 (1H, br d), 7.56 (1H, dd), 7.62 (1H, dd), 7.78 (1H, br d), 7.83 (1H, d), 7.91 (1H, d), 8.08 (1H, d), 8.29 (1H, br s), 8.45 (1H, d), 8.88 (1H, s), 9.20 (1H, s), 9.25 (1H, s), 9.77 (1H, s).<br>[Route 2] |
| 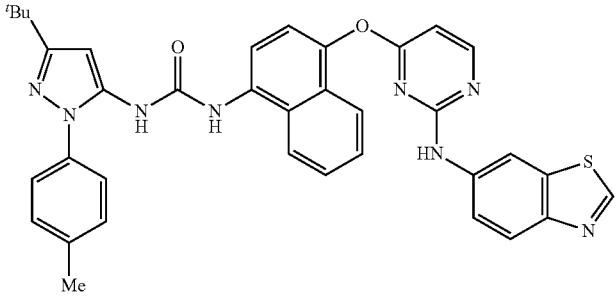<br>35: 1-(4-((2-((benzo[d]thiazol-6-ylamino)pyrimidin-4-yl)oxy)naphthalen-1-yl)-3-(3-(tert-butyl)-1-(p-tolyl)-1H-pyrazol-5-yl)urea. | $R^t$ 2.53 min (Method 2 acidic); m/z 641 $(M + H)^+$ $(ES^+)$; $^1$H NMR δ: 1.29 (9H, s), 2.39 (3H, s), 6.43 (1H, s), 6.70 (1H, d), 7.36-7.39 (3H, over-lapping m), 7.43 (1H, d), 7.50 (2H, d), 7.55 (1H, dd), 7.62 (1H, dd), 7.74 (1H, d), 7.81 (1H, d), 7.97 (1H, br s), 8.04 (1H, d), 8.16 (1H, d), 8.46 (1H, d), 8.99 (1H, s), 9.08 (1H, s), 9.33 (1H, s), 9.90 (1H, s).<br>[Route 2] |
| 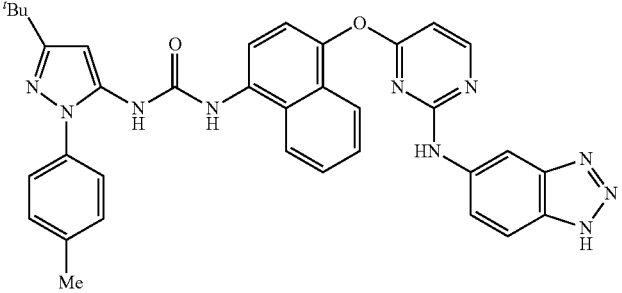<br>36: 1-(4-((2-((1H-benzo[d][1,2,3]triazol-5-yl)amino)pyrimidin-4-yl)oxy)naphthalen-1-yl)-3-(3-(tert-butyl)-1-(p-tolyl)-1H-pyrazol-5-yl)urea. | $R^t$ 2.53 min (Method 2, acidic); m/z 625 $(M + H)^+$ $(ES^+)$; $^1$H NMR δ: 1.30 (9H, s), 2.40 (3H, s), 6.48 (1H, s), 6.60 (1H, d), 7.36-7.39 (3H, over-lapping m), 7.45 (1H, d), 7.49 (2H, d), 7.56 (1H, dd), 7.60-7.66 (2H, over-lapping m), 7.84 (1H, d), 7.91 (1H, d), 8.07-8.10 (2H, over-lapping m), 8.45 (1H, d), 8.97 (1H, s), 9.31 (1H, s), 9.83 (1H, s), 15.13 (1H, br s).<br>[Route 2] |
| 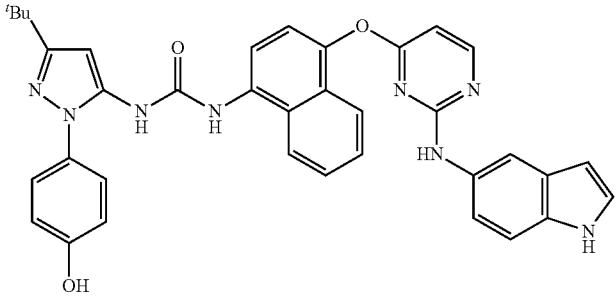<br>37: 1-(4-((2-((1H-indol-5-yl)amino)pyrimidin-4-yl)oxy)naphthalen-1-yl)-3-(3-(tert-butyl)-1-(4-hydroxyphenyl)-1H-pyrazol-5-yl)urea. | $R^t$ 2.11 min (Method 2, acidic); m/z 625 $(M + H)^+$ $(ES^+)$; $^1$H NMR δ: 1.28 (9H, s), 6.09 (1H, s), 6.39 (1H, s), 6.46 (1H, d), 6.94 (2H, m), 7.04-7.07 (2H, over-lapping m), 7.15 (1H, s), 7.35 (2H, m), 7.40 (1H, d), 7.54-7.64 (3H, over-lapping m), 7.82 (1H, dd), 8.01 (1H, d), 8.10 (1H, d), 8.33 (1H, d), 8.77 (1H, s), 9.20 (1H, s), 9.26 (1H, br s), 9.84 (1H, br s), 10.79 (1H, s).<br>[Route 1, CDI, then TBAF deprotection] |

TABLE 3-continued

Additional Compound Examples of the Invention

| Structure, Example No. and Name | Analytical Data [Generic Route] |
|---|---|
| 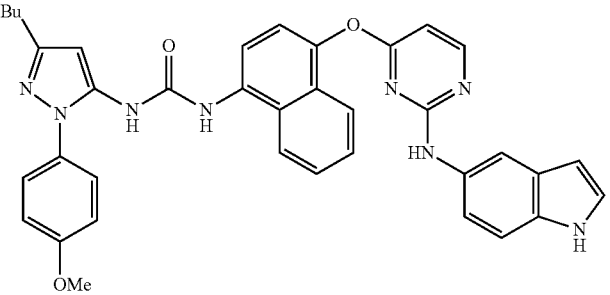<br>38: 1-(4-((2-((1H-indol-5-yl)amino)pyrimidin-4-yl)oxy)naphthalen-1-yl)-3-(3-(tert-butyl)-1-(4-methoxyphenyl)-1H-pyrazol-5-yl)urea. | $R^t$ 2.32 min (Method 2, acidic); m/z 639 (M + H)$^+$ (ES$^+$); $^1$H NMR δ: 1.29 (9H, s), 3.83 (3H, s), 6.09 (1H, br s), 6.41 (1H, s), 6.45 (1H, d), 7.02-7.15 (5H, over-lapping m), 7.41 (1H, d), 7.49-7.62 (5H, over-lapping m), 7.84 (1H, dd), 8.01 (1H, d), 8.10 (1H, d), 8.33 (1H, d), 8.80 (1H, s), 9.17 (1H, s), 9.27 (1H, br s), 10.79 (1H, s).<br>[Route 1, CDI] |
| 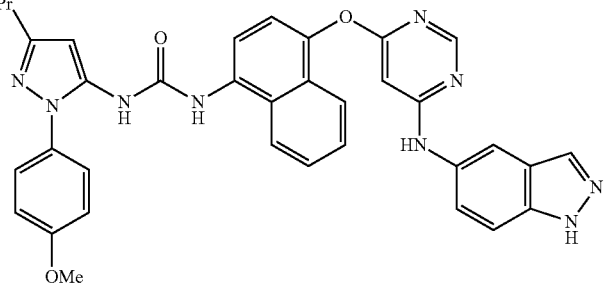<br>39: 1-(4-((6-((1H-indazol-5-yl)amino)pyrimidin-4-yl)oxy)naphthalen-1-yl)-3-(3-isopropyl-1-(4-methoxyphenyl)-1H-pyrazol-5-yl)urea. | $R^t$ 1.99 min (Method 2, basic); m/z 626 (M + H)$^+$ (ES$^+$); m/z 624 (M − H)$^−$ (ES$^−$); $^1$H NMR δ: 1.24 (6H, d), 2.89 (1H, m), 3.84 (3H, s), 6.08 (1H, d), 6.35 (1H, s), 7.12 (2H, m), 7.34 (1H, d), 7.36 (1H, dd), 7.46-7.49 (3H, over-lapping m), 7.56-7.63 (2H, over-lapping m), 7.82 (1H, dd), 7.90 (1H, d), 8.01-8.06 (3H, over-lapping m), 8.28 (1H, s), 8.72 (1H, br s), 9.09 (1H, br s), 9.50 (1H, br s), 12.97 (1H, br s).<br>[Route 1, phenyl chloroformate] |
| 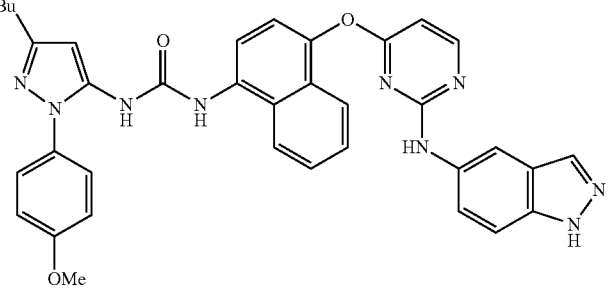<br>40: 1-(4-((2-((1H-indazol-5-yl)amino)pyrimidin-4-yl)oxy)naphthalen-1-yl)-3-(3-(tert-butyl)-1-(4-methoxyphenyl)-1H-pyrazol-5-yl)urea. | $R^t$ 2.98 min (Method 2, acidic); m/z 640 (M + H)$^+$ (ES$^+$); $^1$H NMR δ: 1.29 (9H, s), 3.84 (3H, s), 6.42 (1H, s), 6.58 (1H, d), 7.14 (2H, m), 7.24 (2H, br s), 7.43 (1H, d), 7.50-7.64 (6H, over-lapping m), 7.83 (1H, dd), 8.07 (1H, d), 8.12 (1H, d), 8.39 (1H, d), 8.79 (1H, s), 9.20 (1H, s), 9.53 (1H, s), 12.77 (1H, s).<br>[Route 1, CDI] |
| 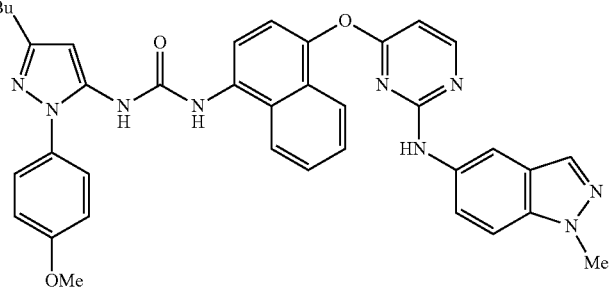<br>41: 1-(3-(tert-butyl)-1-(4-methoxyphenyl)-1H-pyrazol-5-yl)-3-(4-((2-((1-methyl-1H-indazol-5-yl)amino)pyrimidin-4-yl)oxy)naphthalen-1-yl)urea. | $R^t$ 2.33 min (Method 2, acidic); m/z 654 (M + H)$^+$ (ES$^+$); $^1$H NMR δ: 1.29 (9H, s), 3.84 (3H, s), 3.91 (3H, s), 6.43 (1H, s), 6.61 (1H, d), 7.14 (2H, m), 7.26 (1H, br d), 7.36 (1H, d), 7.42 (1H, d), 7.50-7.62 (6H, over-lapping m), 7.81 (1H, dd), 8.05 (1H, d), 8.11 (1H, d), 8.40 (1H, d), 8.80 (1H, s), 9.21 (1H, s), 9.57 (1H, br s).<br>[Route 1, CDI] |

TABLE 3-continued

Additional Compound Examples of the Invention

| Structure, Example No. and Name | Analytical Data [Generic Route] |
|---|---|
| 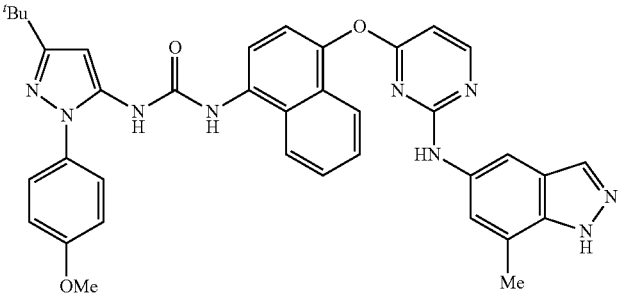<br>42 1-(3-(tert-butyl)-1-(4-methoxyphenyl)-1H-pyrazol-5-yl)-3-(4-((2-((7-methyl-1H-indazol-5-yl)amino)pyrimidin-4-yl)oxy)naphthalen-1-yl)urea. | $R^t$ 2.75 min (Method 2, acidic); m/z 654 (M + H)$^+$ (ES$^+$); $^1$H NMR δ: 1.29 (9H, s), 2.29 (3H, s), 3.84 (3H, s), 6.42 (1H, s), 6.57 (1H, d), 7.02 (1H, br s), 7.14 (2H, m), 7.42 (1H, d), 7.51-7.61 (6H, over-lapping m), 7.82 (1H, d), 8.07 (1H, s), 8.12 (1H, d), 8.38 (1H, d), 8.82 (1H, s), 9.21 (1H, s), 9.44 (1H, br s), 12.84 (1H, s).<br>[Route 1, CDI] |
| 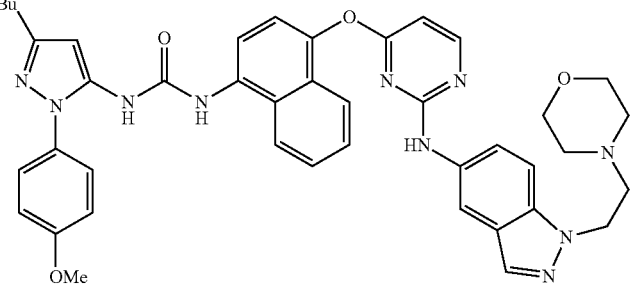<br>43: 1-(3-(tert-butyl)-1-(4-methoxyphenyl)-1H-pyrazol-5-yl)-3-(4-((2-((1-(2-morpholinoethyl)-1H-indazol-5-yl)amino)pyrimidin-4-yl)oxy)naphthalen-1-yl)urea. | $R^t$ 1.82 min (Method 2, acidic); m/z 753 (M + H)$^+$ (ES$^+$); $^1$H NMR δ: 1.29 (9H, s), 2.33-2.35 (4H, over-lapping m), 2.66 (2H, t), 3.43-3.45 (4H, over-lapping m), 3.83 (3H, s), 4.37 (2H, t), 6.43 (1H, s), 6.60 (1H, d), 7.15 (2H, m), 7.26 (1H, m), 7.37 (1H, m), 7.43 (1H, d), 7.50-7.63 (6H, over-lapping m), 7.82 (1H, m), 8.05 (1H, d), 8.12 (1H, d), 8.39 (1H, d), 8.83 (1H, br s), 9.24 (1H, br s), 9.55 (1H, br s).<br>[Route 1, CDI] |
| 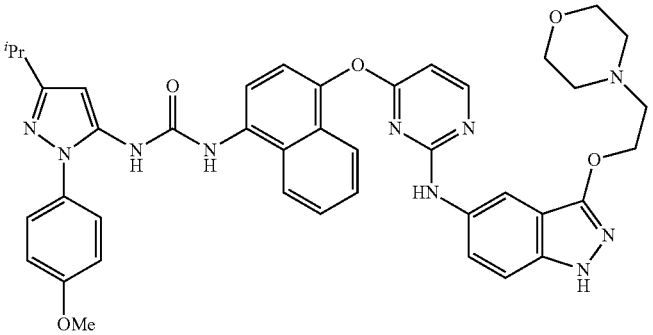<br>44: 1-(3-isopropyl-1-(4-methoxyphenyl)-1H-pyrazol-5-yl)-3-(4-((2-((3-(2-morpholinoethoxy)-1H-indazol-5-yl)amino)pyrimidin-4-yl)oxy)naphthalen-1-yl)urea. | $R^t$ 1.73 min (Method 2, acidic); m/z 755 (M + H)$^+$ (ES$^+$); $^1$H NMR δ: 1.24 (6H, d), 2.48-2.51 (4H, over-lapping m), 2.75 (2H, m), 2.90 (1H, t), 3.55-3.57 (4H, over-lapping m), 3.85 (3H, s), 4.40 (2H, t), 6.36 (1H, s), 6.43 (1H, d), 7.06-7.15 (3H, over-lapping m), 7.38-7.43 (2H, over-lapping m), 7.49 (2H, m), 7.56-7.65 (2H, over-lapping m), 7.83-7.85 (2H, over-lapping m), 7.94 (1H, m), 8.06 (1H, m), 8.37 (1H, d), 8.72 (1H, br s), 9.10 (1H, br s), 9.42 (1H, br s), 11.67 (1H, br s).<br>[Route 1, phenyl chloroformate] |

TABLE 3-continued

Additional Compound Examples of the Invention

| Structure, Example No. and Name | Analytical Data [Generic Route] |
|---|---|
| 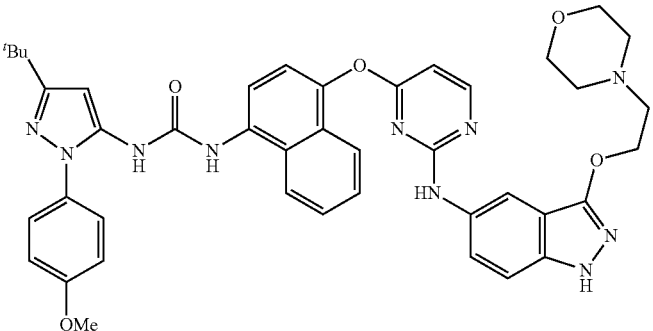<br>45: 1-(3-(tert-butyl)-1-(4-methoxyphenyl)-1H-pyrazol-5-yl)-3-(4-((2-((3-(2-morpholinoethoxy)-1H-indazol-5-yl)amino)pyrimidin-4-yl)oxy)naphthalen-1-yl)urea. | $R^t$ 1.82 min (Method 2, acidic); m/z 769 (M + H)$^+$ (ES$^+$); $^1$H NMR δ: 1.29 (9H, s), 2.48-2.51 (4H, over-lapping m), 2.75 (2H, t), 3.55-3.56 (4H, over-lapping m), 3.84 (3H, s), 4.40 (2H, t), 6.41 (1H, s), 6.43 (1H, d), 7.07-7.14 (3H, over-lapping m), 7.37-7.43 (2H, over-lapping m), 7.49 (2H, m), 7.56-7.64 (2H, over-lapping m), 7.82-7.85 (2H, over-lapping m), 7.95 (1H, d), 8.08 (1H, d), 8.37 (1H, d), 8.78 (1H, br s), 9.16 (1H, br s), 9.44 (1H, br s), 11.70 (1H, br s). [Route 1, phenyl chloroformate] |
| 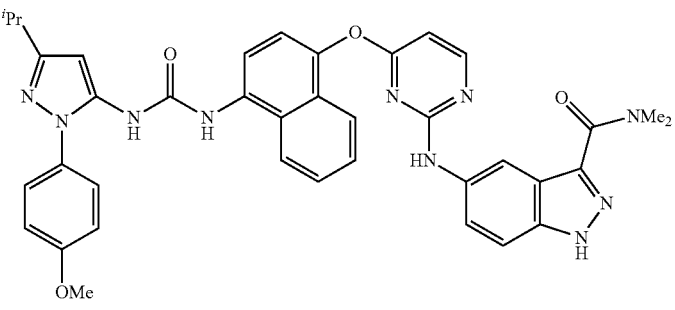<br>46: 5-((4-((4-(3-(3-isopropyl-1-(4-methoxyphenyl)-1H-pyrazol-5-yl)ureido)naphthalen-1-yl)oxy)pyrimidin-2-yl)amino)-N,N-dimethyl-1H-indazole-3-carboxamide. | $R^t$ 2.13 min (Method 2, acidic); m/z 697 (M + H)$^+$ (ES$^+$); $^1$H NMR δ: 1.24 (6H, d), 2.89 (1H, m), 3.05 (3H, s), 3.32 (3H, s), 3.84 (3H, s), 6.36 (1H, s), 6.45 (1H, d), 7.12 (2H, m), 7.30 (1H, d), 7.42 (1H, d), 7.45-7.49 (3H, over-lapping m), 7.55-7.65 (2H, over-lapping m), 7.84 (1H, m), 7.91 (1H, d), 8.05 (1H, d), 8.20 (1H, br s), 8.36 (1H, d), 8.72 (1H, s), 9.09 (1H, s), 9.51 (1H, s), 13.28 (1H, s). [Route 1, CDI] |
| 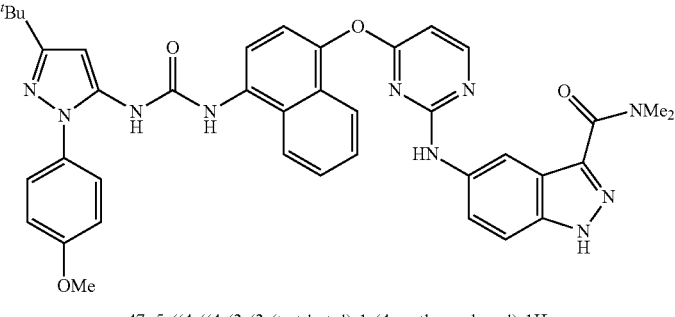<br>47: 5-((4-((4-(3-(3-(tert-butyl)-1-(4-methoxyphenyl)-1H-pyrazol-5-yl)ureido)naphthalen-1-yl)oxy)pyrimidin-2-yl)amino)-N,N-dimethyl-1H-indazole-3-carboxamide. | $R^t$ 2.21 min (Method 2, acidic); m/z 711 (M + H)$^+$ (ES$^+$); $^1$H NMR δ: 1.29 (9H, s), 3.05 (3H, s), 3.32 (3H, s), 3.84 (3H, s), 6.40 (1H, s), 6.44 (1H, d), 7.12 (2H, m), 7.29 (1H, d), 7.42 (1H, d), 7.46-7.50 (3H, over-lapping m), 7.55-7.64 (2H, over-lapping m), 7.84 (1H, m), 7.92 (1H, d), 8.05 (1H, d), 8.20 (1H, br s), 8.36 (1H, d), 8.71 (1H, s), 9.10 (1H, s), 9.49 (1H, s), 13.27 (1H, s). [Route 1, CDI] |
| 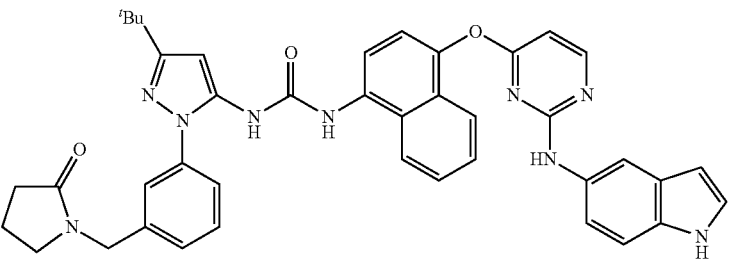<br>48: 1-(4-((2-((1H-indol-5-yl)amino)pyrimidin-4-yl)oxy)naphthalen-1-yl)-3-(3-(tert-butyl)-1-(3-((2-oxopyrrolidin-1-yl)methyl)phenyl)-1H-pyrazol-5-yl)urea. | $R^t$ 2.15 min (Method 2, acidic); m/z 706 (M + H)$^+$ (ES$^+$); $^1$H NMR δ: 1.30 (9H, s), 1.84 (2H, m), 2.25 (2H, m), 3.28 (2H, m), 4.47 (2H, s), 6.09 (1H, br s), 6.43-6.45 (2H, over-lapping m), 7.07-7.15 (3H, over-lapping m), 7.28 (1H, m), 7.40 (1H, d), 7.47 (1H, s), 7.53-7.62 (5H, over-lapping m), 7.84 (1H, m), 8.00 (1H, d), 8.11 (1H, d), 8.32 (1H, d), 8.95 (1H, s), 9.18 (1H, s), 9.26 (1H, s), 10.79 (1H, 2). [Route 1, CDI] |

TABLE 3-continued

Additional Compound Examples of the Invention

| Structure, Example No. and Name | Analytical Data [Generic Route] |
|---|---|
| 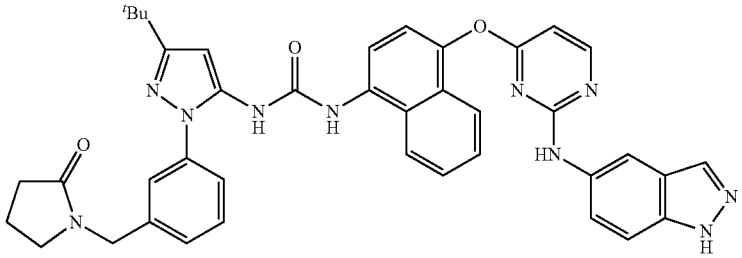<br>49: 1-(4-((2-((1H-indazol-5-yl)amino)pyrimidin-4-yl)oxy)naphthalen-1-yl)-3-(3-(tert-butyl)-1-(3-((2-oxopyrrolidin-1-yl)methyl)phenyl)-1H-pyrazol-5-yl)urea. | $R^t$ 2.17 min (Method 2, acidic); m/z 707 (M + H)$^+$ (ES$^+$); $^1$H NMR δ: 1.30 (9H, s), 1.84 (2H, m), 2.25 (2H, m), 3.28 (2H, m), 4.47 (2H, s), 6.45 (1H, s), 6.57 (1H, d), 7.24-7.28 (3H, over-lapping m), 7.42 (1H, d), 7.47 (1H, s), 7.54-7.64 (6H, over-lapping m), 7.84 (1H, s), 8.06 (1H, d), 8.13 (1H, d), 8.39 (1H, d), 8.91 (1H, s), 9.19 (1H, s), 9.53 (1H, s), 12.77 (1H, s).<br>[Route 1, CDI] |
| 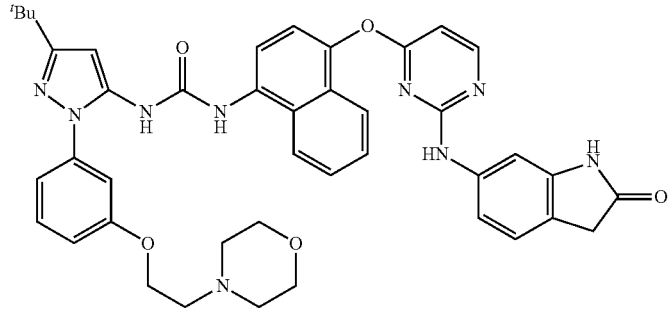<br>50: 1-(3-(tert-butyl)-1-(3-(2-morpholinoethoxy)phenyl)-1H-pyrazol-5-yl)-3-(4-((2-((2-oxoindolin-6-yl)amino)pyrimidin-4-yl)oxy)naphthalen-1-yl)urea. | $R^t$ 2.21 min (Method 2, basic); m/z 754 (M + H)$^+$ (ES$^+$); $^1$H NMR δ: 1.30 (9H, s), 2.42 (4H, t), 2.68 (2H, t), 3.30 (2H, s), 3.49 (4H, t), 4.15 (2H, t), 6.45 (1H, s), 6.49 (1H, d), 6.80 (1H, d), 6.95 (1H, d), 7.01 (1H, ddd), 7.15-7.18 (3H, over-lapping m), 7.40 (1H, d), 7.46 (1H, m), 7.55-7.64 (2H, over-lapping m), 7.82 (1H, dd), 7.91 (1H, d), 8.07 (1H, d), 8.37 (1H, d), 8.78 (1H, br s), 9.15 (1H, br s), 9.48 (1H, br s), 10.17 (1H, br s). [Route 1, CDI] |
| 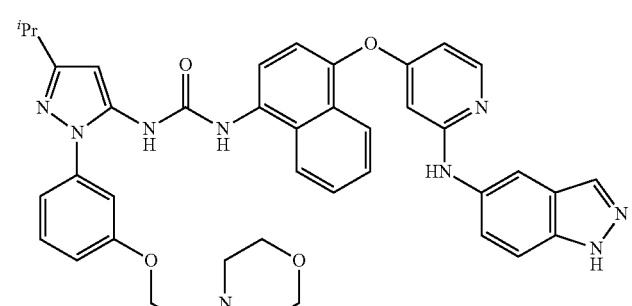<br>51: 1-(4-((2-((1H-indazol-5-yl)amino)pyridin-4-yl)oxy)naphthalen-1-yl)-3-(3-isopropyl-1-(3-(2-morpholinoethoxy)phenyl)-1H-pyrazol-5-yl)urea. | $R^t$ 2.07 min (Method 3); m/z 724 (M + H)$^+$ (ES$^+$); $^1$H NMR δ: 1.25 (6H, d), 2.43 (4H, br t), 2.69 (2H, t), 2.91 (1H, heptet), 3.51 (4H, t), 4.16 (2H, t), 6.07 (1H, d), 6.39 (1H, s), 6.50 (1H, dd), 7.02 (1H, ddd), 7.17-7.18 (2H, overlapping m), 7.29 (1H, dd), 7.37 (1H, d), 7.39 (1H, d), 7.46 (1H, t), 7.60 (1H, m), 7.65 (1H, m), 7.87 (1H, dd), 7.94 (1H, s), 7.95 (1H, d), 8.08 (1H, d), 8.10 (1H, d), 8.19 (1H, s), 8.86 (1H, s), 8.92 (1H, s), 9.23 (1H, s), 12.84 (1H, s).<br>[Route 1, CDI; isolated by preparative HPLC and characterised as a formic acid salt] |
| 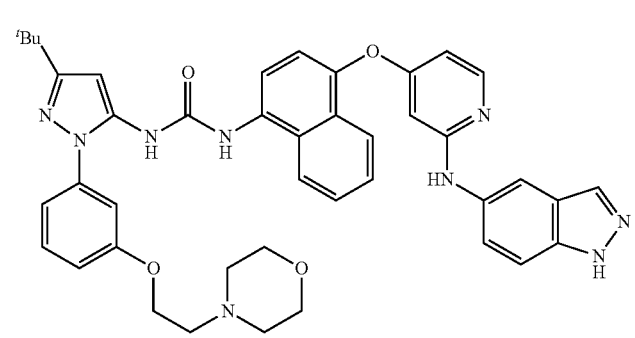<br>52: 1-(4-((2-((1H-indazol-5-yl)amino)pyridin-4-yl)oxy)naphthalen-1-yl)-3-(3-(tert-butyl)-1-(3-(2-morpholinoethoxy)phenyl)-1H-pyrazol-5-yl)urea. | $R^t$ 2.18 min (Method 3); m/z 738 (M + H)$^+$ (ES$^+$); $^1$H NMR δ: 1.30 (9H, s), 2.43 (4H, br t), 2.69 (2H, t), 3.51 (4H, t), 4.16 (2H, t), 6.09 (1H, d), 6.43 (1H, s), 6.49 (1H, dd), 7.02 (1H, ddd), 7.17-7.20 (2H, overlapping m), 7.30 (1H, dd), 7.36 (1H, d), 7.39 (1H, d), 7.46 (1H, t), 7.60 (1H, m), 7.66 (1H, m), 7.88 (1H, dd), 7.93 (1H, s), 7.95 (1H, d), 8.08 (1H, d), 8.10 (1H, d), 8.18 (1H, s), 8.81 (1H, s), 8.84 (1H, s), 9.15 (1H, s), 12.82 (1H, s).<br>[Route 1, CDI] |

TABLE 3-continued

Additional Compound Examples of the Invention

| Structure, Example No. and Name | Analytical Data [Generic Route] |
|---|---|
| 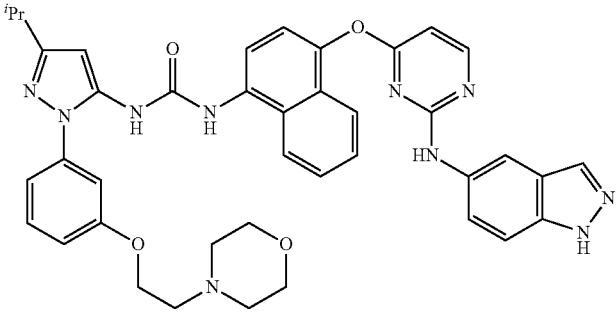<br>53: 1-(4-((2-((1H-indazol-5-yl)amino)pyrimidin-4-yl)oxy)naphthalen-1-yl)-3-(3-isopropyl-1-(3-(2-morpholinoethoxy)phenyl)-1H-pyrazol-5-yl)urea. | $R^t$ 1.91 min (Method 2, basic); m/z 725 (M + H)$^+$ (ES$^+$); $^1$H NMR δ: 1.25 (6H, d), 2.39 (4H, m), 2.66 (2H, t), 2.91 (1H, m), 3.47 (4H, t), 4.15 (2H, t), 6.41 (1H, s), 6.59 (1H, d), 7.00-7.05 (2H, over-lapping m), 7.19-7.24 (4H, over-lapping m), 7.43-7.47 (2H, over-lapping m), 7.54-7.64 (3H, over-lapping m), 7.83 (1H, dd), 8.06 (1H, br s), 8.13 (1H, d), 8.40 (1H, d), 8.95 (1H, s), 9.28 (1H, s), 9.55 (1H, br s), 12.78 (1H, s). [Route 1, CDI] |
| 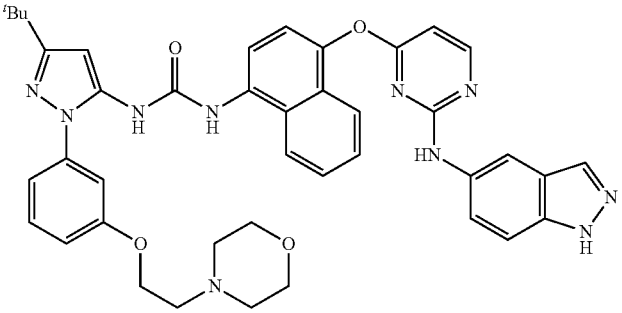<br>54: 1-(4-((2-((1H-indazol-5-yl)amino)pyrimidin-4-yl)oxy)naphthalen-1-yl)-3-(3-(tert-butyl)-1-(3-(2-morpholinoethoxy)phenyl)-1H-pyrazol-5-yl)urea. | $R^t$ 1.75 min (Method 2, acidic); m/z 739 (M + H)$^+$ (ES$^+$); $^1$H NMR δ: 1.30 (9H, s), 2.38-2.40 (4H, over-lapping m), 2.66 (2H, m), 3.46-3.49 (4H, over-lapping m), 4.15 (2H, m), 6.46 (1H, s), 6.58 (1H, d), 7.00-7.02 (2H, over-lapping m), 7.19-7.25 (4H, over-lapping m), 7.42-7.49 (2H, over-lapping m), 7.54-7.64 (3H, over-lapping m), 7.84 (1H, m), 8.06 (1H, d), 8.14 (1H, d), 8.39 (1H, d), 8.92 (1H, s), 9.26 (1H, s), 9.52 (1H, s), 12.77 (1H, s). [Route 1, CDI] |
| 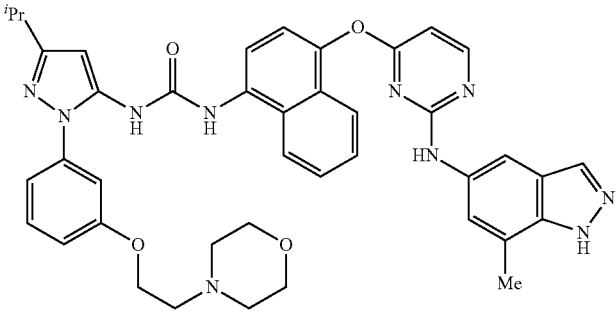<br>55: 1-(3-isopropyl-1-(3-(2-morpholinoethoxy)phenyl)-1H-pyrazol-5-yl)-3-(4-((2-((7-methyl-1H-indazol-5-yl)amino)pyrimidin-4-yl)oxy)naphthalen-1-yl)urea. | $R^t$ 2.15 min (Method 2, basic); m/z 739 (M + H)$^+$ (ES$^+$); $^1$H NMR δ: 1.25 (6H, d), 2.29 (3H, br s), 2.39 (4H, br s), 2.66 (2H, t), 2.91 (1H, m), 3.17 (1H, d), 3.47 (4H, t), 4.15 (2H, t), 6.42 (1H, s), 6.58 (1H, d), 7.01-7.03 (2H, over-lapping m), 7.19-7.20 (2H, over-lapping m), 7.42-7.50 (2H, over-lapping m), 7.54-7.64 (3H, over-lapping m), 7.83 (1H, dd), 8.07 (1H, br d), 8.13 (1H, d), 8.38 (1H, d), 8.93 (1H, s), 9.24 (1H, s), 9.46 (1H, br s), 12.86 (1H, s). [Route 1, CDI] |

TABLE 3-continued

Additional Compound Examples of the Invention

| Structure, Example No. and Name | Analytical Data [Generic Route] |
|---|---|
| 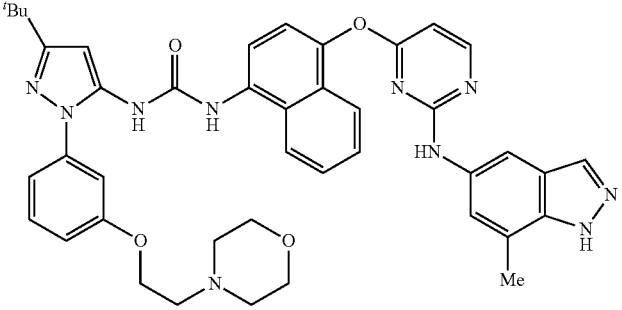<br>56: 1-(3-(tert-butyl)-1-(3-(2-morpholinoethoxy)phenyl)-1H-pyrazol-5-yl)-3-(4-((2-((7-methyl-1H-indazol-5-yl)amino)pyrimidin-4-yl)oxy)naphthalen-1-yl)urea. | $R^t$ 2.33 min (Method 2, basic); m/z 753 $(M + H)^+$ $(ES^+)$; $^1$H NMR δ: 1.30 (9H, s), 2.29 (3H, s), 2.39 (4H, t), 2.66 (2H, t), 3.47 (4H, t), 4.15 (2H, t), 6.45 (1H, s), 6.57 (1H, d), 6.99-7.05 (2H, over-lapping m), 7.19 (1H, d), 7.21 (1H, br s), 7.34-7.63 (6H, over-lapping m), 7.83 (1H, dd), 8.06 (1H, d), 8.13 (1H, d), 8.38 (1H, d), 8.90 (1H, br s), 9.23 (1H, br s), 9.43 (1H, br s), 12.83 (1H, br s). [Route 1, CDI] |
| 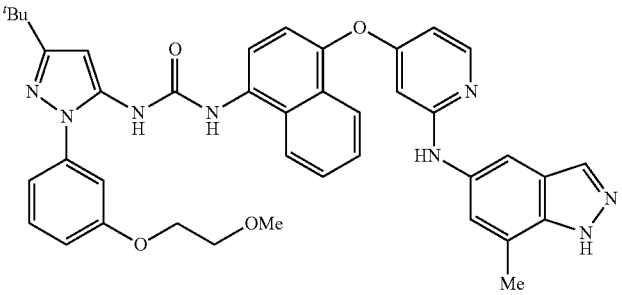<br>57: 1-(3-(tert-butyl)-1-(3-(2-methoxyethoxy)phenyl)-1H-pyrazol-5-yl)-3-(4-((2-((7-methyl-1H-indazol-5-yl)amino)pyridin-4-yl)oxy)naphthalen-1-yl)urea. | $R^t$ 2.89 min (Method 3); m/z 697 $(M + H)^+$ $(ES^+)$; $^1$H NMR δ: 1.29 (9H, s), 2.42 (3H, s), 3.29 (3H, s), 3.66 (2H, m), 4.18 (2H, m), 6.06 (1H, d), 6.43 (1H, s), 6.48 (1H, dd), 7.01-7.03 (2H, overlapping m), 7.16-7.18 (2H, overlapping m), 7.35 (1H, d), 7.46 (1H, t), 7.59 (1H, t), 7.65 (1H, t), 7.86 (1H, d), 7.91 (1H, d), 7.93 (1H, d), 7.96 (1H, s), 8.06 (1H, d), 8.09 (1H, d), 8.77 (1H, br s), 8.82 (1H, br s), 9.16 (1H, s), 12.91 (1H, s). [Route 1, CDI] |
| 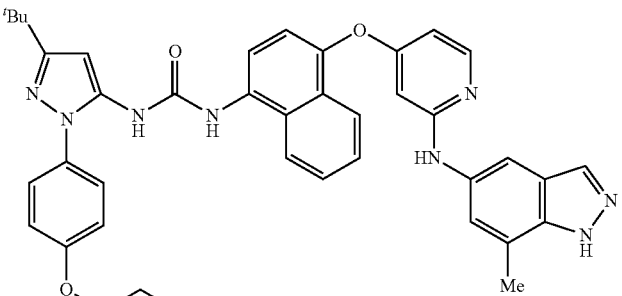<br>58: 1-(3-(tert-butyl)-1-(4-(2-dimethylamino)ethoxy)phenyl)-1H-pyrazol-5-yl)-3-(4-((2-((7-methyl-1H-indazol-5-yl)amino)pyridin-4-yl)oxy)naphthalen-1-yl)urea. | $R^t$ 2.22 min (Method 3); m/z 710 $(M + H)^+$ $(ES^+)$; $^1$H NMR δ: 1.29 (9H, s), 2.25 (6H, s), 2.42 (3H, s), 2.69 (2H, t), 4.14 (2H, t), 6.06 (1H, d), 6.40 (1H, s), 6.48 (1H, dd), 7.03 (1H, s), 7.13 (2H, d), 7.36 (1H, d), 7.48 (2H, d), 7.59 (1H, m), 7.66 (1H, m), 7.86 (1H, d), 7.91 (1H, d), 7.96 (1H, d), 7.97 (1H, s), 8.07 (1H, d), 8.08 (1H, d), 8.74 (1H, br s), 8.78 (1H, br s), 9.13 (1H, s), 12.92 (1H, s). [Route 1, CDI] |

TABLE 3-continued

Additional Compound Examples of the Invention

| Structure, Example No. and Name | Analytical Data [Generic Route] |
|---|---|
| 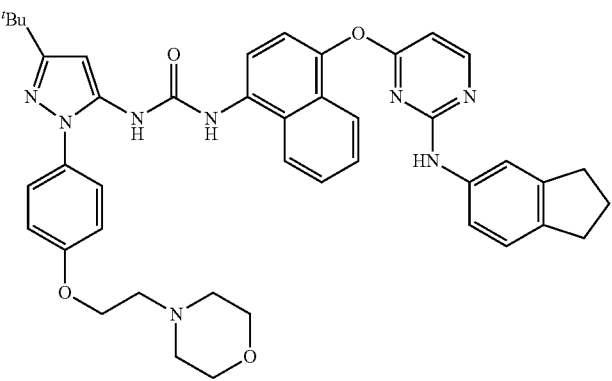<br>59: 1-(3-(tert-butyl)-1-(4-(2-morpholinoethoxy)phenyl)-1H-pyrazol-5-yl)-3-(4-((2-((2,3-dihydro-1H-inden-5-yl)amino)pyrimidin-4-yl)oxy)naphthalen-1-yl)urea. | R$^t$ 3.05 min (Method 3); m/z 739 (M + H)$^+$ (ES$^+$); $^1$H NMR δ: 1.28 (9H, s), 1.87 (2H, m), 2.28 (6H, s), 2.53 (2H, m), 2.65 (2H, t), 3.23 (2H, m), 3.49 (2H, d), 3.60 (2H, m), 3.74 (2H, t), 3.98 (2H, d), 4.44 (2H, t), 6.38 (1H, s), 6.60 (1H, d), 6.86 (1H, m), 6.94 (1H, m), 7.09 (4H, d), 7.16 (2H, m), 7.38 (1H, d), 7.46 (4H, d), 7.54-7.63 (4H, over-lapping m), 7.80 (1H, dd), 7.95 (1H, d), 8.14 (1H, d), 8.36 (1H, d), 8.87 (1H, br s), 9.21 (1H, br s), 9.62 (1H, br s), 10.35 (1H, br s).<br>[Route 2, isolated and characterised as the bis p-toluenesulfonic acid salt] |
| 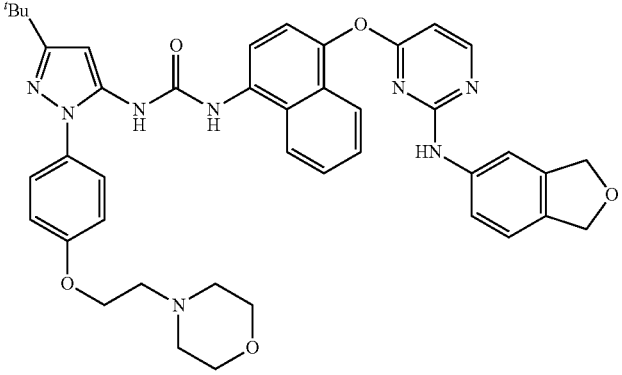<br>60: 1-(3-(tert-butyl)-1-(4-(2-morpholinoethoxy)phenyl)-1H-pyrazol-5-yl)-3-(4-((2-((1,3-dihydroisobenzofuran-5-yl)amino)pyrimidin-4-yl)oxy)naphthalen-1-yl)urea. | R$^t$ 2.81 min (Method 3); m/z 741 (M + H)$^+$ (ES$^+$); $^1$H NMR δ: 1.29 (9H, s), 2.29 (6H, s), 3.24 (2H, m), 3.53 (2H, d), 3.62 (2H, t), 3.76 (2H, t), 3.99 (2H, d), 4.46 (2H, t), 4.58 (2H, m), 4.83 (2H, s), 5.01 (2H, d), 6.40 (1H, s), 6 66 (1H, d), 6.96 (1H, d), 7.12 (4H, d), 7.19-7.28 (2H, over-lapping m), 7.38-7.43 (1H, m), 7.48 (4H, d), 7.54-7.65 (4H, over-lapping m), 7.80 (1H, dd), 7.99 (1H, d), 8.15 (1H, d), 8.41 (1H, d), 8.87 (1H, br s), 9.23 (1H, br s), 9.69 (1H, br s).<br>[Route 2, isolated and characterised as the bis p-toluenesulfonic acid salt] |
| 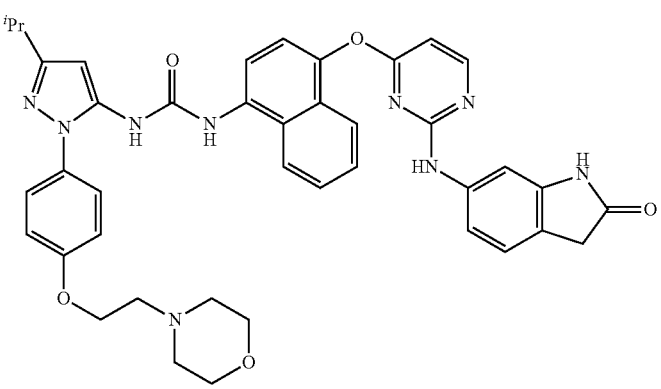<br>61: 1-(3-isopropyl-1-(4-(2-morpholinoethoxy)phenyl)-1H-pyrazol-5-yl)-3-(4-((2-((2-oxoindolin-6-yl)amino)pyrimidin-4-yl)oxy)naphthalen-1-yl)urea. | R$^t$ 2.03 min (Method 2, basic); m/z 740 (M + H)$^+$ (ES$^+$); $^1$H NMR δ: 1.24 (6H, d), 2.45-2.48 (4H, over-lapping m), 2.73 (2H, m), 2.89 (1H, m), 3.30 (2H, s), 3.57-3.59 (4H, over-lapping m), 4.16 (2H, m), 6.37 (1H, s), 6.49 (1H, d), 6.79 (1H, d), 6.94 (1H, d), 7.11-7.13 (3H, over-lapping m), 7.40 (1H, d), 7.47 (2H, m), 7.56-7.62 (2H, over-lapping m), 7.82 (1H, m), 7.90 (1H, d), 8.05 (1H, d), 8.37 (1H, d), 8.69 (1H, s), 9.10 (1H, s), 9.49 (1H, s), 10.18 (1H, s).<br>[Route 1, CDI] |

TABLE 3-continued

Additional Compound Examples of the Invention

| Structure, Example No. and Name | Analytical Data [Generic Route] |
|---|---|
| 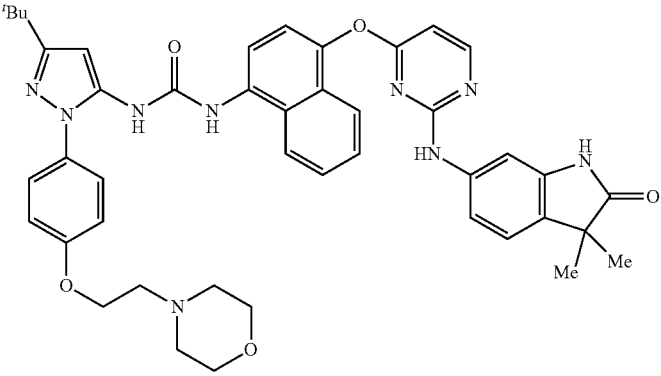<br>62: 1-(3-(tert-butyl)-1-(4-(2-morpholinoethoxy)phenyl)-1H-pyrazol-5-yl)-3-(4-((2-((3,3-dimethyl-2-oxoindolin-6-yl)amino)pyrimidin-4-yl)oxy)naphthalen-1-yl)urea. | $R^t$ 2.31 min (Method 2, basic); m/z 782 (M + H)$^+$ (ES$^+$); m/z 780 (M − H)$^-$ (ES$^-$); $^1$H NMR (400 δ: 1.15 (6H, s), 1.28 (9H, s), 2.47-2.50 (4H, over-lapping m), 2.73 (2H, m), 3.57-3.59 (4H, over-lapping m), 4.16 (2H, m), 6.43 (1H, s), 6.51 (1H, d), 6.93-6.98 (2H, over-lapping m), 7.08-7.14 (3H, over-lapping m), 7.41 (1H, d), 7.47 (2H, m), 7.55-7.62 (2H, over-lapping m), 7.82 (1H, m), 7.89 (1H, d), 8.05 (1H, m), 8.16 (1H, s,), 8.36 (1H, d), 8.76 (1H, s), 9.16 (1H, s), 9.51 (1H, s), 10.15 (1H, s).<br>[Route 2, isolated and characterised as the formate acid salt] |
| 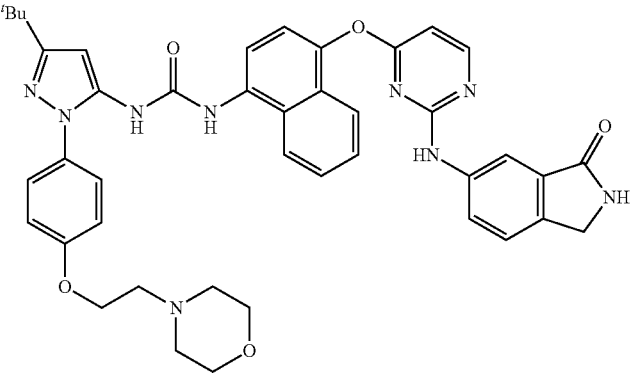<br>63: 1-(3-(tert-butyl)-1-(4-(2-morpholinoethoxy)phenyl)-1H-pyrazol-5-yl)-3-(4-((2-((3-oxoisoindolin-5-yl)amino)pyrimidin-4-yl)oxy)naphthalen-1-yl)urea. | $R^t$ 2.76 min (Method 1, acidic); m/z 754 (M + H)$^+$ (ES$^+$); $^1$H NMR δ: 1.29 (9H, s), 2.49-2.5 (4H, over-lapping m), 2.73 (2H, br s), 3.58 (4H, t), 4.16 (2H, t), 4.22 (2H, s), 6.39 (1H, s), 6.55 (1H, d), 7.12 (2H, d), 7.19 (1H, d), 7.41 (1H, d), 7.47 (2H, d), 7.58-7.60 (3H, over-lapping m), 7.83 (1H, dd), 7.90 (1H, d), 7.93 (1H, br s), 8.06 (1H, d), 8.42-8.43 (2H, over-lapping m), 8.69 (1H, s), 9.10 (1H, s), 9.72 (1H, br s).<br>[Route 2] |
| 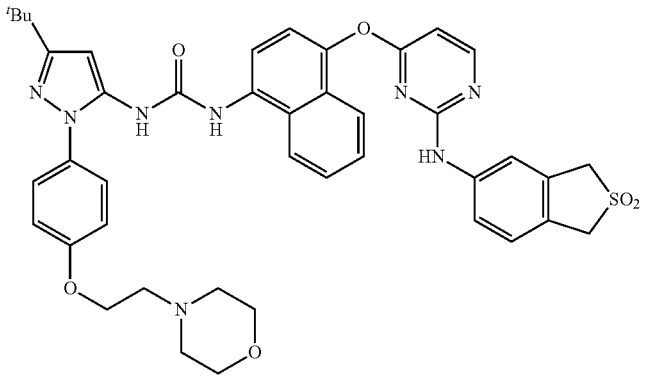<br>64: 1-(3-(tert-butyl)-1-(4-(2-morpholinoethoxy)phenyl)-1H-pyrazol-5-yl)-3-(4-((2-((2,2-dioxido-1,3-dihydrobenzo[c]thiophen-5-yl)amino)pyrimidin-4-yl)oxy)naphthalen-1-yl)urea. | $R^t$ 2.76 min (Method 1, acidic); m/z 789 (M + H)$^+$ (ES$^+$); $^1$H NMR δ: 1.29 (9H, s), 2.49-2.50 (4H, over-lapping m), 2.73 (2H, t), 3.59 (4H, t), 4.10 (2H, br s), 4.17 (2H, t), 4.28 (2H, s), 6.45 (1H, s), 6.66 (1H, d), 7.04 (1H, d), 7.13 (2H, d), 7.21 (1H, d), 7.37 (1H, br s), 7.42 (1H, d), 7.48 (2H, d), 7.56 (1H, m), 7.63 (1H, m), 7.82 (1H, d), 7.99 (1H, d), 8.09 (1H, d), 8.43 (1H, d), 8.73 (1H, s), 9.14 (1H, s), 9.69 (1H, s).<br>[Route 2] |

TABLE 3-continued

Additional Compound Examples of the Invention

| Structure, Example No. and Name | Analytical Data [Generic Route] |
|---|---|
| 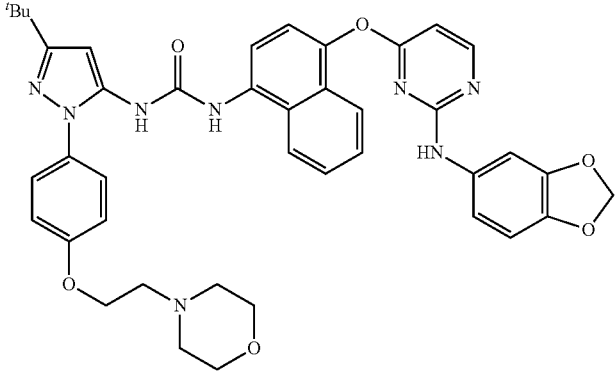<br>65: 1-(4-((2-(benzo[d][1,3]dioxol-5-ylamino)pyrimidin-4-yl)oxy)naphthalen-1-yl)-3-(3-(tert-butyl)-1-(4-(2-morpholinoethoxy)phenyl)-1H-pyrazol-5-yl)urea. | $R^t$ 2.83 min (Method 3); m/z 743 (M + H)$^+$ (ES$^+$); $^1$H NMR δ: 1.30 (9H, s), 2.29 (6H, s), 3.24 (2H, m), 3.53 (2H, d), 3.62 (2H, m), 3.76 (2H, t), 4.00 (2H, m), 4.45 (2H, t), 5.88 (2H, s), 6.40 (1H, s), 6.56-6.58 (2H, overlapping m), 6.75 (1H, m), 6.94 (1H, m), 7.12 (4H, d), 7.18 (2H, m), 7.38 (1H, d), 7.49 (4H, d), 7.55-7.62 (4H, over-lapping m), 7.80 (1H, dd), 7.92 (1H, d), 8.13 (1H, d), 8.36 (1H, d), 8.88 (1H, br s), 9.20 (1H, br s), 9.52 (1H br s).<br>[Route 2, isolated and characterised as the bis p-toluenesulfonic acid salt] |
| 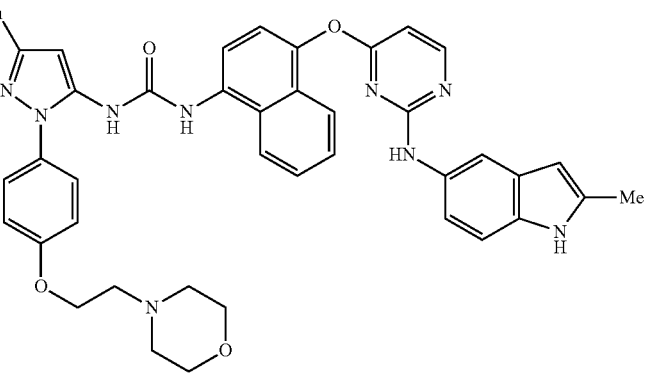<br>66: 1-(3-(tert-butyl)-1-(4-(2-morpholinoethoxy)phenyl)-1H-pyrazol-5-yl)-3-(4-((2-((2-methyl-1H-indol-5-yl)amino)pyrimidin-4-yl)oxy)naphthalen-1-yl)urea. | $R^t$ 2.36 min (Method 2, basic); m/z 752 (M + H)$^+$ (ES$^+$); m/z 750 (M − H)$^-$ (ES$^-$); $^1$H NMR δ: 1.28 (9H, s), 2.36 (3H, s), 2.47-2.50 (4H, over-lapping m), 2.72 (2H, m), 3.57-3.59 (4H, over-lapping m), 4.15 (2H, m), 5.81 (1H, br s), 6.43 (1H, s), 6.46 (1H, d), 6.92 (2H, br s), 7.12 (2H, m), 7.37-7.50 (4H, over-lapping m), 7.53-7.62 (2H, over-lapping m), 7.82 (1H, m), 8.04-8.10 (2H, over-lapping m), 8.32 (1H, d), 8.81 (1H, br s), 9.19 (1H, br s), 9.25 (1H, br s), 10.58 (1H, br s).<br>[Route 2] |
| 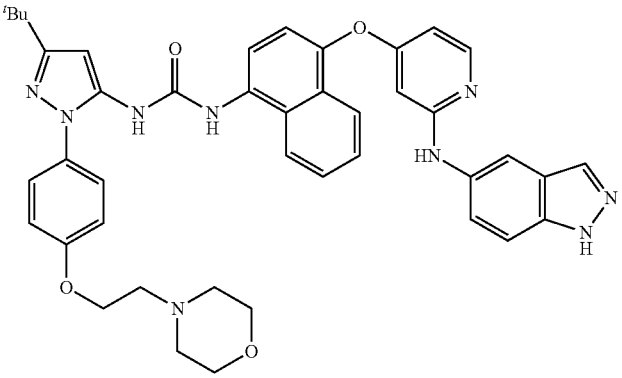<br>67: 1-(3-isopropyl-1-(3-(2-morpholinoethoxy)phenyl)-1H-pyrazol-5-yl)-3-(4-((2-((7-methyl-1H-indazol-5-yl)amino)pyrimidin-4-yl)oxy)naphthalen-1-yl)urea. | $R^t$ 2.18 min (Method 3): m/z 736 (M − H)$^-$ (ES$^-$); $^1$H NMR δ: 1.29 (9H, s), 2.73 (4H, br s), 2.97 (2H, br s), 3.67 (4H, br s), 4.25 (2H, br s), 6.07 (1H, d), 6.39 (1H, s), 6.51 (1H, dd), 7.14 (2H, d), 7.29 (1H, dd), 7.36-7.39 (2H, overlapping m), 7.51 (2H, d), 7.59 (1H, t); 7.66 (1H, t), 7.87 (1H, d), 7.94 (1H, s), 7.96 (1H, d), 8.08 (1H, d), 8.13 (1H, d), 8.19 (1H, d), 8.85 (1H, br s), 8.87 (1H, br s), 9.22 (1H, s), 12.84 (1H, s).<br>[Route 1, CDI] |

TABLE 3-continued

Additional Compound Examples of the Invention

| Structure, Example No. and Name | Analytical Data [Generic Route] |
|---|---|
| 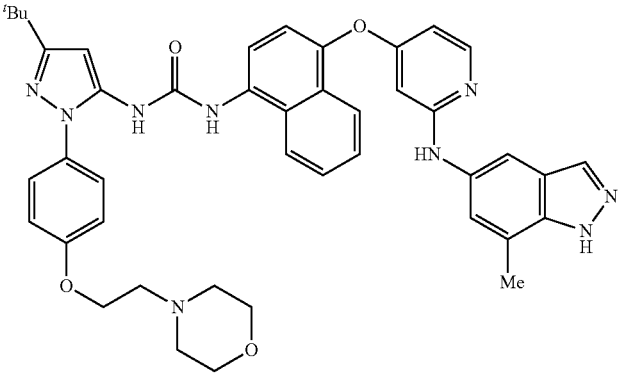\n\n68: 1-(3-(tert-butyl)-1-(4-(2-morpholinoethoxy)phenyl)-1H-pyrazol-5-yl)-3-(4-((2-((7-methyl-1H-indazol-5-yl)amino)pyridin-4-yl)oxy)naphthalen-1-yl)urea. | $R^t$ 2.54 min (Method 3); m/z 752 (M + H)$^+$ (ES$^+$); $^1$H NMR δ: 1.29 (9H, s), 2.42 (3H, s), 2.48 (4H, br s, partially obscured by DMSO peak), 2.74 (2H, br m), 3.59 (4H, t), 4.17 (2H, t), 6.07 (1H, d), 6.40 (1H, s), 6.48 (1H, dd), 7.04 (1H, br s), 7.13 (2H, m), 7.36 (1H, d), 7.48 (2H, m), 7.59 (1H, t), 7.66 (1H, t), 7.87 (1H, d), 7.91 (1H, d), 7.95 (1H, d), 7.96 (1H, s), 8.07 (1H, d), 8.08 (1H, d), 8.73 (1H, br s), 8.78 (1H, br s), 9.12 (1H, s), 12.92 (1H, s). [Route 1, CDI] |
| 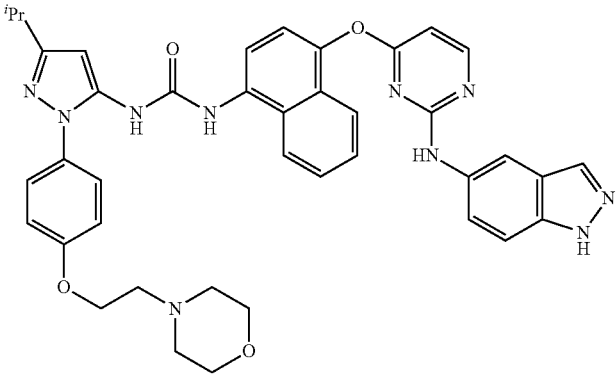\n\n69: 1-(4-((2-((1H-indazol-5-yl)amino)pyrimidin-4-yl)oxy)naphthalen-1-yl)-3-(3-isopropyl-1-(4-(2-morpholinoethoxy)phenyl)-1H-pyrazol-5-yl)urea. | $R^t$ 2.04 min (Method 2, basic); m/z 725 (M + H)$^+$ (ES$^+$); $^1$H NMR δ: 1.24 (6H, d), 2.49 (4H, over-lapping m), 2.71 (2H, m), 2.88 (1H, m), 3.56-3.59 (4H, over-lapping m), 4.15 (2H, m), 6.37 (1H, s), 6.59 (1H, d), 7.13 (2H, m), 7.24 (2H, br s), 7.43 (1H, d), 7.50 (2H, m), 7.48-7.64 (4H, over-lapping m), 7.83 (1H, m), 8.04-8.12 (2H, over-lapping m), 8.39 (1H, d), 8.80 (1H, s), 9.20 (1H, s), 9.55 (1H, s), 12.78 (1H, s). [Route 1, CDI] |
| 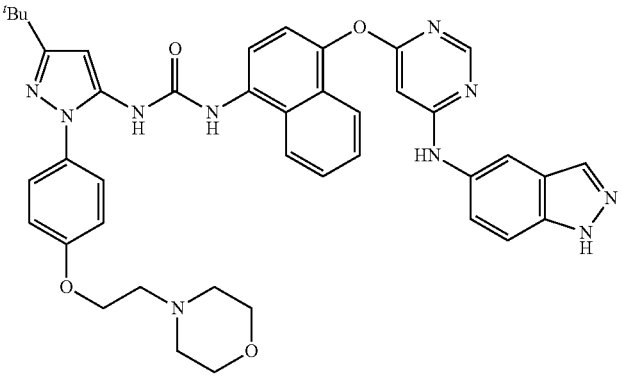\n\n70: 1-(4-((6-((1H-indazol-5-yl)amino)pyrimidin-4-yl)oxy)naphthalen-1-yl)-3-(3-(tert-butyl)-1-(4-(2-morpholinoethoxy)phenyl)-1H-pyrazol-5-yl)urea. | $R^t$ 2.04 min (Method 2, basic); m/z 739 (M + H)$^+$ (ES$^+$); $^1$H NMR δ: 1.28 (9H, s), 2.48 (4H, over-lapping m), 2.73 (2H, t), 3.58 (4H, t), 4.16 (2H, t), 6.08 (1H, s), 6.38 (1H, s), 7.12 (2H, d), 7.33-7.37 (2H, over-lapping m), 7.46-7.49 (3H, over-lapping m), 7.55-7.65 (2H, over-lapping m), 7.82 (1H, d), 7.89 (1H, d), 8.01-8.06 (3H, over-lapping m), 8.28 (1H, s), 8.69 (1H, s), 9.08 (1H, s), 9.50, (1H, s), 12.97 (1H, s). [Route 1, CDI] |

TABLE 3-continued

Additional Compound Examples of the Invention

| Structure, Example No. and Name | Analytical Data [Generic Route] |
|---|---|
| 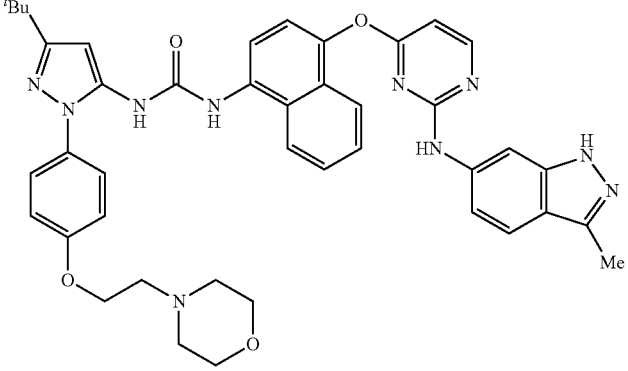<br>71: 1-(3-(tert-butyl)-1-(4-(2-morpholinoethoxy)phenyl)-1H-pyrazol-5-yl)-3-(4-((2-((3-methyl-1H-indazol-6-yl)amino)pyrimidin-4-yl)oxy)naphthalen-1-yl)urea. | $R^t$ 2.39 min (Method 2, basic); m/z 753 (M + H)$^+$ (ES$^+$); $^1$H NMR δ: 1.30 (9H, s), 2.37 (3H, s), 2.49-2.50 (4H, over-lapping m), 2.73 (2H, t), 3.58 (4H, t), 4.16 (2H, t), 6.56-6.57 (2H, over-lapping m), 7.05 (1H, d), 7.14 (2H, m), 7.38 (1H, d), 7.46-7.50 (3H, over-lapping m), 7.56-7.62 (2H, over-lapping m), 7.78 (1H, br s), 7.84 (1H, d), 7.91 (1H, d), 8.04 (1H, d), 8.43 (1H, d), 8.78 (1H, s), 9.17 (1H, s), 9.71 (1H, br s), 12.11 (1H, br s).<br>[Route 2] |
| 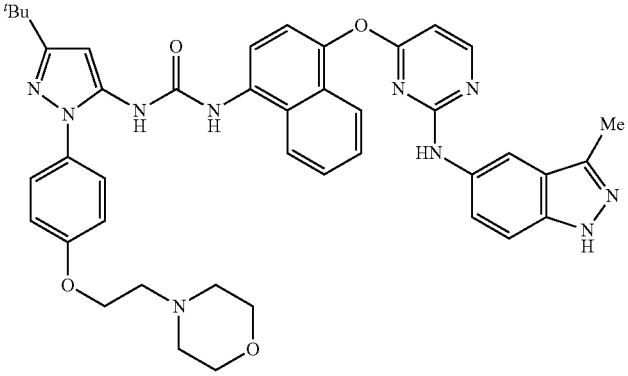<br>72: 1-(3-(tert-butyl)-1-(4-(2-morpholinoethoxy)phenyl)-1H-pyrazol-5-yl)-3-(4-((2-((3-methyl-1H-indazol-5-yl)amino)pyrimidin-4-yl)oxy)naphthalen-1-yl)urea. | $R^t$ 2.67 min (Method 3); m/z 753 (M + H)$^+$ (ES$^+$); $^1$H NMR δ: 1.29 (9H, s), 2.20 (3H s), 2.49-2.52 (4H, over-lapping m), 2.73 (2H, t), 3.57-3.60 (4H, over-lapping m), 4.16 (2H, t), 6.39 (1H, s), 6.51 (1H, d), 7.12-7.19 (2H, over-lapping m), 7.28 (1H, m), 7.42 (1H, m), 7.46-7.50 (2H, over-lapping m), 7.55-7.63 (3H, over-lapping m), 7.81 (1H, m), 7.95 (1H, t), 8.08 (1H, m), 8.15 (1H, s), 8.39 (1H, d), 8.73 (1H, br s), 9.10 (1H, br s), 9.45 (1H, br s), 12.38 (1H, br s).<br>[Route 2] |
| 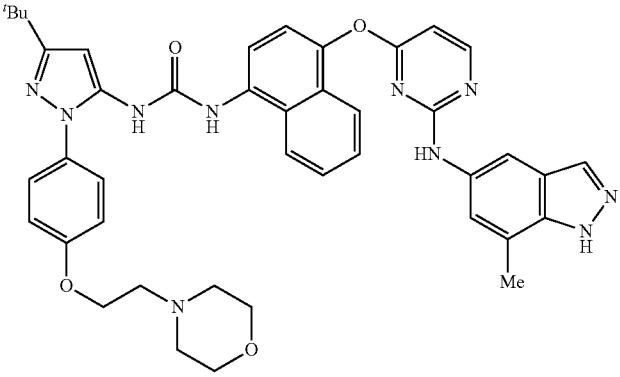<br>73: 1-(3-(tert-butyl)-1-(4-(2-morpholinoethoxy)phenyl)-1H-pyrazol-5-yl)-3-(4-((2-((7-methyl-1H-indazol-5-yl)amino)pyrimidin-4-yl)oxy)naphthalen-1-yl)urea. | $R^t$ 2.31 min (Method 2, basic); m/z 753 (M + H)$^+$ (ES$^+$); $^1$H NMR δ: 1.29 (9H, s), 2.29 (3H, s), 2.47 (4H, t), 2.72 (2H, t), 3.57 (4H, t), 4.15 (2H, t), 6.41 (1H, s), 6.57 (1H, d), 7.02 (1H, br s), 7.13 (2H, m), 7.42-7.63 (7H, over-lapping m), 7.82 (1H, dd), 8.05 (1H, d), 8.11 (1H, d), 8.38 (1H, d), 8.79 (1H, br s), 9.19 (1H, br s), 9.44 (1H, br s), 12.84 (1H, br s).<br>[Route 1, CDI] |

TABLE 3-continued

Additional Compound Examples of the Invention

| Structure, Example No. and Name | Analytical Data [Generic Route] |
|---|---|
| 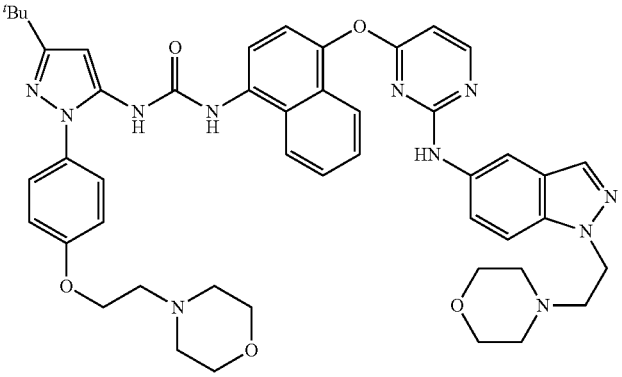<br>74: 1-(3-(tert-butyl)-1-(4-(2-morpholinoethoxy)phenyl)-1H-pyrazol-5-yl)-3-(4-((2-((1-(2-morpholinoethyl)-1H-indazol-5-yl)amino)pyrimidin-4-yl)oxy)naphthalen-1-yl)urea. | R$^t$ 1.36 min (Method 2, acidic); m/z 852 (M + H)$^+$ (ES$^+$); $^1$H NMR δ: 1.30 (9H, s), 2.35 (4H, t), 2.49 (4H, m), 2.67 (2H, t), 2.73 (2H, t), 3.45 (4H, t), 3.58 (4H, t), 4.16 (2H, t), 4.38 (2H, t), 6.43 (1H, s), 6.61 (1H, d), 7.13-7.15 (2H, over-lapping m), 7.26 (1H, m), 7.38 (1H, d), 7.43 (1H, d), 7.50-7.64 (5H, over-lapping m), 7.82 (1H, d), 8.04 (1H, d), 8.11 (1H, d), 8.22 (1H, s), 8.40 (1H, d), 8.83 (1H, s), 9.24 (1H, br s), 9.56 (1H, br s)<br>[Route 1, CDI] |
| 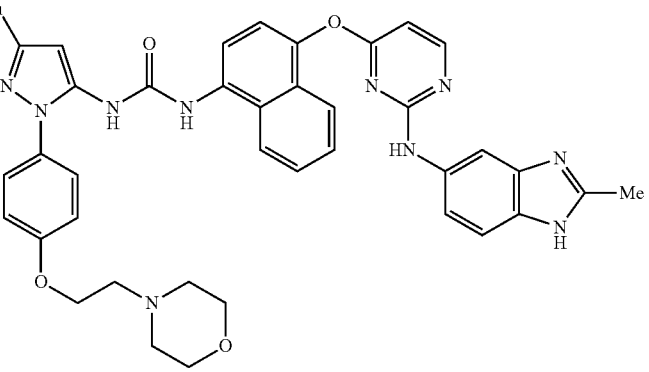<br>75: 1-(3-(tert-butyl)-1-(4-(2-morpholinoethoxy)phenyl)-1H-pyrazol-5-yl)-3-(4-((2-((2-methyl-1H-benzo[d]imidazol-6-yl)amino)pyrimidin-4-yl)oxy)naphthalen-1-yl)urea. | R$^t$ 2.45 min (Method 1, acidic); m/z 753 (M + H)$^+$ (ES$^+$); $^1$H NMR δ: 1.28 (9H, s), 2.49-2.50 (4H, over-lapping m), 2.73 (2H, br s), 3.58 (4H, t), 4.16 (2H, t), 4.28 (3H, s), 6.39 (1H, s), 6.55 (1H, d), 7.12 (2H, d), 7.19 (1H, d), 7.41 (1H, d), 7.47 (2H, d), 7.55-7.60 (3H, over-lapping m), 7.83 (1H, dd), 7.90 (1H, d), 7.93 (1H, br s), 8.06 (1H, d), 8.42-8.43 (2H, over-lapping m), 8.68 (1H, s), 9.10 (1H, s), 9.72 (1H, s).<br>[Route 2] |
| 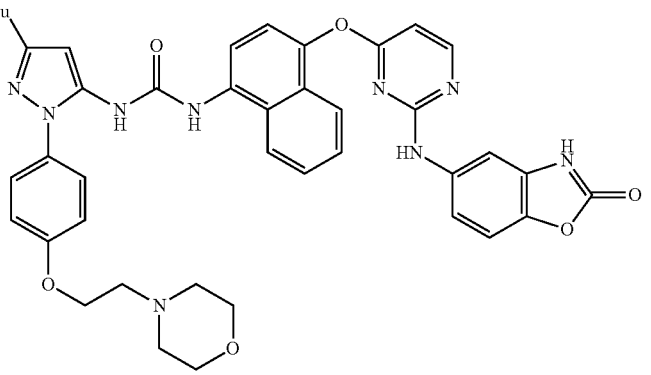<br>76: 1-(3-(tert-butyl)-1-(4-(2-morpholinoethoxy)phenyl)-1H-pyrazol-5-yl)-3-(4-((2-((2-oxo-2,3-dihydrobenzo[d]oxazol-5-yl)amino)pyrimidin-4-yl)oxy)naphthalen-1-yl)urea. | R$^t$ 2.31 min (Method 2, basic); m/z 756 (M + H)$^+$ (ES$^+$); $^1$H NMR δ: 1.28 (9H, s), 2.48-2.50 (4H, over-lapping m), 2.72 (2H, t), 3.58 (4H, t), 4.16 (2H, t), 6.46 (1H, s), 6.53 (1H, d), 6.89 (1H, br s), 7.03 (1H, br s), 7.13 (2H, m), 7.38 (1H, br s), 7.41 (1H, d), 7.48 (2H, m), 7.56-7.62 (2H, over-lapping m), 7.81 (1H, d), 7.88 (1H, d), 8.04 (1H, d), 8.38 (1H, d), 8.71 (1H, s), 9.14 (1H, s), 9.56 (1H, br s), 11.30 (1H, br s).<br>[Route 2] |

TABLE 3-continued

Additional Compound Examples of the Invention

| Structure, Example No. and Name | Analytical Data [Generic Route] |
|---|---|
| 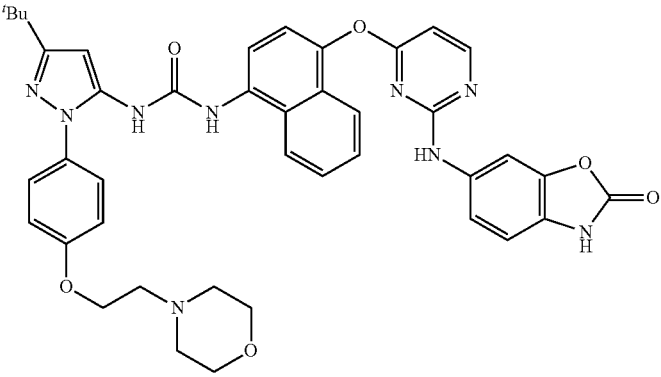<br>77: 1-(3-(tert-butyl)-1-(4-(2-morpholinoethoxy)phenyl)-1H-pyrazol-5-yl)-3-(4-((2-((2-oxo-2,3-dihydrobenzo[d]oxazol-6-yl)amino)pyrimidin-4-yl)oxy)naphthalen-1-yl)urea. | R$^t$ 2.18 min (Method 2, basic); m/z 756 (M + H)$^+$ (ES$^+$); m/z 754 (M − H)$^-$ (ES$^-$); $^1$H NMR δ: 1.28 (9H, s), 2.47-2.49 (4H, over-lapping m), 2.72 (2H, m), 3.57-3.59 (4H, over-lapping m), 4.15 (2H, m), 6.39 (1H, s), 6.53 (1H, d), 6.76 (1H, br d), 7.11-7.14 (3H, over-lapping m), 7.38-7.50 (4H, over-lapping m), 7.54-7.64 (2H, over-lapping m), 7.80 (1H, m), 7.95 (1H, m), 8.08 (1H, d), 8.37 (1H, d), 8.75 (1H, s), 9.13 (1H, s), 9.53 (1H, s), 11.38 (1H br s).<br>[Route 2] |
| 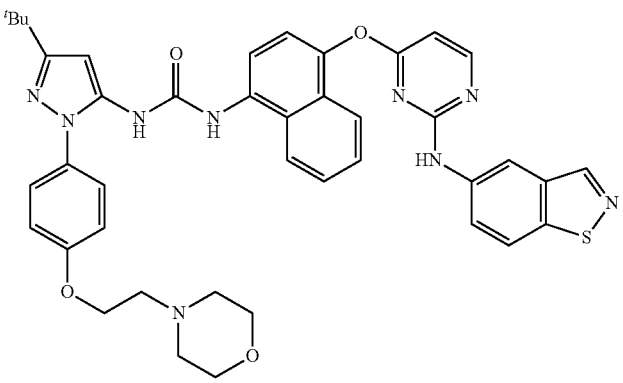<br>78: 1-(4-((2-(benzo[d]isothiazol-5-ylamino)pyrimidin-4-yl)oxy)naphthalen-1-yl)-3-(3-(tert-butyl)-1-(4-(2-morpholinoethoxy)phenyl)-1H-pyrazol-5-yl)urea. | R$^t$ 3.11 min (Method 3); m/z 756 (M + H)$^+$ (ES$^+$); $^1$H NMR δ: 1.30 (9H, s), 2.48-2.51 (4H, over-lapping m), 2.73 (2H, t), 3.59 (4H, t), 4.16 (2H, t), 6.43 (1H, s), 6.71 (1H, d), 7.14 (2H, m), 7.46-7.50 (4H, over-lapping m), 7.51-7.65 (2H, over-lapping m), 7.83-7.87 (2H, over-lapping m), 8.05 (1H, d), 8.11 (1H, d), 8.15 (1H, s), 8.48 (1H, d), 8.53 (1H, m), 8.76 (1H, br s), 9.22 (1H, br s), 9.90 (1H, br s).<br>[Route 2] |
| 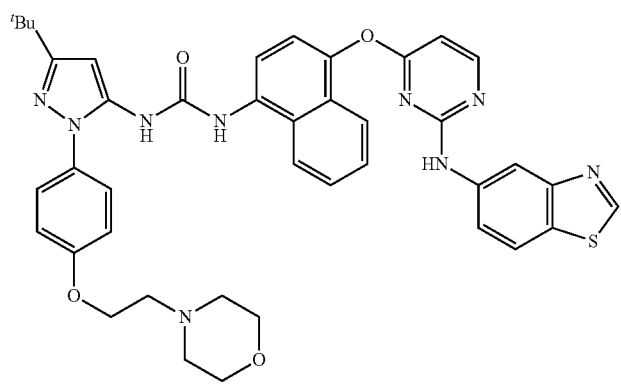<br>79: 1-(4-((2-(benzo[d]thiazol-5-ylamino)pyrimidin-4-yl)oxy)naphthalen-1-yl)-3-(3-(tert-butyl)-1-(4-(2-morpholinoethoxy)phenyl)-1H-pyrazol-5-yl)urea. | R$^t$ 2.35 min (Method 2, basic); m/z 756 (M + H)$^+$ (ES$^+$); m/z 754 (M − H)$^-$ (ES$^-$); $^1$H NMR δ: 1.29 (9H, s), 2.40-2.50 (4H, over-lapping m), 2.73 (2H, m), 3.57-3.59 (4H, over-lapping m), 4.15 (2H, t), 6.40 (1H, s), 6.58 (1H, d), 7.11 (2H, m), 7.42 (1H, d), 7.47 (2H, m), 7.51 (1H, m), 7.54-7.63 (2H, over-lapping m), 7.78 (1H, br d), 7.83 (1H, m), 7.91 (1H, d), 8.06 (1H, m), 8.28 (1H, br s), 8.44 (1H, d), 8.71 (1H, s), 9.08 (1H, s), 9.25 (1H, s), 9.75 (1H, s).<br>[Route 2] |

TABLE 3-continued

Additional Compound Examples of the Invention

| Structure, Example No. and Name | Analytical Data [Generic Route] |
|---|---|
| 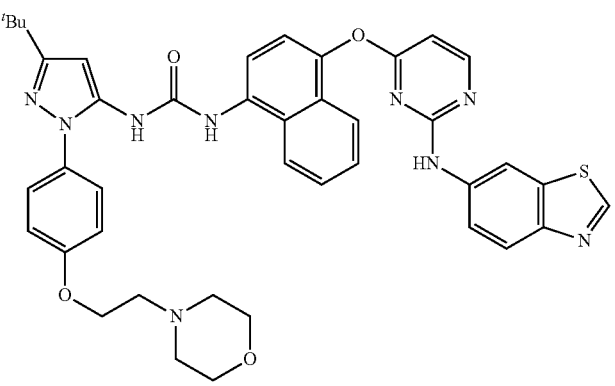<br>80: 1-(4-((2-(benzo[d]thiazol-6-ylamino)pyrimidin-4-yl)oxy)naphthalen-1-yl)-3-(3-(tert-butyl)-1-(4-(2-morpholinoethoxy)phenyl)-1H-pyrazol-5-yl)urea. | R$^t$ 2.83 min (Method 2 acidic); m/z 756 (M + H)$^+$ (ES$^+$); $^1$H NMR δ: 1.30 (9H, s), 2.47-2.50 (4H, over-lapping m), 2.72 (2H, t), 3.58 (4H, t), 4.15 (2H, t), 6.39 (1H, s), 6.68 (1H, d), 7.11 (2H, m): 7.38-7.41 (2H, over-lapping m), 7.50 (2H, m), 7.55-7.61 (2H, over-lapping m), 7.73 (1H, d), 7.82 (1H, d), 7.99-8.01 (2H, over-lapping m), 8.14 (1H, d), 8.46 (1H, d), 8.81 (1H, br s), 9.06 (1H, s), 9.20 (1H, br s), 9.80 (1H, br s). [Route 2] |
| 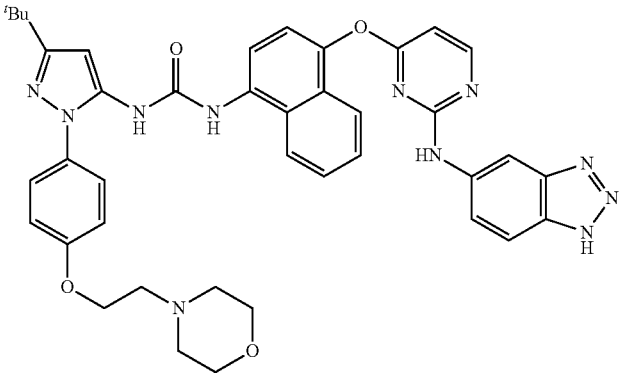<br>81: 1-(4-((2-((1H-benzo[d][1,2,3]triazol-5-yl)amino)pyrimidin-4-yl)oxy)naphthalen-1-yl)-3-(3-(tert-butyl)-1-(4-(2-morpholinoethoxy)phenyl)-1H-pyrazol-5-yl)urea. | R$^t$ 2.22 min (Method 2, basic); m/z 740 (M + H)$^+$ (ES$^+$); m/z 738 (M − H)$^-$ (ES$^-$); $^1$H NMR δ: 1.30 (9H, s), 2.47-2.49 (4H, over-lapping m), 2.72 (2H, m), 3.57-3.59 (4H, over-lapping m), 4.15 (2H, m), 6.49 (1H, br s), 6.60 (1H, d), 7.13 (2H, m), 7.37 (1H, br d), 7.46 (1H, d), 7.49 (2H, m), 7.55-7.67 (3H, over-lapping m), 7.84 (1H, m), 7.91 (1H, d), 8.04-8.09 (2H, over-lapping m), 8.46 (1H, d), 8.80 (1H, s), 9.19 (1H, s), 9.85 (1H, s), 15.15 (1H, br s). [Route 2] |
| 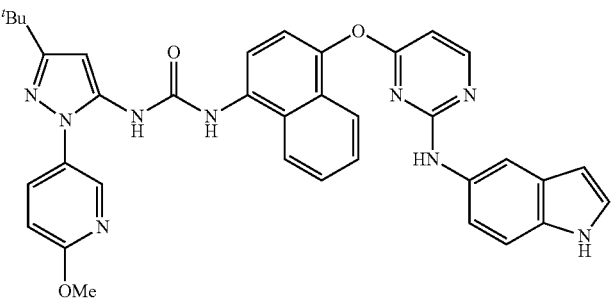<br>82: 1-(4-((2-((1H-indol-5-yl)amino)pyrimidin-4-yl)oxy)naphthalen-1-yl)-3-(3-(tert-butyl)-1-(6-methoxypyridin-3-yl)-1H-pyrazol-5-yl)urea. | R$^t$ 2.32 min (Method 2 acidic); m/z 638 (M − H)$^-$ (ES$^-$); $^1$H NMR δ: 1.29 (9H, s), 3.95 (3H, s), 6.08 (1H, s), 6.44-6.46 (2H, over-lapping m), 7.02-7.07 (3H, over-lapping m), 7.17 (1H, m), 7.42 (1H, d), 7.54-7.64 (3H, over-lapping m), 7.83 (1H, m), 7.93 (1H, dd), 7.99 (1H, d), 8.08 (1H, d), 8.33 (1H, d), 8.42 (1H, d), 8.84 (1H, s), 9.12 (1H, s), 9.27 (1H, s), 10.79 (1H, s). [Route 1, CDI] |

TABLE 3-continued

Additional Compound Examples of the Invention

| Structure, Example No. and Name | Analytical Data [Generic Route] |
|---|---|
| 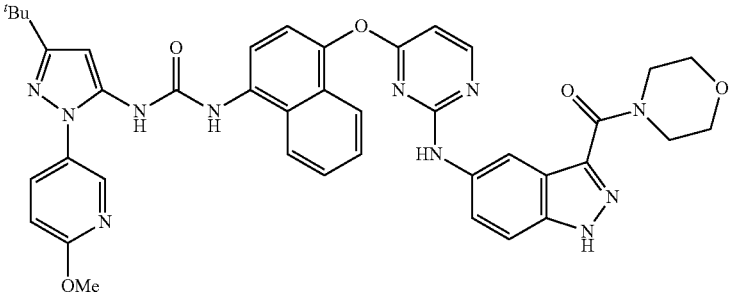<br>83: 1-(3-(tert-butyl)-1-(6-methoxypyridin-3-yl)-1H-pyrazol-5-yl)-3-(4-((2-((3-(morpholine-4-carbonyl)-1H-indazol-5-yl)amino)pyrimidin-4-yl)oxy)naphthalen-1-yl)urea. | $R^t$ 2.15 min (Method 2 acidic); m/z 754 (M + H)$^+$ (ES$^+$); $^1$H NMR δ: 1.29 (9H, s), 3.67 (6H, br s), 3.94 (3H, s), 3.98 (2H, br s), 6.44-6.46 (2H, over-lapping m), 7.03 (1H, d), 7.31 (1H, d), 7.42 (1H, d), 7.48 (1H, m), 7.56-7.65 (2H, over-lapping m), 7.83-7.92 (3H, over-lapping m), 8.04 (1H, d), 8.25 (1H, br s), 8.37 (1H, d), 8.40 (1H, m), 8.78 (1H, s), 9.07 (1H, s), 9.52 (1H, s), 13.34 (1H, s).<br>[Route 1, CDI] |
| 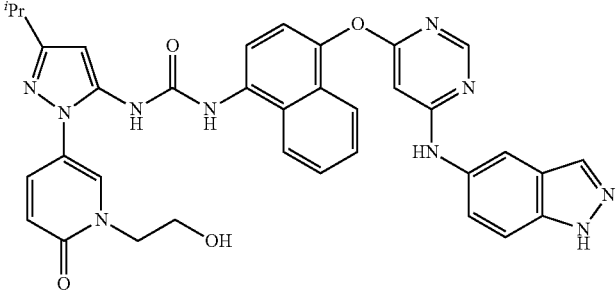<br>84: 1-(4-((6-(1H-indazol-5-yl)amino)pyrimidin-4-yl)oxy)naphthalen-1-yl)-3-(1-(1-(2-hydroxyethyl)-6-oxo-1,6-dihydropyridin-3-yl)-3-isopropyl-1H-pyrazol-5-yl)urea. | $R^t$ 1.66 min (Method 2, basic); m/z 655 (M − H)$^−$ (ES$^−$); $^1$H NMR δ: 1.23 (6H, d), 2.87 (1H, m), 3.70 (2H, m), 4.04 (2H, t), 4.93 (1H, t), 6.09 (1H, d), 6.33 (1H, s), 6.55 (1H, d), 7.34-7.38 (2H, over-lapping m), 7.49 (1H, d), 7.56-7.67 (3H, over-lapping m), 7.83 (1H, dd), 7.91 (1H, d), 8.01-8.08 (4H, over-lapping m), 8.28 (1H, s), 8.82 (1H, br s), 9.02 (1H, br s), 9.51 (1H, br s), 12.97 (1H, br s).<br>[Route 1, phenyl chloroformate then TBAF deprotection] |
| 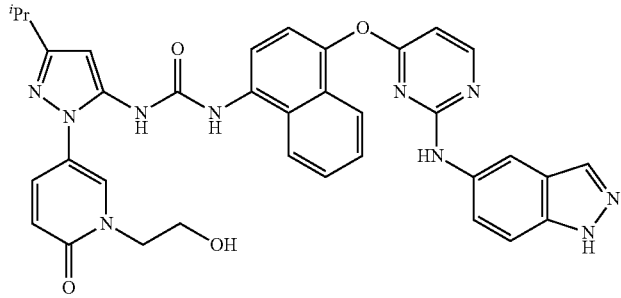<br>85: 1-(4-((2-(1H-indazol-5-yl)amino)pyrimidin-4-yl)oxy)naphthalen-1-yl)-3-(1-(1-(2-hydroxyethyl)-6-oxo-1,6-dihydropyridin-3-yl)-3-isopropyl-1H-pyrazol-5-yl)urea. | $R^t$ 1.77 min (Method 2 acidic); m/z 657 (M + H)$^+$ (ES$^+$); $^1$H NMR δ: 1.24 (6H, d), 2.90 (1H, m), 3.70 (2H, m), 4.06 (2H, t), 4.96 (1H, t), 6.37 (1H, s), 6.56-6.59 (2H, over-lapping m), 7.26 (2H, over-lapping br s), 7.44 (1H, d), 7.55-7.64 (5H, over-lapping m), 7.85 (1H, d), 8.04-8.07 (2H, over-lapping m), 8.16 (1H, d), 8.40 (1H, d), 8.95 (1H, br s), 9.17 (1H, br s), 9.54 (1H, br s), 12.78 (1H, br s).<br>[Route 1, CDI then TBAF deprotection] |
| 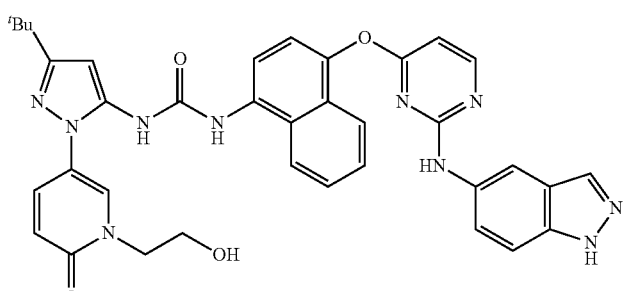<br>86: 1-(4-((2-((1H-indazol-5-yl)amino)pyrimidin-4-yl)oxy)naphthalen-1-yl)-3-(3-(tert-butyl)-1-(1-(2-hydroxyethyl)-6-oxo-1,6-dihydropyridin-3-yl)-1H-pyrazol-5-yl)urea. | $R^t$ 1.90 min (Method 2 acidic); m/z 671 (M + H)$^+$ (ES$^+$); $^1$H NMR δ: 1.29 (9H, s), 3.70 (2H, m), 4.05 (2H, t), 4.96 (1H, t), 6.42 (1H, s), 6.56-6.59 (2H, over-lapping m), 7.26 (2H, br s), 7.44 (1H, d), 7.55-7.66 (5H, over-lapping m), 7.85 (1H, d), 8.04-8.07 (2H, over-lapping m), 8.17 (1H, d), 8.40 (1H, d), 8.96 (1H, br s), 9.19 (1H, br s), 9.54 (1H, br s), 12.78 (1H, br s).<br>[Route 1, CDI] |

TABLE 3-continued

Additional Compound Examples of the Invention

| Structure, Example No. and Name | Analytical Data [Generic Route] |
|---|---|
| 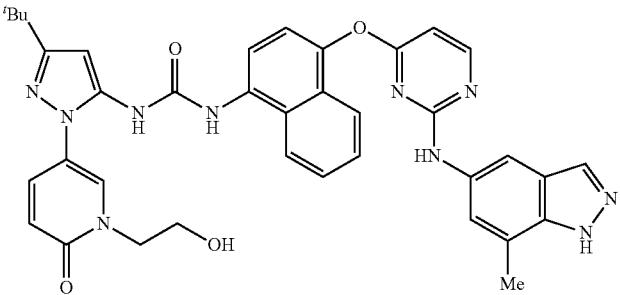<br>87: 1-(3-(tert-butyl)-1-(1-(2-hydroxyethyl)-6-oxo-1,6-dihydropyridin-3-yl)-1H-pyrazol-5-yl)-3-(4-((2-((7-methyl-1H-indazol-5-yl)amino)pyrimidin-4-yl)oxy)naphthalen-1-yl)urea. | $R^t$ 2.01 min (Method 2, basic); m/z 685 (M + H)$^+$ (ES$^+$); $^1$H NMR δ: 1.28 (9H, s), 2.29 (3H, br s), 3.71 (2H, t), 4.05 (2H, t), 4.95 (1H, br s), 6.41 (1H, s), 6.56-6.58 (2H, over-lapping m), 7.03 (1H, br s), 7.43 (2H, d), 7.54-7.66 (4H, over-lapping m), 7.83 (1H, dd), 8.04 (1H, d), 8.06 (1H, d), 8.14 (1H, d), 8.38 (1H, d), 8.90 (1H, br s), 9.13 (1H, br s), 9.44 (1H, br s), 12.83 (1H, br s). [Route 1, CDI then TBAF deprotection] |
| 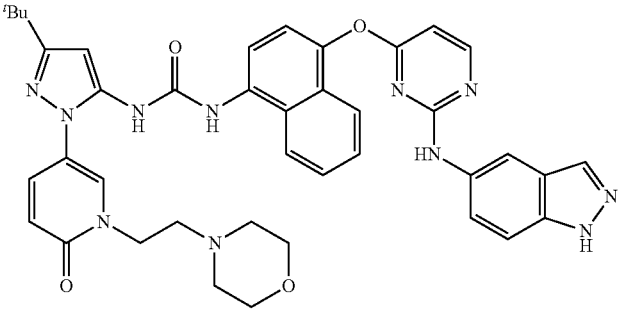<br>88: 1-(4-((2-((1H-indazol-5-yl)amino)pyrimidin-4-yl)oxy)naphthalen-1-yl)-3-(3-(tert-butyl)-1-(1-(2-morpholinoethyl)-6-oxo-1,6-dihydropyridin-3-yl)-1H-pyrazol-5-yl)urea. | $R^t$ 1.69 min (Method 2 acidic); m/z 740 (M + H)$^+$ (ES$^+$); $^1$H NMR δ: 1.28 (9H, s), 2.39 (4H, br s), 2.58 (2H, m), 3.50-3.52 (4H, over-lapping m), 4.07 (2H, m), 6.40 (1H, s), 6.54-6.59 (2H, over-lapping m), 7.24 (2H, br s), 7.44 (1H, d), 7.56-7.66 (5H, over-lapping m), 7.84 (1H, m), 8.09-8.15 (3H, over-lapping m), 8.39 (1H, d), 8.89 (1H, s), 9.16 (1H, s), 9.53 (1H, s), 12.76 (1H, s). [Route 1, CDI] |
| 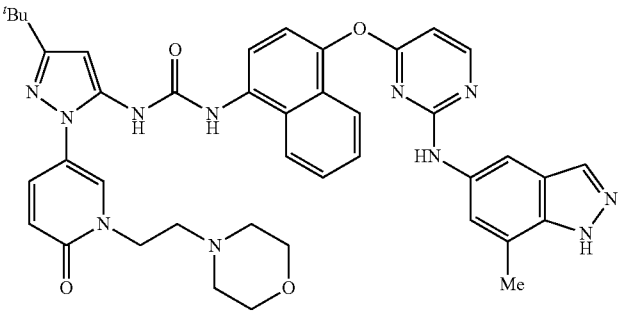<br>89: 1-(3-(tert-butyl)-1-(1-(2-morpholinoethyl)-6-oxo-1,6-dihydropyridin-3-yl)-1H-pyrazol-5-yl)-3-(4-((2-((7-methyl-1H-indazol-5-yl)amino)pyrimidin-4-yl)oxy)naphthalen-1-yl)urea. | $R^t$ 2.17 min (Method 2, basic); m/z 754 (M + H)$^+$ (ES$^+$); m/z 752 (M − H)$^-$ (ES$^-$); $^1$H NMR δ: 1.28 (9H, s), 2.29 (3H, s), 2.39 (4H, t), 2.59 (2H, t), 3.51 (4H, t), 4.07 (2H, t), 6.40 (1H, s), 6.54-6.58 (2H, over-lapping m), 7.02 (1H, br s), 7.36-7.46 (2H, over-lapping m), 7.54-7.66 (4H, over-lapping m), 7.84 (1H, dd), 8.07-8.14 (3H, over-lapping m), 8.38 (1H, d), 8.88 (1H, br s), 9.15 (1H, br s), 9.44 (1H, br s). 12.83 (1H, br s). [Route 1, CDI] |

TABLE 3-continued

Additional Compound Examples of the Invention

| Structure, Example No. and Name | Analytical Data [Generic Route] |
|---|---|
| 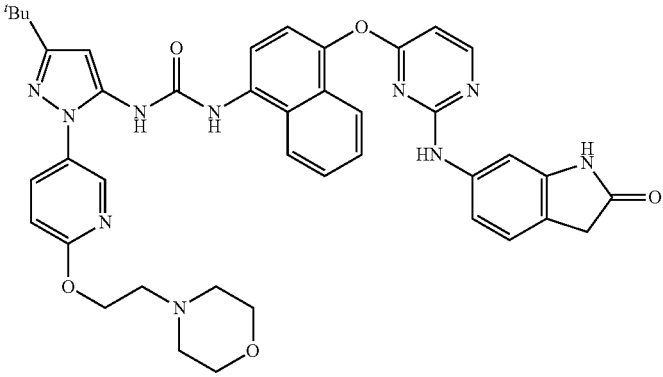<br>90: 1-(3-(tert-butyl)-1-(6-(2-morpholinoethoxy)pyridin-3-yl)-1H-pyrazol-5-yl)-3-(4-((2-((2-oxoindolin-6-yl)amino)pyrimidin-4-yl)oxy)naphthalen-1-yl)urea. | $R^t$ 2.10 min (Method 2, basic); m/z 755 (M + H)$^+$ (ES$^+$); $^1$H NMR δ: 1.29 (9H, s), 2.43-2.51 (4H, over-lapping m), 2.67 (2H, br s), 3.30 (2H, s), 3.58 (4H, br s), 4.45 (2H, br s), 6.44 (1H, s), 6.50 (1H, d), 6.78 (1H, d), 6.93 (1H, d), 7.03 (1H, d), 7.14 (1H, br s), 7.39 (1H, d), 7.54-7.64 (2H, over-lapping m), 7.82 (1H, dd), 7.87 (1H, d), 7.92 (1H, br s), 8.07 (1H, d), 8.37 (1H, d), 8.39 (1H, br s), 8.82 (1H, br s), 9.13 (1H, br s), 9.49 (1H, br s), 10.18 (1H, br s). [Route 1, CDI] |
| 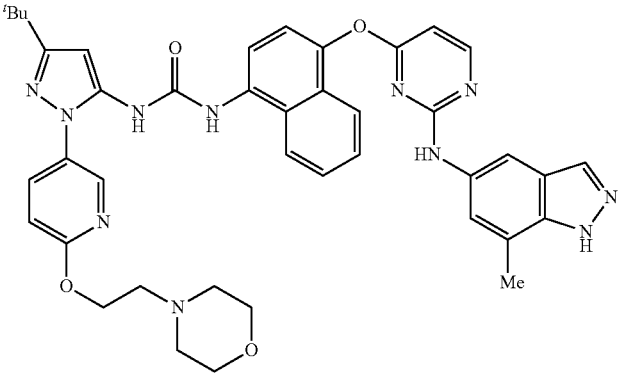<br>91: 1-(3-(tert-butyl)-1-(6-(2-morpholinoethoxy)pyridin-3-yl)-1H-pyrazol-5-yl)-3-(4-((2-((7-methyl-1H-indazol-5-yl)amino)pyrimidin-4-yl)oxy)naphthalen-1-yl)urea. | $R^t$ 2.30 min (Method 2, basic); m/z 754 (M + H)$^+$ (ES$^+$); $^1$H NMR δ: 1.30 (9H, s), 2.29 (3H, s), 2.46 (4H, t), 2.72 (2H, t), 3.56 (4H, t), 4.45 (2H, t), 6.45 (1H, s), 6.57 (1H, d), 7.02-7.04 (2H, over-lapping m), 7.42-7.64 (5H, over-lapping m), 7.83 (1H, dd), 7.93 (1H, dd), 8.01 (1H, d), 8.09 (1H, d), 8.38 (1H, d), 8.39 (1H, dd), 8.86 (1H, br s), 9.16 (1H, br s), 9.44 (1H, br s), 12.84 (1H, br s). [Route 1, CDI] |
| 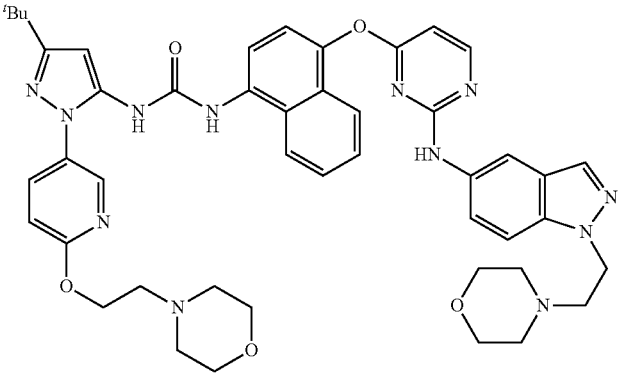<br>92: 1-(3-(tert-butyl)-1-(6-(2-morpholinoethoxy)pyridin-3-yl)-1H-pyrazol-5-yl)-3-(4-((2-((1-(2-morpholinoethyl)-1H-indazol-5-yl)amino)pyrimidin-4-yl)oxy)naphthalen-1-yl)urea. | $R^t$ 1.52 min (Method 2 acidic); m/z 853 (M + H)$^+$ (ES$^+$); $^1$H NMR δ: 1.30 (9H, s), 2.36 (4H, t), 2.47 (4H, t), 2.67 (2H, t), 2.73 (2H, t), 3.46 (4H, t), 3.58 (4H, t), 4.38 (2H, t), 4.46 (2H, t), 6.47 (1H, s), 6.60 (1H, d), 7.04 (1H, d), 7.27 (1H, m), 7.38 (1H, d), 7.44 (1H, d), 7.54-7.65 (3H, over-lapping m), 7.84 (1H, dd), 7.93 (1H, dd), 8.01 (1H, d), 8.10 (1H, d), 8.14 (1H, s), 8.40-8.42 (2H, over-lapping m), 8.86 (1H, br s), 9.17 (1H, br s), 9.55 (1H, br s). [Route 1, CDI] |

Biological Testing: Experimental Methods
Enzyme Binding Assays (Kinomescan)

The kinase enzyme binding activities of compounds disclosed herein were determined using a proprietary assay which measures active site-directed competition binding to an immobilized ligand (Fabian, M. A. et al., *Nature Biotechnol.*, 2005, 23:329-336). These assays were conducted by DiscoverX (formerly Ambit; San Diego, Calif.). The percentage inhibition produced by incubation with a test compound is calculated relative to the non-inhibited control.

Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The inhibitory activities of test compounds against the p38 MAPKα isoform (MAPK14: Invitrogen), are evaluated indirectly by determining the level of activation/phosphorylation of the down-stream molecule, MAPKAP-K2. The p38 MAPKα protein (80 ng/mL, 2.5 μL) is mixed with the test compound (2.5 μL of either 4 μg/mL, 0.4 μg/mL, 0.04 μg/mL or 0.004 μg/mL) for 2 hr at RT. The mix solution (2.5 μL) of the p38α inactive target MAPKAP-K2 (Invitrogen, 600 ng/mL) and FRET peptide (8 μM; a phosphorylation target for MAPKAP-K2) is then added and the kinase reaction is initiated by adding ATP (40 μM, 2.5 μL). The mixture is incubated for 1 hr at RT. Development reagent (protease, 5 μL) is added for 1 hr prior to detection in a fluorescence microplate reader (Varioskan® Flash, ThermoFisher Scientific).

p38 MAPKγ Enzyme Inhibition

The inhibitory activities of compounds of the invention against p38MAPKγ (MAPK12: Invitrogen), are evaluated in a similar fashion to that described hereinabove. The enzyme (800 ng/mL, 2.5 μL) is incubated with the test compound (2.5 μL at either 4 μg/mL, 0.4 μg/mL, 0.04 μg/mL, or 0.004 μg/mL) for 2 hr at RT. The FRET peptides (8 μM, 2.5 μL), and appropriate ATP solution (2.5 μL, 400 μM) is then added to the enzymes/compound mixtures and incubated for 1 hr. Development reagent (protease, 5 μL) is added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 μL) is incubated with the test compound (either 4 μg/mL, 0.4 μg/mL, 0.04 μg/mL, or 0.004 μg/mL, 2.5 μL each) for 2 hr at RT. The FRET peptides (8 μM, 2.5 μL), and appropriate ATP solutions (2.5 μL, 800 μM for c-Src, and 60 μM ATP for Syk) are then added to the enzymes/compound mixtures and incubated for 1 hr. Development reagent (protease, 5 μL) is added for 1 hr prior to detection in a fluorescence microplate reader (Varioskan® Flash, ThermoFisher Scientific).

GSK 3α Enzyme Inhibition

The inhibitory activities of compounds of the invention against the GSK 3α enzyme isoform (Invitrogen), are evaluated by determining the level of activation/phosphorylation of the target peptide. The GSK3-α protein (500 ng/mL, 2.5 μL) is mixed with the test compound (2.5 μL at either 4 μg/mL, 0.4 μg/mL, 0.04 μg/mL, or 0.004 μg/mL) for 2 hr at RT. The FRET peptide (8 μM, 2.5 μL), which is a phosphorylation target for GSK3α, and ATP (40 μM, 2.5 μL) are then added to the enzyme/compound mixture and the resulting mixture incubated for 1 hr. Development reagent (protease, 5 μL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which low ratios indicate high phosphorylation and high ratios indicate low phosphorylation levels. The percentage inhibition of each reaction is calculated relative to non-inhibited control and the 50% inhibitory concentration ($IC_{50}$ value) is then calculated from the concentration-response curve.

Cellular Assays (a) LPS-Induced TNFα/IL-8 Release in d-U937Cells

U937 cells, a human monocytic cell line, are differentiated into macrophage-type cells by incubation with PMA (100 ng/mL) for 48 to 72 hr. Cells are pre-incubated with final concentrations of test compound for 2 hr and are then stimulated with LPS (0.1 μg/mL) (from *E. coli*: O111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 μg/mL of BIRB796 at each concentration of test compound by comparison against vehicle control. The relative 50% effective concentration ($REC_{50}$) is determined from the resultant concentration-response curve. The inhibition of IL-8 production is calculated at each concentration of test compound by comparison with vehicle control. The 50% inhibitory concentration ($IC_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/ml LPS (*Escherichia Coli* 0111:B4 from Sigma Aldrich) for 24 hours under normal tissue culture conditions (37° C., 5% $CO_2$). The supernatant is harvested for determination of IL-8 and TNFα concentrations by sandwich ELISA (Duo-set, R&D systems) and read on the fluorescence microplate reader (Varioskan® Flash, ThermoFisher Scientific). The concentration at 50% inhibition ($IC_{50}$) of IL-8 and TNFα production is calculated from the dose response curve.

(c) IL-2 Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD38 monoclonal antibodies (0.3 ug/ml eBioscience and 3 ug/ml BD Pharmingen respectively). Compound at the desired concentration is then added to the wells and the plate left for 3 days under normal tissue culture conditions. Supernatants are harvested and IL-2 release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hrs) and pre-treated with compounds at the desired concentration for 2 hours before addition of 5 ng/ml of IL-1β (Abcam) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells incubated for 2 hrs and non-adherent cells removed by washing. To differentiate the cells to macrophages the cells are incubated with 5 ng/ml of GM-CSF (Peprotech) for 7 days under normal tissue culture conditions. Compounds are then added to the cells at the desired concentration for a 2 hour pre-treatment before stimulation with 10 ng/ml LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 µg/mL Poly I:C, ±2% Oligofectamine, 25 uL) (Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS (100 µL) and then endogenous peroxidase is quenched by the addition of washing buffer (100 µL, 0.05% Tween in PBS: PBS-Tween) containing 0.1% sodium azide and 1% hydrogen peroxide. Cells are washed with wash-buffer (3×200 µL). and after blocking the wells with 5% milk in PBS-Tween (100 µL) for 1 hr, the cells are incubated with anti-human ICAM-1 antibody (50 µL) (Cell Signaling Technology, Danvers, Mass.) in 1% BSA PBS overnight at 4° C.

The cells are washed with PBS-Tween (3×200 µL) and incubated with the secondary antibody (100 µL) (HRP-conjugated anti-rabbit IgG, Dako Ltd., Glostrup, Denmark). The cells are then incubated with of substrate (50 µL) for 2-20 min, followed by the addition of stop solution (50 µL, 1N $H_2SO_4$). The ICAM-1 signal is detected by reading and reading the absorbance at 450 nm against a reference wavelength of 655 nm using a spectrophotometer. The cells are then washed with PBS-Tween (3×200 µL) and total cell numbers in each well are determined by reading absorbance at 595 nm after Crystal Violet staining (50 µL of a 2% solution in PBS) and elution by 1% SDS solution (100 µL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) Human Biopsy Assay

Intestinal mucosa biopsies are obtained from the inflamed regions of the colon of IBD patients. The biopsy material is cut into small pieces (2-3 mm) and placed on steel grids in an organ culture chamber at 37° C. in a 5% $CO_2$/95% $C_2$ atmosphere in serum-free media. Test compounds at the desired concentration are added to the tissue and incubated for 24 hr in the organ culture chamber. The supernatant is harvested for determination of IL-6, IL-8, IL-1β and TNFα levels by ELISA.

(h) Cell Mitosis Assay

Peripheral blood mononucleocytes (PBMCs) from healthy subjects are separated from whole blood (Quintiles, London, UK) using a density gradient (Histopaque-1077, Sigma-Aldrich, Poole, UK). The PBMCs (3 million cells per sample) are subsequently treated with 2% PHA (Sigma-Aldrich, Poole, UK) for 48 hr, followed by a 20 hr exposure to varying concentrations of test compounds. At 2 hr before collection, PBMCs are treated with demecolcine (0.1 µg/mL) (Invitrogen, Paisley, UK,) to arrest cells in metaphase. To observe mitotic cells, PBMCs are permeabilised and fixed by adding Intraprep (50 µL) (Beckman Coulter, France), and stained with anti-phospho-histone 3 (0.26 ng/L) (#9701; Cell Signalling, Danvers, Mass.) and propidium iodide (1 mg/mL) (Sigma-Aldrich, Poole, UK,) as previously described (Muehlbauer P. A. and Schuler M. J., *Mutation Research*, 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(i) Assessment of HRV16 Induced CPE in MRC5 Cells

MRC-5 cells are infected with HRV16 at an MOI of 1 in DMEM containing 5% FCS and 1.5 mM $MgCl_2$, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 µL, 2% formaldehyde, 10% methanol and 0.175% Methylene Blue) for 2 hr at RT. After washing, 1% SDS in distilled water (100 µL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(j) In vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at an MOI of 0.001 in the LHC8 Media: RPMI-1640 (50:50) containing 15 mM magnesium chloride and incubated for 1 hr at 37° C. for adsorption. The cells are then washed with PBS (3×200 µL), fresh media (200 µL) is added and incubation continued for 4 days. Where appropriate, cells are pre-incubated with the compound or DMSO for 2 hr, and then added again after washout of the virus.

The cells are fixed with 4% formaldehyde in PBS solution (50 µL) for 20 min, washed with WB (3×200 µL), (washing buffer, PBS including 0.5% BSA and 0.05% Tween-20) and incubated with blocking solution (5% condensed milk in PBS) for 1 hr. Cells are then washed with WB (3×200 µL) and incubated for 1 hr at RT with anti-RSV (2F7) F-fusion protein antibody (40 µL) (mouse monoclonal, lot 798760, Cat. No. ab43812, Abcam) in 5% BSA in PBS-tween. After washing, cells are incubated with an HRP-conjugated secondary antibody solution (50 µL) in 5% BSA in PBS-Tween (lot 00053170, Cat. No. P0447, Dako) and then TMB substrate (50 µL) (substrate reagent pack, lot 269472, Cat. No. DY999, R&D Systems, Inc.) was added. This reaction is stopped by the addition of 2N $H_2SO_4$ (50 µL) and the resultant signal is determined colorimetrically (OD: 450 nm with a reference wavelength of 655 nm) in a microplate reader (Varioskan® Flash, ThermoFisher Scientific).

Cells are then washed and a 2.5% crystal violet solution (50 µL) (lot 8656, Cat. No. PL7000, Pro-Lab Diagnostics) is applied for 30 min. After washing with WB, 1% SDS in distilled water (100 µL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{595}$ readings. The percentage inhibition for each well is calculated and the $IC_{50}$ value is calculated from the concentration-response curve generated from the serial dilutions of compound.

(k) the Effect of Test Compounds on Cell Viability: MTT Assay

Differentiated U937 cells are pre-incubated with each test compound (final concentration 1 µg/mL or 10 µg/mL in 200 µL media indicated below) under two protocols: the first for 4 hr in 5% FCS RPMI1640 media and the second in 10% FCS RPMI1640 media for 24 h. The supernatant is replaced with new media (200 µL) and MTT stock solution (10 µL, 5 mg/mL) is added to each well. After incubation for 1 hr the media are removed, DMSO (200 µL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(l) Accumulation of β catenin in d-U937Cells

U937 cells, a human monocytic cell line, are differentiated into macrophage-type cells by incubation with PMA; (100 ng/mL) for between 48 to 72 hr. The cells are then incubated with either final concentrations of test compound or vehicle for 18 hr. The induction of β-catenin by the test compounds is stopped by replacing the media with 4% formaldehyde solution. Endogenous peroxide activity is neutralised by incubating with quenching buffer (100 µL, 0.1% sodium azide, 1% $H_2O_2$ in PBS with 0.05% Tween-20) for 20 min. The cells are washed with washing buffer (200 µL) (PBS containing 0.05% Tween-20) and incubated with blocking solution (200 µL) (5% milk in PBS) for 1 hr, re-washed with washing buffer (200 µL) and then incubated overnight with anti-β-catenin antibody solution (50 µL) in 1% BSA/PBS (BD, Oxford, UK).

After washing with washing buffer (3×200 µL,) (PBS containing 0.05% Tween-20), cells are incubated with an HRP-conjugated secondary antibody solution (100 µL) in 1% BSA/PBS (Dako, Cambridge, UK) and the resultant signal is determined colourimetrically (OD: 450 nm with a reference wavelength of 655 nm) using TMB substrate (50 µL) (R&D Systems, Abingdon, UK). This reaction is stopped by addition of 1N $H_2SO_4$ solution (50 µL). Cells are then washed with washing buffer and 2% crystal violet solution (50 µL) is applied for 30 min. After washing with washing buffer (3×200 µL), 1% SDS (100 µL) is added to each well and the plates are shaken lightly for 1 hr prior to measuring the absorbance at 595 nm (Varioskan® Flash, Thermo-Fisher Scientific).

The measured $OD_{450-555}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising of the Reference Compound (1 µg/mL) which is defined as unity. A signal less than 0.15 of that observed for the standard control is designated as "−ve".

In Vivo Screening: Pharmacodynamics and Anti-inflammatory Activity (A) LPS-induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min). After a further 8 hr the animals are anesthetized, their tracheas cannulated and BALF extracted by infusing and then withdrawing from their lungs 1.0 mL of PBS via the tracheal catheter. Total and differential white cell counts in the BALF samples are measured using a Neubaur haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are shown as mean±S.E.M. (standard error of the mean). The percentage inhibition of neutrophil accumulation is calculated for each treatment relative to vehicle treatment.

(B) DSS-induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with DSS. On Day 0 of the study DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study animals are weighed every day and stool observations are made and recorded as a score, based on stool consistency. At the time of sacrifice on Day +6 the large intestine is removed and the length and weight are recorded. Sections of the colon are taken for either MPO analysis to determine neutrophil infiltration or for histopathology scoring to determine disease severity.

(C) TNBS-induced Colitis in Mice

Non-fasted, 10-12 week old, male BDF1 mice are dosed by oral gavage twice daily with either vehicle (5 mL/kg), reference item (Budesonide 2.5 mg/kg) or test compound (5 or 50 mg/kg) one day before (Day −1) stimulation of the inflammatory response by treatment with 2,4,6-trinitrobenzenesulphonic add (TNBS) (15 mg/mL in 50% ethanol/50% saline). On Day 0 of the study TNBS (200 µL) is administered intra-colonically via a plastic catheter followed by BID dosing of the vehicle, reference or test compound for 2 or 4 days. During the study animals are weighed every day and stool observations are made and recorded as a score, based on stool consistency. At the time of sacrifice on Day 2 (or Day 4) the large intestine is removed and the length and weight recorded. Sections of the colon are taken for either MPO analysis to determine neutrophil infiltration or for histopathology involving scoring to determine disease severity.

Summary of In Vitro and In Vivo Screening Results

The in vitro profile of the compound examples of the present invention, as determined using the protocols described above, are presented below (Tables 4a-c). Comparison is made with a structurally related Reference Compound which is: N-(4-(4-(3-(3-tert-butyl-1-p-tolyl-1H-pyrazol-5-yl)ureido)naphthalen-1-yloxy)pyridin-2-yl)-2-methoxyacetamide, that has been described previously as a potent anti-inflammatory agent with anti-viral activity (Ito, K. et al., WO 2010/112936, PCT/GB2010/050575, 7 Oct. 2010 and Ito, K. et al., WO 2010/067130, PCT/GB2009/051702, 17 Jun. 2010). The compounds of the present invention demonstrate a very similar inhibitory profile to the Reference Compound in the range of kinase enzyme assays with the marked exception of the inhibition they possess against the enzyme GSK3α, which is very much weaker than that displayed by the Reference Compound (Table 4a).

TABLE 4a

The p38 MAPK, c-Src, Syk and GSK3 α Enzyme Profiles of Compound Examples

| Test Compound Example No. | $IC_{50}$ Values for Enzyme Inhibition (nM) | | | |
|---|---|---|---|---|
| | p38 MAPKα | c-Src | Syk | GSK3α |
| Reference Compound | 12 | 5 | 42 | 45 |
| 1 | 187 | 21 | 50 | >1610 |
| 2 | 93 | 4 | 18 | >15600 |
| 3 | 19 | 6 | 95 | 2330 |
| 4 | 19 | 4 | 14 | 1370 |
| 5 | 81 | >1560 | 49 | >1560 |

TABLE 4a-continued

The p38 MAPK, c-Src, Syk and GSK3 α Enzyme Profiles of Compound Examples

| Test Compound Example No. | IC$_{50}$ Values for Enzyme Inhibition (nM) | | | |
|---|---|---|---|---|
| | p38 MAPKα | c-Src | Syk | GSK3α |
| 6 | 177 | 14 | 162 | >16000 |
| 7 | 80 | 10 | 24 | >1600 |
| 8 | 7 | 2 | 8 | 837 |
| 9 | 38 | 4 | 7 | >15600 |
| 10 | 18 | <1 | 2 | 589 |
| 11 | 39 | 6 | 15 | 848 |
| 12 | 77 | 13 | 22 | 3890 |
| 13 | 30 | 3 | 8 | >1560 |
| 14 | 3 | 2 | 7 | 1090 |
| 15 | 22 | <1 | 7 | 1420 |
| 16 | 101 | 22 | 65 | >16100 |
| 17 | 376 | 138 | 280 | >16100 |
| 18 | 1359 | 155 | 92 | 7080 |
| 19 | 12 | 7 | 32 | 1010 |
| 20 | 61 | 113 | 6 | 900 |
| 21 | 21 | 21 | 182 | >16000 |
| 22 | 56 | 19 | 26 | >16000 |
| 23 | 30 | 16 | 57 | 12500 |
| 24 | 245 | 102 | 1086 | 2180 |
| 25 | 523 | 46 | 756 | >16000 |
| 26 | 145 | 12 | 180 | >15700 |
| 27 | 263 | 11 | 17 | >1570 |
| 28 | >1520 | 164 | 711 | >1520 |
| 29 | 57 | 12 | 29 | 582 |
| 30 | 89 | 17 | >1600 | 301 |
| 31 | 33 | 6 | 199 | 1610 |
| 32 | 79 | 14 | 14 | >1600 |
| 33 | 369 | 23 | 671 | 5140 |
| 34 | 308 | 18 | >1560 | 1620 |
| 35 | 439 | 18 | >1560 | >15600 |
| 36 | 92 | 14 | 75 | 2100 |
| 37 | 332 | 16 | 142 | >1600 |
| 38 | 184 | 10 | 26 | >1560 |
| 39 | 10 | 11 | 39 | >16000 |
| 40 | 68 | 8 | 24 | >15600 |
| 41 | 128 | 16 | 81 | >15300 |
| 42 | 67 | 5 | 5 | >1530 |
| 43 | 15 | 2 | 21 | 485 |
| 44 | 5 | 2 | 2 | 203 |
| 45 | 17 | 5 | 3 | 407 |
| 46 | 12 | <1 | 2 | 908 |
| 47 | 32 | <1 | 5 | 472 |
| 48 | 70 | 4 | 18 | >1420 |
| 49 | 29 | 5 | 12 | 1350 |
| 50 | 31 | <1 | 2 | 1170 |
| 51 | 2 | <1 | <1 | 4900 |
| 52 | 22 | 3 | 18 | 4970 |
| 53 | 8 | 4 | 3 | 11300 |
| 54 | 11 | 7 | 9 | 1980 |
| 55 | 7 | <1 | <1 | >13500 |
| 56 | 46 | 2 | 3 | >13300 |
| 57 | 74 | 19 | 15 | 4700 |
| 58 | <1 | <1 | NT | 1260 |
| 59 | 98 | 23 | 28 | >9230 |
| 60 | 94 | 2 | 13 | 686 |
| 61 | 14 | <1 | 7 | 1540 |
| 62 | 98 | 5 | 9 | 1700 |
| 63 | 14 | <1 | 10 | 184 |
| 64 | 67 | 3 | 20 | 437 |
| 65 | 239 | 23 | 141 | 2840 |
| 66 | 335 | 15 | 19 | 2850 |
| 67 | 5 | <1 | <1 | 3040 |
| 68 | 40 | 3 | <1 | 3040 |
| 69 | 18 | 3 | 5 | 1280 |
| 70 | 33 | 13 | 14 | 3250 |
| 71 | 269 | 12 | 9 | 3440 |
| 72 | 13 | 2 | 3 | 2290 |
| 73 | 69 | 5 | 4 | 1800 |
| 74 | 27 | <1 | 1 | 597 |
| 75 | 36 | <1 | <1 | 4950 |
| 76 | 48 | 15 | 34 | 777 |
| 77 | 417 | 27 | 93 | 2290 |
| 78 | 139 | 8 | 33 | 2420 |
| 79 | 149 | 8 | 36 | 730 |
| 80 | 86 | 9 | 25 | 461 |
| 81 | 66 | 5 | 14 | 641 |
| 82 | 63 | 10 | 26 | >1560 |
| 83 | 10 | 107 | 63 | 3780 |
| 84 | <1.5 | 3 | 12 | 278 |
| 85 | 8 | <2 | 15 | 2530 |
| 86 | 7 | <1 | 16 | 827 |
| 87 | 45 | 2 | 4 | 1100 |
| 88 | 32 | 3 | 10 | 2430 |
| 89 | 47 | <1 | 3 | 2780 |
| 90 | 44 | <1 | <1 | 267 |
| 91 | 20 | 1 | 1 | 1210 |
| 92 | 5 | <1 | <1 | 569 |

The kinase binding profile of compound Example 12 of the present invention and the Reference Compound were compared with sorafenib against B-RAF p38 MAPK, HCK, cSrc, Syk, and GSK3α at 500 nM. The profile of Sorafenib was consistent with that previously described (Strumberg D. Drugs Today (Barc)., 2005, 41:773-84.). However, compound Example 12 displayed a very different phenotype, demonstrating profound inhibition of binding versus p38MAPK, HCK, cSrc and Syk kinases, without significant effect against B-RAF or GSK3α (Table 4b).

TABLE 4b

Comparison of the Enzyme Binding Profile of Compound Example 12 with the Reference Compound and Sorafenib.

| Test Compound Example No. | % Inhibition for kinase binding at 500 nM | | | | | | |
|---|---|---|---|---|---|---|---|
| | p38 MAPKα | p38 MAPKγ | HCK | cSrc | Syk | B-Raf | GSK3α |
| Reference compound | 100% | 100% | 100% | 100% | 95% | 70% | 84% |
| Sorafenib | 77% | 28% | 22% | 0% | 14% | 50% | 26% |
| 12 | 66% | 52% | 100% | 100% | 100% | 0% | 31% |

The compounds of the present invention demonstrate a similar profile to the Reference Compound in cellular assays that reveal anti-inflammatory properties against endotoxin mediated release of both TNFα and IL-8, as well as versus the virus mimic: polyIC induced ICAM-1 expression (Table 4c).

TABLE 4c

Inhibition of LPS induced TNFα and IL-8 Release (assay (a) above) and PolyIC induced ICAM-1 Expression or Compound Examples

| Test Compound: Example No. | LPS Induced Release of Cytokine in d-937 Cells (nM) | | Poly IC induced ICAM1 in BEAS2B (nM) |
|---|---|---|---|
| | TNFα REC$_{50}$ | IL-8 IC$_{50}$ | IC$_{50}$ |
| Ref. Compound | 0.13 | 1.3 | 2.1 |
| 1 | 1.7 | 2.2 | 4.7 |
| 2 | 1.4 | 1.7 | 1.4 |
| 3 | 5.2 | 34.8 | 6.8 |
| 4 | 2.4 | 2.0 | 2.4 |
| 5 | 1.1 | 1.7 | 0.6 |
| 6 | 1.6 | 5.3 | 1.7 |

TABLE 4c-continued

Inhibition of LPS induced TNFα and IL-8 Release (assay (a) above) and PolyIC induced ICAM-1 Expression or Compound Examples

| Test Compound: | LPS Induced Release of Cytokine in d-937 Cells (nM) | | Poly IC induced ICAM1 in BEAS2B (nM) |
|---|---|---|---|
| Example No. | TNFα REC$_{50}$ | IL-8 IC$_{50}$ | IC$_{50}$ |
| 7 | 6.2 | 17.2 | 16.1 |
| 8 | NT | 3.6 | 16.8 |
| 9 | 1.6 | 3.9 | 1.2 |
| 10 | 1.4 | 1.2 | 3.9 |
| 11 | 8.5 | 25.2 | 7.9 |
| 12 | 1.6 | 2.0 | 21.6 |
| 13 | 1.6 | 0.5 | 2.4 |
| 14 | 7.5 | 18.4 | 52.4 |
| 15 | 1.6 | 1.6 | 2.1 |
| 16 | 2.0 | 2.6 | 8.9 |
| 17 | 8.7 | 7.4 | 8.4 |
| 18 | 2.8 | 5.7 | 1.9 |
| 19 | 1.8 | 1.9 | 2.4 |
| 20 | 1.7 | 2.2 | 6.3 |
| 21 | 1.7 | 5.0 | 3.0 |
| 22 | 4.7 | 1.5 | 2.5 |
| 23 | 3.3 | 2.7 | 4.3 |
| 24 | 4.7 | 16.9 | 2.4 |
| 25 | 0.8 | 1.7 | 14.1 |
| 26 | 2.2 | 2.2 | 2.3 |
| 27 | 2.0 | 0.7 | 2.4 |
| 28 | 1.6 | 1.7 | 3.4 |
| 29 | 9.9 | 21.1 | 0.9 |
| 30 | 1.8 | 7.7 | 4.7 |
| 31 | 0.3 | 0.6 | 2.3 |
| 32 | 1.7 | 0.6 | 14.3 |
| 33 | 3.8 | 3.3 | 2.7 |
| 34 | 0.9 | 3.4 | 6.3 |
| 35 | 11.0 | 22.2 | 2.7 |
| 36 | 17.2 | 2.3 | 6.3 |
| 37 | 2.5 | 5.9 | 3.7 |
| 38 | 1.8 | 1.1 | 2.5 |
| 39 | 5.8 | 15.3 | 160 |
| 40 | 1.5 | 7.2 | 2.4 |
| 41 | 1.6 | 123 | 1.9 |
| 42 | 1.7 | 1.4 | 1.4 |
| 43 | 1.3 | 1.8 | 2.4 |
| 44 | 0.4 | 0.8 | 1.4 |
| 45 | 0.9 | 1.6 | 1.2 |
| 46 | 1.8 | 21.1 | 2.3 |
| 47 | 0.9 | 3.3 | 0.5 |
| 48 | 5.3 | 16.6 | 6.9 |
| 49 | 2.5 | 9.7 | 2.2 |
| 50 | 16.4 | 34.0 | 2.7 |
| 51 | NT | NT | 23.8 |
| 52 | NT | NT | 10.2 |
| 53 | 49.1 | 173 | 38.5 |
| 54 | 8.7 | 24.8 | 10.3 |
| 55 | 3.9 | 43.4 | 50.8 |
| 56 | 4.9 | 11.0 | 11.9 |
| 57 | 1.1 | 2.3 | 4.4 |
| 58 | NT | NT | 8.3 |
| 59 | 12.6 | 16.8 | 0.1 |
| 60 | 1.8 | 10.3 | 1.4 |
| 61 | 18.7 | 84.7 | >135 |
| 62 | 7.3 | 22.7 | 11.6 |
| 63 | 1.5 | 2.8 | 0.3 |
| 64 | 1.1 | 1.3 | 0.01 |
| 65 | 5.3 | 20.9 | 6.7 |
| 66 | 6.4 | 16.0 | 6.9 |
| 67 | 1.5 | 0.3 | 2.5 |
| 68 | NT | NT | 7.6 |
| 69 | 0.4 | 3.4 | 8.1 |
| 70 | 2.5 | 2.7 | 4.1 |
| 71 | 11.1 | >1330 | 2.2 |
| 72 | 1.6 | 1.7 | 165 |
| 73 | NT | 2.6 | 2.2 |
| 74 | 3.6 | 192 | 2.7 |
| 75 | 14.2 | 43.9 | 16.3 |
| 76 | 12.5 | 0.3 | 2.2 |
| 77 | 3.5 | 3.1 | 8.6 |
| 78 | 4.7 | 7.4 | 7.9 |
| 79 | 10.5 | 12.4 | 7.0 |
| 80 | 1.5 | 1.9 | 1.9 |
| 81 | 1.4 | 1.6 | 10.0 |
| 82 | 1.8 | 2.4 | 2.7 |
| 83 | 0.7 | 8.7 | 2.9 |
| 84 | 147 | 217 | >152 |
| 85 | 19.7 | 54.4 | 70.2 |
| 86 | 2.2 | 4.1 | 8.3 |
| 87 | 1.7 | 2.3 | 1.0 |
| 88 | 18.8 | 153 | 35.9 |
| 89 | 10.8 | 28.8 | 17.1 |
| 90 | 1.6 | 4.1 | 14.6 |
| 91 | NT | 1.6 | 1.9 |
| 92 | 1.5 | 11.5 | 5.3 |

The biological profiles of the compounds of the present invention are similar to those exhibited by the Reference Compound in cellular systems measuring their effects on respiratory virus replication as determined for HRV induced expression of CPE and RSV induced expression of F-protein (Table 4d).

TABLE 4d

The Effects of Compound Examples on Viral Propagation: HRV-16 induced expression of CPE and on RSV induced F-protein expression.

| Test Compound Example No. | IC$_{50}$ Values (nM) or % Inhibition Observed[1] | |
|---|---|---|
| | HRV induced CPE in MRC5 Cells | RSV induced F-protein in HBECs |
| Ref. Compound | 4.7 | 22.0 |
| 2 | 89% | NT |
| 4 | NT | 96% |
| 5 | 100% | NT |
| 12 | 92% | NT |
| 15 | 56% | NT |
| 17 | NT | 65% |
| 18 | NT | 56% |
| 22 | NT | 4.6 |
| 23 | 3.0 | NT |
| 24 | NT | 45% |
| 30 | NT | 57% |
| 31 | NT | 73% |
| 34 | NT | 74% |
| 35 | 100% | 71% |
| 40 | NT | 4.8 |
| 54 | 0.4 | NT |
| 56 | 6.7 | NT |
| 88 | 75% | NT |
| 89 | 9.6 | NT |

[1]Test compounds were screened at concentrations up to 0.32 ng/mL against HRV and 0.04 μg/mL against RSV;
NT = not tested.

However, advantageously, the compounds of the present invention in general show markedly less activity in assays systems that measure their impact on cell viability and cell division (mitosis) indicating that they are likely to possess an improved side effect profile and a superior therapeutic index over the Reference Compound (Table 4e).

TABLE 4e

Effect of Compound Examples on Cellular Viability and Cell Division

| Test Compound Example No. | MTT Assay [1] Cell viability at time point in d-U937 cells 4 h | MTT Assay [1] Cell viability at time point in d-U937 cells 24 h | Mitosis Assay % inhibition in PBMC cells at 5 μg/mL |
|---|---|---|---|
| Ref. Compd. | −ve | +ve | 87.8 |
| 1 | −ve | −ve | NT |
| 2 | −ve | −ve | NT |
| 3 | −ve | −ve | NT |
| 4 | −ve | −ve | NT |
| 5 | −ve | −ve | NT |
| 6 | −ve | −ve | NT |
| 7 | −ve | −ve | NT |
| 8 | −ve | −ve | NT |
| 9 | −ve | −ve | 23.7 |
| 10 | −ve | −ve | NT |
| 11 | −ve | −ve | NT |
| 12 | −ve | −ve | 58.6 |
| 13 | −ve | −ve | NT |
| 14 | −ve | −ve | NT |
| 15 | −ve | −ve | NT |
| 16 | −ve | −ve | NT |
| 17 | −ve | −ve | NT |
| 18 | −ve | −ve | NT |
| 19 | −ve | −ve | NT |
| 20 | −ve | −ve | NT |
| 21 | −ve | −ve | NT |
| 22 | −ve | −ve | 52.7 |
| 23 | −ve | −ve | 70.7 |
| 24 | −ve | −ve | NT |
| 25 | −ve | −ve | NT |
| 26 | −ve | −ve | NT |
| 27 | −ve | −ve | NT |
| 28 | −ve | −ve | NT |
| 29 | −ve | −ve | NT |
| 30 | −ve | −ve | NT |
| 31 | −ve | −ve | NT |
| 32 | −ve | −ve | NT |
| 33 | −ve | −ve | NT |
| 34 | −ve | −ve | NT |
| 35 | −ve | −ve | NT |
| 36 | −ve | −ve | 41.2 |
| 37 | −ve | −ve | NT |
| 38 | −ve | −ve | NT |
| 39 | −ve | −ve | NT |
| 40 | −ve | −ve | 30.5 |
| 41 | +ve | −ve | NT |
| 42 | −ve | +ve | NT |
| 43 | −ve | −ve | NT |
| 44 | −ve | −ve | NT |
| 45 | −ve | −ve | NT |
| 46 | −ve | −ve | NT |
| 47 | −ve | −ve | NT |
| 48 | −ve | −ve | NT |
| 49 | −ve | −ve | NT |
| 50 | −ve | −ve | NT |
| 51 | −ve | −ve | NT |
| 52 | −ve | −ve | NT |
| 53 | −ve | −ve | NT |
| 54 | −ve | −ve | NT |
| 55 | −ve | −ve | NT |
| 56 | −ve | +ve | NT |
| 57 | −ve | −ve | NT |
| 58 | −ve | −ve | NT |
| 59 | −ve | −ve | NT |
| 60 | −ve | −ve | NT |
| 61 | −ve | −ve | NT |
| 62 | −ve | −ve | NT |
| 63 | −ve | −ve | NT |
| 64 | −ve | −ve | NT |
| 65 | −ve | −ve | NT |
| 66 | −ve | −ve | NT |
| 67 | −ve | −ve | NT |
| 68 | −ve | −ve | NT |
| 69 | −ve | −ve | NT |
| 70 | −ve | −ve | 62.4 |
| 71 | −ve | −ve | NT |
| 72 | −ve | −ve | NT |
| 73 | −ve | −ve | NT |
| 74 | −ve | −ve | NT |
| 75 | −ve | −ve | NT |
| 76 | −ve | −ve | NT |
| 77 | −ve | −ve | NT |
| 78 | −ve | −ve | NT |
| 79 | −ve | −ve | NT |
| 80 | −ve | −ve | NT |
| 81 | −ve | −ve | NT |
| 82 | −ve | −ve | NT |
| 83 | −ve | −ve | NT |
| 84 | −ve | −ve | NT |
| 85 | −ve | −ve | NT |
| 86 | −ve | −ve | NT |
| 87 | −ve | −ve | NT |
| 88 | −ve | −ve | NT |
| 89 | −ve | +ve | 26.7 |
| 90 | −ve | −ve | 15.4 |
| 91 | −ve | −ve | NT |
| 92 | −ve | −ve | NT |

[1] Cell Viability Screen: −ve and +ve indicate that the value is below and above respectively, the no significant effect threshold, defined as 30% inhibition at 1 μg/mL at the time point indicated.

A number of compound examples of the invention were selected for additional profiling in vivo. The potential of these compounds to increase cellular concentrations of β-catenin was assessed and was found to be negative, that is, their inductive effect at a test concentration of 10 μg/mL was less than 15% of the effect produced by the Reference Compound at 1 μg/mL. Treatment of mice with the test substances was found to produce profound inhibitory effects on LPS-induced neutrophil accumulation in the lungs. As the compounds were administered only once, 8 hr before the endotoxin challenge, these experiments reveal that the drug substances had a long duration of action in this inflammatory model (Table 5).

TABLE 5

The Effects of Treatment with Selected Compound Examples on LPS-Induced Airways Neutrophilia in Mice.

| Test Compound Example No. | Neutrophil numbers (×10⁵/mL, +/−SEM) in BAL for drug substances dosed 8 hr pre-LPS challenge (% Inhibition)[1] Vehicle Control | Neutrophil numbers (×10⁵/mL, +/−SEM) in BAL for drug substances dosed 8 hr pre-LPS challenge (% Inhibition)[1] Test Substance at 0.2 mg/mL |
|---|---|---|
| Ref. Compd. | 14.0 ± 2.3 | 5.6 ± 0.86(60) |
| 12 | 14.1 ± 2.3 | 7.6 ± 1.5(46) |
| 13 | 17.1 ± 2.5 | 8.5 ± 1.4(50) |
| 22 | 16.4 ± 2.3 | 7.0 ± 1.2(57) |
| 42 | 17.1 ± 2.5 | 8.5 ± 1.5(50) |
| 56 | 16.4 ± 2.3 | 10.2 ± 1.9(38) |

[1] N = 8 animals per group

The biological profiles of the compound examples of the present invention, revealed above, indicate that the compounds of formula (I) possess anti-inflammatory properties similar to those of the Reference Compound, disclosed earlier. In addition the pharmacological effects are sustained in vivo for up to 8 hr that suggests they will show a long duration of action in therapeutic use. Advantageously the compounds of formula (I) have a narrower spectrum of kinase inhibitory activity than the Reference Compound, that is typical of many prior art molecules designed for this purpose and show reduced potential for adverse effects on cellular viability and on cell division. The pharmacological profiles exhibited by the compounds of formula (I) are thereby consistent with potent anti-inflammatory agents that are associated with a decreased risk of inducing toxicity in clinical use.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:
1. A compound of formula (I):

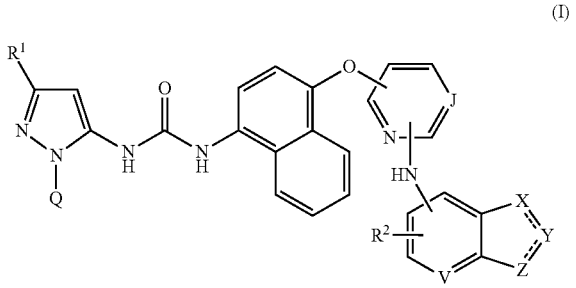

wherein:
R$^1$ represents C$_{1-6}$ alkyl, C$_{1-6}$ hydroxyalkyl, C$_{0-2}$ alkylene-C$_{3-8}$ cycloalkyl optionally substituted by C$_{1-3}$ alkyl, halo substituted C$_{1-6}$ alkyl or a 4-6 membered heterocycle optionally substituted with C$_{1-3}$ alkyl, Q represents thienyl, phenyl, pyridine or pyridone, each optionally substituted by 1 to 3 substituents independently selected from the group consisting of hydroxyl, halogen, C$_{1-6}$ alkyl, C$_{1-6}$ alkoxy, C$_{1-6}$ haloalkoxy, C$_{1-6}$ hydroxyalkyl, OC$_{2-6}$alkyleneOR$^A$, OC$_{2-6}$ alkyleneOC$_{2-6}$ alkyleneOR$^A$, OC$_{2-6}$alkyleneNR$^A$R$^A$ C$_{1-6}$ alkylene-5-10 membered heterocycle, and C$_{0-3}$ alkylene-O—C$_{1-6}$ alkylene-5-10 membered heterocycle, R$^A$ represents H or C$_{1-3}$ alkyl,
R$^2$ represents H, C$_{1-3}$ alkyl, C$_{1-3}$ alkoxy or halo,
J represents CH or N,
V represents CR$^2$ or N,
X represents S, N, NR$^3$, CR$^4$, C═O, O, CR$^5$R$^6$, or —OCR$^5$R$^6$-thereby forming a six membered ring,
Y represents O, N, NR$^7$, CR$^8$, C═O, SO$_n$ or CR$^9$R$^{10}$,
Z represents O, S, N, NR$^{11}$, C═O, CR$^{12}$, CR$^{12}$R$^{13}$, or —OCR$^{12}$R$^{13}$-thereby forming a six membered ring,
R$^3$ represents H, C$_{1-3}$ alkyl or C$_{1-6}$ alkylene-5-10 membered heterocycle,
R$^4$ represents H, hydroxyl, C$_{1-8}$ alkyl, C$_{2-8}$ alkenyl, C$_{2-8}$ alkynyl, C$_{1-3}$ haloalkyl, C$_{0-6}$ alkyleneNR$^{14}$R$^{15}$ or C$_{1-6}$ alkylene-5-10 membered heterocycle, wherein each alkylene group or alkyl group optionally bears 1oxo substituent and optionally one or two carbons in the alkylene chain or alkyl chain is replaced by a heteroatom selected from the group consisting of O,N, NR$^{14}$ and S(O)$_p$, R$^5$ represents H or C$_{1-3}$ alkyl,
R$^6$ represents H or C$_{1-3}$ alkyl,
R$^7$ represents H, C$_{1-3}$ alkyl or C$_{1-6}$ alkylene-5-10 membered heterocycle,
R$^8$ represents H, hydroxyl, C$_{1-8}$ alkyl, C$_{2-8}$ alkenyl, C$_{2-8}$ alkynyl, C$_{1-3}$ haloalkyl, C$_{0-6}$ alkyleneNR$^{14}$R$^{15}$ or C$_{1-6}$ alkylene-5-10 membered heterocycle, wherein each alkylene group or alkyl group optionally bears 1oxo substituent and optionally one or two carbons in the alkylene chain or alkyl chain is replaced by a heteroatom selected from the group consisting of O, N, NR$^{14}$ and S(O)$_p$, R$^9$ represents H or C$_{1-3}$ alkyl,
R$^{10}$ represents H or C$_{1-3}$ alkyl,
R$^{11}$ represents H, C$_{1-3}$ alkyl or C$_{1-6}$ alkylene-5-10 membered heterocycle,
R$^{12}$ represents H, hydroxyl, C$_{1-8}$ alkyl, C$_{2-8}$ alkenyl, C$_{2-8}$ alkynyl, C$_{1-3}$ haloalkyl, C$_{0-6}$ alkyleneNR$^{14}$R$^{15}$ or C$_{1-6}$ alkylene-5-10 membered heterocycle, wherein each alkylene group or alkyl group optionally bears 1oxo substituent and optionally one or two carbons in the alkylene chain or alkyl chain is replaced by a heteroatom selected from the group consisting of O N, NR$^{14}$ and S(O)$_p$, R$^{13}$ represents H or C$_{1-3}$ alkyl,
R$^{14}$ represents H or C$_{1-3}$ alkyl,
R$^{15}$ represents H or C$_{1-3}$ alkyl,
a dashed bond represents, as required by valency, a double or single bond,
n represents 0, 1 or 2,
P represents 0, 1 or 2,
with the proviso that when Z represents —OCR$^{12}$R$^{13}$-then X represents S, N, NR$^3$, CR$^4$, C═O, O or CR$^5$R$^6$;

or a pharmaceutically acceptable salt thereof, including all stereoisomers and tautomers thereof.

2. A compound according to claim 1 of formula (IA):

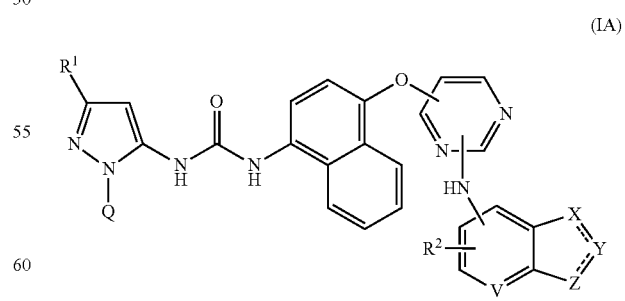

wherein:
R$^1$, R$^2$Q, V, X, Y and Z are as defined for claim 1, or a pharmaceutically acceptable salt thereof, including all stereoisomers and tautomers thereof.

3. A compound according to claim 1 of formula (IB):

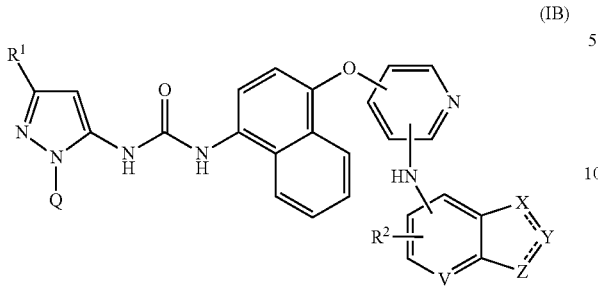

wherein:
R¹, R²Q, X, V, Y and Z are as defined for claim 1, or a pharmaceutically acceptable salt thereof, including all stereoisomers and tautomers thereof.

4. A compound according to claim 1 of formula (IC):

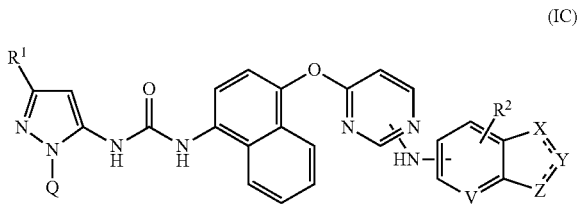

wherein:
R¹, R²Q, X, V, Y and Z are as defined in claim 1, or a pharmaceutically acceptable salt thereof, including all stereoisomers and tautomers thereof.

5. A compound according to claim 1 of formula (ID):

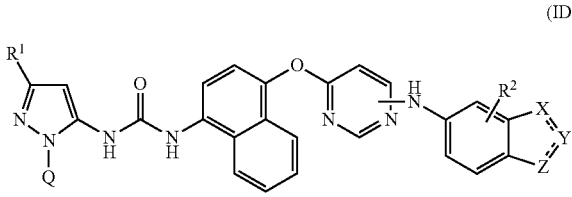

wherein:
R¹, R², Q, X, Y and Z are as defined in claim 1, or a pharmaceutically acceptable salt thereof, including all stereoisomers and tautomers thereof.

6. A compound according to claim 1 selected from the group consisting of:
  1-(4-((2-((1H-indol-5-yl)amino)pyrimidin-4-yl)oxy) naphthalen-1-yl)-3-(3-(tert-butyl)-1-(p-tolyl)-1H-pyrazol-5-yl)urea;
  1-(3-(tert-butyl)-1-(p-tolyl)-1H-pyrazol-5-yl)-3-(4-((2-((2-oxoindolin-6-yl)amino)pyrimidin-4-yl)oxy)naphthalen-1-yl)urea;
  5-((4-((4-(3-(3-(tert-butyl)-1-(p-tolyl)-1H-pyrazol-5-yl) ureido)naphthalen-1-yl)oxy)pyrimidin-2-yl)amino)-N-(2-morpholinoethyl)-1H-indazole-3-carboxamide;
  1-(3-(tert-butyl)-1-(p-tolyl)-1H-pyrazol-5-yl)-3-(4-((2 ((1-methyl-1H -benzo[d]imidazol-5-yl)amino)pyrimidin-4-yl)oxy)naphthalen-1-yl)urea;
  1-(4-((2-((3-aminobenzo [d]isoxazol-5-yl)amino)pyrimidin-4-yl)oxy)naphthalen-1-yl)-3-(3-(tert-butyl)-1-(p-tolyl)-1H-pyrazol-5-yl)urea;
  1-(4-((2-((1H-pyrazolo[3,4-b]pyridin-5-yl)amino)pyrimidin-4-yl)oxy)naphthalen-1-yl)-3-(3-(tert-butyl)-1-(p-tolyl)-1H-pyrazol-5-yl)urea;
  1-(4-((2-((1H-indazol-5-yl)amino)pyrimidin-4-yl)oxy) naphthalen-1-yl)-3-(3-(tert -butyl)-1-(4-hydroxyphenyl)-1H-pyrazol-5-yl)urea;
  1-(4-((2-((1H-indazol-5-yl)amino)pyrimidin-4-yl)oxy) naphthalen-1-yl)-3-(1-(4-methoxyphenyl)-3-(tetrahydrofuran-3-yl)-1H-pyrazol-5-yl)urea;
  1-(3-isopropyl-1-(4-methoxyphenyl)-1H-pyrazol-5-yl)-3-(4-((2((7-methyl-1H -indazol-5-yl)amino)pyrimidin-4-yl)oxy)naphthalen-1-yl)urea;
  1-(3-(tert-butyl)-1-(3-((2-oxopyrrolidin-1-yl)methyl)phenyl)-1H-pyrazol-5-yl)-3-(4-((2-((7-methyl-1H-indazol-5-yl)amino)pyrimidin-4-yl)oxy)naphthalen-1-yl) urea;
  1-(3-(tert-butyl)-1-(4-(2-morpholinoethoxy)phenyl)-1H-pyrazol-5-yl)-3-(4-((2-((2,3-dihydrobenzo [b][1,4]dioxin-6-yl)amino)pyrimidin-4-yl)oxy)naphthalen-1-yl) urea;
  1-(4-((2-((1H-indazol-5-yl)amino)pyrimidin-4-yl)oxy) naphthalen-1-yl)-3-(3-(tert -butyl)-1-(4-(2-morpholinoethoxy)phenyl)-1H-pyrazol-5-yl)urea;
  1-(4-((2-((1H-indazol-5-yl)amino)pyrimidin-4-yl)oxy) naphthalen-1-yl)-3-(3-(tert -butyl)-1-(6-methoxypyridin-3-yl)-1H-pyrazol-5-yl)urea;
  1-(4-((6-((1H-indazol-5-yl)amino)pyrimidin-4-yl)oxy) naphthalen-1-yl)-3-(3-(tert -butyl)-1-(1-(2-hydroxyethyl)-6-oxo-1,6-dihydropyridin-3-yl)1H-pyrazol-5-yl) urea;
  1-(4-((2-((1H-indazol-5-yl)amino)pyrimidin-4-yl)oxy) naphthalen-1-yl)-3-(3-(tert -butyl)-1-(6-(2-morpholinoethoxy)pyridin-3-yl)-1H-pyrazol-5-yl)urea;
  1-(3-(tert-butyl)-1-(p-tolyl)-1H-pyrazol-5-yl)-3-(4-((2-((1-methyl-1H-indol-5-yl)amino)pyrimidin-4-yl)oxy) naphthalen-1-yl)urea;
  1-(3-(tert-butyl)-1-(p-tolyl)-1H-pyrazol-5-yl)-3-(4((2-((2-oxoindolin-5-yl)amino)pyrimidin-4-yl)oxy)naphthalen-1-yl)urea;
  1-(3-(tert-butyl)-1-(p-tolyl)-1H-pyrazol-5-yl)-3-(4((2-((1-methyl-2-oxoindolin-5-yl)amino)pyrimidin-4-yl) oxy)naphthalen-1-yl)urea;
  1-(4-((2-((1H-indazol-5-yl)amino)pyrimidin-4-yl)oxy) naphthalen-1-yl)-3-(3-(tert -butyl)-1-(p-tolyl)-1H-pyrazol-5-yl)urea;
  1-(4-((6-((1H-indazol-5-yl)amino)pyrimidin-4-yl)oxy) naphthalen-1-yl)-3-(3-(tert -butyl)-1-(p-tolyl)-1H-pyrazol-5-yl)urea;
  1-(4-((2-((1H-indazol-6-yl)amino)pyrimidin-4-yl)oxy) naphthalen-1-yl)-3-(3-(tert -butyl)-1-(p-tolyl)-1H-pyrazol-5-yl)urea;
  1-(3-(tert-butyl)-1-(p-tolyl)-1H-pyrazol-5-yl)-3-(4((2-((1-methyl-1H-indazol-5-yl)amino)pyrimidin-4-yl) oxy)naphthalen-1-yl)urea;
  1-(3-(tert-butyl)-1-(p-tolyl)-1H-pyrazol-5-yl)-3-(4((2-((7-methyl-1H-indazol-5-yl)amino)pyrimidin-4-yl) oxy)naphthalen-1-yl)urea;
  1-(3-(tert-butyl)-1-(p-tolyl)-1H-pyrazol-5-yl)-3-(4((2-((7-chloro-1H-indazol-5-yl)amino)pyrimidin-4-yl) oxy)naphthalen-1-yl)urea;
  1-(3-(tert-butyl)-1-(p-tolyl)-1H-pyrazol-5-yl)-3-(4((2-((1-(2-morpholinoethyl)-1H-indazol-5-yl)amino)pyrimidin-4-yl)oxy)naphthalen-1-yl)urea;
  1-(4-((2-((1H-benzo [d]imidazol-5-yl)amino)pyrimidin-4-yl)oxy)naphthalen-1-yl)-3-(3-(tert-butyl)-1-(p-tolyl)-1H-pyrazol-5-yl)urea;

1-(3-(tert-butyl)-1-(p-tolyl)-1H-pyrazol-5-yl)-3-(4((2-((1-methyl-1H-benzo[d]imidazol-6-yl)amino)pyrimidin-4-yl)oxy)naphthalen-1-yl)urea;

1-(3-(tert-butyl)-1-(p-tolyl)-1H-pyrazol-5-yl)-3-(4((2-((1-methyl-1H-benzo[d]imidazol-6-yl)amino)pyrimidin-4-yl)oxy)naphthalen-1-yl)urea;

1-(4-((2-((1H-pyrrolo[2,3-b]pyridin-5-yl)amino)pyrimidin-4-yl)oxy)naphthalen-1-yl)-3-(3-(tert-butyl)-1-(p-toyl)-1H-pyrazol-5-yl)urea;

1-(4-((2-(benzo[d][1,3]dioxol-5-ylamino)pyrimidin-4-yl)oxy)naphthalen-1-yl)-3-(3-(tert-butyl)-1-(p-toyl)-1H-pyrazol-5-yl)urea;

1-(4-((2-(benzo[d][1,3]dioxol-5-ylamino)pyrimidin-4-yl)oxy)naphthalen-1-yl)-3-(3-(tert-butyl)-1-(p-toyl)-1H-pyrazol-5-yl)urea;

1-(4-((2-(benzo[d]thiazol-5-ylamino)pyrimidin-4-yl)oxy)naphthalen-1-yl)-3-(3-(tert-butyl)-1-(p-toyl)-1H-pyrazol-5-yl)urea;

1-(4-((2-(benzo[d]thiazol-6-ylamino)pyrimidin-4-yl)oxy)naphthalen-1-yl)-3-(3-(tert-butyl)-1-(p-toyl)-1H-pyrazol-5-yl)urea;

1-(4-((2-((1H-benzo[d][1,2,3]triazol-5-yl)amino)pyrimidin-4-yl)oxy)naphthalen-1-yl)-3-(3-(tert-butyl)-1-(p-tolyl)-1H-pyrazol-5-yl)urea;

1-(4-((2-((1H-indol-5-yl)amino)pyrimidin-4-yl)oxy)naphthalen-1-yl)-3-(3-(tert-butyl)-1-(4-hydroxyphenyl)-1H-pyrazol-5-yl)urea;

1-(4-((2-((1H-indol-5-yl)amino)pyrimidin-4-yl)oxy)naphthalen-1-yl)-3-(3-(tert-butyl)-1-(4-methoxyphenyl)-1H-pyrazol-5-yl)urea;

1-(4-(((6-((1H-indazol-5-yl)amino)pyrimidin-4-yl)oxy)naphthalen-1-yl)-3-(3-isopropyl-1-(4-methoxyphenyl)-1H-pyrazol-5-yl)urea;

1-(4-((2-((1H-indazol-5-yl)amino)pyrimidin-4-yl)oxy)naphthalen-1-yl)-3-(3-(tert-butyl)-1-(4-methoxyphenyl)-1H-pyrazol-5-yl)urea;

1-(3-(tert-butyl)-1-(4-methoxyphenyl)-1H-pyrazol-5-yl)-3-(4((2-((1-methyl-1H-indazol-5-yl)amino)pyrimidin-4-yl)oxy)naphthalen-1-yl)urea;

1-(3-(tert-butyl)-1-(4-methoxyphenyl)-1H-pyrazol-5-yl)-3-(4((2-((7-methyl-1H-indazol-5-yl)amino)pyrimidin-4-yl)oxy)naphthalen-1-yl)urea;

1-(3-(tert-butyl)-1-(4-methoxyphenyl)-1H-pyrazol-5-yl)-3-(4((2-((1-(2-morpholinoethyl)-1H-indazol-5-yl)amino)pyrimidin-4-yl)oxy)naphthalen-1-yl)urea;

1-(3-isopropyl-1-(4-methoxyphenyl)-1H-pyrazol-5-yl)-3-(4((2-((3-(2-morpholinoethoxy)-1H-indazol-5-yl)amino)pyrimidin-4-yl)oxy)naphthalen-1-yl)urea;

1-(3-(tert-butyl)-1-(4-methoxyphenyl)-1H-pyrazol-5-yl)-3-(4((2-((3-(2-morpholinoethoxy)-1H-indazol-5-yl)amino)pyrimidin-4-yl)oxy)naphthalen-1-yl)urea;

5-((4-((4-(3-(3-isopropyl-1-(4-methoxyphenyl)-1H-pyrazol-5-yl)ureido)naphthalen-1-yl)oxy)pyrimidin-2-yl)amino)-N,N-dimethyl-1H-indazole-3-carboxamide;

5-((4((4-(3-(3-(tert-butyl)-1-(4-methoxyphenyl)-1H-pyrazol-5-yl)ureido)naphthalen-1-yl)oxy)pyrimidin-2-yl)amino)-N,N-dimethyl-1H-indazole-3-carboxamide;

1-(4-((2-((1H-indol-5-yl)amino)pyrimidin-4-yl)oxy)naphthalen-1-yl)-3-(3-(tert-butyl)-1-(3-((2-oxopyrrolidin-1-yl)methyl)phenyl)-1H-pyrazol-5-yl)urea;

1-(4-((2-((1H-indazol-5-yl)amino)pyrimidin-4-yl)oxy)naphthalen-1-yl)-3-(3-(tert-butyl)-1-(3-((2-oxopyrrolidin-1-yl)methyl)phenyl)-1H-pyrazol-5-yl)urea;

1-(3-(tert-butyl)-1-(3-(2-morpholinoethoxy)phenyl)-1H-pyrazol-5-yl)-3-(4-((2-((2-oxoindolin-6-yl)amino)pyrimidin-4-yl)oxy)naphthalen-1-yl)urea;

1-(4-((2-((1H-indazol-5-yl)amino)pyrimidin-4-yl)oxy)naphthalen-1-yl)-3-(3-isopropyl-1-(3-(2-morpholinoethoxy)phenyl)-1H-pyrazol-5-yl)urea;

1-(4-((2-((1H-indazol-5-yl)amino)pyrimidin-4-yl)oxy)naphthalen-1-yl)-3-(3-(tert-butyl)-1-(3-(2-morpholinoethoxy)phenyl)-1H-pyrazol-5-yl)urea;

1-(3-isopropyl-1-(3-(2-morpholinoethoxy)phenyl)-1H-pyrazol-5-yl)-3-(4-((2-((7-methyl-1H-indazol-5-yl)amino)pyrimidin-4-yl)oxy)naphthalen-1-yl)urea;

1-(3-(tert-butyl)-1-(3-(2-morpholinoethoxy)phenyl)-1H-pyrazol-5-yl)-3-(4-((2-((7-methyl-1H-indazol-5-yl)amino)pyrimidin-4-yl)oxy)naphthalen-1-yl)urea;

1-(3-(tert-butyl)-1-(4(2-morpholinoethoxy)phenyl)-1H-pyrazol-5-yl)-3-(4-((2-((2,3-dihydro-1H-inden-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((1,3-dihydroisobenzofuran-5-yl)amino)pyrimidin-4-yl)oxy)naphthalen-1-yl)urea;

1-(3-isopropyl-1-(4-(2-morpholinoethoxy)phenyl)-1H-pyrazol-5-yl)-3-(4-((2-((2-oxoindolin-6-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((3,3-dimethyl-2-oxoindolin-6-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((3-oxoisoindolin-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((2,2-dioxido-1,3-dihydrobenzo[c]thiophen-5-yl)amino)pyrimidin-4-yl)oxy)naphthalen-1-yl)urea;

1-(4-((2-(benzo[d][1,3]dioxol 5-ylamino)pyrimidin-4-yl)oxy)naphthalen-1-yl)-3-(3-(tert-butyl)-1-(4-(2-morpholinoethoxy)phenyl)-1H-pyrazol-5-yl)urea;

1-(3-(tert-butyl)-1-(4-(2-morpholinoethoxy)phenyl)-1H-pyrazol-5-yl)-3-(4-((2-((2-methyl-1H-indol 5-yl)amino)pyrimidin-4-yl)oxy)naphthalen-1-yl)urea;

1-(4-((2-((1H-indazol-5-yl)amino)pyrimidin-4-yl)oxy)naphthalen-1-yl)-3-(3-isopropyl-1-(4-(2-morpholinoethoxy)phenyl)-1H-pyrazol-5-yl)urea;

1-(4-(((6-((1H-indazol-5-yl)amino)pyrimidin-4-yl)oxy)naphthalen-1-yl)-3-(3-(tert-butyl)-1-(4-(2-morpholinoethoxy)phenyl)-1H-pyrazol-5-yl)urea;

1-(3-(tert-butyl)-1-(4-(2-morpholinoethoxy)phenyl)-1H-pyrazol-5-yl)-3-(4-((2-((3-methyl-1H-indazol-6-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((7-methyl-1H-indazol-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((1-(2-morpholinoethyl)-1H-indazol-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((2-methyl-1H-benzo[d]imidazol-6-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((2-oxo-2,3-dihydrobenzo[d]oxazol-5-yl)amino)pyrimidin-4-yl)oxy)naphthalen-1-yl)urea;

1-(3-(tert-butyl)-1-(4-(2-morpholinoethoxy)phenyl)-1H-pyrazol-5-yl)-3-(4-((2-((2-oxo-2,3-dihydrobenzo[d]oxazol-6-yl)amino)pyrimidin-4-yl)oxy)naphthalen-1-yl)urea;

1-(4-((2-(benzo [d]isothiazol-5-ylamino)pyrimidin-4-yl)oxy)naphthalen-1-yl)-3-(3-(tert-butyl)-1-(4-(2-morpholinoethoxy)phenyl)-1H-pyrazol-5-yl)urea;

1-(4-((2-(benzo [d]thiazol-5-ylamino)pyrimidin-4-yl)oxy)naphthalen-1-yl)-3-(3-(tert-butyl)-1-(4-(2-morpholinoethoxy)phenyl)-1H-pyrazol-5-yl)urea;

1-(4-((2-(benzo [d]thiazol-6-ylamino)pyrimidin-4-yl)oxy)naphthalen-1-yl)-3-(3-(tert-butyl)-1-(4-(2-morpholinoethoxy)phenyl)-1H-pyrazol-5-yl)urea;

1-(4-((2-((1H-benzo [d][1,2,3]triazol-5-yl)amino)pyrimidin-4-yl)oxy)naphthalen-1-yl)-3-(3-(tert-butyl)-1-(4-(2-morpholinoethoxy)phenyl)-1H-pyrazol-5-yl)urea;

1-(4-((2-((1H-indol-5-yl)amino)pyrimidin-4-yl)oxy)naphthalen-1-yl)-3-(3-(tert-butyl)-1-(6-methoxypyridin-3-yl)-1H-pyrazol-5-yl)urea;

1-(3-(tert-butyl)-1-(6-methoxypyridin-3-yl)-1H-pyrazol-5-yl)-3-(4-((2-((3-(morpholine-4-carbonyl)-1H-indazol-5-yl)amino)pyrimidin-4-yl)oxy)naphthalen-1-yl)urea;

1-(4-((6-((1H-indazol-5-yl)amino)pyrimidin-4-yl)oxy)naphthalen-1-yl)-3-(1-(1-(2-hydroxyethyl)-6-oxo-1,6-dihydropyridin-3-yl)-3-isopropyl-1H-pyrazol-5-yl)urea;

1-(4-((2-((1H-indazol-5-yl)amino)pyrimidin-4-yl)oxy)naphthalen-1-yl)-3-(1-(1-(2-hydroxyethyl)-6-oxo-1,6-dihydropyridin-3-yl)-3-isopropyl-1H-pyrazol-5-yl)urea;

1-(4-((2-((1H-indazol-5-yl)amino)pyrimidin-4-yl)oxy)naphthalen-1-yl)-3-(3-(tert -butyl)-1-(1-(2-hydroxyethyl)-6-oxo-1,6-dihydropyridin-3-yl)-1H-pyrazol-5-yl)urea;

1-(3-(tert-butyl)-1-(1-(2-hydroxyethyl)-6-oxo-1,6-dihydropyridin-3-yl)-1H -pyrazol-5-yl)-3-(4-((2-((7-methyl-1H-indazol-5-yl)amino)pyrimidin-4-yl)oxy)naphthalen-1-yl)urea;

1-(4-((2-((1H-indazol-5-yl)amino)pyrimidin-4-yl)oxy)naphthalen-1-yl)-3-(3-(tert -butyl)-1-(1-(2-morpholinoethyl)-6-oxo-1,6-dihydropyridin-3-yl)-1H-pyrazol-5-yl)urea;

1-(3-(tert-butyl)-1-(1-(2-morpholinoethyl)-6-oxo-1,6-dihydropyridin-3-yl)-1H -pyrazol-5-yl)-3-(4((2-((7-methyl-1H-indazol-5-yl)amino)pyrimidin-4-yl)oxy)naphthalen-1 -yl)urea;

1-(3-(tert-butyl)-1-(6-(2-morpholinoethoxy)pyridin-3-yl)-1H-pyrazol-5-yl)-3-(4-((2-((2-oxoindolin-6-yl)amino)pyrimidin-4-yl)oxy)naphthalen-1-yl)urea;

1-(3-(tert-butyl)-1-(6-(2-morpholinoethoxy)pyridin-3-yl)-1H-pyrazol-5-yl)-3-(4-((2-((7-methyl-1H-indazol-5-yl)amino)pyrimidin-4-yl)oxy)naphthalen-1-yl)urea;

1-(3-(tert-butyl)-1-(6-(2-morpholinoethoxy)pyridin-3-yl)-1H-pyrazol-5-yl)-3-(4-((2-((1-(2-morpholinoethyl)-1H-indazol-5-yl)amino)pyrimidin-4-yl)oxy)naphthalen-1-yl)urea;

methyl 5-((4-((4-(3-(3-(tert-butyl)-1-(p-tolyl)-1H-pyrazol-5-yl)ureido)naphthalen-1-yl)oxy)pyrimidin-2-yl)amino)-1H-indazole-3-carboxylate;

1-(3-(tert-butyl)-1-(4-(2-morpholinoethoxy)phenyl)-1H-pyrazol-5-yl)-3-(4((2-((1-(tetrahydro-2H-pyran-2-yl)-1H-indazol-5-yl)amino)pyrimidin-4-yl)oxy)naphthalen-1-yl)urea;

and pharmaceutically acceptable salts of any one thereof.

7. A pharmaceutical composition comprising a compound according to claim 1, in combination with one or more pharmaceutically acceptable diluents or carriers.

8. A combination product comprising:
(A) a compound according to claim 1; and
(B) another therapeutic agent,
wherein each of components (A) and (B) is formulated in admixture with a pharmaceutically-acceptable adjuvant, diluent or carrier.

9. A method of treatment of a condition selected from the group consisting of Chronic Obstructive Pulmonary Disease (COPD), asthma, paediatric asthma, cystic fibrosis, sarcoidosis, idiopathic pulmonary fibrosis, allergic rhinitis, rhinitis, sinusitis, allergic conjunctivitis, conjunctivitis, diabetic retinopathy, macular oedema, post-operative cataract inflammation, uveitis (including posterior, anterior and pan uveitis), allergic dermatitis, contact dermatitis, atopic dermatitis, psoriasis, ulcerative colitis, Crohn's disease, rheumatoid arthritis and osteoarthritis which comprises administering to a subject having said condition an effective amount of a compound according to claim 1.

10. A method according to claim 9, wherein the condition is selected from the group consisting of COPD and asthma.

11. A method according to claim 9, wherein said COPD is chronic bronchitis or emphysema.

12. A method according to claim 9, wherein said macular oedema is wet macular oedema or dry macular oedema.

* * * * *